United States Patent
Gifford et al.

(10) Patent No.: US 11,673,936 B2
(45) Date of Patent: Jun. 13, 2023

(54) METHOD OF COMPACT PEPTIDE VACCINES USING RESIDUE OPTIMIZATION

(71) Applicant: Think Therapeutics, Inc., Newton, MA (US)

(72) Inventors: David Kenneth Gifford, Newton, MA (US); Brandon Carter, Cambridge, MA (US)

(73) Assignee: Think Therapeutics, Inc., Newton, MA (US)

(*) Notice: Subject to any disclaimer, the term of this patent is extended or adjusted under 35 U.S.C. 154(b) by 0 days.

(21) Appl. No.: 17/863,603

(22) Filed: Jul. 13, 2022

(65) Prior Publication Data

US 2023/0041112 A1    Feb. 9, 2023

Related U.S. Application Data

(63) Continuation of application No. 17/389,875, filed on Jul. 30, 2021, now Pat. No. 11,421,015, which is a continuation of application No. 17/114,237, filed on Dec. 7, 2020, now Pat. No. 11,161,892.

(51) Int. Cl.
| | |
|---|---|
| *A61K 39/00* | (2006.01) |
| *A61K 38/00* | (2006.01) |
| *C07K 14/74* | (2006.01) |
| *C07K 14/435* | (2006.01) |
| *A61K 38/17* | (2006.01) |
| *G01N 33/569* | (2006.01) |
| *G16B 20/30* | (2019.01) |
| *G16B 5/20* | (2019.01) |
| *G16B 30/00* | (2019.01) |
| *G16B 20/40* | (2019.01) |
| *G16B 35/10* | (2019.01) |
| *G16B 15/20* | (2019.01) |
| *G16B 5/00* | (2019.01) |

(52) U.S. Cl.
CPC .... *C07K 14/70539* (2013.01); *A61K 39/0011* (2013.01); *G01N 33/56977* (2013.01); *G16B 5/00* (2019.02); *G16B 5/20* (2019.02); *G16B 15/20* (2019.02); *G16B 20/30* (2019.02); *G16B 20/40* (2019.02); *G16B 30/00* (2019.02); *G16B 35/10* (2019.02); *A61K 38/00* (2013.01)

(58) Field of Classification Search
CPC ........ A61K 38/00; A61K 39/00; A61K 38/08; A61K 2039/605; C07K 14/70539
See application file for complete search history.

(56) References Cited

U.S. PATENT DOCUMENTS

| | | | |
|---|---|---|---|
| 5,961,978 A | 10/1999 | Gaudernack et al. | |
| 6,602,510 B1 | 8/2003 | Fikes et al. | |
| 7,488,718 B2 | 2/2009 | Scheinberg et al. | |
| 7,756,644 B2 | 7/2010 | Fridman et al. | |
| 8,007,810 B2 | 8/2011 | Fikes et al. | |
| 8,653,237 B2 | 2/2014 | Liu et al. | |
| 8,741,576 B2 | 6/2014 | Tangri et al. | |
| 8,765,687 B2 | 7/2014 | Scheinberg et al. | |
| 9,340,577 B2 | 5/2016 | Grey et al. | |
| 9,913,884 B2 | 3/2018 | Fikes et al. | |
| 10,335,473 B2 | 7/2019 | Eriksen | |
| 10,456,457 B2 | 10/2019 | Eriksen | |
| 10,556,943 B2 | 2/2020 | Knutson et al. | |
| 10,596,239 B2 | 3/2020 | Eriksen | |
| 10,738,355 B2 | 8/2020 | Sahin et al. | |
| 11,058,751 B1 | 7/2021 | Gifford et al. | |
| 11,161,892 B1 | 11/2021 | Gifford et al. | |
| 11,222,711 B2 | 1/2022 | Sahin et al. | |
| 11,235,039 B1 | 2/2022 | Gifford et al. | |
| 2002/0155093 A1 | 10/2002 | Houghton et al. | |
| 2002/0164346 A1 | 11/2002 | Nicolette | |
| 2003/0220239 A1 | 11/2003 | Simard et al. | |
| 2003/0224036 A1 | 12/2003 | Fikes et al. | |
| 2004/0037843 A1 | 2/2004 | Fikes et al. | |
| 2004/0072240 A1 | 4/2004 | Kosmatopoulos et al. | |

(Continued)

FOREIGN PATENT DOCUMENTS

| | | |
|---|---|---|
| WO | WO-97/33602 A1 | 9/1997 |
| WO | WO-99/63945 A2 | 12/1999 |

(Continued)

OTHER PUBLICATIONS

U.S. Appl. No. 17/243,096, Gifford et al.
U.S. Appl. No. 17/551,679, Gifford et al.
U.S. Appl. No. 17/815,086, Gifford et al.
Abelin et al., "Defining HLA-II Ligand Processing and Binding Rules with Mass Spectrometry Enhances Cancer Epitope Prediction," Immunity, Oct. 15, 2019, vol. 51(4), pp. 766-779; e1-e17, and Update (Feb. 9, 2021, 54(2):388). 34 pages.

(Continued)

*Primary Examiner* — Barry A Chestnut
(74) *Attorney, Agent, or Firm* — Wilmer Cutler Pickering Hale and Dorr LLP

(57) ABSTRACT

A system for selecting an immunogenic peptide composition comprising a processor and a memory storing processor-executable instructions that, when executed by the processor, cause the processor to create a first peptide set by selecting a plurality of base peptides, wherein at least one peptide of the plurality of base peptides is associated with a disease, create a second peptide set by adding to the first peptide set a modified peptide, wherein the modified peptide comprises a substitution of at least one residue of a base peptide selected from the plurality of base peptides, and create a third peptide set by selecting a subset of the second peptide set, wherein the selected subset of the second peptide set has a predicted vaccine performance, wherein the predicted vaccine performance has a population coverage above a predetermined threshold, and wherein the subset comprises at least one peptide of the second peptide set.

30 Claims, 10 Drawing Sheets

Specification includes a Sequence Listing.

(56) References Cited

U.S. PATENT DOCUMENTS

| | | |
|---|---|---|
| 2006/0018915 A1 | 1/2006 | Ishioka et al. |
| 2006/0093617 A1 | 5/2006 | Buyse et al. |
| 2007/0054262 A1 | 3/2007 | Baker et al. |
| 2007/0098776 A1 | 5/2007 | Fikes et al. |
| 2011/0002963 A1 | 1/2011 | Weinschenk et al. |
| 2011/0182926 A1 | 7/2011 | La Monica et al. |
| 2011/0257890 A1 | 10/2011 | Weinschenk et al. |
| 2014/0178421 A1 | 6/2014 | Kosmatopoulos |
| 2016/0101170 A1 | 4/2016 | Hacohen et al. |
| 2016/0125129 A1 | 5/2016 | Sahin et al. |
| 2018/0066017 A1 | 3/2018 | Hunt et al. |
| 2018/0102585 A1 | 4/2018 | Forster |
| 2018/0134804 A1 | 5/2018 | Scheinberg et al. |
| 2018/0141998 A1 | 5/2018 | Nguyen et al. |
| 2019/0175727 A1 | 6/2019 | Huang et al. |
| 2019/0307868 A1 | 10/2019 | Rooney |
| 2019/0322714 A1 | 10/2019 | Petit et al. |
| 2020/0061166 A1 | 2/2020 | Sahin et al. |
| 2020/0069782 A1 | 3/2020 | Biskup et al. |
| 2020/0105378 A1 | 4/2020 | Abelin et al. |
| 2020/0237885 A1 | 7/2020 | Levey et al. |
| 2021/0154280 A1 | 5/2021 | Martin et al. |
| 2021/0177954 A1 | 6/2021 | Juneja |
| 2021/0177955 A1 | 6/2021 | Petit et al. |
| 2021/0196806 A1 | 7/2021 | Yelensky et al. |
| 2021/0268086 A1 | 9/2021 | Zhong et al. |
| 2021/0268091 A1 | 9/2021 | Juneja |
| 2021/0275657 A1 | 9/2021 | Juneja et al. |
| 2021/0290746 A1 | 9/2021 | Sahin et al. |
| 2022/0160848 A1 | 5/2022 | Gifford et al. |
| 2022/0194999 A1 | 6/2022 | Krishna et al. |

FOREIGN PATENT DOCUMENTS

| | | |
|---|---|---|
| WO | WO-2005/042698 A2 | 5/2005 |
| WO | WO-2009/002418 A2 | 12/2008 |
| WO | WO-2016/172722 A1 | 10/2016 |
| WO | WO-2016/187508 | 11/2016 |
| WO | WO-2018/102585 A1 | 6/2018 |
| WO | WO-2018/187356 A2 | 10/2018 |
| WO | WO-2019/246286 | 12/2019 |
| WO | WO-2020/037239 A1 | 2/2020 |
| WO | WO-2020/154617 A1 | 7/2020 |
| WO | WO-2020/252039 A1 | 12/2020 |
| WO | WO-2021/055594 | 3/2021 |
| WO | WO-2021/087840 A1 | 5/2021 |
| WO | WO-2022/036142 A2 | 2/2022 |
| WO | WO-2022/132596 A2 | 6/2022 |

OTHER PUBLICATIONS

Alhadj-Ali et al., "Metabolic and immune effects of immunotherapy with proinsulin peptide in human new-onset type 1 diabetes," Science Translation Medicine, Aug. 9, 2017, vol. 9;9(402):eaaf7779. 9 pages.

Alvarez, B. et al., "NNAlign_MA; MHC Peptidome Deconvolution for Accurate MHC Binding Motif Characterization and Improved T-cell Epitope Predictions", Molecular & Cellular Proteomics, Dec. 2019, vol. 18(12), pp. cover, 2459-2477 (20 pages).

Asahara et al., "Phase I/II clinical trial using HLA-A24-restricted peptide vaccine derived from KIF20A for patients with advanced pancreatic cancer," Journal of Translational Medicine, Nov. 16, 2013, vol. 11:291. 13 pages.

Bae et al., "Myeloma-Specific Multiple Peptides Able to Generate Cytotoxic T Lymphocytes: A Potential Therapeutic Application in Muliple Myeloma and other Plasma Cell Disorders," Clinical Cancer Research, published online Jul. 2, 2012, vol. 18(17), pages.

Berzofsky et al., "Progress on new vaccine strategies for the immunotherapy and prevention of cancer," The Journal of Clinical Investigation, Jun. 2004, vol. 113(11), pp. 1515-1525.

Berzofsky et al., "Strategies for designing and optimizing new generation vaccines," Nature Reviews: Immunology, vol. 1(3), Dec. 2001, pp. 209-219.

Berzofsky, "Epitope selection and design of synthetic vaccines. Molecular approaches to enhancing immunogenicity and cross-reactivity of engineered vaccines," Annals of the New York Academy of Sciences, Aug. 12, 1993, vol. 690(1), pp. 256-264.

Bhasin, M. and Raghava, G.P.S., "Prediction of Promiscuous and High-Affinity Mutated MHC Binders", Hybridoma and Hybridomics, Nov. 4, 2003, vol. 22, 229-234, (8 pages).

Candia et al., "On Peptides and Altered Peptide Ligands: From Origin, Mode of Action and Design to Clinical Application (Immunotherapy)," International Archives of Allergy and Immunology, published online Sep. 20, 2016; vol. 170(4), pp. 211-233.

Chicz et al., "Predominant naturally processed peptides bound to HLA-DR1 are derived from MHC-related molecules and are heterogeneous in size," Nature, Aug. 27, 1992, vol. 358(6389), pp. 764-768.

Cleveland et al., "Routine large-scale production of monoclonal antibodies in a protein-free culture medium," Journal of Immunological Methods, Jan. 28, 1983, vol. 56, Issue 2, pp. 221-234.

Croft et al., "Most viral peptides displayed by class I MHC on infected cells are immunogenic," Proceedings of the National Academy of Sciences, Feb. 19, 2019, vol. 116(8), pp. 3112-3117.

Dai et al., "Machine learning optimization of peptides for presentation by class II MHCs," bioRxiv, posted Aug. 18, 2020 (https://doi.org/10.1101/2020.08.18.256081). 35 pages.

Dastagir et al., "Efficient Presentation of Multiple Endogenous Epitopes to Both CD4+ and CD8+ Diabetogenic T Cells for Tolerance," Molecular Therapy: Methods & Clinical Development, Mar. 2017, vol. 4, pp. 27-38.

Dey et al., "A Bioinformatics approach to designing a Zika virus vaccine," Computational Biology and Chemistry, available online Mar. 10, 2017, vol. 68, pp. 143-152.

Dyall et al., "Heteroclitic Immunization Induces Tumor Immunity," J. Exp. Med., Nov. 2, 1998, vol. 188(9), pp. 1553-1561.

Fong et al., "Altered peptide ligand vaccination with Flt3 ligand expanded dendritic cells for tumor immunotherapy," PNAS, Jul. 17, 2001, vol. 98(15), pp. 8809-8814.

Gibson et al., "Proinsulin multi-peptide immunotherapy induces antigen-specific regulatory T cells and limits autoimmunity in a humanized model," Clinical Experimental Immunology, Dec. 2015, vol. 182(3), pp. 251-260.

Guevara-Patino et al., "Optimization of a self antigen for presentation of multiple epitopes in cancer immunity," The Journal of Clinical Investigation, May 2006, vol. 116(5), pp. cover, 1382-1390.

Hollingsworth et al., "Turning the corner on therapeutic cancer vaccines," npj Vaccines, published online Feb. 8, 2019, vol. 4(7), pp. 1-10.

Hong et al., "Epitope-optimized alpha-fetoprotein genetic vaccines prevent carcinogen-induced murine autochthonous hepatocellular carcinoma," Hepatology, Apr. 2014, vol. 59(4), pp. 1448-1458.

Hoppes et al., "Altered Peptide Ligands Revisited: Vaccine Design through Chemically Modified HLA-A2-Restricted T Cell Epitopes," Journal of Immunology, published online Oct. 13, 2014, vol. 193, pp. 4803-4813. (12 pages).

Houghton et al., "Immunological validation of the EpitOptimizer program for streamlined design of heteroclitic epitopes," Vaccine, available online Jun. 4, 2007, vol. 25(29), pp. 5330-5342.

International Search Report and Written Opinion dated Mar. 28, 2022, in the International Application No. PCT/US2021/060013. 14 pages.

International Search Report and Written Opinion dated Oct. 14, 2022, in the International Application No. PCT/US22/26354. 21 pages.

Jain et al., "Synthetic Tumor-Specific Breakpoint Peptide Vaccine in Patients With Chronic Myeloid Leukemia and Minimal Residual Disease," Cancer, Sep. 1, 2009, vol. 115, pp. 3924-3934.

Jaravine et al., "Assessment of cancer and virus antigens for cross-reactivity in human tissues," Bioinformatics, Jan. 1, 2017, vol. 33, No. 1, pp. 104-111.

Jaravine et al., "Expitope 2.0: a tool to assess immunotherapeutic antigens for their potential cross-reactivity against naturally expressed proteins in human tissues," BMC Cancer, Dec. 28, 2017, vol. 17:892. 9 pages.

(56) References Cited

OTHER PUBLICATIONS

Jurtz, V. et al., "NetMHCpan-4.0: Improved Peptide-MHC Class I Interaction Predictions Integrating Eluted Ligand and Peptide Binding Affinity Data", The Journal of Immunology, prepublished online Oct. 4, 2017, vol. 199, pp. 3360-3368 (9 pages).

Keogh et al., "Identification of new epitopes from four different tumor-associated antigens: Recognition of naturally processed epitopes correlates with HLA-A*0201-binding affinity," The Journal of Immunology, Jul. 15, 2001, vol. 167(2), pp. 787-796. 11 pages.

Klinger et al., "Multiplex identification of antigen-specific T cell receptors using a combination of immune assays and immune receptor sequencing," PLOS One, Oct. 28, 2015, vol. 10(10), e0141561. 21 pages.

Kranz et al., "Systemic RNA delivery to dendritic cells exploits antiviral defence for cancer immunotherapy," Nature, Jun. 16, 2016, vol. 534(7607), pp. 396-401, and Methods. 16 pages.

Kreiter, et al., "Increased antigen presentation efficiency by coupling antigens to MHC class I trafficking signals," The Journal of Immunology, Jan. 2008, vol. 180(1), pp. 309-318, and Corrections. 12 pages.

Krienke, C. et al., "A noninflammatory mRNA vaccine for treatment of experimental autoimmune encephalomyelitis", Science, Jan. 8, 2021, vol. 371, pp. 145-153 (10 pages).

Liu et al. "Computationally Optimized SARS-CoV-2 MHC Class I and II Vaccine Formulations Predicted to Target Human Haplotype Distributions," Cell Systems, Aug. 26, 2020, vol. 11(2), pp. 131-144, e1-e6, Supplementary Table. 23 pages.

Liu et al., "Maximum n-times Coverage for COVID-19 Vaccine Design," arXiv (arXiv:2101.10902v1), submitted Jan. 24, 2021. 13 pages.

Liu et al., "Predicted Cellular Immunity Population Coverage Gaps for SARS-CoV-2 Subunit Vaccines and their Augmentation by Compact Peptide Sets," bioRxiv, posted Oct. 21, 2020, 29 pages. (https://www.biorxiv.org/content/10.1101/2020.08.04.200691v2).

Liu et al., "Predicted Cellular Immunity Population Coverage Gaps for SARS-CoV-2 Subunit Vaccines and their Augmentation by Compact Peptide Sets," Cell Systems, Journal Pre-proof, Nov. 26, 2020. (https://doi.org/10.1016/j.cels.2020.11.010). 36 pages.

Longmate et al., "Population coverage by HLA class-I restricted cytotoxic T-lymphocyte epitopes," Immunogenetics (2001), published online Dec. 19, 2000, vol. 52, pp. 165-173.

Maa et al., "Biopharmaceutical Powders: Particle Formation and Formulation Considerations," Current Pharmaceutical Biotechnology, Nov. 2000, vol. 1, No. 3, pp. 283-302.

Mahanty et al., "Immunogenicity of infectious pathogens and vaccine antigens," BMC Immunology, published online May 29, 2015, vol. 16(1), pp. 1-6.

Mashiba et al., "Identification of CTL epitopes in hepatitis C virus by a genome-wide computational scanning and a rational design of peptide vaccine," Immunogenetics, published online Jan. 16, 2007, vol. 59, pp. 197-209.

Merriam-Webster, "Prevent", available online at https://www.merriam-webster.com/dictionary/prevent. 10 pages. Accessed on Sep. 24, 2021.

Mösch et al., "Machine Learning for Cancer Immunotherapies Based on Epitope Recognition by T Cell Receptors," Frontiers in Genetics, Nov. 19, 2019, vol. 10, Article 1141. 17 pages.

Nair et al., "A simple practice guide for dose conversion between animals and human," Journal of Basic and Clinical Pharmacy, Article Review, Mar.-May 2016, vol. 7, Issue 2, pp. 27-31.

Ng et al., "In silico-guided sequence modifications of K-ras epitopes improve immunological outcome against G12V and G13D mutant KRAS antigens," PeerJ, published Jul. 20, 2018, 6:e5056. doi: 10.7717/peerj.5056. 21 pages.

Nielsen et al., "NNAlign: a platform to construct and evaluate artificial neural network models of receptor-ligand interactions," Nucleic Acids Research, published online Apr. 12, 2017, vol. 45, pp. W344-W349.

Nielsen et al., "The role of the proteasome in generating cytotoxic T-cell epitopes: insights obtained from improved predictions of proteasomal cleavage," Immunogenetics, published online Mar. 3, 2005, vol. 57, pp. 33-41.

Nielsen, M. and Lund, O., "NN-align. An artificial neural network-based alignment algorithm for MHC class II peptide binding prediction", BMC Bioinformatics, Sep. 18, 2009, vol. 10:296, pp. 1-10 (10 pages).

Nielsen, M. et al., "Quantitative Predictions of Peptide Binding to Any HLA-DR Molecule of Known Sequence: NetMHCIIpan", PLoS Computational Biology, Jul. 4, 2008, vol. 4(7):e1000107, pp. 1-10 (10 pages).

O'Donnell, T.J. et al., "MHCflurry 2.0: Improved Pan-Allele Prediction of MHC Class I-Presented Peptides by Incorporating Antigen Processing", Cell Systems, Jul. 22, 2020, vol. 11, pp. cover, 42-48 (15 pages).

O'Donnell, T.J. et al., "MHCflurry: Open-Source Class I MHC Binding Affinity Prediction", Cell Systems, Jul. 25, 2018, vol. 7, pp. cover, 129-132 (9 pages).

Ogishi et al., "Quantitative Prediction of the Landscape of T Cell Epitope Immunogenicity in Sequence Space," Frontiers in Immunology, Apr. 16, 2019, vol. 10, Article 827. 20 pages.

Park et al., "Accurate structure prediction of peptide-MHC complexes for identifying highly immunogenic antigens," Mol. Immunol., Nov. 2013, vol. 56(0):81-90. NIH Author Manuscript. 25 pages.

Reynisson et al., "NetMHCpan-4.1 and NetMHCIIpan-4.0: improved predictions of MHC antigen presentation by concurrent motif deconvolution and integration of MS MHC eluted ligand data," Nucleic Acids Research, published online May 14, 2020; vol. 48(W1), pp. W449-W454.

Rist et al., "HLA peptide length preferences control CD8+ T cell responses," The Journal of Immunology, published online Jun. 7, 2013, vol. 191(2), pp. 561-571. 12 pages.

Rosenberg et al., "Immunologic and therapeutic evaluation of a synthetic peptide vaccine for the treatment of patients with metastatic melanoma," Nature Medicine, Mar. 1998, vol. 4(3), pp. 321-327.

Sahin et al., "Personalized RNA mutanome vaccines mobilize poly-specific therapeutic immunity against cancer," Nature, Jul. 13, 2017, vol. 547(7662), pp. 222-226, and Methods. 19 pages.

Schipper et al., "Minimal Phenotype Panels, A Method for Achieving Maximum Population Coverage with a Minimum of HLA Antigens," Human Immunology, vol. 51, Dec. 1996, pp. 95-98.

Sette et al., "Peptides and Methods for Creating Synthetic Peptides With Modulated Binding Affinity for HLA Molecules," Application for U.S. non-provisional utility patent, U.S. Appl. No. 09/226,775, filed Jan. 6, 1999—not published, abandoned. 133 pages.

Sette et al., "The Relationship Between Class I Binding Affinity and Immunogenicity of Potential Cytotoxic T Cell Epitopes," The Journal of Immunology, Dec. 15, 1994, vol. 153, pp. 5586-5592.

Shimokawa, C. et al., "CD8+ regulatory T cells are critical in prevention of autoimmune-mediated diabetes", Nature Communications, Apr. 22, 2020, vol. 11:1922, pp. 1-9 (9 pages).

Sim et al., "Correction—High-affinity oligoclonal TCRs define effective adoptive T cell therapy targeting mutant KRAS-G12D," Proc. Natl. Acad. Sci. USA, Nov. 3, 2020, vol. 117(44), pp. 27743-27744.

Sim et al., "High-affinity oligoclonal TCRs define effective adoptive T cell therapy targeting mutant KRAS-G12D," Proc. Natl. Acad. Sci. USA, first published May 27, 2020, vol. 117(23), pp. 12826-12835.

Slansky et al., "Enhanced antigen-specific antitumor immunity with altered peptide ligands that stabilize the MHC-peptide-TCR complex," Immunity, Oct. 2000, vol. 13(4), pp. 529-538.

Slota et al., "ELISpot for measuring human immune responses to vaccines," Expert Review of Vaccines, Mar. 2011, vol. 10(3), pp. 299-306. NIH Author Manuscript. 14 pages.

Soria-Guerra et al., "An overview of bioinformatics tools for epitope prediction: implications on vaccine development," Journal of Biomedical Informatics (2015), available online Nov. 10, 2014, vol. 53, pp. 405-414.

(56) References Cited

OTHER PUBLICATIONS

Takahashi et al., "Induction of Broadly Cross-Reactive Cytotoxic T Cells Recognizing an HIV-1 Envelope Determinant," Science, Jan. 17, 1992, vol. 255(5042), pp. 333-336.

Tangri et al., "Structural Features of Peptide Analogs of Human Histocompatibility Leukocyte Antigen Class I Epitopes That Are More Potent and Immunogenic than Wild-Type Peptide," Journal of Experimental Medicine, Sep. 17, 2001, vol. 194(6), pp. 833-846.

Tapia-Calle et al., "A PBMC-Based System to Assess Human T Cell Responses to Influenza Vaccine Candidates In Vitro," Vaccines, Nov. 13, 2019, vol. 7(4):181. 26 pages.

Toussaint, N.C. et al., "A Mathematical Framework for the Selection of an Optimal Set of Peptides for Epitope-Based Vaccines", PLoS Computational Biology, Dec. 26, 2008, vol. 4(12):e1000246, pp. 1-10 (10 pages).

Trolle et al., "The length distribution of class I-restricted T cell epitopes is determined by both peptide supply and MHC allele-specific binding preference," The Journal of Immunology, Feb. 15, 2016, vol. 196(4), 1480-1487. HSS Author Manuscript. 21 pages.

Vita et al., "The Immune Epitope Database (IEDB): 2018 update," Nucleic Acids Research (2019), published online Oct. 24, 2018, vol. 47, database issue D339-D343. 5 pages.

Woodham et al., "Nanobody-Antigen Conjugates Elicit HPV-Specific Antitumor Immune Responses," Cancer Immunology Research, Jul. 2018, vol. 6(7); pp. 870-880.

Zaremba et al., "Identification of an enhancer agonist cytotoxic T lymphocyte peptide from human carcinoembryonic antigen," Cancer Research, Oct. 15, 1997, vol. 57(20), pp. 4570-4577.

Zhang et al., "Cancer vaccines: Targeting KRAS-driven cancers," Expert Review of Vaccines, published online Mar. 14, 2020, vol. 19(2), pp. 163-173. 12 pages.

Zirlik et al., "Cytotoxic T cells generated against heteroclitic peptides kill primary tumor cells independent of the binding affinity of the native tumor antigen peptide," Blood, Dec. 1, 2006, Vo. 108, No. 12, pp. 3865-3870.

Fikes et al., "Design of multi-epitope, analogue-based cancer vaccines," Expert Opinion on Biological Therapy, published online Mar. 3, 2005, vol. 3:6, pp. 985-993. 10 pages.

Aurisicchio et al., "A novel minigene scaffold for therapeutic cancer vaccines," OncoImmunology, published online Jan. 16, 2014, vol. 3, e27529, pp. 1-13. 14 pages.

Fridman et al., "An efficient T-cell epitope discovery strategy using in silico prediction and the iTopia assay platform," OncoImmunology, published online Nov. 30, 2012, vol. 1:8, pp. 1258-1270 and Supplemental Material. 21 pages.

Zhang et al., "Epitope-based minigene vaccine targeting fibroblast activation protein α induces specific immune responses and antitumor effect in 4 T1 murine breast cancer model," International Immunopharmacology, available online Sep. 21, 2022, vol. 112, 109237, pp. 1-10.

Factoring of disease presentation type probabilities and for each presentation, probability of targets presented

| Disease | Target 1<br>KRAS G12D | Target 2<br>KRAS G12V | ... | Target m<br>KRAS G12R |
|---|---|---|---|---|
| Presentation 1<br>0.032<br>(Pancreas) | 0.328 | 0.226 | | 0.151 |
| Presentation 2<br>0.082<br>(Colon and rectum) | 0.279 | 0.214 | | 0.093 |
| ... | | | | |
| Presentation 3<br>0.127<br>(Bronchus and lung) | 0.019 | 0.038 | | 0.000 |

FIG. 5

```
def merge_multi(lists):
    values = []

# While any list in lists has elements remaining
    while max(map(lambda l: len(l), lists)) > 0:
        # Find list with largest value at its head.
        cur_max = None
        cur_max_idx = None
        for idx, l in enumerate(lists):
            if not l:  # List is empty.
                continue
            if cur_max is None or l[0] > cur_max:
                cur_max = l[0]
                cur_max_idx = idx
        # Pop that value from list l.
        values.append((lists[cur_max_idx].pop(0), cur_max_idx))

return values
```

METHOD OF COMPACT PEPTIDE VACCINES USING RESIDUE OPTIMIZATION

This application is a continuation of U.S. application Ser. No. 17/389,875, filed Jul. 30, 2021, which is a continuation of U.S. application Ser. No. 17/114,237, filed Dec. 7, 2020, each of which is incorporated by reference herein in their entireties.

This patent disclosure contains material that is subject to copyright protection. The copyright owner has no objection to the facsimile reproduction of the patent document or the patent disclosure as it appears in the U.S. Patent and Trademark Office patent file or records, but otherwise reserves any and all copyright rights.

INCORPORATION BY REFERENCE

All documents cited herein are incorporated herein by reference in their entirety.

SEQUENCE LISTING

The instant application contains a Sequence Listing which has been submitted electronically in XML format and is hereby incorporated by reference in its entirety. The XML file, created on Sep. 13, 2022, is named 2215269_00124US1_SL.xml and is 1,337,250 bytes in size.

TECHNICAL FIELD

The present invention relates generally to compositions, systems, and methods of peptide vaccines. More particularly, the present invention relates to compositions, systems, and methods of designing peptide vaccines to treat or prevent disease optimized based on predicted population immunogenicity.

BACKGROUND

The goal of a peptide vaccine is to train the immune system to recognize and expand its capacity to engage cells that display target peptides to improve the immune response to cancerous cells or pathogens. A peptide vaccine can also be administered to someone who is already diseased to increase their immune response to a causal cancer, other diseases, or pathogen. Alternatively, a peptide vaccine can be administered to induce the immune system to have therapeutic tolerance to one or more peptides. There exists a need for compositions, systems, and methods of peptide vaccines based on prediction of the target peptides that will be displayed to protect a host from cancer, other disease, or pathogen infection.

SUMMARY OF THE INVENTION

In one aspect, the invention provides for a system for selecting an immunogenic peptide composition comprising a processor, and a memory storing processor-executable instructions that, when executed by the processor, cause the processor to create a first peptide set by selecting a plurality of base peptides, wherein at least one peptide of the plurality of base peptides is associated with a disease, create a second peptide set by adding to the first peptide set a modified peptide, wherein the modified peptide comprises a substitution of at least one residue of a base peptide selected from the plurality of base peptides, and create a third peptide set by selecting a subset of the second peptide set, wherein the selected subset of the second peptide set has a predicted vaccine performance, wherein the predicted vaccine performance has a population coverage above a predetermined threshold, and wherein the subset comprises at least one peptide of the second peptide set.

In some embodiments, the plurality of base peptides of the first peptide set is derived from a target protein, wherein the target protein is a tumor neoantigen or a pathogen proteome. In some embodiments, selecting the plurality of base peptides to create the first peptide set comprises sliding a window of size n across an amino acid sequence encoding the target protein, wherein n is between about 8 amino acids and about 25 amino acids in length, and wherein n is a length of each peptide of the plurality of base peptides of the first peptide set. In some embodiments, a peptide of the plurality of base peptides binds to an HLA class I molecule or an HLA class II molecule. In some embodiments, the substitution of the at least one residue comprises substituting an amino acid at an anchor residue position for a different amino acid at the anchor residue position. In some embodiments, the system further comprises filtering the first peptide set to exclude a peptide with a predicted binding core that contains a target residue in an anchor position. In some embodiments, the second peptide set comprises the first peptide set. In some embodiments, the prediction to be bound by the one or more HLA alleles is computed using a binding affinity of less than about 1000 nM. In some embodiments, the predicted vaccine performance is determined by computing a plurality of peptide-HLA immunogenicities of the third peptide set to at least one HLA allele. In some embodiments, each peptide-HLA immunogenicity of the plurality of peptide-HLA immunogenicities of the third peptide set is based on a predicted binding affinity of less than about 500 nM. In some embodiments, the predicted vaccine performance is based on a population coverage, wherein the population coverage is computed based on a frequency of an HLA haplotype in a human population. In some embodiments, the predicted vaccine performance is based on a population coverage, wherein the population coverage is computed based on a frequency of at least two HLA alleles in a human population. In some embodiments, the plurality of base peptides is present in a single subject. In some embodiments, the predicted vaccine performance is an expected number of peptide-HLA hits. In some embodiments, the disease is cancer, and wherein the cancer is selected from the group consisting of pancreas, colon, rectum, kidney, bronchus, lung, uterus, cervix, bladder, liver, and stomach. In some embodiments, the plurality of base peptides of the first peptide set comprises at least one self-peptide.

In another aspect, the invention provides for a non-transitory computer-readable storage medium comprising computer-readable instructions for determining an immunogenic peptide composition that, when executed by a processor cause the processor to create a first peptide set by selecting a plurality of base peptides, wherein a first base peptide and a second base peptide of the plurality of base peptides are each scored for binding by two or more HLA alleles, wherein the first base peptide and the second base peptide are each predicted to be bound by one or more HLA alleles, and wherein the first base peptide and the second base peptide are associated with a disease, create a second peptide set comprising the first base peptide, the second base peptide, a first modified peptide, and a second modified peptide, wherein the first modified peptide comprises a substitution of at least one residue of the first base peptide, and wherein the second modified peptide comprises a substitution of at least one residue of the second base peptide, and create a third peptide set by selecting a subset of the second peptide set, wherein the selected subset of the second peptide set has a predicted vaccine performance, and wherein the predicted vaccine performance is a function of a peptide-HLA immunogenicity of at least one peptide of the third peptide set with respect to the two or more HLA alleles.

In some embodiments, the plurality of base peptides of the first peptide set is derived from a target protein, wherein the target protein is a tumor neoantigen or a pathogen proteome. In some embodiments, selecting the plurality of base peptides to create the first peptide set comprises sliding a window of size n across an amino acid sequence encoding the target protein, wherein n is between about 8 amino acids and about 25 amino acids in length, and wherein n is a length of each peptide of the plurality of base peptides of the first peptide set. In some embodiments, a peptide of the plurality of base peptides binds to an HLA class I molecule or an HLA class II molecule. In some embodiments, the substitution of the at least one residue comprises substituting an amino acid at an anchor residue position for a different amino acid at the anchor residue position. In some embodiments, the non-transitory computer-readable storage medium of further comprises filtering the first peptide set to exclude a peptide with a predicted binding core that contains a target residue in an anchor position. In some embodiments, the second peptide set comprises the first peptide set. In some embodiments, the prediction to be bound by the two or more HLA alleles is computed using a binding affinity of less than about 1000 nM. In some embodiments, the plurality of base peptides of the first peptide set comprises at least one self-peptide.

In another aspect, the invention provides for a system for selecting an immunogenic peptide composition comprising a processor, and a memory storing processor-executable instructions that, when executed by the processor, cause the processor to create a first peptide set by selecting a plurality of base peptides, wherein a first base peptide of the plurality of base peptides is scored for binding by three or more HLA alleles, wherein the first base peptide is predicted to be bound by one or more HLA alleles, and wherein the first base peptide is associated with a disease, create a second peptide set comprising the first base peptide and a modified peptide, wherein the modified peptide comprises a substitution of at least one residue of the first base peptide, and create a third peptide set by selecting a subset of the second peptide set, wherein the selected subset of the second peptide set has a predicted vaccine performance, and wherein the predicted vaccine performance is a function of a peptide-HLA immunogenicity of at least one peptide of the third peptide set with respect to the three or more HLA alleles.

In some embodiments, the first base peptide is scored for binding based on data obtained from experimental assays. In some embodiments, the predicted vaccine performance includes a peptide-HLA immunogenicity of the modified peptide bound to the first HLA allele of the one or more HLA alleles if the first base peptide is predicted to be bound to the first HLA allele of the one or more HLA alleles with a first binding core, wherein the first binding core is a binding core of the first base peptide, wherein the first binding core is identical to a second binding core, and wherein the second binding core is a binding core of the modified peptide bound to the first HLA allele.

In another aspect, the invention provides for a non-transitory computer-readable storage medium comprising computer-readable instructions for determining an immunogenic peptide composition that, when executed by a processor cause the processor to create a first peptide set by selecting a plurality of base peptides, wherein at least one peptide of the plurality of base peptides is associated with a disease, create a second peptide set comprising a first base peptide selected from the first base peptide set and a modified peptide, wherein the modified peptide comprises a substitution of at least one residue of the first base peptide, and create a third peptide set by selecting a subset of the second peptide set, wherein the selected subset of the second peptide set has a predicted vaccine performance, wherein the predicted vaccine performance has an expected number of peptide-HLA hits above a predetermined threshold, and wherein the subset comprises at least one peptide of the second peptide set.

In some embodiments, the first base peptide binds to an HLA class I molecule or an HLA class II molecule.

In another aspect, the invention provides for a system for selecting an immunogenic peptide composition comprising a processor, and a memory storing processor-executable instructions that, when executed by the processor, cause the processor to create a first peptide set by selecting a first plurality of peptides, wherein the first plurality of peptides comprises a plurality of target peptides that are associated with a first disease, and wherein the first peptide set has a first predicted vaccine performance value, create a second peptide set by selecting a second plurality of peptides, wherein the second plurality of peptides comprises a plurality of target peptides that are associated with a second disease, and wherein the second peptide set has a second predicted vaccine performance value, create a first weighted peptide set by multiplying a first weight by the first predicted vaccine performance value, create a second weighted peptide set multiplying a second weight by the second predicted vaccine performance value, and create a third peptide set by combining the first weighted peptide set and the second weighted peptide set.

In some embodiments, the first predicted vaccine performance value and the second predicted vaccine performance value are computed based on a population coverage of a vaccine. In some embodiments, the first predicted vaccine performance value and the second predicted vaccine performance value are computed based on an expected number of peptide-HLA hits. In some embodiments, the first plurality of peptides is derived from a tumor neoantigen or a pathogen proteome. In some embodiments, the second plurality of peptides is derived from a tumor neoantigen or a pathogen proteome. In some embodiments, the first disease is cancer, and wherein the cancer is selected from the group consisting of pancreas, colon, rectum, kidney, bronchus, lung, uterus, cervix, bladder, liver, and stomach. In some embodiments, the second disease is cancer, and wherein the cancer is selected from the group consisting of pancreas, colon, rectum, kidney, bronchus, lung, uterus, cervix, bladder, liver, and stomach. In some embodiments, the first plurality of peptides comprises a peptide that binds to an HLA class I molecule or an HLA class II molecule. In some embodiments, the second plurality of peptides comprises a peptide that binds to an HLA class I molecule or an HLA class II molecule.

BRIEF DESCRIPTION OF THE DRAWINGS

The following figures depict illustrative embodiments of the invention.

FIG. 5 shows probabilities of disease presentations for pancreas, colon/rectum, and bronchus/lung and respective probabilities of target presentations for KRAS G12D, KRAS G12V, and KRAS G12R targets.

FIG. 9 shows an example Python implementation of the MERGEMULTI function for combined vaccine design procedures.

DETAILED DESCRIPTION

Figure 1:
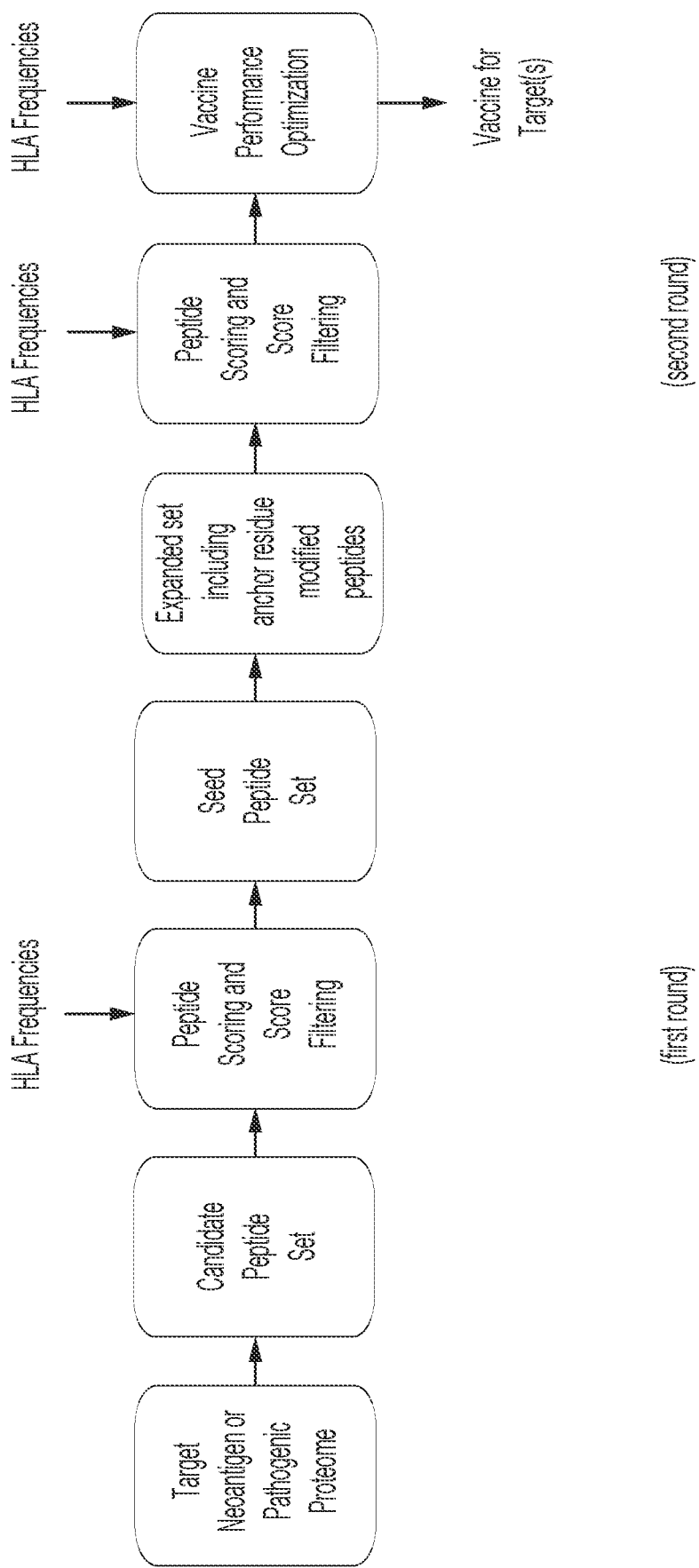
FIG. 1 is a flow chart of a vaccine optimization method.

In some embodiments, the disclosure provides for peptide vaccines that incorporate peptide sequences that will be displayed by Major Histocompatibility Complex (MHC) molecules on cells and train the immune system to recognize cancer or pathogen diseased cells. In some embodiments, the disclosure provides for peptide vaccines that that incorporate peptide sequences that will be displayed by Major Histocompatibility Complex (MHC) molecules on cells to induce therapeutic tolerance in antigen-specific immunotherapy for autoimmune diseases (Alhadj Ali et al., 2017, Gibson, et al. 2015). In some embodiments, a peptide vaccine is a composition that consists of one or more peptides. In some embodiments, a peptide vaccine is an mRNA or DNA construct administered for expression in vivo that encodes for one or more peptides.

Peptide display by an MHC molecule is necessary, but not sufficient, for a peptide to be immunogenic and cause the recognition of the resulting peptide-MHC complex by an individual's T cells to trigger T cell activation, expansion, and immune memory. In some embodiments, experimental data from assays such as the ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) is used for scoring peptide display (e.g., binding affinity) by an MHC molecule (e.g., HLA allele). In some embodiments, experimental data from assays such as the ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) can be combined with machine learning based predictions for scoring peptide display (e.g., binding affinity) by an MHC molecule (e.g., HLA allele). In some embodiments, the MHCflurry or NetMHCpan (Reynisson et al., 2020) computational methods (as known in the art) are used to predict MHC class I display of a peptide by an HLA allele (see Table 1). In some embodiments, the NetMHCIIpan computational method (Reynisson et al., 2020) is used to predict MHC class II display of a peptide by an HLA allele (see Table 2).

A peptide is displayed by an MHC molecule when it binds within the groove of the MHC molecule and is transported to the cell surface where it can be recognized by a T cell receptor. A target peptide refers to a foreign peptide or a self-peptide. In some embodiments, a peptide that is part of the normal proteome in a healthy individual is a self-peptide, and a peptide that is not part of the normal proteome is a foreign peptide. Foreign peptides can be generated by mutations in normal self-proteins in tumor cells that create epitopes called neoantigens, or by pathogenic infections. In some embodiments, a neoantigen is any subsequence of a human protein, where the subsequence contains one or more altered amino acids or protein modifications that do not appear in a healthy individual. Therefore, in this disclosure, foreign peptide refers to an amino acid sequence encoding a fragment of a target protein/peptide (or a full-length protein/peptide), the target protein/peptide consisting of: a neoantigen protein, a pathogen proteome, or any other undesired protein that is non-self and is expected to be bound and displayed by an HLA allele.

For example, KRAS gene mutations are the most frequently mutated oncogenes in cancer, but they have been very difficult to treat with small molecule therapeutics. The KRAS protein is part of a signaling pathway that controls cellular growth, and point mutations in the protein can cause constitutive pathway activation and uncontrolled cell growth. Single amino acid KRAS mutations result in minor changes in protein structure, making it difficult to engineer small molecule drugs that recognize a mutant specific binding pocket and inactivate KRAS signaling. KRAS oncogenic mutations include the mutation of position 12 from glycine to aspartic acid (G12D), glycine to valine (G12V), glycine to arginine (G12R), or glycine to cystine (G12C); or the mutation of position 13 from glycine to aspartic acid (G13D). The corresponding foreign peptides contain these mutations.

A challenge for the design of peptide vaccines is the diversity of human MHC alleles (HLA alleles) that each have specific preferences for the peptide sequences they will display. The Human Leukocyte Antigen (HLA) loci, located within the MHC, encode the HLA class I and class II molecules. There are three classical class I loci (HLA-A, HLA-B, and HLA-C) and three loci that encode class II molecules (HLA-DR, HLA-DQ, and HLA-DP). An individual's HLA type describes the alleles they carry at each of these loci. Peptides of length of between about 8 and about 11 residues can bind to HLA class I (or MHC class I) molecules whereas those of length of between about 13 and about 25 bind to HLA class II (or MHC class II) molecules (Rist et al., 2013; Chicz et al., 1992). Human populations that originate from different geographies have differing frequencies of HLA alleles, and these populations exhibit linkage disequilibrium between HLA loci that result in population specific haplotype frequencies. In some embodiments, methods are disclosed for creating effective vaccines that includes consideration of the HLA allelic frequency in the target population, as well as linkage disequilibrium between HLA genes to achieve a set of peptides that is likely to be robustly displayed.

The present disclosure provides for compositions, systems, and methods of vaccine designs that produce immunity to single or multiple targets. In some embodiments, a target is a neoantigen protein sequence, a pathogen proteome, or any other undesired protein sequence that is non-self and is expected to be bound and displayed by an HLA molecule (also referred to herein as an HLA allele). When a target is present in an individual, it may result in multiple peptide sequences that are displayed by a variety of HLA alleles. In some embodiments, it may be desirable to create a vaccine that includes selected self-peptides, and thus these selected self-peptides are considered to be the target peptides for this purpose.

The term peptide-HLA binding is defined to be the binding of a peptide to an HLA allele, and can either be computationally predicted, experimentally observed, or computationally predicted using experimental observations. The metric of peptide-HLA binding can be expressed as affinity, percentile rank, binary at a predetermined threshold, probability, or other metrics as are known in the art. The term peptide-HLA immunogenicity is defined as the activation of T cells based upon their recognition of a peptide when bound by an HLA allele. Peptide-HLA immunogenicity can vary from individual to individual, and the metric for peptide-HLA immunogenicity can be expressed as a probability, a binary indicator, or other metric that relates to the likelihood that a peptide-HLA combination will be immunogenic. In some embodiments, peptide-HLA immunogenicity is defined as the induction of immune tolerance based upon the recognition of a peptide when bound by an HLA allele. Peptide-HLA immunogenicity can be computationally predicted, experimentally observed, or computationally predicted using experimental observations. In some embodiments, peptide-HLA immunogenicity is based only upon peptide-HLA binding, since peptide-HLA binding is necessary for peptide-HLA immunogenicity. In some embodiments, peptide-HLA immunogenicity data or computational predictions of peptide-HLA immunogenicity can be included and combined with scores for peptide display in the methods disclosed herein. One way of combining the scores is using immunogenicity data for peptides assayed for immunogenicity in diseased or vaccinated individuals, and assigning peptides to the HLA allele that displayed them in the individual by choosing the HLA allele that computational methods predict has the highest likelihood of display. For peptides that are not experimentally assayed, computational predictions of display can be used. In some embodiments, different computational methods of predicting peptide-HLA immunogenicity or peptide-HLA binding can be combined (Liu et al., 2020b). For a given set of peptides and a set of HLA alleles, the term peptide-HLA hits is the number of unique combinations of peptides and HLA alleles that exhibit peptide-HLA immunogenicity or binding at a predetermined threshold. For example, a peptide-HLA hit of 2 can mean that one peptide is predicted to be bound (or trigger T cell activation) by two different HLA alleles, two peptides are predicted to be bound (or trigger T cell activation) by two different HLA alleles, or two peptides are predicted to be bound (or trigger T cell activation) by the same HLA allele. For a given set of peptides and HLA frequencies, HLA haplotype frequencies, or HLA diplotype frequencies, the expected number of peptide-HLA hits is the average number of peptide-HLA hits in each set of HLAs that represent an individual, weighted by their frequency of occurrence.

Since immunogenicity may vary from individual to individual, one method to increase the probability of vaccine efficacy is to use a diverse set of target peptides (e.g., at least two peptides) to increase the chances that some subset of them will be immunogenic in a given individual. Prior research using mouse models has shown that most MHC displayed peptides are immunogenic, but immunogenicity varies from individual to individual as described in Croft et al. (2019). In some embodiments, experimental peptide-HLA immunogenicity data are used to determine which target peptides and their modifications will be effective immunogens in a vaccine.

Considerations for the design of peptide vaccines are outlined in Liu et al., Cell Systems 11, Issue 2, p. 131-146 (Liu et al., 2020) and (Liu et al., 2020b) which are incorporated by reference in their entireties herein.

Certain target peptides may not bind with high affinity to a wide range of HLA molecules. To increase the binding of target peptides to HLA molecules, their amino acid composition can be altered to change one or more anchor residues or other residues. Anchor residues are amino acids that interact with an HLA molecule and have the largest influence on the affinity of a peptide for an HLA molecule. Peptides with altered anchor residues are called heteroclitic peptides. In some embodiments, heteroclitic peptides include target peptides with residue modifications at non-anchor positions. In some embodiments, heteroclitic peptides include target peptides with residue modifications that include unnatural amino acids and amino acid derivatives. Modifications to create heteroclitic peptides can improve the binding of peptides to both MHC class I and MHC class II molecules, and the modifications required can be both peptide and MHC class specific. Since peptide anchor residues face the MHC molecule groove, they are less visible than other peptide residues to T cell receptors. Thus, heteroclitic peptides have been observed to induce a T cell response where the stimulated T cells also respond to unmodified peptides. It has been observed that the use of heteroclitic peptides in a vaccine can improve a vaccine's effectiveness (Zirlik et al., 2006). In some embodiments, the immunogenicity of heteroclitic peptides are experimentally determined and their ability to activate T cells that also recognize the corresponding base (also called seed) peptide of the heteroclitic peptide is determined, as is known in the art. In some embodiments, these assays of the immunogenicity and cross-reactivity of heteroclitic peptides are performed when the heteroclitic peptides are displayed by specific HLA alleles.

Peptide Vaccines to Induce Immunity to One or More Targets

In some embodiments, a method is provided for formulating peptide vaccines using a single vaccine design for one or more targets. In some embodiments, a single target is a foreign protein with a specific mutation (e.g., KRAS G12D). In some embodiments, a single target is a self-protein (e.g., a protein that is overexpressed in tumor cells such as cancer/testis antigens). In some embodiments, multiple targets can be used (e.g. both KRAS G12D and KRAS G13D).

In some embodiments, the method includes extracting peptides to construct a candidate set from all target proteome sequences (e.g., entire KRAS G12D protein) as described in Liu et al. (2020).

Figure 2:
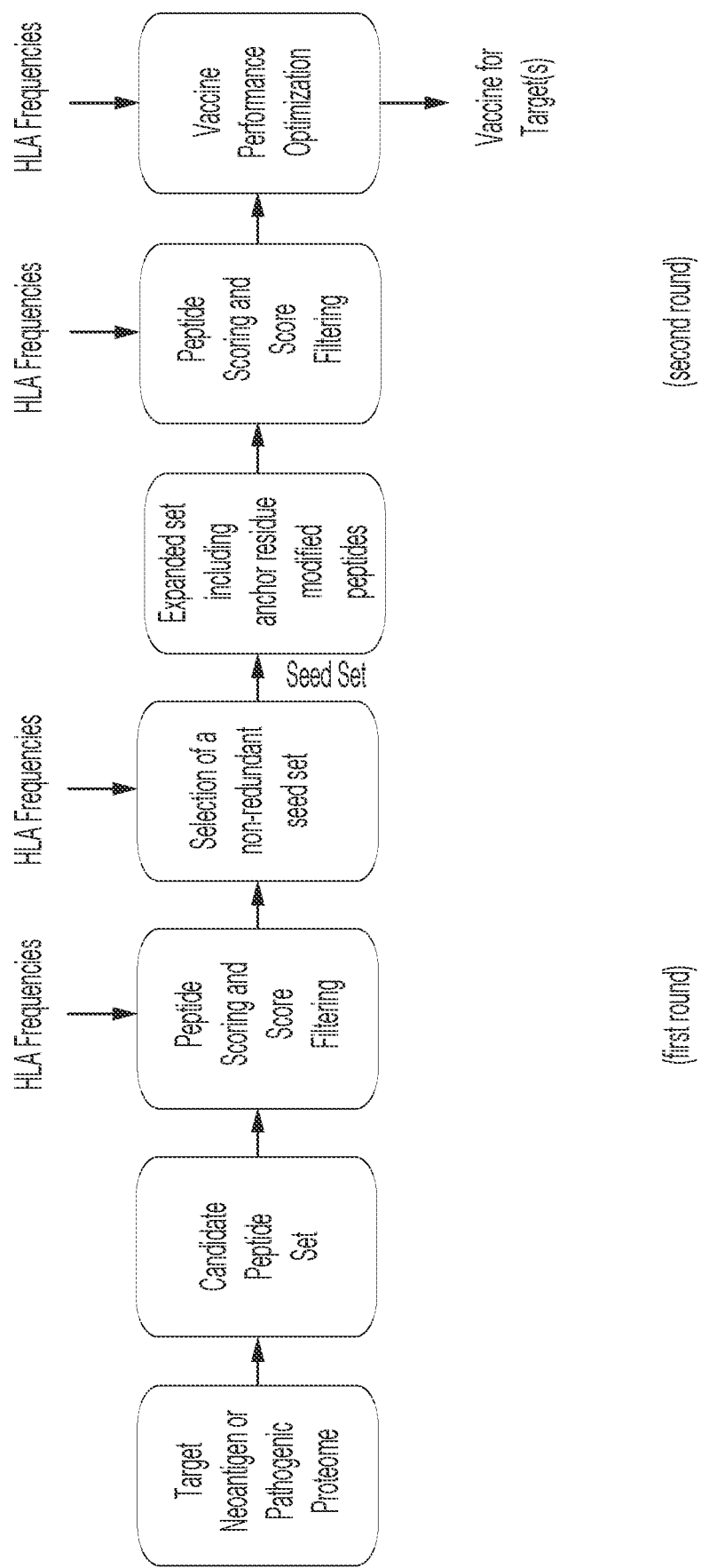
FIG. 2 is a flow chart of vaccine optimization method with seed set compression.

FIGS. 1 and 2 depict flow charts for example vaccine design methods that can be used for MHC class I or MHC class II vaccine design. In some embodiments, extracted target peptides are of amino acid length of between about 8 and about 10 (e.g., for MHC class I binding (Rist et al., 2013)). In some embodiments, the extracted target peptides presented by MHC class I molecules are longer than 10 amino acid residues, such as 11 residues (Trolle et al., 2016). In some embodiments, extracted target peptides are of length between about 13 and about 25 (e.g., for class II binding (Chicz et al., 1992)). In some embodiments, sliding windows of various size ranges described herein are used over the entire proteome. In some embodiments, other target peptide lengths for MHC class I and class II sliding windows can be utilized. In some embodiments, computational predictions of proteasomal cleavage are used to filter or select peptides in the candidate set. One computational method for predicting proteasomal cleavage is described by Nielsen et al. (2005). In some embodiments, peptide mutation rates, glycosylation, cleavage sites, or other criteria can be used to filter peptides as described in Liu et al. (2020). In some embodiments, peptides can be filtered based upon evolutionary sequence variation above a predetermined threshold. Evolutionary sequence variation can be computed with respect to other species, other pathogens, other pathogen strains, or other related organisms. In some embodiments, a first peptide set is the candidate set.

As shown in FIGS. 1-2, in some embodiments, the next step of the method includes scoring the target peptides in the candidate set for peptide-HLA binding to all considered HLA alleles as described in Liu et al. (2020) and Liu et al. (2020b). In some embodiments, a first peptide set is the candidate set after scoring the target peptides. Scoring can be accomplished for human HLA molecules, mouse H-2 molecules, swine SLA molecules, or MHC molecules of any species for which prediction algorithms are available or can be developed. Thus, vaccines targeted at non-human species can be designed with the method. Scoring metrics can include the affinity for a target peptide to an HLA allele in nanomolar, eluted ligand, presentation, and other scores that can be expressed as percentile rank or any other metric. The candidate set may be further filtered to exclude peptides whose predicted binding cores do not contain a particular pathogenic or neoantigen target residue of interest or whose predicted binding cores contain the target residue in an anchor position. The candidate set may also be filtered for target peptides of specific lengths, such as length 9 for MHC class I, for example. In some embodiments, scoring of target peptides is accomplished with experimental data or a combination of experimental data and computational prediction methods. When computational models are unavailable to make peptide-HLA binding predictions for particular (peptide, HLA) pairs, the binding value for such pairs can be defined by the mean, median, minimum, or maximum immunogenicity value taken over supported pairs, a fixed value (such as zero), or inferred using other techniques, including a function of the prediction of the most similar (peptide, HLA) pair available in the scoring model.

In some embodiments, a base set (also referred to as seed set herein) is constructed by selecting peptides from the scored candidate set using individual peptide-HLA binding or immunogenicity criteria (e.g., first peptide set) (FIG. 1). The criteria used for scoring peptide-HLA binding during the scoring procedure can accommodate different goals during the base set selection and vaccine design phases. For example, a target peptide with peptide-HLA binding affinities of 500 nM may be displayed by an individual that is diseased, but at a lower frequency than a target peptide with a 50 nM peptide-HLA binding affinity. In some embodiments, during the scoring of a candidate set to qualify peptides for membership in the base set as potential immune system targets, 1000 nM or other less constrained affinity criteria than 50 nM may be utilized. During the combinatorial design phase of a vaccine, a more constrained affinity criteria may be used (e.g., when selecting a third peptide set), such a 50 nM, to increase the probability that a vaccine peptide will be found and displayed by HLA molecules. In some embodiments, peptides are scored for third peptide set potential inclusion that have peptide-HLA binding affinities less than about 500 nM. In some embodiments, peptides are selected for the base set that have peptide-HLA binding affinities less than about 1000 nM. Alternatively, predictions of peptide-HLA immunogenicity can be used to qualify target peptides for base set inclusion. In some embodiments, experimental observations of the immunogenicity of peptides in the context of their display by HLA alleles or experimental observation of the binding of peptides to HLA alleles can be used to score peptides for binding to HLA alleles or peptide-HLA immunogenicity. In some embodiments, computational predictions of the immunogenicity of a peptide in the context of display by HLA alleles can used for scoring such as the methods of Ogishi et al. (2019).

In some embodiments, the method further includes running the OptiVax-Robust algorithm as described in Liu et al. (2020) using the HLA haplotype frequencies of a population on the scored candidate set to construct a base set (also referred to as seed set herein) of target peptides (FIG. 2). In some embodiments, HLA diplotype frequencies can be provided to OptiVax. OptiVax-Robust includes algorithms to eliminate peptide redundancy that arises from the sliding window approach with varying window sizes, but other redundancy elimination measures can be used to enforce minimum edit distance constraints between target peptides in the candidate set. The size of the seed set is determined by a point of diminishing returns of population coverage as a function of the number of target peptides in the seed set. Other criteria can also be used, including a minimum number of vaccine target peptides, maximum number of vaccine target peptides, and desired predicted population coverage. In some embodiments, a predetermined population coverage is less than about 0.4, between about 0.4 and 0.5, between about 0.5 and 0.6, between about 0.6 and 0.7, between about 0.7 and 0.8, between about 0.8 and 0.9, or greater than about 0.9. Another possible criterion is a minimum number of expected peptide-HLA binding hits in each individual. In alternate embodiments, the method further includes running the OptiVax-Unlinked algorithm as described in Liu et al. (2020) instead of OptiVax-Robust.

The OptiVax-Robust method uses binary predictions of peptide-HLA immunogenicity, and these binary predictions can be generated as described in Liu et al. (2020b). The OptiVax-Unlinked method uses the probability of target peptide binding to HLA alleles and can be generated as described in Liu et al. (2020). In some embodiments, OptiVax-Unlinked and EvalVax-Unlinked are used with the probabilities of peptide-HLA immunogenicity. Either method can be used for the purposes described herein, and thus the term "OptiVax" refers to either the Robust or Unlinked method. In some embodiments, the HLA haplotype or HLA allele frequencies of a population provided to OptiVax for vaccine design describe the world's population. In alternative embodiments, the HLA haplotype or HLA allele frequencies of a population provided to OptiVax for vaccine design are specific to a geographic region. In alternative embodiments, the HLA haplotype or HLA allele frequencies of a population provided to OptiVax for vaccine design are specific to an ancestry. In alternative embodiments, the HLA haplotype or HLA allele frequencies of a population provided to OptiVax for vaccine design are specific to a race. In alternative embodiments, the HLA haplotype or HLA allele frequencies of a population provided to OptiVax for vaccine design are specific to individuals with risk factors such as genetic indicators of risk, age, exposure to chemicals, alcohol use, chronic inflammation, diet, hormones, immunosuppression, infectious agents, obesity, radiation, sunlight, or tobacco use. In alternative embodiments, the HLA haplotype or HLA allele frequencies of a population provided to OptiVax for vaccine design are specific to individuals that carry certain HLA alleles. In alternative embodiments, the HLA diplotypes provided to OptiVax for vaccine design describe a single individual, and are used to design an individualized vaccine.

In some embodiments, the base (or seed) set of target peptides (e.g., first peptide set) that results from OptiVax application to the candidate set of target peptides describes a set of unmodified target peptides that represent a possible compact vaccine design (Seed Set in FIG. 2). In some embodiments, the seed set (e.g., first peptide set) is based upon filtering candidate peptides by predicted or observed affinity or immunogenicity with respect to HLA molecules (Seed Set in FIG. 1). However, to improve the display of the target peptides in a wide range of HLA haplotypes as possible, some embodiments include modifications of the seed (or base) set. In some embodiments, experimental assays can be used to ensure that a modified seed (or base) peptide activates T cells that also recognize the base/seed peptide.

For a given target peptide, the optimal anchor residue selection may depend upon the HLA allele that is binding to and displaying the target peptide and the class of the HLA allele (MHC class I or class II). A seed peptide set (e.g., first peptide set) can become an expanded set by including anchor residue modified peptides of either MHC class I or II peptides (FIGS. 1-2). Thus, one aspect of vaccine design is considering how to select a limited set of heteroclitic peptides that derive from the same target peptide for vaccine inclusion given that different heteroclitic peptides will have different and potentially overlapping population coverages.

In some embodiments, all possible anchor modifications for each base set of target peptide are considered. There are typically two anchor residues in peptides bound by MHC class I molecules, typically at positions 2 and 9 for 9-mer peptides. At each anchor position, 20 possible amino acids are attempted in order to select the best heteroclitic peptides. Thus, for MHC class I binding, 400 (i.e., 20 amino acids by 2 positions=$20^2$) minus 1 heteroclitic peptides are generated for each base target peptide. There are typically four anchor residues in peptides bound by MHC class II molecules, typically at positions 1, 4, 6, and 9 of the 9-mer binding core. Thus, for MHC class II binding there are 160,000 (i.e., 20 amino acids by 4 positions=$20^4$) minus 1 heteroclitic peptides generated for each base target peptide. Other methods, including Bayesian optimization, can be used to select optimal anchor residues to create heteroclitic peptides from each seed (or base) set peptide. Other methods are presented in "Machine learning optimization of peptides for presentation by class II MHCs" by Dai et al. (2020), incorporated in its entirety herein. In some embodiments, the anchor positions are determined by the HLA allele that presents a peptide, and thus the set of heteroclitic peptides includes for each set of HLA specific anchor positions, all possible anchor modifications.

In some embodiments, for all of the target peptides in the base/seed set, new peptide sequences with all possible anchor residue modifications (e.g., MHC class I or class II) are created resulting in a new heteroclitic base set (Expanded set in FIGS. 1-2) that includes all of the modifications. In some embodiments, for all of the target peptides in the base/seed set, new peptide sequences with anchor residue modifications (e.g., MHC class I or class II) at selected anchor locations are created resulting in a new heteroclitic base set (Expanded set in FIGS. 1-2) that includes the selected modifications. In some embodiments, the anchor residue positions used for modifying peptides are selected from anchor residue positions determined by the HLA alleles considered during vaccine evaluation. In some embodiments, the heteroclitic base set (Expanded set in FIGS. 1-2) also includes the original seed (or base) set (Seed Peptide Set in FIGS. 1-2). In some embodiments, the heteroclitic base set includes amino acid substitutions at non-anchor residues. In some embodiments, modifications of base peptide residues is accomplished to alter binding to T cell receptors to improve therapeutic efficacy (Candia, et al. 2016). In some embodiments, the heteroclitic base set includes amino acid substitutions of non-natural amino acid analogs. The heteroclitic base set is scored for HLA affinity, peptide-HLA immunogenicity, or other metrics as described herein (another round of Peptide Filtering and Scoring as shown in FIGS. 1-2). The scoring predictions may be further updated for pairs of heteroclitic peptide and HLA allele, eliminating pairs where a heteroclitic peptide is predicted to be displayed by an allele but the seed (or base) peptide from which it was derived is not predicted to be displayed by the allele. The scoring predictions may also be filtered to ensure that predicted binding cores of the heteroclitic peptide displayed by a particular HLA allele align exactly in position with the binding cores of the respective seed (or base) set target peptide for that HLA allele. In some embodiments, the scoring predictions are filtered for an HLA allele to ensure that the heteroclitic peptides considered for that HLA allele are only modified at anchor positions determined by that HLA allele. Scoring produces a metric of peptide-HLA immunogenicity for peptides and HLA alleles that can be either binary, a probability of immunogenicity, or other metric of immunogenicity such as peptide-HLA affinity or percent rank, and can be based on computational predictions, experimental observations, or a combination of both computational predictions and experimental observations. In some embodiments, probabilities of peptide-HLA immunogenicity are utilized by OptiVax-Unlinked. In some embodiments, heteroclitic peptides are included in experimental assays such as MIRA (Klinger et al., 2015) to determine their immunogenicity with respect to specific HLA alleles. In some embodiments, the methods of Liu et al. (2020b), can be used to incorporate MIRA data for heteroclitic peptides into a model of peptide-HLA immunogenicity. In some embodiments, the immunogenicity of heteroclitic peptides are experimentally determined and their ability to activate T cells that also recognize the corresponding seed (or base) peptide of the heteroclitic peptide is performed as is known in the art to qualify the heteroclitic peptide for vaccine inclusion. In some embodiments, these assays of the immunogenicity and cross-reactivity of heteroclitic peptides are performed when the heteroclitic peptides are displayed by specific HLA alleles. In some embodiments, computational predictions of the immunogenicity of a heteroclitic peptide in the context of display by HLA alleles can used for scoring such as the methods of Ogishi et al. (2019).

In some embodiments, the next step involves inputting the heteroclitic base set (also referred to as Expanded set as shown in FIGS. 1-2) to OptiVax to select a compact set of vaccine peptides that maximizes predicted vaccine performance (Vaccine Performance Optimization; FIGS. 1-2). In some embodiments, predicted vaccine performance is a function of expected peptide-HLA binding affinity (e.g., a function of the distribution of peptide-HLA binding affinities across all peptide-HLA combinations for a given peptide set, or weighted by the occurrence of the HLA alleles in a population or individual). In some embodiments, predicted vaccine performance is the expected population coverage of a vaccine. In some embodiments, predicted vaccine performance is the expected number peptide-HLA hits produced by a vaccine in a population or individual. In some embodiments, predicted vaccine performance requires a minimum expected number of peptide-HLA hits (e.g., 1, 2, 3, 4, 5, 6, 7, 8, or more) produced by a vaccine. In some embodiments, predicted vaccine performance is a function of population coverage and expected number of peptide-HLA hits desired produced by a vaccine. In some embodiments, predicted vaccine performance is a metric that describes the overall immunogenic properties of a vaccine where all of the peptides in the vaccine are scored for peptide-HLA immunogenicity for two or more HLA alleles (e.g., three or more HLA alleles). In some embodiments, predicted vaccine performance excludes immunogenicity contributions by selected HLA alleles above a maximum number of peptide-HLA hits (e.g., 1, 2, 3, 4, 5, 6, 7, 8, or more). In some embodiments, predicted vaccine performance excludes immunogenicity contributions of individual HLA diplotypes above a maximum number of peptide-HLA hits (e.g., 1, 2, 3, 4, 5, 6, 7, 8, or more). In some embodiments, predicted vaccine performance is the fraction of covered HLA alleles, which is the expected fraction of HLA alleles in each individual that have a minimum number of peptides (e.g., 1, 2, 3, 4, 5, 6, 7, 8, or more) with predicted peptide-HLA immunogenicity produced by a vaccine. In some embodiments, predicted vaccine performance is the expected fraction of HLA alleles in a single individual that have a minimum number of peptides (e.g., 1, 2, 3, 4, 5, 6, 7, 8, or more) with predicted peptide-HLA immunogenicity produced by a vaccine.

Predicted vaccine performance refers to a metric. Predicted vaccine performance can be expressed as a single numerical value, a plurality of numerical values, any number of non-numerical values, and a combination thereof. The value or values can be expressed in any mathematical or symbolic term and on any scale (e.g., nominal scale, ordinal scale, interval scale, or ratio scale).

A seed (or base) peptide and all of the modified peptides that are derived from that seed (or base) peptide comprise a single peptide family. In some embodiments, in the component of vaccine performance that is based on peptide-HLA immunogenicity for a given HLA allele, a maximum number of peptides (e.g., 1, 2, 3, 4, 5, 6, 7, 8, or more) that are in the same peptide family are given computational immunogenicity credit for that HLA allele. This limit on peptide family immunogenicity limits the credit caused by many modified versions of the same base peptide. In some embodiments, the methods described herein are included for running OptiVax with an EvalVax objective function that corresponds to a desired metric of predicted vaccine performance. In some embodiments, population coverage means the proportion of a subject population that presents one or more immunogenic peptides that activate T cells responsive to a seed (or base) target peptide. The metric of population coverage is computed using the HLA haplotype frequency in a given population such as a representative human population. In some embodiments, the metric of population coverage is computed using marginal HLA frequencies in a population. Maximizing population coverage means selecting a peptide set (either a base peptide set, a modified peptide set, or a combination of base and modified peptides; e.g., a first peptide set, second peptide set, or third peptide set) that collectively results in the greatest fraction of the population that has at least a minimum number (e.g., 1, 2, 3, 4, 5, 6, 7, 8, or more) of immunogenic peptide-HLA bindings based on proportions of HLA haplotypes in a given population (e.g., representative human population). In some embodiments, this process includes the OptiVax selection of heteroclitic peptides (as described in this disclosure) that activate T cells that respond to their corresponding seed (or base) peptide and the heteroclitic base peptides to improve population coverage. In some embodiments, the seed (or base) target peptides are always included in the final vaccine design. In some embodiments, peptides are only considered as candidates for a vaccine design (e.g., included in a first, second, and/or third peptide set) if they have been observed to be immunogenic in clinical data, animal models, or tissue culture models.

Although heteroclitic peptides are used as exemplary embodiments in this disclosure, any modified peptide could be used in place of a heteroclitic peptide. A modified peptide is a peptide that has one or more amino acid substitutions of a target base/seed peptide. The amino acid substitution could be located at an anchor position or any other non-anchor position.

In some embodiments, a candidate vaccine peptide (e.g., a base peptide or a modified peptide) is eliminated from vaccine inclusion if it activates T cells that recognize self-peptides (e.g., this can be achieved at the first and/or second round of Peptide Filtering and Sorting as shown in FIGS. 1-2). In some embodiments, a candidate vaccine peptide (e.g., a base peptide or a modified peptide) is computationally eliminated from vaccine inclusion if its outward facing amino acids when bound by an HLA allele are similar to outward facing self-peptide residues that are presented by the same HLA allele, where similarity can be defined by identity or defined similarity metrics such as BLOSUM matrices (BLOSUM matrices are known in the art). Testing a vaccine peptide for its ability to activate T cells that recognize self-peptides can be experimentally accomplished by the vaccination of animal models followed by ELISPOT or other immunogenicity assay or with human tissue protocols. In both cases, models with HLA alleles that present the vaccine peptide are used. In some embodiments, human primary blood mononuclear cells (PBMCs) are stimulated with a vaccine peptide, the T cells are allowed to grow, and then T cell activation with a self-peptide is assayed as described in Tapia-Calle et al. (2019) or other methods as known in the art. In some embodiments, the vaccine peptide is excluded from vaccine inclusion if the T cells are activated by the self-peptide. In some embodiments, computational predictions of the ability of a peptide to activate T cells that also recognize self-peptides can be utilized. These predictions can be based upon the modeling of the outward facing residues from the peptide-HLA complex and their interactions with other peptide residues. In some embodiments, a candidate vaccine peptide (e.g., a base peptide or a modified peptide) is eliminated from vaccine inclusion or experimentally tested for cross-reactivity if it is predicted to activate T cells that also recognize self-peptides based upon the structural similarity of the peptide-MHC complex of the candidate peptide (e.g., a base peptide or a modified peptide) and the peptide-MHC complex of a self-peptide. One method for the prediction of peptide-MHC structure is described by Park et al. (2013).

In some embodiments, a candidate heteroclitic vaccine peptide (e.g., a modified peptide) is eliminated from vaccine inclusion if it does not activate T cells that recognize its corresponding base/seed target peptide (second round of Peptide Filtering and Scoring, FIGS. 1-2). Testing a candidate heteroclitic peptide (e.g., a modified peptide) for its ability to activate T cells that recognize its corresponding seed (or base) target peptide with respect to the same HLA allele can be experimentally accomplished by the vaccination of animal models followed by ELISPOT or other immunogenicity assay or with human tissue protocols. In both cases, models with HLA alleles that present the heteroclitic peptide are used. In some embodiments, human PBMCs are stimulated with the heteroclitic peptide, the T cells are allowed to grow, and then T cell activation with the seed (or base) target peptide is assayed as described in Tapia-Calle et al. (2019) or using other methods known in the art. In some embodiments, computational predictions of the ability of a heteroclitic peptide to activate T cells that also recognize the corresponding seed (or base) target peptide can be utilized. These predictions can be based upon the modeling of the outward facing residues from the peptide-HLA complex and their interactions with other peptide residues. In some embodiments, the structural similarity of the peptide-HLA complex of a heteroclitic peptide and the peptide-HLA complex of the corresponding seed (or base) target is used to qualify heteroclitic peptides for vaccine inclusion or to require experimental immunogenicity testing before vaccine inclusion.

Figure 3:
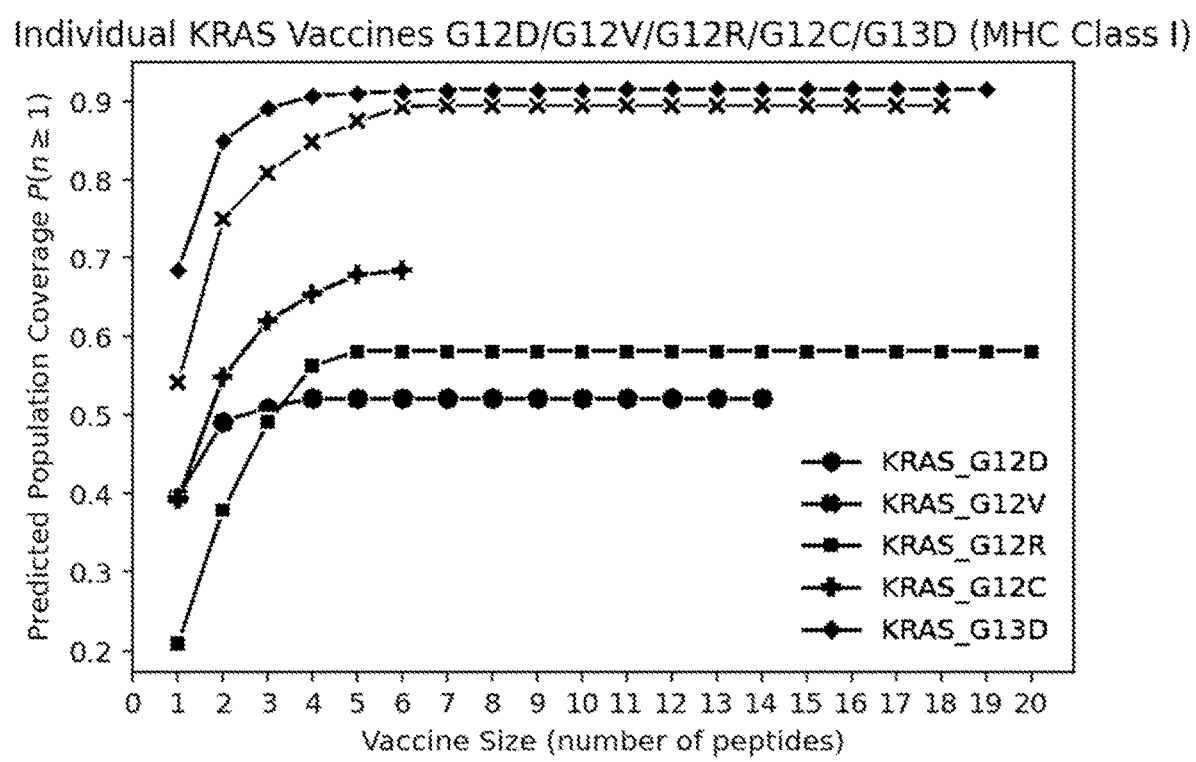
FIG. 3 shows predicted population coverage for single target MHC class I vaccines by vaccine size for KRAS G12D, KRAS G12V, KRAS G12R, KRAS G12C, and KRAS G13D targets.
Figure 4:
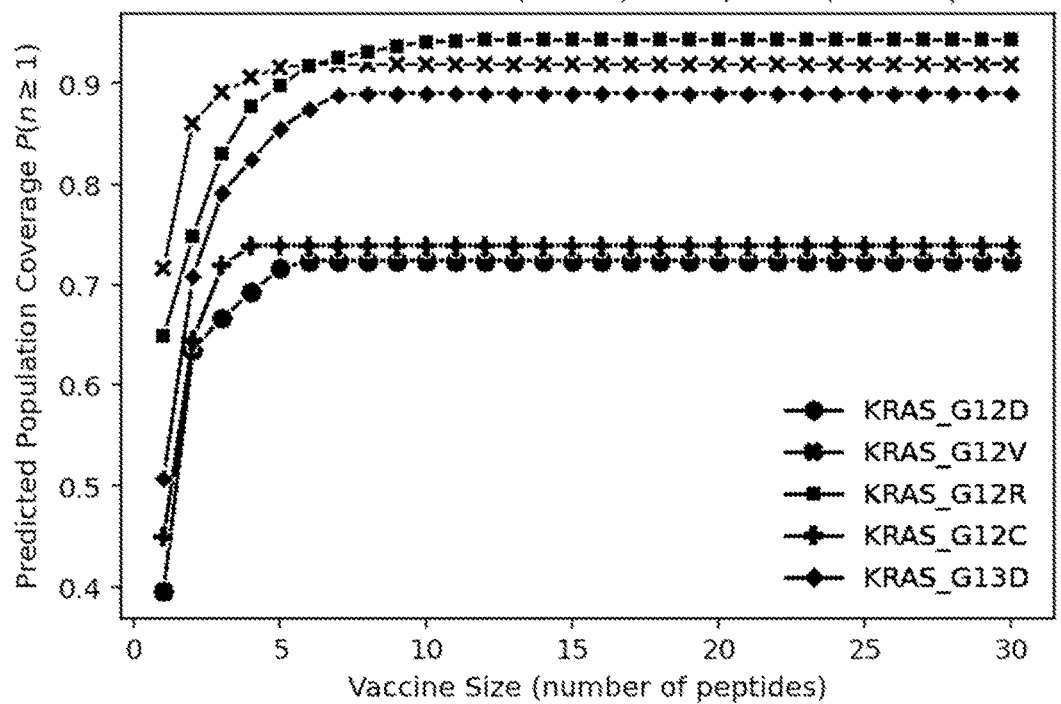
FIG. 4 shows predicted population coverage for single target MHC class II vaccines by vaccine size for KRAS G12D, KRAS G12V, KRAS G12R, KRAS G12C, and KRAS G13D targets.

FIG. 3 (MHC class I) and FIG. 4 (MHC class II) show the predicted population coverage of OptiVax-Robust selected single target-specific vaccines with differing number of peptides designed for the KRAS mutations G12D, G12V, G12R, G12C, and G13D. FIGS. 4-5 show that as the number of peptides increases for a vaccine, its predicted population coverage increases. The population coverage shown in FIGS. 4-5 are of those individuals that have the specific mutation that the vaccine is designed to cover. An increase in peptide count will also typically cause the average number of peptide-HLA hits in each individual to increase within the population.

OptiVax can be used to design a vaccine to maximize the fraction/proportion of the population whose HLA molecules are predicted to bind to and display at least p peptides from the vaccine. In some embodiments, this prediction (e.g., scoring) includes experimental immunogenicity data to directly predict at least p peptides will be immunogenic. The number p is input to OptiVax, and OptiVax can be run multiple times with varying values for p to obtain a predicted optimal target peptide set for different peptide counts p. Larger values of p will increase the redundancy of a vaccine at the cost of more peptides to achieve a desired population coverage. In some embodiments, it may not be possible to achieve a given population coverage given a specific heteroclitic base set. In some embodiments, the number p is a function of the desired size of a vaccine.

The methods described herein can be used to design separate vaccine formulations for MHC class I and class II based immunity.

In some embodiments, this procedure is used to create a vaccine for an individual. In some embodiments, the target peptides present in the individual are determined by sequencing the individual's tumor RNA or DNA, and identifying mutations that produce foreign peptides. One embodiment of this method is described in U.S. Pat. No. 10,738,355, incorporated in its entirety herein. In some embodiments, peptide sequencing methods are used to identify target peptides in the individual. One embodiment of this is described in U.S. Publication No.: 2011/0257890. In some embodiments, the target peptides used for the individual's vaccine are selected when a self-peptide, foreign peptide, or RNA encoding a self-peptide or foreign peptide is observed in a specimen from the individual is present at a predetermined level. The target peptides in the individual are used to construct a vaccine as described in the disclosure herein. For vaccine design, OptiVax is provided a diplotype comprising the HLA type of the individual. In an alternative embodiment, the HLA type of an individual is separated into multiple diplotypes with frequencies that sum to one, where each diplotype comprises one or more HLA alleles from the individual and a notation that the other allele positions should not be evaluated. The use of multiple diplotypes will cause OptiVax's objective function to increase the chance that immunogenic peptides will be displayed by all of the constructed diplotypes. This achieves the objective of maximizing the number of distinct HLA alleles in the individual that exhibit peptide-HLA immunogenicity and thus improves the allelic coverage of the vaccine in the individual.

Figure 10:
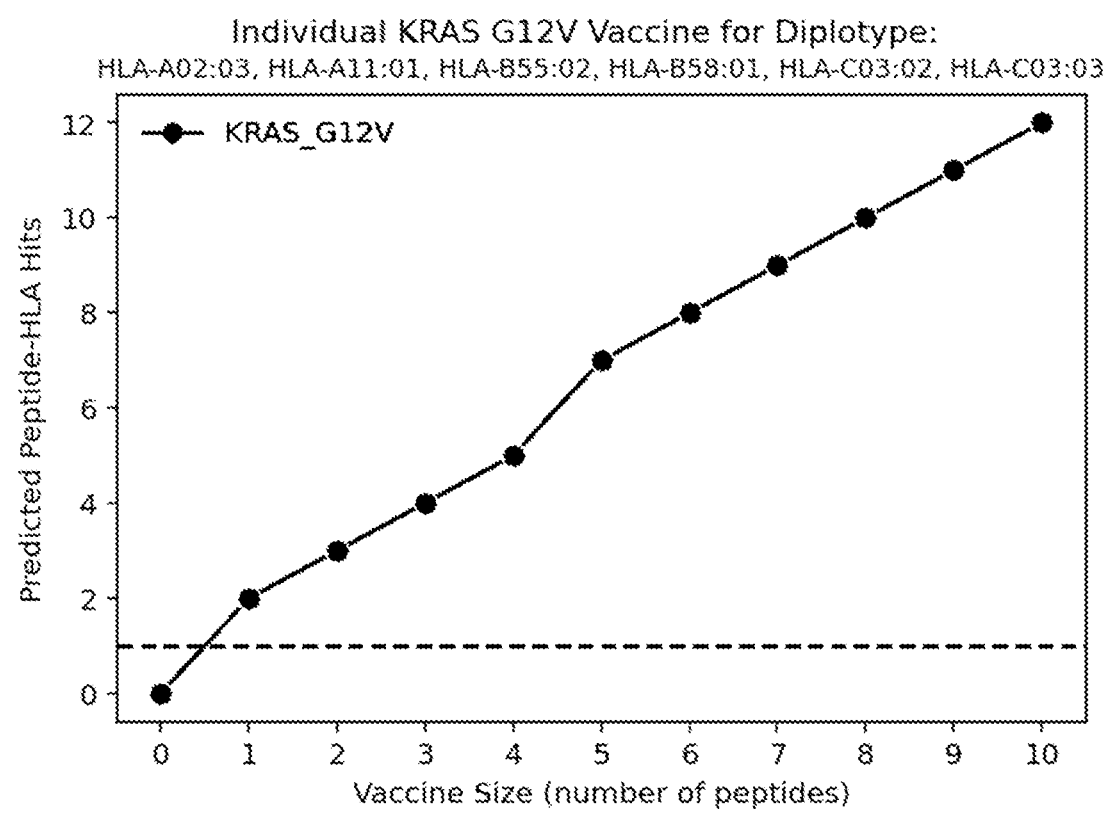
FIG. 10 shows predicated peptide-HLA hits by vaccine size for a KRAS G12V vaccine for the HLA diplotype HLA-A02:03, HLA-A11:01, HLA-B55:02, HLA-B58:01, HLA-C03:02, HLA-C03:03.

FIG. 10 shows the predicted vaccine performance (predicted number of peptide-HLA hits) of ten example G12V MHC class I vaccines for a single individual with the MHC class I HLA diplotype HLA-A02:03, HLA-A11:01, HLA-B55:02, HLA-B58:01, HLA-C03:02, HLA-C03:03. OptiVax was used to design ten G12V MHC class I vaccines for this HLA diplotype with peptide counts ranging from 1 to 10. For the results in FIG. 10, OptiVax was run with six synthetic diplotypes, each equally weighted, each with one HLA allele from the individual's HLA diplotype, and the other allele positions marked to not be evaluated. The 10 peptide vaccine in FIG. 10 comprises SEQ ID NO: 3 (GAVGVGKSL), SEQ ID NO: 4 (LMVVGAVGV), SEQ ID NO: 7 (VVGAVGVGK), SEQ ID NO: 14 (GPVGVGKSV), SEQ ID NO: 69 (LMVVGAVGI), SEQ ID NO: 72 (LMVVGAVGL), SEQ ID NO: 131 (GAVGVGKSM), SEQ ID NO: 138 (GPVGVGKSA), SEQ ID NO: 142 (VTGAVGVGK), and SEQ ID NO: 198 (VAGAVGVGM). Two peptides, SEQ ID NO: 3 (GAVGVGKSL) and SEQ ID NO: 131 (GAVGVGKSM), are predicted to bind two of the HLA alleles with an affinity of 50 nM or less.

MHC Class I Vaccine Design Procedure

In some embodiments, MHC class I vaccine design procedures consist of the following computations steps.

In some embodiments, the inputs for the computation are:

$P_{1 \ldots n}$: Peptide sequence (length n) containing the neoantigen or pathogenic target(s) of interest (e.g., KRAS G12D, KRAS G12V, KRAS G12R, KRAS G12C, KRAS G13D). $P_i$ denotes the amino acid at position i.

t: Position of target mutation in P, $t \in [1, \ldots n]$ (e.g., t=12 for KRAS G12D).

$\tau_1$: Threshold for potential presentation of peptides by MHC for peptide-MHC scoring (e.g., 500 nM binding affinity)

$\tau_2$: Threshold for predicted display of peptides by MHC for peptide-MHC scoring (e.g., 50 nM binding affinity)

$\mathcal{H}$: Set of HLA alleles (for HLA-A, HLA-B, HLA-C loci)

F: $\mathcal{H}^3 \to \mathbb{R}$: Population haplotype frequencies (for OptiVax optimization and coverage evaluation).

N: Parameter for EvalVax and OptiVax objective function. Specifies minimum number of predicted per-individual hits for population coverage objective to consider the individual covered. Default=1 (computes $P(n \geq 1)$ population coverage).

In some embodiments, Peptide-HLA Scoring Functions used are:

ScorePotential: $P \times \mathcal{H} \to \mathbb{R}$ : Scoring function mapping a (peptide, HLA allele) pair to a prediction of peptide-HLA display. If predicted affinity $\leq \tau_1$, then returns 1, else returns 0. Options include MHCflurry, NetMHCpan, PUFFIN, ensembles, or alternative metrics or software may be used, including models calibrated against immunogenicity data.

ScoreDisplay: $P \times \mathcal{H} \to \mathbb{R}$ : Scoring function mapping a (peptide, HLA allele) pair to a prediction of peptide-HLA display. If predicted affinity $\leq \tau_2$, then returns 1, else returns 0. Options include MHCflurry, NetMHCpan, PUFFIN, ensembles, or alternative metrics or software may be used, including models calibrated against immunogenicity data.

Next, from the seed protein sequence (P), a set $\mathcal{P}$ of windowed native peptides spanning the protein sequence(s) is constructed. In some embodiments, 9-mers are produced, but this process can be performed with any desired window lengths and the resulting peptide sets combined.

$$\mathcal{P} = \{P_{j \ldots j+8} | j \in [t-8, \ldots, t], j \neq \{t-8, t-1\}\}$$

The second condition $j \neq \{t-8, t-1\}$ excludes peptides where the mutation at t is in positions P2 or P9 of the windowed 9-mer peptide (i.e., the anchor positions).

Next, each peptide sequence in $\mathcal{P}$ is scored against all HLA alleles in $\mathcal{H}$ for potential presentation using ScorePotential (with threshold $\tau_1 = 500$ nM) and store results in a $|\mathbb{R}| \times |\mathcal{H}|$ matrix S:

$$S[p,h] = \text{ScorePotential}(p,h) \forall p \in \mathcal{P}, h \in \mathcal{H}$$

Note that S is a binary matrix where 1 indicates the HLA is predicted to potentially present the peptide, and 0 indicates no potential presentation.

Define Base Set of Peptides $B \subseteq \mathcal{P}$:

$$B = \{p \in \mathcal{P} \mid \exists h s.t. S[p,h]=1\}$$

Thus, B contains the native peptides that are predicted to be potentially presented by at least 1 HLA.

Create a Set of all Heteroclitic Peptides B' Stemming from Peptides in B:

$$B' = \bigcup_{b \in B} \text{ANCHOR-MODIFIED}(b)$$

where ANCHOR-MODIFIED(b) returns a set of all 399 anchor-modified peptides stemming from b (with all possible modifications to the amino acids at P2 and P9).

Next, all heteroclitic candidate peptides (e.g., modified peptides) in B' are scored against all HLA alleles in $\mathcal{H}$ for predicted display using ScoreDisplay (with threshold $\tau_2 = 50$ nM), and store results in binary $|B'| \times |\mathcal{H}|$ matrix $S_1'$:

$$S_1'[b',h] = \text{ScoreDisplay}(b',h) \forall b' \in B', h \in \mathcal{H}$$

Next, an updated scoring matrix $S_2'$ is computed for heteroclitic peptides conditioned on the potential presentation of the corresponding base peptides by each HLA:

$$S_2'[b', h] = \begin{cases} S_1'[b', h], & \text{if } S[b, h] = 1 \\ 0, & \text{otherwise} \end{cases} \forall b' \in B', h \in \mathcal{H}$$

where each heteroclitic peptide $b' \in B'$ is a mutation of base peptide $b \in B$. This condition enforces that if h was not predicted to potentially present b, then all heteroclitic peptides b' derived from b will not be displayed by h (even if h would otherwise be predicted to display b').

In some embodiments, OptiVax-Robust is used to design a final peptide set (e.g., third peptide set) from the union of base peptides and heteroclitic peptides $B \cup B'$ (with corresponding scoring matrices S and $S_2'$ for B and B', respectively). Let $\mathcal{V}_k$ denote the compact set of vaccine peptides output by OptiVax containing k peptides. Note that $\mathcal{V}_{k+1}$ is not necessarily a superset of $\mathcal{V}_k$. (In alternate embodiments, OptiVax can be used to augment the base set B with peptides from B' using scoring matrix $S_2'$ to return set $\mathcal{A}_k$, and the final vaccine set $\mathcal{V}_{k+|B|}$ consists of peptides $B \cup \mathcal{A}_k$.)

In some embodiments, this procedure is repeated independently for each target of interest, and the resulting independent vaccine sets can be merged into a combined vaccine as described below.

MHC Class II Vaccine Design Procedure

In some embodiments, MHC class II vaccine design procedures consist of the following computations steps.

In some embodiments, the inputs for the computation are:

$P_{1 \ldots n}$: Peptide sequence(s) (length n) containing the neoantigen(s) of interest (e.g., KRAS G12D, KRAS G12V, KRAS G12R, KRAS G12C, KRAS G13D). $P_i$ denotes the amino acid at position i.

t: Position of target mutation in P, $t \in [1, \ldots, n]$ (e.g., t=12 for KRAS G12D).

$\tau_1$: Threshold for potential presentation of peptides by MHC for peptide-MHC scoring (e.g., 500 nM binding affinity)

$\tau_2$: Threshold for predicted display of peptides by MHC for peptide-MHC scoring (e.g., 50 nM binding affinity)

$\mathcal{H}$ : Set of HLA alleles (for HLA-DR, HLA-DQ, HLA-DP loci)

F: $\mathcal{H}^3 \to \mathbb{R}$ : Population haplotype frequencies (for OptiVax optimization and coverage evaluation).

N: Parameter for EvalVax and OptiVax objective function. Specifies minimum number of predicted per-individual hits for population coverage objective to consider the individual covered. Default=1 (computes $P(n \geq 1)$ population coverage).

In some embodiments, Peptide-HLA Scoring Functions used are:

ScorePotential: $P \times \mathcal{H} \to \mathbb{R}$ : Scoring function mapping a (peptide, HLA allele) pair to a prediction of display. If predicted affinity $\leq \tau_1$, then returns 1, else returns 0. Options include NetMHCIIpan, PUFFIN, ensembles, or alternative metrics or software may be used, including models calibrated against immunogenicity data.

ScoreDisplay: $P \times \mathcal{H} \to \mathbb{R}$ : Scoring function mapping a (peptide, HLA allele) pair to a prediction of peptide-HLA display. If predicted affinity $\leq \tau_2$, then returns 1, else returns 0. Options include NetMHCIIpan, PUFFIN, ensembles, or alternative metrics or software may be used, including models calibrated against immunogenicity data.

FindCore: $P \times \mathcal{H} \to [1, \ldots, n]$: Function mapping a (peptide, HLA allele) pair to a prediction of the 9-mer binding core. The core may be specified as the offset position (index) into the peptide where the core begins.

Next, from the seed protein sequence (P), a set $\mathcal{P}$ of peptides spanning the protein sequence are constructed. Here, we extract all windowed peptides of length 13-25 spanning the target mutation, but this process can be performed using any desired window lengths (e.g., only 15-mers).

$$\mathcal{P} = \bigcup_{k \in [13,\ldots,25]} \mathcal{P}_k$$

$$\mathcal{P} = \{P_{j\ldots j+(k-1)} | j \in [t-(k-1),\ldots,t]\}$$

where $\mathcal{P}_k$ contains all sliding windows of length k, which are combined to form $\mathcal{P}$. Note that here (unlike MHC class I), no peptides are excluded based on binding core or anchor residue positions (for MHC class II, filtering is performed as described in this disclosure).

Next, each peptide sequence in P is scored against all HLA alleles in $\mathcal{H}$ for potential presentation using SCOREPOTENTIAL (with threshold $\tau_1=500$ nM) and store results in $|\mathcal{P}| \times |\mathcal{H}|$ matrix $S_1$:

$$S_1[p,h] = \text{ScorePotential}(p,h) \forall p \in \mathcal{P}, h \in \mathcal{H}$$

Note that $S_1$ is a binary matrix where 1 indicates the HLA is predicted to potentially present the peptide, and 0 indicates no potential presentation.

For each (peptide, HLA allele) pair (p, h), identify/predict the 9-mer binding core using FINDCORE. The predicted binding core is recorded in a matrix C:

$$C[p,h] = \text{FindCore}(p,h) \forall p \in \mathcal{P}, h \in \mathcal{H}$$

Next, an updated scoring matrix $S_2$ is computed for native peptides in $\mathcal{P}$:

$$S_2[p, h] = \begin{cases} S_1[p, h], & \text{if } C[p, h] \text{ specifies } P_t \text{ at a non-anchor postion inside core} \\ 0, & \text{otherwise} \end{cases}$$

$$\forall p \in \mathcal{P}, h \in \mathcal{H}$$

where $P_t$ is the target residue of interest (e.g., the mutation site of KRAS G12D). This condition enforces the target residue to fall within the binding core at a non-anchor position for all (peptide, HLA allele) pairs with non-zero scores in $S_2$, and allows the binding core to vary by allele per peptide (as the binding cores of a particular peptide may differ based on the HLA allele presenting the peptide). Thus, for each pair (p, h), if the predicted binding core C[p, h] specifies the target residue $P_t$ at an anchor position (P1, P4, P6, or P9 of the 9-mer core), or if $P_t$ is not contained within the binding core, then $S_2[p, h]=0$. In an alternate embodiment, $P_t$ can be located outside of the core or inside the core in a non-anchor position.

Next, OptiVax-Robust is run with peptides $\mathcal{P}$ and scoring matrix $S_2$ to identify a non-redundant base set of peptides $B \subseteq \mathcal{P}$. (In alternate embodiments, B can be chosen as the entire set $\mathcal{P}$ rather than identifying a non-redundant base set.)

Next, a set of all heteroclitic peptides B' is created stemming from peptides in B:

$$B' = \bigcup_{b \in \cup B} \{\text{ANCHOR} - \text{MODIFIED}(b, c) \forall c \mid \exists h \text{ s.t. } S_2[b, h] = 1\}$$

where ANCHOR-MODIFIED(b,c) returns a set of all $20^4-1$ anchor-modified peptides stemming from b with all possible modifications to the amino acids at P1, P4, P6, and P9 of the 9-mer binding core c. Thus, for each base peptide b, the heteroclitic set B' contains all anchor-modified peptides b' with modifications to all unique cores of b identified for any HLA alleles that potentially present b with a valid core position as indicated by scoring matrix $S_2$.

Next, all heteroclitic candidate peptides (e.g., modified peptides) in B' are scored against all HLA alleles in $\mathcal{H}$ for predicted display using SCOREDISPLAY (with threshold $\tau_2=50$ nM), and store results in binary $|B'| \times |\mathcal{H}|$ matrix $S_1'$:

$$S_1'[b',h] = \text{ScoreDisplay}(b',h) \forall b' \in B', h \in \mathcal{H}$$

For each (heteroclitic peptide, HLA allele) pair (b',h), identify/predict the 9-mer binding core using FINDCORE. The predicted binding core is recorded in a matrix C':

$$C'[b',h] = \text{FindCore}(b',h) \forall b' \in B', h \in \mathcal{H}$$

An updated scoring matrix $S_2'$ is computed for heteroclitic peptides conditioned on the identified binding cores of a heteroclitic and base peptides occurring at the same offset by a particular HLA:

$$S_2'[b', h] = \begin{cases} S_1'[b', h], & \text{if } C'[b', h] = C[b, h] \\ 0, & \text{otherwise} \end{cases} \forall b' \in B', h \in \mathcal{H}$$

where each heteroclitic peptide b'∈B' is a mutation of base peptide b∈B. This condition enforces the binding core of the heteroclitic peptide b' to be at the same relative position as the base peptide b, and, implicitly, enforces that the target residue $P_t$ still falls in a non-anchor position within the 9-mer binding core (Step 3).

An updated scoring matrix $S_3'$ is computed for heteroclitic peptides conditioned on the potential presentation of the corresponding base peptides by each HLA:

$$S_3'[b', h] = \begin{cases} S_2'[b', h], & \text{if } S[b, h] = 1 \\ 0, & \text{otherwise} \end{cases} \forall b' \in B', h \in \mathcal{H}$$

where each heteroclitic peptide b'∈B' is a mutation of base peptide b∈B. This condition enforces that if h was not predicted to display b, then all heteroclitic peptides b' derived from b will not be displayed by h (even if h would otherwise be predicted to display b').

OptiVax-Robust is used to design a final peptide set (e.g., third peptide set) from the union of base peptides and heteroclitic peptides B∪B' (with corresponding scoring matrices $S_2$ and $S_3'$ for B and B', respectively). Let $\mathcal{V}_k$ denote the compact set of vaccine peptides output by OptiVax containing k peptides. Note that $\mathcal{V}_{k+1}$ is not necessarily a superset of $\mathcal{V}_k$. (In alternate embodiments, OptiVax can be used to augment the base set B with peptides from B' using scoring matrix $S_2'$ to return set $\mathcal{A}_k$, and the final vaccine set $\mathcal{V}_{k+|B|}$ consists of peptides $B \cup \mathcal{A}_k$.)

In some embodiments, this procedure is repeated independently for each single target of interest, and the resulting independent vaccine sets can be merged into a combined vaccine as described below.

Methods for Combining Multiple Vaccines

The above described methods will produce an optimized target peptide set (e.g., third peptide set) for one or more individual targets. In some embodiments, a method is provided for designing separate vaccines for MHC class I and class II based immunity for multiple targets (e.g., two or more targets such as KRAS G12D and KRAS G12V).

In some embodiments, a method is disclosed for producing a combined peptide vaccine for multiple targets by using a table of presentations for a disease that is based upon empirical data from sources such as the Cancer Genome Atlas (TCGA). FIG. 5 shows one embodiment for factoring disease presentation type probabilities (pancreatic cancer, colon/rectum cancer, and bronchus/lung cancer) by probability, for each disease presentation, of target presented for various KRAS mutation targets (KRAS G12D, KRAS G12V, and KRAS G12R). A presentation is a unique set of targets that are presented by one form of a disease (e.g., distinct type of cancer as shown in FIG. 5). For each presentation, FIG. 5 shows an example of the probability of that presentation, and the probability that a given target is observed. For a given presentation, there can be one or more targets, each having a probability. In some embodiments, the method for multi-target vaccine design will allocate peptide resources for inducing disease immunity based on the presentation and respective target probabilities as shown in FIG. 5, for example. In some embodiments, presentations correspond to the prevalence of targets in different human populations or different risk groups. The probability of a target in a population is computed by summing for each possible presentation the probability of that presentation times the probability of the target in that presentation.

Figure 6:
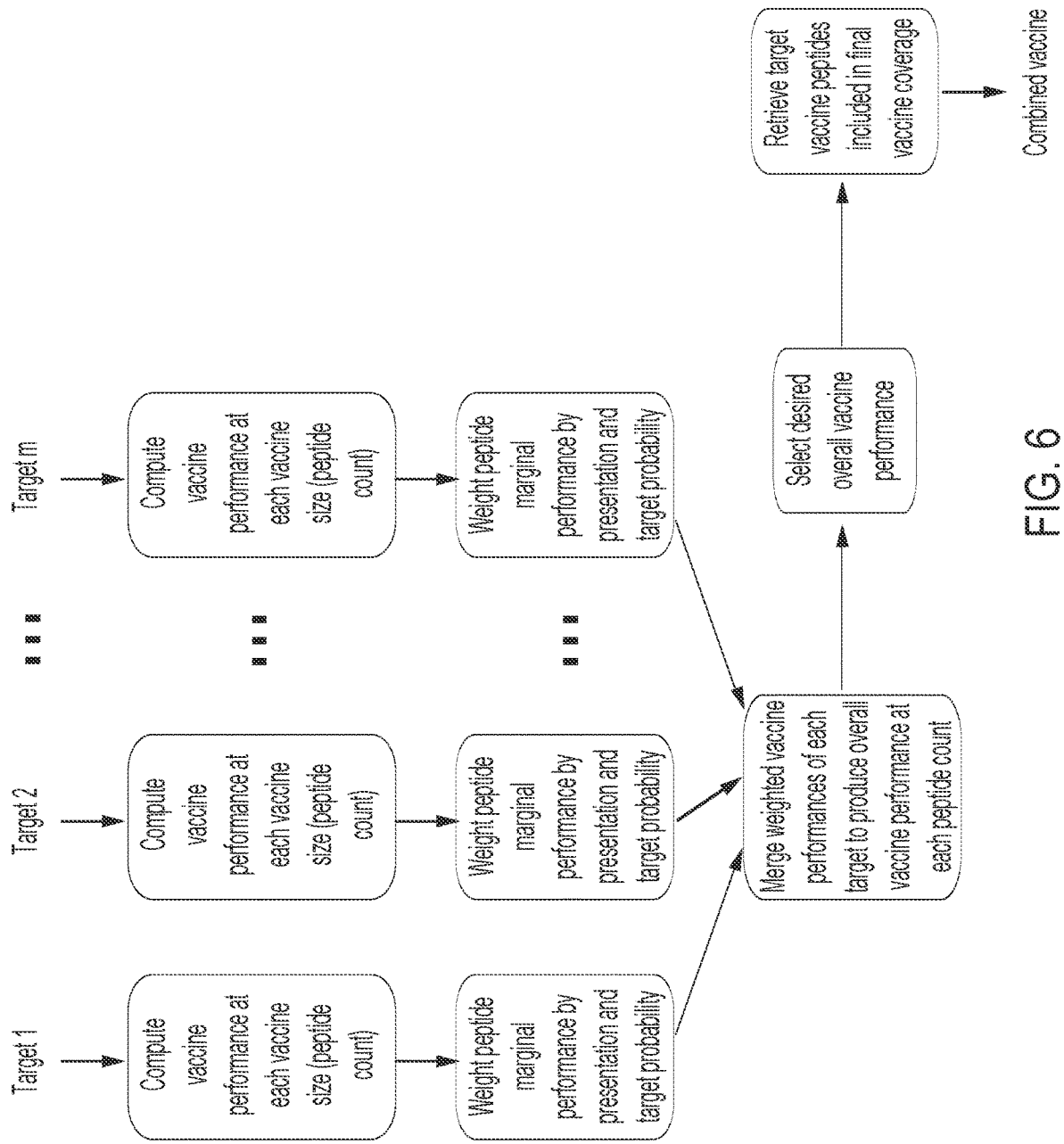
FIG. 6 is a flow chart for multiple target (combined) vaccine optimization methods.

Referring to FIG. 6, in some embodiments, the method first includes designing an individual peptide vaccine for each target to create a combined vaccine design for multiple targets. This initially results in sets of target-specific vaccine designs. In some embodiments, the marginal predicted vaccine performance of each target-specific vaccine at size k is defined by predicted vaccine performance at size k minus the predicted vaccine performance of the vaccine at size k minus one (see FIGS. 3-4). The composition of a vaccine may change as the number of peptides used in the vaccine increases, and thus for computing contributions to a combined vaccine the marginal predicted vaccine performance of each target-specific vaccine is used instead of a specific set of peptides.

In some embodiments, the weighted marginal predicted vaccine performance of a target-specific vaccine design for each target specific vaccine size is computed as shown in FIG. 6. For a given target specific vaccine size, its weighted predicted vaccine performance is computed by multiplying its predicted vaccine performance times the probability of the target in the population (e.g., by using values as shown in FIG. 5). The marginal weighted predicted vaccine performance for a target specific vaccine is its weighted coverage at size k minus its coverage a size k minus one (e.g., see FIGS. 3-4). The marginal weighted predicted vaccine performance of a target specific vaccine of size one is its weighted predicted vaccine performance. The marginal weighted predicted vaccine performances for all vaccines are combined into a single list, and the combined list is sorted from largest to least by the weighted marginal predicted vaccine performances of the target specific vaccines as shown in FIG. 6. The combined vaccine of size n is then determined by the first n elements of this list. The peptides for the combined vaccine are determined by the individual peptide target vaccines whose sizes add to n and whose weighted predicted vaccine performances sums to the same sum as the first n elements of the sorted list. This maximizes the predicted vaccine performance of the combined vaccine of size n.

In some embodiments, the combined multiple target vaccine can be designed on its overall predicted coverage for the disease described depending on the presentation table used (e.g., see FIG. 5), by its predicted coverage for a specific indication, and/or by its predicted coverage for a specific target by adjusting the weighting used for predicted vaccine performance accordingly. Once a desired level of coverage is selected, the peptides of the combined vaccine are determined by the contributions of target-specific designs. For example, if the combined vaccine includes a target-specific vaccine of size k, then the vaccine peptides for this target at size k are used in the combined vaccine.

Figure 7:
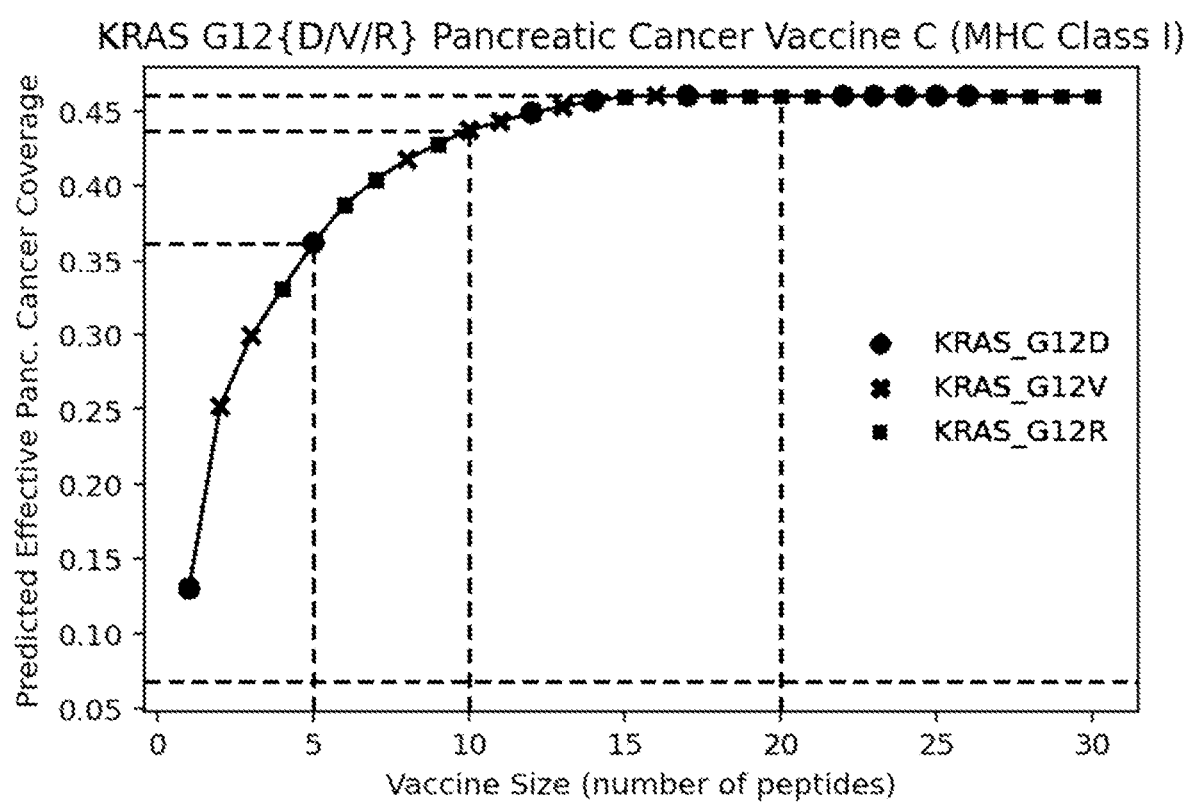
FIG. 7 shows predicted population coverage for pancreatic cancer multiple target (combined) MHC class I vaccines by vaccine size for KRAS G12D, KRAS G12V, and KRAS G12R targets.
Figure 8:
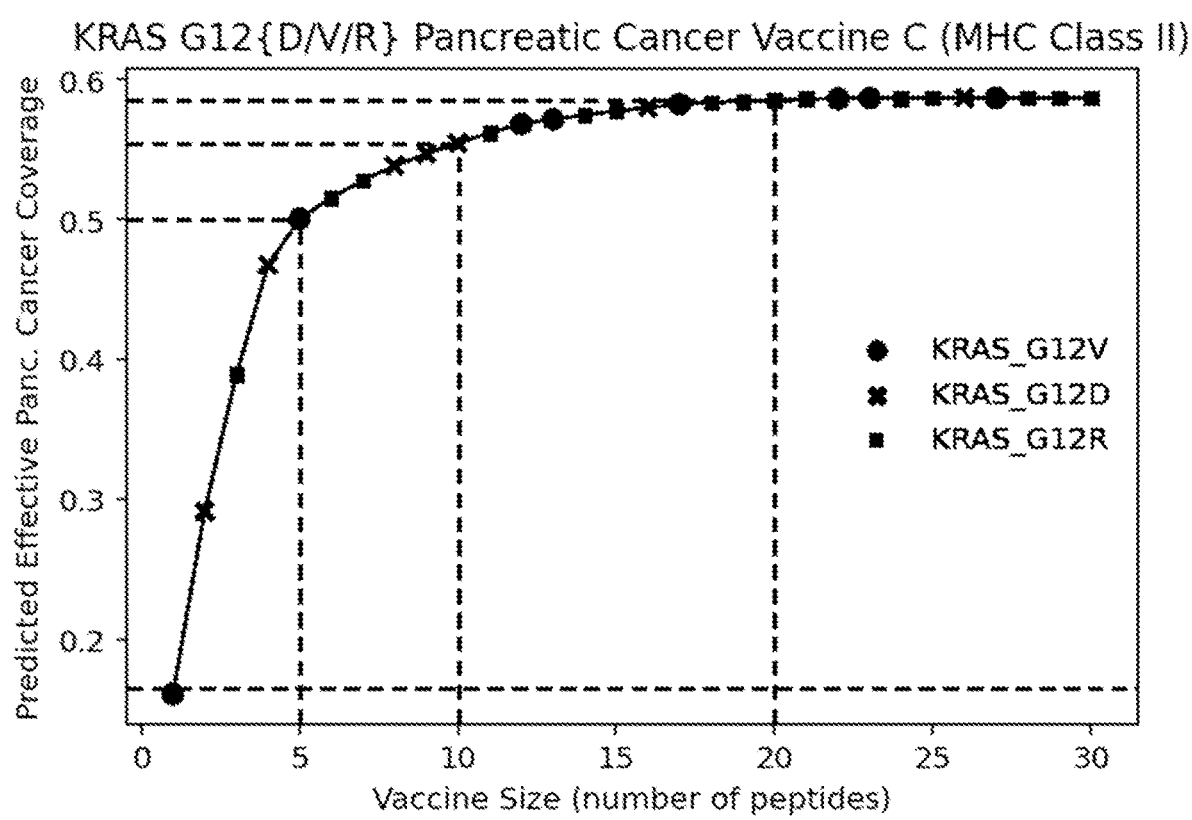
FIG. 8 shows predicted population coverage for pancreatic cancer multiple target (combined) MHC class II vaccines by vaccine size for KRAS G12D, KRAS G12V, and KRAS G12R targets.

As an example of one embodiment, FIG. 5 shows three mutations (KRAS G12D, G12V, and G12R) and their respective probabilities of occurring in an individual with pancreatic cancer. FIG. 3 (MHC class I) and FIG. 4 (MHC class II) show the population coverage of target-specific vaccines for the KRAS G12D, G12V, G12R, G12C, and G13D targets using the methods for vaccines described herein. The marginal population coverage of each target-specific vaccine at a given vaccine size is the improvement in coverage at that size and the size less one. The coverage with no peptides is zero. The marginal coverage of each target-specific vaccine is multiplied by the probability of the target in the population as determined by the proportions as shown in FIG. 5 for the pancreas (pancreatic cancer). These weighted marginal coverages of all target-specific vaccines are sorted to determine the best target-specific compositions, and the resulting list describes the composition of a combined vaccine at each size k by taking the first k elements of the list. As an example of one embodiment, FIG. 7 (MHC Class I) and FIG. 8 (MHC Class II) show the target specific contributions at each vaccine size for a combined KRAS vaccine for the three mutations KRAS G12D, G12V, and G12R. The methods for combined vaccine protocol described herein was used to compute the examples in FIGS. 7 and 8. At each combined vaccine size, different components of the target-specific vaccines are utilized. Table 1 (below) contains the peptides present in independent (single target) and combined (multiple target) MHC class I vaccine designs for the KRAS G12D, G12V, G12R, G12C, and G13D targets. Table 2 (below) contains the contains the peptides present in independent (single target) MHC class II vaccine designs for the KRAS G12D, G12V, G12R, G12C, and G13D targets, and any subset of the individual/single target vaccines can be combined to create an MHC class II vaccine for two or more multiple targets. For alternate embodiments, Sequence Listing provides heteroclitic peptides useful in MHC class I vaccines for the KRAS G12D, G12V, G12R, G12C, and G13D targets.

Combined Vaccine Design Procedure

In some embodiments, the procedure described herein is used to combine individual compact vaccines optimized for different targets into a single optimized combined vaccine.

In some embodiments, the computational inputs for the procedure are:

$\mathcal{T}$: Set of neoantigen or pathogenic targets of interest (e.g., KRAS G12D, KRAS G12V, KRAS G12R)

$\mathcal{V}$: Vaccine sets optimized individually for each target. Let $\mathcal{V}_{t,k}$ denote the optimal vaccine set of exactly k peptides for target $t \in \mathcal{T}$ (e.g., as computed by the procedures describe above). Note that $\mathcal{V}_{t,k+1}$ may not necessarily be a superset of $\mathcal{V}_{t,k}$.

W: $\mathcal{T} \to [0,1]$: Target weighting function mapping each target $t \in \mathcal{T}$ to a probability or weight of t in a particular presentation of interest (e.g., pancreatic cancer; see Exhibit A, Table 1 for example).

POPULATIONCOVERAGE: $\mathcal{V} \to [0,1]$: Function mapping a peptide set into population coverage (e.g., EvalVax). This function may also take as input additional parameters, including HLA haplotype frequencies and a minimum per-individual number of peptide-HLA hits N (here, we compute coverage as P(n≥1) using EvalVax-Robust).

For each target t (individually) and vaccine size (peptide count) k, the unweighted population coverage $c_{t,k}$ is computed:

$$c_{t,k} = \text{PopulationCoverage}(\mathcal{V}_{t,k}) \forall t \in \mathcal{T}, k$$

Note that for each target t, $c_{t,k}$ is generally monotonically increasing and concave down for increasing values of k (each additional peptide increases coverage but with decreasing returns).

For each target t (individually), the marginal coverage $m_{t,k}$ is computed of the k-th peptide added to the vaccine set:

$$m_{t,k} = \begin{cases} c_{t,k} & \text{if } k = 1 \\ c_{t,k} - c_{t,k-1}, & \text{otherwise} \end{cases} \forall t \in \mathcal{T}, k$$

Note that for each target t, $m_{t,k}$ should be a monotonically decreasing function in k (by Step 1 above).

The weighted marginal population coverage $\tilde{m}_{t,k}$ is computed using weights of each target in W:

$$\tilde{m}_{t,k} = W(t) \cdot m_{t,k} \forall t \in \mathcal{T}, k$$

The weighted marginal population coverage gives the effective marginal coverage of the k-th peptide in the vaccine weighted by the prevalence of the target in the presentation (by multiplication with the probability/weight of the target in the presentation).

The individual vaccines are combined into a combined vaccine via the MERGEMULTI procedure called on the weighted marginal population coverage lists $\tilde{m}_t = [\tilde{m}_{t,k}, k \in 1, 2, \ldots]$. FIG. 9 shows an example Python implementation of the MERGEMULTI function. This procedure takes as input multiple sorted (descending) lists and merges them into a single sorted (descending) list. Let M indicate the output of MERGEMULTI where each element $M_k$ contains both the marginal weighted coverage and source (target) of the k-th peptide in the combined vaccine. The combined vaccine contains peptides from different targets. In particular, the combined vaccine with k peptides contains $C_{t,k} = \Sigma_{j \leq k}\mathbb{1}\{M_k \text{ from t}\}$ peptides from target t. Note that $C_{t,k} \in [0, \ldots k]$ and $\Sigma_t C_{t,k} = k$ ($C_{t,k}$ gives the distribution of the k peptides in the combined vaccine across the targets).

The optimal combined vaccine set $\hat{\mathcal{V}}_k$ is defined as:

$$\hat{v}_k = \bigcup_{t \in \mathcal{T}} v_{t,C_{t,k}}$$

Thus, the combined vaccine with k peptides is the combination of the optimal individual ($C_{t,k}$)-peptide vaccines. The marginal weighted coverage values of the combine vaccine $M_k$ can be cumulatively summed over k to give the overall effective (target-weighted) population coverage of the combined vaccine containing k peptides as $\Sigma_{j \leq K} M_k$ (taking into account both the probabilities/weights of the targets in the presentation and the expected population coverage of peptides based on HLA display). The final vaccine size k can vary based upon the specific population coverage goals of the vaccine.

MHC Class I Peptide Sequences

In some embodiments, a peptide vaccine (single target or combined multiple target vaccine) comprises about five, ten, or twenty MHC class I peptides with each peptide consisting of 8 or more amino acids. In some embodiments, an MHC class I peptide vaccine is intended for one or more of the KRAS G12D, G12V, and G12R targets. In some embodiments, the amino acid sequence of a first peptide in a five-peptide combined vaccine comprises SEQ ID NO: 1. GADGVGKSM (SEQ ID NO: 1). In some embodiments, the amino acid sequence of a second peptide in a five-peptide combined vaccine comprises SEQ ID NO: 2. LMVVGADGV (SEQ ID NO: 2). In some embodiments, the amino acid sequence of a third peptide in a five-peptide combined vaccine comprises SEQ ID NO: 3. GAVGVGKSL (SEQ ID NO: 3). In some embodiments, the amino acid sequence of a fourth peptide in a five-peptide combined vaccine comprises SEQ ID NO: 4. LMVVGAVGV (SEQ ID NO: 4). In some embodiments, the amino acid sequence of a fifth peptide in a five-peptide combined vaccine comprises SEQ ID NO: 5. VTGARGVGK (SEQ ID NO: 5). An example combined vaccine for the KRAS G12D, G12V, and G12R targets with five peptides (SEQ ID NO: 1 to SEQ ID NO: 5) is predicted to have a weighted population coverage of 0.3620.

In some embodiments, any one of the peptides (peptides 1-5) in the five-peptide vaccine comprise an amino acid sequence 80, 81, 82, 83, 84, 85, 86, 87, 88, 89, 90, 91, 92, 93, 94, 95, 96, 97, 98 or 99% identical to SEQ ID NO: 1, SEQ ID NO: 2, SEQ ID NO: 3, SEQ ID NO: 4, or SEQ ID NO: 5.

In some embodiments, the amino acid sequence of peptides 1 to 5 in a ten-peptide combined vaccine comprise SEQ ID NO: 1, SEQ ID NO: 2, SEQ ID NO: 3, SEQ ID NO: 4, and SEQ ID NO: 5. In some embodiments, the amino acid sequence of a sixth peptide in a ten-peptide combined vaccine comprises SEQ ID NO: 6. VMGAVGVGK (SEQ ID NO: 6). In some embodiments, the amino acid sequence of a seventh peptide in a ten-peptide combined vaccine comprises SEQ ID NO: 7. VVGAVGVGK (SEQ ID NO: 7). In some embodiments, the amino acid sequence of an eight peptide in a ten-peptide combined vaccine comprises SEQ ID NO: 8. GARGVGKSY (SEQ ID NO: 8). In some embodiments, the amino acid sequence of a ninth peptide in a ten-peptide combined vaccine comprises SEQ ID NO: 9. GPRGVGKSA (SEQ ID NO: 9). In some embodiments, the amino acid sequence of a tenth peptide in a ten-peptide combined vaccine comprises SEQ ID NO: 10. LMVVGARGV (SEQ ID NO: 10). An example combined vaccine for the KRAS G12D, G12V, and G12R targets with ten peptides (SEQ ID NO: 1 to SEQ ID NO: 10) is predicted to have a weighted population coverage of 0.4374.

In some embodiments, any one of the peptides (peptides 1-10) in the ten-peptide vaccine comprise an amino acid sequence 80, 81, 82, 83, 84, 85, 86, 87, 88, 89, 90, 91, 92, 93, 94, 95, 96, 97, 98 or 99% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In some embodiments, the amino acid sequence of peptides 1 to 10 in a twenty-peptide combined vaccine comprise SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. In some embodiments, the amino acid sequence of an $11^{th}$ peptide in a twenty-peptide combined vaccine comprises SEQ ID NO: 11. GADGVGKSL (SEQ ID NO: 11). In some embodiments, the amino acid sequence of a $12^{th}$ peptide in a twenty-peptide combined vaccine comprises SEQ ID NO: 12. GADGVGKSY (SEQ ID NO: 12). In some embodiments, the amino acid sequence of a $13^{th}$ peptide in a twenty-peptide combined vaccine comprises SEQ ID NO: 13. GYDGVGKSM (SEQ ID NO: 13). In some embodiments, the amino acid sequence of a 14th peptide in a twenty-peptide combined vaccine comprises SEQ ID NO: 14. GPVGVGKSV (SEQ ID NO: 14). In some embodiments, the amino acid sequence of a 15th peptide in a twenty-peptide combined vaccine comprises SEQ ID NO: 15. LTVVGAVGV (SEQ ID NO: 15). In some embodiments, the amino acid sequence of a 16th peptide in a twenty-peptide combined vaccine comprises SEQ ID NO: 16. VVGAVGVGR (SEQ ID NO: 16). In some embodiments, the amino acid sequence of a 17th peptide in a twenty-peptide combined vaccine comprises SEQ ID NO: 17. GARGVGKSM (SEQ ID NO: 17). In some embodiments, the amino acid sequence of an 18th peptide in a twenty-peptide combined vaccine comprises SEQ ID NO: 18. GPRGVGKSV (SEQ ID NO: 18). In some embodiments, the amino acid sequence of a 19th peptide in a twenty-peptide combined vaccine comprises SEQ ID NO: 19. LLVVGARGV (SEQ ID NO: 19). In some embodiments, the amino acid sequence of a 20th peptide in a twenty-peptide combined vaccine comprises SEQ ID NO: 20. VAGARGVGM (SEQ ID NO: 20). An example combined vaccine for the KRAS G12D, G12V, and G12R targets with twenty peptides (SEQ ID NO: 1 to SEQ ID NO: 20) is predicted to have a weighted population coverage of 0.4604.

In some embodiments, any one of the peptides (peptides 1-20) in the twenty-peptide vaccine comprise an amino acid sequence 80, 81, 82, 83, 84, 85, 86, 87, 88, 89, 90, 91, 92, 93, 94, 95, 96, 97, 98 or 99% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20

Table 1 shows MHC class I peptide sequences described herein including the respective SEQ ID NO, amino acid sequence corresponding to the SEQ ID NO, KRAS protein target (with specific mutation), the seed amino acid sequence (i.e., the amino acid sequence of the wild type KRAS fragment), the amino acid substitution (if any) for heteroclitic peptides at positions 2 and 9, and notes detailing embodiments in which the peptide may be included in a 5, 10, or 20 combined peptide vaccine as described herein. Table 1 also includes additional peptide sequences comprising SEQ ID NOs: 21-41. In some embodiments, any combination of peptides listed in Table 1 (SEQ ID NOs: 1-41) may be used to create a combined peptide vaccine having between about 2 and about 40 peptides. In some embodiments, any one of the peptides (peptides 1-41; SEQ ID NOs: 1-41) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1-41.

TABLE 1

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 1 | GADGVGKSM | KRAS G12D | GADGVGKSA | — | A9M | Individual KRAS G12D (MHCflurry); Combined (5 peptide) (MHCflurry); Combined (10 peptide) (MHCflurry); Combined (20 peptide) (MHCflurry) |
| SEQ ID NO: 2 | LMVVGADGV | KRAS G12D | LVVVGADGV | V2M | — | Individual KRAS G12D (MHCflurry); Individual KRAS G12D (NetMHCpan); Combined (5 peptide) (MHCflurry); Combined (10 peptide) (MHCflurry); Combined (20 peptide) (MHCflurry) |
| SEQ ID NO: 3 | GAVGVGKSL | KRAS G12V | GAVGVGKSA | — | A9L | Individual KRAS G12V (MHCflurry); Combined (5 peptide) (MHCflurry); Combined (10 peptide) (MHCflury); Combined (20 peptide) (MHCflurry) |
| SEQ ID NO: 4 | LMVVGAVGV | KRAS G12V | LVVVGAVGV | V2M | — | Individual KRAS G12V (MHCflurry); Individual KRAS G12V (NetMHCpan); Combined (5 peptide) (MHCflury); Combined (10 peptide) (MHCflury); Combined (20 peptide) (MHCflurry) |

TABLE 1-continued

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 5 | VTGARGVGK | KRAS G12R | VVGARGVGK | V2T | — | Individual KRAS G12R (MHCflurry); Combined (5 peptide) (MHCflury); Combined (10 peptide) (MHCflury); Combined (20 peptide) (MHCflurry) |
| SEQ ID NO: 6 | VMGAVGVGK | KRAS G12V | VVGAVGVGK | V2M | — | Individual KRAS G12V (MHCflurry); Combined (10 peptide) (MHCflury); Combined (20 peptide) (MHCflurry) |
| SEQ ID NO: 7 | VVGAVGVGK | KRAS G12V | VVGAVGVGK | — | — | Individual KRAS G12V (MHCflurry); Individual KRAS G12V (NetMHCpan); Combined (10 peptide) (MHCflury); Combined (20 peptide) (MHCflurry) |
| SEQ ID NO: 8 | GARGVGKSY | KRAS G12R | GARGVGKSA | — | A9Y | Individual KRAS G12R (MHCflurry); Combined (10 peptide) (MHCflury); Combined (20 peptide) (MHCflurry) |
| SEQ ID NO: 9 | GPRGVGKSA | KRAS G12R | GARGVGKSA | A2P | — | Individual KRAS G12R (MHCflurry); Combined (10 peptide) (MHCflury); Combined (20 peptide) (MHCflurry) |
| SEQ ID NO: 10 | LMVVGARGV | KRAS G12R | LVVVGARGV | V2M | — | Individual KRAS G12R (MHCflurry); Individual KRAS G12R (NetMHCpan); Combined (10 peptide) (MHCflury); Combined (20 peptide) (MHCflurry) |
| SEQ ID NO: 11 | GADGVGKSL | KRAS G12D | GADGVGKSA | — | A9L | Individual KRAS G12D (MHCflurry); Combined (20 peptide) (MHCflurry) |
| SEQ ID NO: 12 | GADGVGKSY | KRAS G12D | GADGVGKSA | — | A9Y | Individual KRAS G12D (MHCflurry); Combined (20 peptide) (MHCflurry) |
| SEQ ID NO: 13 | GYDGVGKSM | KRAS G12D | GADGVGKSA | A2Y | A9M | Individual KRAS G12D (MHCflurry); Combined (20 peptide) (MHCflurry) |
| SEQ ID NO: 14 | GPVGVGKSV | KRAS G12V | GAVGVGKSA | A2P | A9V | Combined (20 peptide) (MHCflurry) |
| SEQ ID NO: 15 | LTVVGAVGV | KRAS G12V | LVVVGAVGV | V2T | — | Individual KRAS G12V (NetMHCpan); Combined (20 peptide) (MHCflury) |

TABLE 1-continued

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 16 | VVGAVGVGR | KRAS G12V | VVGAVGVK | — | K9R | Individual KRAS G12V (MHCflurry); Individual KRAS G12V (NetMHCpan); Combined (20 peptide) (MHCflurry) |
| SEQ ID NO: 17 | GARGVGKSM | KRAS G12R | GARGVGKSA | — | A9M | Combined (20 peptide) (MHCflurry) |
| SEQ ID NO: 18 | GPRGVGKSV | KRAS G12R | GARGVGKSA | A2P | A9V | Combined (20 peptide) (MHCflurry) |
| SEQ ID NO: 19 | LLVVGARGV | KRAS G12R | LVVVGARGV | V2L | — | Individual KRAS G12R (NetMHCpan); Combined (20 peptide) (MHCflurry) |
| SEQ ID NO: 20 | VAGARGVGM | KRAS G12R | VVGARGVGK | V2A | K9M | Individual KRAS G12R (MHCflurry); Combined (20 peptide) (MHCflurry) |
| SEQ ID NO: 21 | LTVVGADGV | KRAS G12D | LVVVGADGV | V2T | — | Individual KRAS G12D (NetMHCpan) |
| SEQ ID NO: 22 | LLVVGADGV | KRAS G12D | LVVVGADGV | V2L | — | Individual KRAS G12D (NetMHCpan) |
| SEQ ID NO: 23 | LMVVGADGL | KRAS G12D | LVVVGADGV | V2M | V9L | Individual KRAS G12D (NetMHCpan) |
| SEQ ID NO: 24 | VMGAVGVGR | KRAS G12V | VVGAVGVK | V2M | K9R | Individual KRAS G12V (NetMHCpan) |
| SEQ ID NO: 25 | VMGARGVGK | KRAS G12R | VVGARGVGK | V2M | — | Individual KRAS G12R (NetMHCpan) |
| SEQ ID NO: 26 | GACGVGKSL | KRAS G12C | GACGVGKSA | — | A9L | Individual KRAS G12C (MHCflurry) |
| SEQ ID NO: 27 | LMVVGACGV | KRAS G12C | LVVVGACGV | V2M | — | Individual KRAS G12C (MHCflurry); Individual KRAS G12C (NetMHCpan) |
| SEQ ID NO: 28 | LTVVGACGV | KRAS G12C | LVVVGACGV | V2T | — | Individual KRAS G12C (MHCflurry); Individual KRAS G12C (NetMHCpan) |
| SEQ ID NO: 29 | VTGACGVGK | KRAS G12C | VVGACGVGK | V2T | — | Individual KRAS G12C (MHCflurry) |
| SEQ ID NO: 30 | VVGACGVGR | KRAS G12C | VVGACGVGK | — | K9R | Individual KRAS G12C (MHCflurry) |
| SEQ ID NO: 31 | AADVGKSAM | KRAS G13D | AGDVGKSAL | G2A | L9M | Individual KRAS G13D (MHCflurry); Individual KRAS G13D (NetMHCpan) |
| SEQ ID NO: 32 | AEDVGKSAM | KRAS G13D | AGDVGKSAL | G2E | L9M | Individual KRAS G13D (MHCflurry) |
| SEQ ID NO: 33 | AYDVGKSAM | KRAS G13D | AGDVGKSAL | G2Y | L9M | Individual KRAS G13D (MHCflurry) |
| SEQ ID NO: 34 | DAGKSALTV | KRAS G13D | DVGKSALTI | V2A | I9V | Individual KRAS G13D (MHCflurry) |
| SEQ ID NO: 35 | GAGDVGKSM | KRAS G13D | GAGDVGKSA | — | A9M | Individual KRAS G13D (MHCflurry) |

TABLE 1-continued

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 36 | LQVVGACGV | KRAS G12C | LVVVGACGV | V2Q | — | Individual KRAS G12C (NetMHCpan) |
| SEQ ID NO: 37 | VMGACGVGK | KRAS G12C | VVGACGVGK | V2M | — | Individual KRAS G12C (NetMHCpan) |
| SEQ ID NO: 38 | VMGACGVGR | KRAS G12C | VVGACGVGK | V2M | K9R | Individual KRAS G12C (NetMHCpan) |
| SEQ ID NO: 39 | AADVGKSAL | KRAS G13D | AGDVGKSAL | G2A | — | Individual KRAS G13D (NetMHCpan) |
| SEQ ID NO: 40 | ASDVGKSAL | KRAS G13D | AGDVGKSAL | G2S | — | Individual KRAS G13D (NetMHCpan) |
| SEQ ID NO: 41 | ASDVGKSAM | KRAS G13D | AGDVGKSAL | G2S | L9M | Individual KRAS G13D (NetMHCpan) |

Additional amino acid sequences of MHC class I heteroclitic peptides are provided in Sequence Listings (SEQ ID NOs: 67-1522). In some embodiments, any combination of MHC class I peptides disclosed herein (SEQ ID NOs: 1-41 and 67-1522) may be used to create a combined peptide vaccine having between about 2 and about 40 peptides. In some embodiments, any one of the peptides (SEQ ID NOs: 1-41 and 67-1522) in the combined vaccine comprises or contains an amino acid sequence 80, 81, 82, 83, 84, 85, 86, 87, 88, 89, 90, 91, 92, 93, 94, 95, 96, 97, 98 or 99% identical to any of SEQ ID NOs: 1-41 or 67-1522.

MHC Class II Peptide Sequences

In some embodiments, a peptide vaccine (single target or combined multiple target vaccine) comprises about 2 to 40 MHC class II peptides with each peptide consisting of about 20 amino acids. In some embodiments, an MHC class II peptide vaccine is intended for one or more of the KRAS G12D, G12V, G12R, G12C, and G13D targets.

Table 2 summarizes MHC class II peptide sequences described herein including the respective SEQ ID NO, amino acid sequence corresponding to the SEQ ID NO, the amino acid sequence corresponding to the peptide's binding core, the KRAS protein target (with specific mutation), the seed amino acid sequence (i.e., the amino acid sequence of the wild type KRAS fragment), the seed amino acid sequence of the binding core, and the amino acid substitution (if any) for heteroclitic peptides at positions 1, 4, 6, and 9. Table 2 includes peptide sequences comprising SEQ ID NOs: 42-66. SEQ ID NOs: 42-65 (Table 2) encode for recombinant peptides. In some embodiments, any combination of peptides listed in Table 2 (SEQ ID NOs: 42-66) may be used to create a single target (individual) or combined peptide vaccine having between about 2 and about 40 peptides. In some embodiments, any one of the peptides (peptides 42-66; SEQ ID NOs: 42-66) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 42-66.

TABLE 2

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 42 | EYKFVVFGSDGAGKS | FVVFGSDGA | KRAS G12D | EYKLVVGADGVGKS | LVVGADGV | L1F | V4F | A6S | V9A | Individual KRAS G12D (NetMHCIIpan) |
| SEQ ID NO: 43 | EYKFVVIGNDGAGKSALTIQLIQN | FWIGNDGA | KRAS G12D | EYKLVVGADGVGKSALTIQLIQN | LVVGADGV | L1F | V4I | A6N | V9A | Individual KRAS G12D (NetMHCIIpan) |
| SEQ ID NO: 44 | EYKFVVLGADGAGKS | FVVLGADGA | KRAS G12D | EYKLVVGADGVGKS | LVVGADGV | L1F | V4L | — | V9A | Individual KRAS G12D (NetMHCIIpan) |

TABLE 2-continued

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 45 | MTEYKFVVSGADGIGKSALT | FVVSGADGI | KRAS G12D | MTEYKLVVVGADGVGKSALT | LVVVGADGV | L1F | V4S | — | V9I | Individual KRAS G12D (NetMHCIIpan) |
| SEQ ID NO: 46 | MTEYKFVVYGSDGIGKSALT | FVVYGSDGI | KRAS G12D | MTEYKLVVVGADGVGKSALT | LVVVGADGV | L1F | V4Y | A6S | V9I | Individual KRAS G12D (NetMHCIIpan) |
| SEQ ID NO: 47 | EYKFVVIGRVGHGKS | FVVIGRVGH | KRAS G12V | EYKLVVVGAVGVGKS | LVVVGAVGV | L1F | V4I | A6R | V9H | Individual KRAS G12V (NetMHCIIpan) |
| SEQ ID NO: 48 | EYKFVVLGTVGHGKS | FVVLGTVGH | KRAS G12V | EYKLVVVGAVGVGKS | LVVVGAVGV | L1F | V4L | A6T | V9H | Individual KRAS G12V (NetMHCIIpan) |
| SEQ ID NO: 49 | EYKFVVYGNVGMGKS | FVVYGNVGM | KRAS G12V | EYKLVVVGAVGVGKS | LVVVGAVGV | L1F | V4Y | A6N | V9M | Individual KRAS G12V (NetMHCIIpan) |
| SEQ ID NO: 50 | EYKIVVAGNVGIGKS | IVVAGNVGI | KRAS G12V | EYKLVVVGAVGVGKS | LVVVGAVGV | L1I | V4A | A6N | V9I | Individual KRAS G12V (NetMHCIIpan) |
| SEQ ID NO: 51 | TEYKIVVMGNVGYGK | IVVMGNVGY | KRAS G12V | TEYKLVVVGAVGVGK | LVVVGAVGV | L1I | V4M | A6N | V9Y | Individual KRAS G12V (NetMHCIIpan) |
| SEQ ID NO: 52 | MTEYKFVVFGSRGVGKSALT | FVVFGSRGV | KRAS G12R | MTEYKLVVVGARGVGKSALT | LVVVGARGV | L1F | V4F | A6S | — | Individual KRAS G12R (NetMHCIIpan) |
| SEQ ID NO: 53 | MTEYKFVVIGNRGVGKSALT | FVVIGNRGV | KRAS G12R | MTEYKLVVVGARGVGKSALT | LVVVGARGV | L1F | V4I | A6N | — | Individual KRAS G12R (NetMHCIIpan) |
| SEQ ID NO: 54 | MTEYKFVVIGVRGDGKSALT | FVVIGVRGD | KRAS G12R | MTEYKLVVVGARGVGKSALT | LVVVGARGV | L1F | V4I | A6V | V9D | Individual KRAS G12R (NetMHCIIpan) |

TABLE 2-continued

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 55 | MTEYKFVVMGSRGAGKSALT | FVVMGSRGA | KRAS G12R | MTEYKLVVVGARGVVGKSALT | LVVVGARGV | L1F | V4M | A6S | V9A | Individual KRAS G12R (NetMHCIIpan) |
| SEQ ID NO: 56 | VVVIARGVPKSLLTI | IARGVPKSL | KRAS G12R | VVVGARGVGKSALTI | GARGVGKSA | G1I | — | G6P | A9L | Individual KRAS G12R (NetMHCIIpan) |
| SEQ ID NO: 57 | EYKFVVFGNCGAGKS | FVVFGNCGA | KRAS G12C | EYKLVVVGACGVGKS | LVVVGACGV | L1F | V4F | A6N | V9A | Individual KRAS G12C (NetMHCIIpan) |
| SEQ ID NO: 58 | EYKFVVSGACGVGKS | FVVSGACGV | KRAS G12C | EYKLVVVGACGVGKS | LVVVGACGV | L1F | V4S | — | — | Individual KRAS G12C (NetMHCIIpan) |
| SEQ ID NO: 59 | EYKFVVSGNCGLGKS | FVVSGNCGL | KRAS G12C | EYKLVVVGACGVGKS | LVVVGACGV | L1F | V4S | A6N | V9L | Individual KRAS G12C (NetMHCIIpan) |
| SEQ ID NO: 60 | EYKLVVMGPCGAGKS | LVVMGPCGA | KRAS G12C | EYKLVVVGACGVGKS | LVVVGACGV | — | V4M | A6P | V9A | Individual KRAS G12C (NetMHCIIpan) |
| SEQ ID NO: 61 | KLVIVGICKVGHSAL | IVGICKVGH | KRAS G12C | KLVVVGACGVGKSAL | VVGACGVGK | VI1 | A4I | G6K | K9H | Individual KRAS G12C (NetMHCIIpan) |
| SEQ ID NO: 62 | EYKFVVFGNGDLGKS | FVVFGNGDL | KRAS G13D | EYKLVVVGAGDVGKS | LVVVGAGDV | L1F | V4F | A6N | V9L | Individual KRAS G13D (NetMHCIIpan) |
| SEQ ID NO: 63 | EYKFVVMGNGDSGKS | FVVMGNGDS | KRAS G13D | EYKLVVVGAGDVGKS | LVVVGAGDV | L1F | V4M | A6N | V9S | Individual KRAS G13D (NetMHCIIpan) |
| SEQ ID NO: 64 | EYKFVVSGSGDVGKS | FVVSGSGDV | KRAS G13D | EYKLVVVGAGDVGKS | LVVVGAGDV | L1F | V4S | A6S | | Individual KRAS G13D (NetMHCIIpan) |

TABLE 2-continued

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 65 | EYKIVVMGRGDMGKS | IVVMGRGDM | KRAS G13D | EYKLVVVGAGDVGKS | LVVVGAGDV | L1I | V4M | A6R | V9M | Individual KRAS G13D (NetM HCIIpan) |
| SEQ ID NO: 66 | YKLVVVGAGDVGKSA | — | KRAS G13D | — | — | — | — | — | — | Individual KRAS G13D (NetM HCIIpan) |

In some embodiments, any combination of MHC class I and/or MHC class II peptides disclosed herein (SEQ ID NOs: 1-1522) may be used to create a single target (individual) or combined peptide vaccine having between about 2 and about 40 peptides. In some embodiments, any one of the peptides (peptides 1-1522; SEQ ID NOs: 1-1522) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1-1522.

mRNA and DNA Vaccines

In some embodiments, vaccine peptides are encoded as mRNA or DNA molecules and are administered for expression in vivo as is known in the art. One example of the delivery of vaccines by mRNA is found in Kranz et al. (2016), incorporated herein by reference. In one embodiment, a construct comprises 10 peptides, including a five-peptide MHC class I combined pancreatic cancer vaccine (targets: KRAS G12D, G12V, G12R) and a five-peptide MHC class II combined pancreatic cancer vaccine (targets: KRAS G12D, G12V, G12R), as optimized by the procedure described herein. Peptides are prepended with a secretion signal sequence at the N-terminus and followed by an MHC class I trafficking signal (MITD) (Kreiter et al., 2008; Sahin et al., 2017). The MITD has been shown to route antigens to pathways for HLA class I and class II presentation (Kreiter et al., 2008). Here we combine all peptides of each MHC class into a single construct using non-immunogenic glycine/serine linkers from Sahin et al. (2017), though it is also plausible to construct individual constructs containing single peptides with the same secretion and MITD signals as demonstrated by Kreiter et al. (2008).

In some embodiments, the amino acid sequence encoded by the mRNA vaccine comprises SEQ ID NO: 1523. Underlined amino acids correspond to the signal peptide (or leader) sequence. Bolded amino acids correspond to MHC class I (9 amino acids in length; 5 peptides) and MHC class II (13-25 amino acids in length; 5 peptides) peptide sequences. Italicized amino acids correspond to the trafficking signal.
MRVTAPRTLILLLSGALALTETWAGSGGSGGGSGG
GADGVGKSMGGSGGGSGGL MVVGAD-
GVGGSGGGGSGGGAVGVGKSLGGSGGGGSG-
GLMVVGAVGVGGSGGGGS GGVT-
GARGVGKGGSGGGGSGGEYKFVVLGTVGHGKSGG
SGGGGSGGEYKIVVAG NVGIGKSGGSGGGGSGGEYKFVVFGSD-
GAGKSGGSGGGGSGGMTEYKFVVSGADGI
GKSALTGGSGGGGSGGMTEYKFVVIGNRGVGK-
SALTGGSLGGGGSGIVGIVAGLAVL AVVVIGAV-
VATVMCRRKSSGGKGGSYSQAASSDSAQGSDVSLTA
(SEQ ID NO: 1523).

In some embodiments, the vaccine is an mRNA vaccine comprising a nucleic acids sequence encoding the amino acid sequence consisting of SEQ ID NO: 1523. In some embodiments, the nucleic acid sequence of the mRNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 1523.

In some embodiments, the vaccine is a DNA vaccine comprising a nucleic acids sequence encoding the amino acid sequence consisting of SEQ ID NO: 1523. In some embodiments, the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 1523.

In some embodiments, one or more MHC class I and/or MHC class II peptides disclosed herein (SEQ ID NO: 1-1522) can be encoded in one or more mRNA or DNA molecules and administered for expression in vivo. In some embodiments between about 2 and about 40 peptide sequences are encoded in one or more mRNA constructs. In some embodiments, between about 2 and about 40 peptide sequences are encoded in one or more DNA constructs (i.e., nucleic acids encoding the amino acids sequences comprising on or more of SEQ ID NOs: 1-1522). In some embodiments, the amino acid sequence of the mRNA vaccine or the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to any of SEQ ID NOs: 1-1522.

Non-Limiting Embodiments of the Subject Matter

In one aspect, the invention provides for a system for selecting an immunogenic peptide composition comprising a processor, and a memory storing processor-executable instructions that, when executed by the processor, cause the processor to create a first peptide set by selecting a plurality of base peptides, wherein at least one peptide of the plurality of base peptides is associated with a disease, create a second peptide set by adding to the first peptide set a modified peptide, wherein the modified peptide comprises a substitution of at least one residue of a base peptide selected from the plurality of base peptides, and create a third peptide set by selecting a subset of the second peptide set, wherein the selected subset of the second peptide set has a predicted vaccine performance, wherein the predicted vaccine performance has a population coverage above a predetermined threshold, and wherein the subset comprises at least one peptide of the second peptide set.

In some embodiments, the plurality of base peptides of the first peptide set is derived from a target protein, wherein the target protein is a tumor neoantigen or a pathogen proteome. In some embodiments, selecting the plurality of base peptides to create the first peptide set comprises sliding a window of size n across an amino acid sequence encoding the target protein, wherein n is between about 8 amino acids and about 25 amino acids in length, and wherein n is a length of each peptide of the plurality of base peptides of the first peptide set. In some embodiments, a peptide of the plurality of base peptides binds to an HLA class I molecule or an HLA class II molecule. In some embodiments, the substitution of the at least one residue comprises substituting an amino acid at an anchor residue position for a different amino acid at the anchor residue position. In some embodiments, the system further comprises filtering the first peptide set to exclude a peptide with a predicted binding core that contains a target residue in an anchor position. In some embodiments, the second peptide set comprises the first peptide set. In some embodiments, the prediction to be bound by the one or more HLA alleles is computed using a binding affinity less than about 1000 nM. In some embodiments, the predicted vaccine performance is determined by computing a plurality of peptide-HLA immunogenicities of the third peptide set to at least one HLA allele. In some embodiments, each peptide-HLA immunogenicity of the plurality of peptide-HLA immunogenicities of the third peptide set is based on a predicted binding affinity of less than about 500 nM. In some embodiments, the predicted vaccine performance is based on a population coverage, wherein the population coverage is computed based on a frequency of an HLA haplotype in a human population. In some embodiments, the predicted vaccine performance is based on a population coverage, wherein the population coverage is computed based on a frequency of at least two HLA alleles in a human population. In some embodiments, the plurality of base peptides is present in a single subject. In some embodiments, the predicted vaccine performance is an expected number of peptide-HLA hits. In some embodiments, the disease is cancer, and wherein the cancer is selected from the group consisting of pancreas, colon, rectum, kidney, bronchus, lung, uterus, cervix, bladder, liver, and stomach. In some embodiments, the plurality of base peptides of the first peptide set comprises at least one self-peptide.

In another aspect, the invention provides for a non-transitory computer-readable storage medium comprising computer-readable instructions for determining an immunogenic peptide composition that, when executed by a processor cause the processor to create a first peptide set by selecting a plurality of base peptides, wherein a first base peptide and a second base peptide of the plurality of base peptides are each scored for binding by two or more HLA alleles, wherein the first base peptide and the second base peptide are each predicted to be bound by one or more HLA alleles, and wherein the first base peptide and the second base peptide are associated with a disease, create a second peptide set comprising the first base peptide, the second base peptide, a first modified peptide, and a second modified peptide, wherein the first modified peptide comprises a substitution of at least one residue of the first base peptide, and wherein the second modified peptide comprises a substitution of at least one residue of the second base peptide, and create a third peptide set by selecting a subset of the second peptide set, wherein the selected subset of the second peptide set has a predicted vaccine performance, and wherein the predicted vaccine performance is a function of a peptide-HLA immunogenicity of at least one peptide of the third peptide set with respect to the two or more HLA alleles.

In some embodiments, the plurality of base peptides of the first peptide set is derived from a target protein, wherein the target protein is a tumor neoantigen or a pathogen proteome. I n some embodiments, selecting the plurality of base peptides to create the first peptide set comprises sliding a window of size n across an amino acid sequence encoding the target protein, wherein n is between about 8 amino acids and about 25 amino acids in length, and wherein n is a length of each peptide of the plurality of base peptides of the first peptide set. In some embodiments, a peptide of the plurality of base peptides binds to an HLA class I molecule or an HLA class II molecule. In some embodiments, the substitution of the at least one residue comprises substituting an amino acid at an anchor residue position for a different amino acid at the anchor residue position. In some embodiments, the non-transitory computer-readable storage medium of further comprises filtering the first peptide set to exclude a peptide with a predicted binding core that contains a target residue in an anchor position. In some embodiments, the second peptide set comprises the first peptide set. In some embodiments, the prediction to be bound by the two or more HLA alleles is computed using a binding affinity less than about 1000 nM. In some embodiments, the plurality of base peptides of the first peptide set comprises at least one self-peptide.

In another aspect, the invention provides for a system for selecting an immunogenic peptide composition comprising a processor, and a memory storing processor-executable instructions that, when executed by the processor, cause the processor to create a first peptide set by selecting a plurality of base peptides, wherein a first base peptide of the plurality of base peptides is scored for binding by three or more HLA alleles, wherein the first base peptide is predicted to be bound by one or more HLA alleles, and wherein the first base peptide is associated with a disease, create a second peptide set comprising the first base peptide and a modified peptide, wherein the modified peptide comprises a substitution of at least one residue of the first base peptide, and create a third peptide set by selecting a subset of the second peptide set, wherein the selected subset of the second peptide set has a predicted vaccine performance, and wherein the predicted vaccine performance is a function of a peptide-HLA immunogenicity of at least one peptide of the third peptide set with respect to the three or more HLA alleles.

In some embodiments, the first base peptide is scored for binding based on data obtained from experimental assays. In some embodiments, the predicted vaccine performance includes a peptide-HLA immunogenicity of the modified peptide bound to the first HLA allele of the one or more HLA alleles if the first base peptide is predicted to be bound to the first HLA allele of the one or more HLA alleles with a first binding core, wherein the first binding core is a binding core of the first base peptide, wherein the first binding core is identical to a second binding core, and wherein the second binding core is a binding core of the modified peptide bound to the first HLA allele.

In another aspect, the invention provides for a non-transitory computer-readable storage medium comprising computer-readable instructions for determining an immunogenic peptide composition that, when executed by a processor cause the processor to create a first peptide set by selecting a plurality of base peptides, wherein at least one peptide of the plurality of base peptides is associated with a disease, create a second peptide set comprising a first base peptide selected from the first base peptide set and a modified peptide, wherein the modified peptide comprises a substitution of at least one residue of the first base peptide, and create a third peptide set by selecting a subset of the second peptide set, wherein the selected subset of the second peptide set has a predicted vaccine performance, wherein the predicted vaccine performance has an expected number of peptide-HLA hits above a predetermined threshold, and wherein the subset comprises at least one peptide of the second peptide set.

In some embodiments, the first base peptide binds to an HLA class I molecule or an HLA class II molecule.

In another aspect, the invention provides for a system for selecting an immunogenic peptide composition comprising a processor, and a memory storing processor-executable instructions that, when executed by the processor, cause the processor to create a first peptide set by selecting a first plurality of peptides, wherein the first plurality of peptides comprises a plurality of target peptides that are associated with a first disease, and wherein the first peptide set has a first predicted vaccine performance value, create a second peptide set by selecting a second plurality of peptides, wherein the second plurality of peptides comprises a plurality of target peptides that are associated with a second disease, and wherein the second peptide set has a second predicted vaccine performance value, create a first weighted peptide set by multiplying a first weight by the first predicted vaccine performance value, create a second weighted peptide set multiplying a second weight by the second predicted vaccine performance value, and create a third peptide set by combining the first weighted peptide set and the second weighted peptide set.

In some embodiments, the first predicted vaccine performance value and the second predicted vaccine performance value are computed based on a population coverage of a vaccine. In some embodiments, the first predicted vaccine performance value and the second predicted vaccine performance value are computed based on an expected number of peptide-HLA hits. In some embodiments, the first plurality of peptides is derived from a tumor neoantigen or a pathogen proteome. In some embodiments, the second plurality of peptides is derived from a tumor neoantigen or a pathogen proteome. In some embodiments, the first disease is cancer, and wherein the cancer is selected from the group consisting of pancreas, colon, rectum, kidney, bronchus, lung, uterus, cervix, bladder, liver, and stomach. In some embodiments, the second disease is cancer, and wherein the cancer is selected from the group consisting of pancreas, colon, rectum, kidney, bronchus, lung, uterus, cervix, bladder, liver, and stomach. In some embodiments, the first plurality of peptides comprises a peptide that binds to an HLA class I molecule or an HLA class II molecule. In some embodiments, the second plurality of peptides comprises a peptide that binds to an HLA class I molecule or an HLA class II molecule.

Compositions

In some embodiments, a peptide vaccine comprises one or more peptides of this disclosure and is administered in a pharmaceutical composition that includes a pharmaceutically acceptable carrier. In some embodiments, the peptide vaccine is comprised of the third peptide set, as described in this disclosure. In some embodiments, the pharmaceutical composition is in the form of a spray, aerosol, gel, solution, emulsion, lipid nanoparticle, nanoparticle, or suspension.

The composition is preferably administered to a subject with a pharmaceutically acceptable carrier. Typically, in some embodiments, an appropriate amount of a pharmaceutically acceptable salt is used in the formulation, which in some embodiments can render the formulation isotonic.

In certain embodiments, the peptides are provided as an immunogenic composition comprising any one of the peptides described herein and a pharmaceutically acceptable carrier. In certain embodiments, the immunogenic composition further comprises an adjuvant. In certain embodiments, the peptides are conjugated with other molecules to increase their effectiveness as is known by those practiced in the art. For example, peptides can be coupled to antibodies that recognize cell surface proteins on antigen presenting cells to enhance vaccine effectiveness. One such method for increasing the effectiveness of peptide delivery is described in Woodham, et al. (2018). In certain embodiments for the treatment of autoimmune disorders, the peptides are delivered with a composition and protocol designed to induce tolerance as is known in the art. Example methods for using peptides for immune tolerization are described in Alhadj Ali, et al. (2017) and Gibson, et al. (2015).

In some embodiments, the pharmaceutically acceptable carrier is selected from the group consisting of saline, Ringer's solution, dextrose solution, and a combination thereof. Other suitable pharmaceutically acceptable carriers known in the art are contemplated. Suitable carriers and their formulations are described in Remington's Pharmaceutical Sciences, 2005, Mack Publishing Co. The pH of the solution is preferably from about 5 to about 8, and more preferably from about 7 to about 7.5. The formulation may also comprise a lyophilized powder. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of peptides being administered.

The phrase pharmaceutically acceptable carrier as used herein means a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier is acceptable in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol;

esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term carrier denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency. The composition may also include additional agents such as an isotonicity agent, a preservative, a surfactant, and, a divalent cation, preferably, zinc.

The composition can also include an excipient, or an agent for stabilization of a peptide composition, such as a buffer, a reducing agent, a bulk protein, amino acids (such as e.g., glycine or praline) or a carbohydrate. Bulk proteins useful in formulating peptide compositions include albumin. Typical carbohydrates useful in formulating peptides include but are not limited to sucrose, mannitol, lactose, trehalose, or glucose.

Surfactants may also be used to prevent soluble and insoluble aggregation and/or precipitation of peptides or proteins included in the composition. Suitable surfactants include but are not limited to sorbitan trioleate, soya lecithin, and oleic acid. In certain cases, solution aerosols are preferred using solvents such as ethanol. Thus, formulations including peptides can also include a surfactant that can reduce or prevent surface-induced aggregation of peptides by atomization of the solution in forming an aerosol. Various conventional surfactants can be employed, such as polyoxyethylene fatty acid esters and alcohols, and polyoxyethylene sorbitol fatty acid esters. Amounts will generally range between 0.001% and 4% by weight of the formulation. In some embodiments, surfactants used with the present disclosure are polyoxyethylene sorbitan mono-oleate, polysorbate 80, polysorbate 20. Additional agents known in the art can also be included in the composition.

In some embodiments, the pharmaceutical compositions and dosage forms further comprise one or more compounds that reduce the rate by which an active ingredient will decay, or the composition will change in character. So called stabilizers or preservatives may include, but are not limited to, amino acids, antioxidants, pH buffers, or salt buffers. Nonlimiting examples of antioxidants include butylated hydroxy anisole (BHA), ascorbic acid and derivatives thereof, tocopherol and derivatives thereof, butylated hydroxy anisole and cysteine. Nonlimiting examples of preservatives include parabens, such as methyl or propyl p-hydroxybenzoate and benzalkonium chloride. Additional nonlimiting examples of amino acids include glycine or proline.

The present invention also teaches the stabilization (preventing or minimizing thermally or mechanically induced soluble or insoluble aggregation and/or precipitation of an inhibitor protein) of liquid solutions containing peptides at neutral pH or less than neutral pH by the use of amino acids including proline or glycine, with or without divalent cations resulting in clear or nearly clear solutions that are stable at room temperature or preferred for pharmaceutical administration.

In one embodiment, the composition is a pharmaceutical composition of single unit or multiple unit dosage forms. Pharmaceutical compositions of single unit or multiple unit dosage forms of the invention comprise a prophylactically or therapeutically effective amount of one or more compositions (e.g., a compound of the invention, or other prophylactic or therapeutic agent), typically, one or more vehicles, carriers, or excipients, stabilizing agents, and/or preservatives. Preferably, the vehicles, carriers, excipients, stabilizing agents and preservatives are pharmaceutically acceptable.

In some embodiments, the pharmaceutical compositions and dosage forms comprise anhydrous pharmaceutical compositions and dosage forms. Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Suitable vehicles are well known to those skilled in the art of pharmacy, and non-limiting examples of suitable vehicles include glucose, sucrose, starch, lactose, gelatin, rice, silica gel, glycerol, talc, sodium chloride, dried skim milk, propylene glycol, water, sodium stearate, ethanol, and similar substances well known in the art. Saline solutions and aqueous dextrose and glycerol solutions can also be employed as liquid vehicles. Whether a particular vehicle is suitable for incorporation into a pharmaceutical composition or dosage form depends on a variety of factors well known in the art including, but not limited to, the way in which the dosage form will be administered to a patient and the specific active ingredients in the dosage form. Pharmaceutical vehicles can be sterile liquids, such as water and oils, including those of petroleum, animal, vegetable or synthetic origin, such as peanut oil, soybean oil, mineral oil, sesame oil and the like.

The invention also provides that a pharmaceutical composition can be packaged in a hermetically sealed container such as an ampoule or sachette indicating the quantity. In one embodiment, the pharmaceutical composition can be supplied as a dry sterilized lyophilized powder in a delivery device suitable for administration to the lower airways of a patient. The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for administration may be in the form of powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention (e.g., peptides) as an active ingredient.

A liquid composition herein can be used as such with a delivery device, or they can be used for the preparation of pharmaceutically acceptable formulations comprising peptides that are prepared for example by the method of spray drying. The methods of spray freeze-drying peptides/proteins for pharmaceutical administration disclosed in Maa et al., Curr. Pharm. Biotechnol., 2001, 1, 283-302, are incorporated herein. In another embodiment, the liquid solutions herein are freeze spray dried and the spray-dried product is collected as a dispersible peptide-containing powder that is therapeutically effective when administered to an individual.

The compounds and pharmaceutical compositions of the present invention can be employed in combination therapies, that is, the compounds and pharmaceutical compositions can be administered concurrently with, prior to, or subsequent to, one or more other desired therapeutics or medical procedures (e.g., peptide vaccine can be used in combination therapy with another treatment such as chemotherapy, radiation, pharmaceutical agents, and/or another treatment). The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another therapeutic or prophylactic).

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The current invention provides for dosage forms comprising peptides suitable for treating cancer or other diseases. The dosage forms can be formulated, e.g., as sprays, aerosols, nanoparticles, liposomes, or other forms known to one of skill in the art. See, e.g., Remington's Pharmaceutical Sciences; Remington: The Science and Practice of Pharmacy supra; Pharmaceutical Dosage Forms and Drug Delivery Systems by Howard C., Ansel et al., Lippincott Williams & Wilkins; 7th edition (Oct. 1, 1999).

Generally, a dosage form used in the acute treatment of a disease may contain larger amounts of one or more of the active ingredients it comprises than a dosage form used in the chronic treatment of the same disease. In addition, the prophylactically and therapeutically effective dosage form may vary among different conditions. For example, a therapeutically effective dosage form may contain peptides that has an appropriate immunogenic action when intending to treat cancer or other disease. On the other hand, a different effective dosage may contain peptides that has an appropriate immunogenic action when intending to use the peptides of the invention as a prophylactic (e.g., vaccine) against cancer or another disease/condition. These and other ways in which specific dosage forms encompassed by this invention will vary from one another and will be readily apparent to those skilled in the art. See, e.g., Remington's Pharmaceutical Sciences, 2005, Mack Publishing Co.; Remington: The Science and Practice of Pharmacy by Gennaro, Lippincott Williams & Wilkins; 20th edition (2003); Pharmaceutical Dosage Forms and Drug Delivery Systems by Howard C. Ansel et al., Lippincott Williams & Wilkins; 7th edition (Oct. 1, 1999); and Encyclopedia of Pharmaceutical Technology, edited by Swarbrick, J. & J. C. Boylan, Marcel Dekker, Inc., New York, 1988, which are incorporated herein by reference in their entirety.

The pH of a pharmaceutical composition or dosage form may also be adjusted to improve delivery and/or stability of one or more active ingredients. Similarly, the polarity of a solvent carrier, its ionic strength, or tonicity can be adjusted to improve delivery. Compounds such as stearates can also be added to pharmaceutical compositions or dosage forms to alter advantageously the hydrophilicity or lipophilicity of one or more active ingredients to improve delivery. In this regard, stearates can also serve as a lipid vehicle for the formulation, as an emulsifying agent or surfactant, and as a delivery enhancing or penetration-enhancing agent. Different salts, hydrates, or solvates of the active ingredients can be used to adjust further the properties of the resulting composition.

Compositions can be formulated with appropriate carriers and adjuvants using techniques to yield compositions suitable for immunization. The compositions can include an adjuvant, such as, for example but not limited to, alum, poly IC, MF-59, squalene-based adjuvants, or liposomal based adjuvants suitable for immunization.

In some embodiments, the compositions and methods comprise any suitable agent or immune modulation which could modulate mechanisms of host immune tolerance and release of the induced antibodies. In certain embodiments, an immunomodulatory agent is administered in at time and in an amount sufficient for transient modulation of the subject's immune response so as to induce an immune response which comprises antibodies against for example tumor neoantigens (i.e., tumor-specific antigens (TSA)).

Expression Systems

In certain aspects, the invention provides culturing a cell line that expresses any one of the peptides of the invention in a culture medium comprising any of the peptides described herein.

Various expression systems for producing recombinant proteins/peptides are known in the art, and include, prokaryotic (e.g., bacteria), plant, insect, yeast, and mammalian expression systems. Suitable cell lines, can be transformed, transduced, or transfected with nucleic acids containing coding sequences for the peptides of the invention in order to produce the molecule of interest. Expression vectors containing such a nucleic acid sequence, which can be linked to at least one regulatory sequence in a manner that allows expression of the nucleotide sequence in a host cell, can be introduced via methods known in the art. Practitioners in the art understand that designing an expression vector can depend on factors, such as the choice of host cell to be transfected and/or the type and/or amount of desired protein to be expressed. Enhancer regions, which are those sequences found upstream or downstream of the promoter region in non-coding DNA regions, are also known in the art to be important in optimizing expression. If needed, origins of replication from viral sources can be employed, such as if a prokaryotic host is utilized for introduction of plasmid DNA. However, in eukaryotic organisms, chromosome integration is a common mechanism for DNA replication. For stable transfection of mammalian cells, a small fraction of cells can integrate introduced DNA into their genomes. The expression vector and transfection method utilized can be factors that contribute to a successful integration event. For stable amplification and expression of a desired protein, a vector containing DNA encoding a protein of interest is stably integrated into the genome of eukaryotic cells (for example mammalian cells), resulting in the stable expression of transfected genes. A gene that encodes a selectable marker (for example, resistance to antibiotics or drugs) can be introduced into host cells along with the gene of interest in order to identify and select clones that stably express a gene encoding a protein of interest. Cells containing the gene of interest can be identified by drug selection wherein cells that have incorporated the selectable marker gene will survive in the presence of the drug. Cells that have not incorporated the gene for the selectable marker die. Surviving cells can then be screened for the production of the desired protein molecule.

A host cell strain, which modulates the expression of the inserted sequences, or modifies and processes the nucleic acid in a specific fashion desired also may be chosen. Such modifications (for example, glycosylation and other post-translational modifications) and processing (for example, cleavage) of peptide/protein products may be important for the function of the peptide/protein. Different host cell strains have characteristic and specific mechanisms for the post-translational processing and modification of proteins and gene products. As such, appropriate host systems or cell lines can be chosen to ensure the correct modification and processing of the target protein expressed. Thus, eukaryotic host cells possessing the cellular machinery for proper processing of the primary transcript, glycosylation, and phosphorylation of the gene product may be used.

Various culturing parameters can be used with respect to the host cell being cultured. Appropriate culture conditions for mammalian cells are well known in the art (Cleveland W L, et al., J Immunol Methods, 1983, 56(2): 221-234) or can be determined by the skilled artisan (see, for example, Animal Cell Culture: A Practical Approach 2nd Ed., Rickwood, D. and Hames, B. D., eds. (Oxford University Press: New York, 1992)). Cell culturing conditions can vary according to the type of host cell selected. Commercially available medium can be utilized.

Peptides of the invention can be purified from any human or non-human cell which expresses the polypeptide, including those which have been transfected with expression constructs that express peptides of the invention. For protein recovery, isolation and/or purification, the cell culture medium or cell lysate is centrifuged to remove particulate cells and cell debris. The desired polypeptide molecule is isolated or purified away from contaminating soluble proteins and polypeptides by suitable purification techniques. Non-limiting purification methods for proteins include: size exclusion chromatography; affinity chromatography; ion exchange chromatography; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. Purification procedures that can select for carbohydrates can also be used, e.g., ion-exchange soft gel chromatography, or HPLC using cation- or anionexchange resins, in which the more acidic fraction(s) is/are collected.

Methods of Treatment

In one embodiment, the subject matter disclosed herein relates to a preventive medical treatment started after following diagnosis of cancer in order to prevent the disease from worsening or curing the disease. In one embodiment, the subject matter disclosed herein relates to prophylaxis of subjects who are believed to be at risk for cancer or have previously been diagnosed with cancer (or another disease). In one embodiment, said subjects can be administered the peptide vaccine described herein or pharmaceutical compositions thereof. The invention contemplates using any of the peptides produced by the systems and methods described herein. In one embodiment, the peptide vaccines described herein can be administered subcutaneously via syringe or any other suitable method know in the art.

The compound(s) or combination of compounds disclosed herein, or pharmaceutical compositions may be administered to a cell, mammal, or human by any suitable means. Non-limiting examples of methods of administration include, among others, (a) administration though oral pathways, which includes administration in capsule, tablet, granule, spray, syrup, or other such forms; (b) administration through non-oral pathways such as intraocular, intranasal, intraauricular, rectal, vaginal, intraurethral, transmucosal, buccal, or transdermal, which includes administration as an aqueous suspension, an oily preparation or the like or as a drip, spray, suppository, salve, ointment or the like; (c) administration via injection, including subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; (e) administration topically; as deemed appropriate by those of skill in the art for bringing the compound or combination of compounds disclosed herein into contact with living tissue; (f) administration via inhalation, including through aerosolized, nebulized, and powdered formulations; and (g) administration through implantation.

As will be readily apparent to one skilled in the art, the effective in vivo dose to be administered and the particular mode of administration will vary depending upon the age, weight and species treated, and the specific use for which the compound or combination of compounds disclosed herein are employed. The determination of effective dose levels, that is the dose levels necessary to achieve the desired result, can be accomplished by one skilled in the art using routine pharmacological methods. Typically, human clinical applications of products are commenced at lower dose levels, with dose level being increased until the desired effect is achieved. Alternatively, acceptable in vitro studies can be used to establish useful doses and routes of administration of the compositions identified by the present methods using established pharmacological methods. Effective animal doses from in vivo studies can be converted to appropriate human doses using conversion methods known in the art (e.g., see Nair A B, Jacob S. A simple practice guide for dose conversion between animals and human. Journal of basic and clinical pharmacy. 2016 March; 7(2):27.)

Methods of Prevention

In some embodiments, the peptides prepared using methods of the invention can be used as a vaccine to promote an immune response against cancer (e.g., against tumor neoantigens). In some embodiments, the invention provides compositions and methods for induction of immune response, for example induction of antibodies to tumor neoantigens. In some embodiments, the antibodies are broadly neutralizing antibodies. In some embodiments, the peptides prepared using methods of the invention can be used as a vaccine to promote an immune response against a pathogen. In some embodiments, the peptides prepared using methods of the invention can be used to promote immune tolerance as an autoimmune disease therapeutic.

The compositions, systems, and methods disclosed herein are not to be limited in scope to the specific embodiments described herein. Indeed, various modifications of the compositions, systems, and methods in addition to those described will become apparent to those of skill in the art from the foregoing description.

What is claimed is:

1. A method of forming an immunogenic peptide composition, the method comprising:
using a processor to perform the steps of:
determining a plurality of peptide-HLA binding scores for a first peptide sequence, wherein the first peptide sequence is associated with a tumor neoantigen, a pathogen proteome, or a self-protein;
determining whether the first peptide sequence has a peptide-HLA binding score that passes a threshold with respect to at least one HLA allele;
creating a first peptide set comprising at least two modified peptide sequences that each comprise a substitution of at least one amino acid residue of the first peptide sequence;
determining a plurality of peptide-HLA binding scores for each peptide sequence in the first peptide set; and
creating a second peptide set by selecting a subset of the first peptide set, wherein the selecting comprises excluding a peptide-HLA binding score with respect to a first HLA allele for a modified peptide sequence of the at least two modified peptide sequences if a peptide-HLA binding score for the first peptide sequence does not pass the threshold with respect to the first HLA allele;
performing an experimental assay to obtain a peptide-HLA immunogenicity metric for at least one peptide sequence of the second peptide set; and forming an immunogenic peptide composition comprising the at least one peptide sequence of the second peptide set for which the experimental assay was performed.

2. The method of claim 1, wherein selecting the subset of the first peptide set further comprises computing a population coverage.

3. The method of claim 2, wherein the selected subset of the first peptide set has a population coverage that corresponds to a proportion of a human population of at least about 0.7.

4. The method of claim 2, wherein the population coverage is computed with respect to at least three HLA alleles.

5. The method of claim 2, wherein the population coverage is computed based on a frequency of an HLA allele in a human population.

6. The method of claim 1, wherein selecting the subset of the first peptide set further comprises computing a predicted vaccine performance.

7. The method of claim 6, wherein computing the predicted vaccine performance is based on an HLA type of a subject.

8. The method of claim 1, wherein each peptide sequence of the first peptide set binds to an HLA class I molecule or an HLA class II molecule.

9. The method of claim 1, further comprising excluding from the second peptide set a peptide sequence with a predicted binding core that contains a target amino acid residue in an anchor position.

10. The method of claim 1, wherein the threshold is a binding affinity of less than about 1000 nM.

11. The method of claim 1, wherein the immunogenic peptide composition comprises nucleic acid sequences encoding an amino acid sequence of the at least one peptide sequence of the second peptide set.

12. A method of forming an immunogenic peptide composition, the method comprising:
using a processor to perform the steps of:
determining a plurality of peptide-HLA immunogenicity metrics for a first peptide sequence, wherein the first peptide sequence is associated with a tumor neoantigen, a pathogen proteome, or a self-protein;
determining whether the first peptide sequence has a peptide-HLA immunogenicity metric that passes a threshold with respect to at least one HLA allele;
creating a first peptide set comprising at least two modified peptide sequences that each comprise a substitution of at least one amino acid residue of the first peptide sequence;
determining a plurality of peptide-HLA immunogenicity metrics for each peptide sequence in the first peptide set; and
creating a second peptide set by selecting a subset of the first peptide set, wherein the selecting comprises excluding a peptide-HLA immunogenic metric with respect to a first HLA allele for a modified peptide sequence of the at least two modified peptide sequences if a peptide-HLA immunogenicity metric for the first peptide sequence does not pass the threshold with respect to the first HLA allele;
performing an experimental assay to obtain a peptide-HLA immunogenicity metric for at least one peptide sequence of the second peptide set; and
forming an immunogenic peptide composition comprising the at least one peptide sequence of the second peptide set for which the experimental assay was performed.

13. The method of claim 12, wherein selecting the subset of the first peptide set further comprises computing a population coverage.

14. The method of claim 13, wherein the selected subset of the first peptide set has a population coverage that corresponds to a proportion of a human population of at least about 0.7.

15. The method of claim 13, wherein the population coverage is computed with respect to at least three HLA alleles.

16. The method of claim 13, wherein the population coverage is computed based on a frequency of an HLA allele in a human population.

17. The method of claim 12, wherein selecting the subset of the first peptide set further comprises computing a predicted vaccine performance.

18. The method of claim 17, wherein computing the predicted vaccine performance is based on an HLA type of a subject.

19. The method of claim 12, wherein each peptide sequence of the first peptide set binds to an HLA class I molecule or an HLA class II molecule.

20. The method of claim 12, further comprising excluding from the second peptide set a peptide sequence with a predicted binding core that contains a target amino acid residue in an anchor position.

21. The method of claim 12, wherein the threshold is a binding affinity of less than about 1000 nM.

22. The method of claim 12, wherein the immunogenic peptide composition comprises nucleic acid sequences encoding an amino acid sequence of the at least one peptide sequence of the second peptide set.

23. A method of forming an immunogenic peptide composition, the method comprising:
using a processor to perform the steps of:
determining a plurality of peptide-HLA binding scores for a first peptide sequence, wherein the first peptide sequence is associated with a tumor neoantigen, a pathogen proteome, or a self-protein;
creating a first peptide set comprising at least three modified peptide sequences that each comprise a substitution of at least one amino acid residue of the first peptide sequence;
determining a plurality of peptide-HLA binding scores for each peptide sequence in the first peptide set;
determining whether each of the at least three modified peptide sequences has a peptide-HLA binding score that passes a threshold with respect to at least one HLA allele; and
creating a second peptide set by selecting a subset of the first peptide set, wherein the selecting comprises excluding a peptide-HLA binding score with respect to a first HLA allele for a modified peptide sequence of the at least three modified peptide sequences if a peptide-HLA binding score for the modified peptide sequence does not pass the threshold with respect to the first HLA allele;
performing an experimental assay to obtain a peptide-HLA immunogenicity metric for at least two peptide sequences of the second peptide set; and
forming an immunogenic peptide composition comprising the at least two peptide sequences of the second peptide set for which the experimental assay was performed.

24. The method of claim 23, wherein selecting the subset of the first peptide set further comprises computing a population coverage, wherein the population coverage is computed with respect to at least three HLA alleles, and wherein the population coverage is computed based on a frequency of an HLA haplotype in a human population.

25. The method of claim 23, wherein selecting the subset of the first peptide set further comprises computing a predicted vaccine performance.

26. The method of claim 25, wherein computing the predicted vaccine performance is based on an HLA type of a subject.

27. The method of claim 23, wherein each peptide sequence of the first peptide set binds to an HLA class I molecule or an HLA class II molecule.

28. The method of claim 23, further comprising excluding from the second peptide set a peptide sequence with a predicted binding core that contains a target amino acid residue in an anchor position.

29. The method of claim 23, wherein the threshold is a binding affinity of less than about 50 nM.

30. The method of claim 23, wherein the immunogenic peptide composition comprises nucleic acid sequences encoding an amino acid sequence of the at least one peptide sequence of the second peptide set.

* * * * *

```
                              SEQUENCE LISTING

Sequence total quantity: 1523
SEQ ID NO: 1           moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 1
GADGVGKSM                                                                    9

SEQ ID NO: 2           moltype = AA  length = 9
FEATURE                Location/Qualifiers
source                 1..9
                       organism = synthetic construct
                       mol_type = protein
                       note = Seed: LVVVGADGV (KRAS G12D)
SEQUENCE: 2
LMVVGADGV                                                                    9

SEQ ID NO: 3           moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 3
GAVGVGKSL                                                                    9

SEQ ID NO: 4           moltype = AA  length = 9
FEATURE                Location/Qualifiers
source                 1..9
                       organism = synthetic construct
                       mol_type = protein
                       note = Seed: LVVVGAVGV (KRAS G12V)
SEQUENCE: 4
LMVVGAVGV                                                                    9

SEQ ID NO: 5           moltype = AA  length = 9
FEATURE                Location/Qualifiers
source                 1..9
                       organism = synthetic construct
                       mol_type = protein
                       note = Seed: VVGARGVGK (KRAS G12R)
SEQUENCE: 5
VTGARGVGK                                                                    9

SEQ ID NO: 6           moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 6
VMGAVGVGK                                                                    9

SEQ ID NO: 7           moltype = AA  length = 9
FEATURE                Location/Qualifiers
source                 1..9
                       organism = Homo sapiens
                       mol_type = protein
                       note = Native (KRAS G12V)
SEQUENCE: 7
VVGAVGVGK                                                                    9
```

```
SEQ ID NO: 8              moltype = AA   length = 9
FEATURE                   Location/Qualifiers
source                    1..9
                          organism = synthetic construct
                          mol_type = protein
                          note = Seed: GARGVGKSA (KRAS G12R)
SEQUENCE: 8
GARGVGKSY                                                                    9

SEQ ID NO: 9              moltype = AA   length = 9
FEATURE                   Location/Qualifiers
source                    1..9
                          organism = synthetic construct
                          mol_type = protein
                          note = Seed: GARGVGKSA (KRAS G12R)
SEQUENCE: 9
GPRGVGKSA                                                                    9

SEQ ID NO: 10             moltype = AA   length = 9
FEATURE                   Location/Qualifiers
source                    1..9
                          organism = synthetic construct
                          mol_type = protein
                          note = Seed: LVVVGARGV (KRAS G12R)
SEQUENCE: 10
LMVVGARGV                                                                    9

SEQ ID NO: 11             moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 11
GADGVGKSL                                                                    9

SEQ ID NO: 12             moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 12
GADGVGKSY                                                                    9

SEQ ID NO: 13             moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 13
GYDGVGKSM                                                                    9

SEQ ID NO: 14             moltype = AA   length = 9
FEATURE                   Location/Qualifiers
source                    1..9
                          organism = synthetic construct
                          mol_type = protein
                          note = Seed: GAVGVGKSA (KRAS G12V)
SEQUENCE: 14
GPVGVGKSV                                                                    9

SEQ ID NO: 15             moltype = AA   length = 9
FEATURE                   Location/Qualifiers
source                    1..9
                          organism = synthetic construct
                          mol_type = protein
                          note = Seed: LVVVGAVGV (KRAS G12V)
SEQUENCE: 15
LTVVGAVGV                                                                    9

SEQ ID NO: 16             moltype = AA   length = 9
FEATURE                   Location/Qualifiers
source                    1..9
                          organism = synthetic construct
                          mol_type = protein
                          note = Seed: VVGAVGVGK (KRAS G12V)
```

```
SEQUENCE: 16
VVGAVGVGR                                                                          9

SEQ ID NO: 17         moltype = AA   length = 9
FEATURE               Location/Qualifiers
source                1..9
                      organism = synthetic construct
                      mol_type = protein
                      note = Seed: GARGVGKSA (KRAS G12R)
SEQUENCE: 17
GARGVGKSM                                                                          9

SEQ ID NO: 18         moltype = AA   length = 9
FEATURE               Location/Qualifiers
source                1..9
                      organism = synthetic construct
                      mol_type = protein
                      note = Seed: GARGVGKSA (KRAS G12R)
SEQUENCE: 18
GPRGVGKSV                                                                          9

SEQ ID NO: 19         moltype = AA   length = 9
FEATURE               Location/Qualifiers
source                1..9
                      organism = synthetic construct
                      mol_type = protein
                      note = Seed: LVVGARGV (KRAS G12R)
SEQUENCE: 19
LLVVGARGV                                                                          9

SEQ ID NO: 20         moltype = AA   length = 9
FEATURE               Location/Qualifiers
source                1..9
                      organism = synthetic construct
                      mol_type = protein
                      note = Seed: VVGARGVGK (KRAS G12R)
SEQUENCE: 20
VAGARGVGM                                                                          9

SEQ ID NO: 21         moltype = AA   length = 9
FEATURE               Location/Qualifiers
source                1..9
                      organism = synthetic construct
                      mol_type = protein
                      note = Seed: LVVGADGV (KRAS G12D)
SEQUENCE: 21
LTVVGADGV                                                                          9

SEQ ID NO: 22         moltype = AA   length = 9
FEATURE               Location/Qualifiers
source                1..9
                      organism = synthetic construct
                      mol_type = protein
                      note = Seed: LVVGADGV (KRAS G12D)
SEQUENCE: 22
LLVVGADGV                                                                          9

SEQ ID NO: 23         moltype = AA   length = 9
FEATURE               Location/Qualifiers
source                1..9
                      organism = synthetic construct
                      mol_type = protein
                      note = Seed: LVVGADGV (KRAS G12D)
SEQUENCE: 23
LMVVGADGL                                                                          9

SEQ ID NO: 24         moltype = AA   length = 9
FEATURE               Location/Qualifiers
source                1..9
                      organism = synthetic construct
                      mol_type = protein
                      note = Seed: VVGAVGVGK (KRAS G12V)
SEQUENCE: 24
VMGAVGVGR                                                                          9

SEQ ID NO: 25         moltype = AA   length = 9
FEATURE               Location/Qualifiers
source                1..9
                      organism = synthetic construct
```

```
                            mol_type = protein
                            note = Seed: VVGARGVGK (KRAS G12R)
SEQUENCE: 25
VMGARGVGK                                                               9

SEQ ID NO: 26               moltype = AA  length = 9
FEATURE                     Location/Qualifiers
source                      1..9
                            organism = synthetic construct
                            mol_type = protein
                            note = Seed: GACGVGKSA (KRAS G12C)
SEQUENCE: 26
GACGVGKSL                                                               9

SEQ ID NO: 27               moltype = AA  length = 9
FEATURE                     Location/Qualifiers
source                      1..9
                            organism = synthetic construct
                            mol_type = protein
                            note = Seed: LVVVGACGV (KRAS G12C)
SEQUENCE: 27
LMVVGACGV                                                               9

SEQ ID NO: 28               moltype = AA  length = 9
FEATURE                     Location/Qualifiers
source                      1..9
                            organism = synthetic construct
                            mol_type = protein
                            note = Seed: LVVVGACGV (KRAS G12C)
SEQUENCE: 28
LTVVGACGV                                                               9

SEQ ID NO: 29               moltype = AA  length = 9
FEATURE                     Location/Qualifiers
source                      1..9
                            organism = synthetic construct
                            mol_type = protein
                            note = Seed: VVGACGVGK (KRAS G12C)
SEQUENCE: 29
VTGACGVGK                                                               9

SEQ ID NO: 30               moltype = AA  length = 9
FEATURE                     Location/Qualifiers
source                      1..9
                            organism = synthetic construct
                            mol_type = protein
                            note = Seed: VVGACGVGK (KRAS G12C)
SEQUENCE: 30
VVGACGVGR                                                               9

SEQ ID NO: 31               moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 31
AADVGKSAM                                                               9

SEQ ID NO: 32               moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 32
AEDVGKSAM                                                               9

SEQ ID NO: 33               moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 33
AYDVGKSAM                                                               9

SEQ ID NO: 34               moltype = AA  length = 9
FEATURE                     Location/Qualifiers
```

```
source                     1..9
                           organism = synthetic construct
                           mol_type = protein
                           note = Seed: DVGKSALTI (KRAS G13D)
SEQUENCE: 34
DAGKSALTV                                                                          9

SEQ ID NO: 35              moltype = AA  length = 9
FEATURE                    Location/Qualifiers
source                     1..9
                           organism = synthetic construct
                           mol_type = protein
                           note = Seed: GAGDVGKSA (KRAS G13D)
SEQUENCE: 35
GAGDVGKSM                                                                          9

SEQ ID NO: 36              moltype = AA  length = 9
FEATURE                    Location/Qualifiers
source                     1..9
                           organism = synthetic construct
                           mol_type = protein
                           note = Seed: LVVVGACGV (KRAS G12C)
SEQUENCE: 36
LQVVGACGV                                                                          9

SEQ ID NO: 37              moltype = AA  length = 9
FEATURE                    Location/Qualifiers
source                     1..9
                           organism = synthetic construct
                           mol_type = protein
                           note = Seed: VVGACGVGK (KRAS G12C)
SEQUENCE: 37
VMGACGVGK                                                                          9

SEQ ID NO: 38              moltype = AA  length = 9
FEATURE                    Location/Qualifiers
source                     1..9
                           organism = synthetic construct
                           mol_type = protein
                           note = Seed: VVGACGVGK (KRAS G12C)
SEQUENCE: 38
VMGACGVGR                                                                          9

SEQ ID NO: 39              moltype = AA  length = 9
FEATURE                    Location/Qualifiers
source                     1..9
                           organism = synthetic construct
                           mol_type = protein
                           note = Seed: AGDVGKSAL (KRAS G13D)
SEQUENCE: 39
AADVGKSAL                                                                          9

SEQ ID NO: 40              moltype = AA  length = 9
FEATURE                    Location/Qualifiers
source                     1..9
                           organism = synthetic construct
                           mol_type = protein
                           note = Seed: AGDVGKSAL (KRAS G13D)
SEQUENCE: 40
ASDVGKSAL                                                                          9

SEQ ID NO: 41              moltype = AA  length = 9
FEATURE                    Location/Qualifiers
source                     1..9
                           organism = synthetic construct
                           mol_type = protein
                           note = Seed: AGDVGKSAL (KRAS G13D)
SEQUENCE: 41
ASDVGKSAM                                                                          9

SEQ ID NO: 42              moltype = AA  length = 15
FEATURE                    Location/Qualifiers
source                     1..15
                           organism = synthetic construct
                           mol_type = protein
                           note = Seed: EYKLVVVGADGVGKS (KRAS G12D)
SEQUENCE: 42
EYKFVVFGSD GAGKS                                                                  15
```

| | | |
|---|---|---|
| SEQ ID NO: 43<br>FEATURE<br>source | moltype = AA length = 24<br>Location/Qualifiers<br>1..24<br>organism = synthetic construct<br>mol_type = protein<br>note = Seed: EYKLVVVGADGVGKSALTIQLIQN (KRAS G12D) | |
| SEQUENCE: 43<br>EYKFVVIGND GAGKSALTIQ LIQN | | 24 |
| SEQ ID NO: 44<br>FEATURE<br>source | moltype = AA length = 15<br>Location/Qualifiers<br>1..15<br>organism = synthetic construct<br>mol_type = protein<br>note = Seed: EYKLVVVGADGVGKS (KRAS G12D) | |
| SEQUENCE: 44<br>EYKFVVLGAD GAGKS | | 15 |
| SEQ ID NO: 45<br>FEATURE<br>source | moltype = AA length = 20<br>Location/Qualifiers<br>1..20<br>organism = synthetic construct<br>mol_type = protein<br>note = Seed: MTEYKLVVVGADGVGKSALT (KRAS G12D) | |
| SEQUENCE: 45<br>MTEYKFVVSG ADGIGKSALT | | 20 |
| SEQ ID NO: 46<br>FEATURE<br>source | moltype = AA length = 20<br>Location/Qualifiers<br>1..20<br>organism = synthetic construct<br>mol_type = protein<br>note = Seed: MTEYKLVVVGADGVGKSALT (KRAS G12D) | |
| SEQUENCE: 46<br>MTEYKFVVYG SDGIGKSALT | | 20 |
| SEQ ID NO: 47<br>FEATURE<br>source | moltype = AA length = 15<br>Location/Qualifiers<br>1..15<br>organism = synthetic construct<br>mol_type = protein<br>note = Seed: EYKLVVVGAVGVGKS (KRAS G12V) | |
| SEQUENCE: 47<br>EYKFVVIGRV GHGKS | | 15 |
| SEQ ID NO: 48<br>FEATURE<br>source | moltype = AA length = 15<br>Location/Qualifiers<br>1..15<br>organism = synthetic construct<br>mol_type = protein<br>note = Seed: EYKLVVVGAVGVGKS (KRAS G12V) | |
| SEQUENCE: 48<br>EYKFVVLGTV GHGKS | | 15 |
| SEQ ID NO: 49<br>FEATURE<br>source | moltype = AA length = 15<br>Location/Qualifiers<br>1..15<br>organism = synthetic construct<br>mol_type = protein<br>note = Seed: EYKLVVVGAVGVGKS (KRAS G12V) | |
| SEQUENCE: 49<br>EYKFVVYGNV GMGKS | | 15 |
| SEQ ID NO: 50<br>FEATURE<br>source | moltype = AA length = 15<br>Location/Qualifiers<br>1..15<br>organism = synthetic construct<br>mol_type = protein<br>note = Seed: EYKLVVVGAVGVGKS (KRAS G12V) | |
| SEQUENCE: 50<br>EYKIVVAGNV GIGKS | | 15 |
| SEQ ID NO: 51<br>FEATURE<br>source | moltype = AA length = 15<br>Location/Qualifiers<br>1..15<br>organism = synthetic construct<br>mol_type = protein<br>note = Seed: TEYKLVVVGAVGVGK (KRAS G12V) | |
| SEQUENCE: 51 | | |

```
TEYKIVVMGN VGYGK                                                          15

SEQ ID NO: 52          moltype = AA  length = 20
FEATURE                Location/Qualifiers
source                 1..20
                       organism = synthetic construct
                       mol_type = protein
                       note = Seed: MTEYKLVVVGARGVGKSALT (KRAS G12R)
SEQUENCE: 52
MTEYKFVVFG SRGVGKSALT                                                     20

SEQ ID NO: 53          moltype = AA  length = 20
FEATURE                Location/Qualifiers
source                 1..20
                       organism = synthetic construct
                       mol_type = protein
                       note = Seed: MTEYKLVVVGARGVGKSALT (KRAS G12R)
SEQUENCE: 53
MTEYKFVVIG NRGVGKSALT                                                     20

SEQ ID NO: 54          moltype = AA  length = 20
FEATURE                Location/Qualifiers
source                 1..20
                       organism = synthetic construct
                       mol_type = protein
                       note = Seed: MTEYKLVVVGARGVGKSALT (KRAS G12R)
SEQUENCE: 54
MTEYKFVVIG VRGDGKSALT                                                     20

SEQ ID NO: 55          moltype = AA  length = 20
FEATURE                Location/Qualifiers
source                 1..20
                       organism = synthetic construct
                       mol_type = protein
                       note = Seed: MTEYKLVVVGARGVGKSALT (KRAS G12R)
SEQUENCE: 55
MTEYKFVVMG SRGAGKSALT                                                     20

SEQ ID NO: 56          moltype = AA  length = 15
FEATURE                Location/Qualifiers
source                 1..15
                       organism = synthetic construct
                       mol_type = protein
                       note = Seed: VVVGARGVGKSALTI (KRAS G12R)
SEQUENCE: 56
VVVIARGVPK SLLTI                                                          15

SEQ ID NO: 57          moltype = AA  length = 15
FEATURE                Location/Qualifiers
source                 1..15
                       organism = synthetic construct
                       mol_type = protein
                       note = Seed: EYKLVVVGACGVGKS (KRAS G12C)
SEQUENCE: 57
EYKFVVFGNC GAGKS                                                          15

SEQ ID NO: 58          moltype = AA  length = 15
FEATURE                Location/Qualifiers
source                 1..15
                       organism = synthetic construct
                       mol_type = protein
                       note = Seed: EYKLVVVGACGVGKS (KRAS G12C)
SEQUENCE: 58
EYKFVVSGAC GVGKS                                                          15

SEQ ID NO: 59          moltype = AA  length = 15
FEATURE                Location/Qualifiers
source                 1..15
                       organism = synthetic construct
                       mol_type = protein
                       note = Seed: EYKLVVVGACGVGKS (KRAS G12C)
SEQUENCE: 59
EYKFVVSGNC GLGKS                                                          15

SEQ ID NO: 60          moltype = AA  length = 15
FEATURE                Location/Qualifiers
source                 1..15
                       organism = synthetic construct
                       mol_type = protein
```

```
                         note = Seed: EYKLVVVGACGVGKS (KRAS G12C)
SEQUENCE: 60
EYKLVVMGPC GAGKS                                                   15

SEQ ID NO: 61            moltype = AA  length = 15
FEATURE                  Location/Qualifiers
source                   1..15
                         organism = synthetic construct
                         mol_type = protein
                         note = Seed: KLVVVGACGVGKSAL (KRAS G12C)
SEQUENCE: 61
KLVIVGICKV GHSAL                                                   15

SEQ ID NO: 62            moltype = AA  length = 15
FEATURE                  Location/Qualifiers
source                   1..15
                         organism = synthetic construct
                         mol_type = protein
                         note = Seed: EYKLVVVGAGDVGKS (KRAS G13D)
SEQUENCE: 62
EYKFVVFGNG DLGKS                                                   15

SEQ ID NO: 63            moltype = AA  length = 15
FEATURE                  Location/Qualifiers
source                   1..15
                         organism = synthetic construct
                         mol_type = protein
                         note = Seed: EYKLVVVGAGDVGKS (KRAS G13D)
SEQUENCE: 63
EYKFVVMGNG DSGKS                                                   15

SEQ ID NO: 64            moltype = AA  length = 15
FEATURE                  Location/Qualifiers
source                   1..15
                         organism = synthetic construct
                         mol_type = protein
                         note = Seed: EYKLVVVGAGDVGKS (KRAS G13D)
SEQUENCE: 64
EYKFVVSGSG DVGKS                                                   15

SEQ ID NO: 65            moltype = AA  length = 15
FEATURE                  Location/Qualifiers
source                   1..15
                         organism = synthetic construct
                         mol_type = protein
                         note = Seed: EYKLVVVGAGDVGKS (KRAS G13D)
SEQUENCE: 65
EYKIVVMGRG DMGKS                                                   15

SEQ ID NO: 66            moltype = AA  length = 15
FEATURE                  Location/Qualifiers
source                   1..15
                         organism = Homo sapiens
                         mol_type = protein
                         note = Native (KRAS G13D)
SEQUENCE: 66
YKLVVVGAGD VGKSA                                                   15

SEQ ID NO: 67            moltype = AA  length = 9
FEATURE                  Location/Qualifiers
source                   1..9
                         organism = synthetic construct
                         mol_type = protein
                         note = Seed: LVVVGACGV (KRAS G12C)
SEQUENCE: 67
LLVVGACGV                                                           9

SEQ ID NO: 68            moltype = AA  length = 9
FEATURE                  Location/Qualifiers
source                   1..9
                         organism = synthetic construct
                         mol_type = protein
                         note = Seed: LVVVGAVGV (KRAS G12V)
SEQUENCE: 68
LLVVGAVGV                                                           9

SEQ ID NO: 69            moltype = AA  length = 9
FEATURE                  Location/Qualifiers
source                   1..9
```

```
                          organism = synthetic construct
                          mol_type = protein
                          note = Seed: LVVVGAVGV (KRAS G12V)
SEQUENCE: 69
LMVVGAVGI                                                              9

SEQ ID NO: 70             moltype = AA   length = 9
FEATURE                   Location/Qualifiers
source                    1..9
                          organism = synthetic construct
                          mol_type = protein
                          note = Seed: LVVVGACGV (KRAS G12C)
SEQUENCE: 70
LMVVGACGI                                                              9

SEQ ID NO: 71             moltype = AA   length = 9
FEATURE                   Location/Qualifiers
source                    1..9
                          organism = synthetic construct
                          mol_type = protein
                          note = Seed: LVVVGACGV (KRAS G12C)
SEQUENCE: 71
LLVVGACGI                                                              9

SEQ ID NO: 72             moltype = AA   length = 9
FEATURE                   Location/Qualifiers
source                    1..9
                          organism = synthetic construct
                          mol_type = protein
                          note = Seed: LVVVGAVGV (KRAS G12V)
SEQUENCE: 72
LMVVGAVGL                                                              9

SEQ ID NO: 73             moltype = AA   length = 9
FEATURE                   Location/Qualifiers
source                    1..9
                          organism = synthetic construct
                          mol_type = protein
                          note = Seed: LVVVGACGV (KRAS G12C)
SEQUENCE: 73
LMVVGACGL                                                              9

SEQ ID NO: 74             moltype = AA   length = 9
FEATURE                   Location/Qualifiers
source                    1..9
                          organism = synthetic construct
                          mol_type = protein
                          note = Seed: LVVVGACGV (KRAS G12C)
SEQUENCE: 74
LLVVGACGL                                                              9

SEQ ID NO: 75             moltype = AA   length = 9
FEATURE                   Location/Qualifiers
source                    1..9
                          organism = synthetic construct
                          mol_type = protein
                          note = Seed: LVVVGACGV (KRAS G12C)
SEQUENCE: 75
LIVVGACGV                                                              9

SEQ ID NO: 76             moltype = AA   length = 9
FEATURE                   Location/Qualifiers
source                    1..9
                          organism = synthetic construct
                          mol_type = protein
                          note = Seed: LVVVGAVGV (KRAS G12V)
SEQUENCE: 76
LLVVGAVGI                                                              9

SEQ ID NO: 77             moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 77
ATDVGKSAL                                                              9

SEQ ID NO: 78             moltype = AA   length = 9
```

| FEATURE | Location/Qualifiers |
|---|---|
| source | 1..9<br>organism = synthetic construct<br>mol_type = protein<br>note = Seed: LVVVGACGV (KRAS G12C) |

SEQUENCE: 78
LMVVGACGA                                                                     9

| SEQ ID NO: 79 | moltype = AA length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 79
AIDVGKSAL                                                                     9

| SEQ ID NO: 80 | moltype = AA length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 80
AVDVGKSAL                                                                     9

| SEQ ID NO: 81 | moltype = AA length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 81
AFDVGKSAL                                                                     9

| SEQ ID NO: 82 | moltype = AA length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 82
AADVGKSAV                                                                     9

| SEQ ID NO: 83 | moltype = AA length = 9 |
|---|---|
| FEATURE | Location/Qualifiers |
| source | 1..9<br>organism = synthetic construct<br>mol_type = protein<br>note = Seed: LVVVGAVGV (KRAS G12V) |

SEQUENCE: 83
LMVVGAVGA                                                                     9

| SEQ ID NO: 84 | moltype = AA length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 84
AADVGKSAI                                                                     9

| SEQ ID NO: 85 | moltype = AA length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 85
AFDVGKSAM                                                                     9

| SEQ ID NO: 86 | moltype = AA length = 9 |
|---|---|
| FEATURE | Location/Qualifiers |
| source | 1..9<br>organism = synthetic construct<br>mol_type = protein<br>note = Seed: GADGVGKSA (KRAS G12D) |

SEQUENCE: 86
GTDGVGKSL                                                                     9

```
SEQ ID NO: 87              moltype = AA   length = 9
FEATURE                    Location/Qualifiers
source                     1..9
                           organism = synthetic construct
                           mol_type = protein
                           note = Seed: AGDVGKSAL (KRAS G13D)
SEQUENCE: 87
AYDVGKSAL                                                                     9

SEQ ID NO: 88              moltype = AA   length = 9
FEATURE                    Location/Qualifiers
source                     1..9
                           organism = synthetic construct
                           mol_type = protein
                           note = Seed: GADGVGKSA (KRAS G12D)
SEQUENCE: 88
GSDGVGKSL                                                                     9

SEQ ID NO: 89              moltype = AA   length = 9
FEATURE                    Location/Qualifiers
source                     1..9
                           organism = synthetic construct
                           mol_type = protein
                           note = Seed: AGDVGKSAL (KRAS G13D)
SEQUENCE: 89
ATDVGKSAM                                                                     9

SEQ ID NO: 90              moltype = AA   length = 9
FEATURE                    Location/Qualifiers
source                     1..9
                           organism = synthetic construct
                           mol_type = protein
                           note = Seed: LVVVGAVGV (KRAS G12V)
SEQUENCE: 90
LLVVGAVGL                                                                     9

SEQ ID NO: 91              moltype = AA   length = 9
FEATURE                    Location/Qualifiers
source                     1..9
                           organism = synthetic construct
                           mol_type = protein
                           note = Seed: AGDVGKSAL (KRAS G13D)
SEQUENCE: 91
AIDVGKSAM                                                                     9

SEQ ID NO: 92              moltype = AA   length = 9
FEATURE                    Location/Qualifiers
source                     1..9
                           organism = synthetic construct
                           mol_type = protein
                           note = Seed: AGDVGKSAL (KRAS G13D)
SEQUENCE: 92
ALDVGKSAL                                                                     9

SEQ ID NO: 93              moltype = AA   length = 9
FEATURE                    Location/Qualifiers
source                     1..9
                           organism = synthetic construct
                           mol_type = protein
                           note = Seed: AGDVGKSAL (KRAS G13D)
SEQUENCE: 93
AWDVGKSAL                                                                     9

SEQ ID NO: 94              moltype = AA   length = 9
FEATURE                    Location/Qualifiers
source                     1..9
                           organism = synthetic construct
                           mol_type = protein
                           note = Seed: LVVVGAVGV (KRAS G12V)
SEQUENCE: 94
LIVVGAVGV                                                                     9

SEQ ID NO: 95              moltype = AA   length = 9
FEATURE                    Location/Qualifiers
source                     1..9
                           organism = synthetic construct
                           mol_type = protein
                           note = Seed: AGDVGKSAL (KRAS G13D)
```

```
SEQUENCE: 95
ATDVGKSAI                                                                        9

SEQ ID NO: 96            moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 96
AVDVGKSAM                                                                        9

SEQ ID NO: 97            moltype = AA  length = 9
FEATURE                  Location/Qualifiers
source                   1..9
                         organism = synthetic construct
                         mol_type = protein
                         note = Seed: GADGVGKSA (KRAS G12D)
SEQUENCE: 97
GIDGVGKSL                                                                        9

SEQ ID NO: 98            moltype = AA  length = 9
FEATURE                  Location/Qualifiers
source                   1..9
                         organism = synthetic construct
                         mol_type = protein
                         note = Seed: GADGVGKSA (KRAS G12D)
SEQUENCE: 98
GVDGVGKSL                                                                        9

SEQ ID NO: 99            moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 99
ATDVGKSAV                                                                        9

SEQ ID NO: 100           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 100
ASDVGKSAV                                                                        9

SEQ ID NO: 101           moltype = AA  length = 9
FEATURE                  Location/Qualifiers
source                   1..9
                         organism = synthetic construct
                         mol_type = protein
                         note = Seed: GARGVGKSA (KRAS G12R)
SEQUENCE: 101
GPRGVGKSL                                                                        9

SEQ ID NO: 102           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 102
ASDVGKSAI                                                                        9

SEQ ID NO: 103           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 103
AFDVGKSAF                                                                        9

SEQ ID NO: 104           moltype = AA  length = 9
FEATURE                  Location/Qualifiers
source                   1..9
                         organism = synthetic construct
```

-continued

```
                        mol_type = protein
                        note = Seed: GADGVGKSA (KRAS G12D)
SEQUENCE: 104
GTDGVGKSM                                                              9

SEQ ID NO: 105          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 105
GSDGVGKSM                                                              9

SEQ ID NO: 106          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 106
AIDVGKSAV                                                              9

SEQ ID NO: 107          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 107
AVDVGKSAI                                                              9

SEQ ID NO: 108          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 108
AIDVGKSAI                                                              9

SEQ ID NO: 109          moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 109
LLVVGACGA                                                              9

SEQ ID NO: 110          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 110
AADVGKSAF                                                              9

SEQ ID NO: 111          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 111
AVDVGKSAV                                                              9

SEQ ID NO: 112          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 112
GLDGVGKSL                                                              9

SEQ ID NO: 113          moltype = AA  length = 9
FEATURE                 Location/Qualifiers
```

```
                        -continued source                  1..9
                        organism = synthetic construct
                        mol_type = protein
                        note = Seed: GARGVGKSA (KRAS G12R)
SEQUENCE: 113
GPRGVGKSM                                                                        9

SEQ ID NO: 114          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 114
AWDVGKSAM                                                                        9

SEQ ID NO: 115          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 115
ALDVGKSAM                                                                        9

SEQ ID NO: 116          moltype = AA  length = 9
FEATURE                 Location/Qualifiers
source                  1..9
                        organism = synthetic construct
                        mol_type = protein
                        note = Seed: GADVGKSA (KRAS G12D)
SEQUENCE: 116
GADGVGKSV                                                                        9

SEQ ID NO: 117          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 117
AMDVGKSAL                                                                        9

SEQ ID NO: 118          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 118
GAVGVGKSY                                                                        9

SEQ ID NO: 119          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 119
AFDVGKSAI                                                                        9

SEQ ID NO: 120          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 120
VTGAVGVGR                                                                        9

SEQ ID NO: 121          moltype = AA  length = 9
FEATURE                 Location/Qualifiers
source                  1..9
                        organism = synthetic construct
                        mol_type = protein
                        note = Seed: GADVGKSA (KRAS G12D)
SEQUENCE: 121
GIDGVGKSM                                                                        9
```

```
SEQ ID NO: 122         moltype = AA   length = 9
FEATURE                Location/Qualifiers
source                 1..9
                       organism = synthetic construct
                       mol_type = protein
                       note = Seed: LVVVGAVGV (KRAS G12V)
SEQUENCE: 122
LQVVGAVGV                                                                   9

SEQ ID NO: 123         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 123
GADGVGKSI                                                                   9

SEQ ID NO: 124         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 124
GVDGVGKSM                                                                   9

SEQ ID NO: 125         moltype = AA   length = 9
FEATURE                Location/Qualifiers
source                 1..9
                       organism = synthetic construct
                       mol_type = protein
                       note = Seed: LVVVGADGV (KRAS G12D)
SEQUENCE: 125
LMVVGADGI                                                                   9

SEQ ID NO: 126         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 126
AIDVGKSAF                                                                   9

SEQ ID NO: 127         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 127
GADGVGKSF                                                                   9

SEQ ID NO: 128         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 128
AYDVGKSAF                                                                   9

SEQ ID NO: 129         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 129
GLDGVGKSM                                                                   9

SEQ ID NO: 130         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 130
```

```
AFDVGKSAV                                                                          9

SEQ ID NO: 131          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 131
GAVGVGKSM                                                                          9

SEQ ID NO: 132          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 132
GPRGVGKSI                                                                          9

SEQ ID NO: 133          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 133
ATDVGKSAF                                                                          9

SEQ ID NO: 134          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 134
GMDGVGKSL                                                                          9

SEQ ID NO: 135          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 135
GTDGVGKSI                                                                          9

SEQ ID NO: 136          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 136
AVDVGKSAF                                                                          9

SEQ ID NO: 137          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 137
AGDVGKSAM                                                                          9

SEQ ID NO: 138          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 138
GPVGVGKSA                                                                          9

SEQ ID NO: 139          moltype = AA  length = 9
FEATURE                 Location/Qualifiers
source                  1..9
                        organism = synthetic construct
                        mol_type = protein
```

```
                        note = Seed: GADGVGKSA (KRAS G12D)
SEQUENCE: 139
GTDGVGKSV                                                            9

SEQ ID NO: 140          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 140
ASDVGKSAF                                                            9

SEQ ID NO: 141          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 141
GSDGVGKSV                                                            9

SEQ ID NO: 142          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 142
VTGAVGVGK                                                            9

SEQ ID NO: 143          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 143
GSDGVGKSI                                                            9

SEQ ID NO: 144          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 144
AWDVGKSAF                                                            9

SEQ ID NO: 145          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 145
GAGDVGKSY                                                            9

SEQ ID NO: 146          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 146
GSDGVGKSF                                                            9

SEQ ID NO: 147          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 147
GTDGVGKSF                                                            9

SEQ ID NO: 148          moltype = AA   length = 9
FEATURE                 Location/Qualifiers
source                  1..9
```

```
                                organism = synthetic construct
                                mol_type = protein
                                note = Seed: AGDVGKSAL (KRAS G13D)
SEQUENCE: 148
AMDVGKSAM                                                                       9

SEQ ID NO: 149                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 149
GVDGVGKSI                                                                       9

SEQ ID NO: 150                  moltype = AA  length = 9
FEATURE                         Location/Qualifiers
source                          1..9
                                organism = synthetic construct
                                mol_type = protein
                                note = Seed: AGDVGKSAL (KRAS G13D)
SEQUENCE: 150
ALDVGKSAV                                                                       9

SEQ ID NO: 151                  moltype = AA  length = 9
FEATURE                         Location/Qualifiers
source                          1..9
                                organism = synthetic construct
                                mol_type = protein
                                note = Seed: AGDVGKSAL (KRAS G13D)
SEQUENCE: 151
AYDVGKSAI                                                                       9

SEQ ID NO: 152                  moltype = AA  length = 9
FEATURE                         Location/Qualifiers
source                          1..9
                                organism = synthetic construct
                                mol_type = protein
                                note = Seed: GAVGVGKSA (KRAS G12V)
SEQUENCE: 152
GAVGVGKSF                                                                       9

SEQ ID NO: 153                  moltype = AA  length = 9
FEATURE                         Location/Qualifiers
source                          1..9
                                organism = synthetic construct
                                mol_type = protein
                                note = Seed: AGDVGKSAL (KRAS G13D)
SEQUENCE: 153
ALDVGKSAI                                                                       9

SEQ ID NO: 154                  moltype = AA  length = 9
FEATURE                         Location/Qualifiers
source                          1..9
                                organism = synthetic construct
                                mol_type = protein
                                note = Seed: LVVVGADGV (KRAS G12D)
SEQUENCE: 154
LLVVGADGL                                                                       9

SEQ ID NO: 155                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 155
GIDGVGKSF                                                                       9

SEQ ID NO: 156                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 156
GMDGVGKSM                                                                       9

SEQ ID NO: 157                  moltype = AA  length = 9
```

| | | |
|---|---|---|
| FEATURE | Location/Qualifiers | |
| source | 1..9 | |
| | organism = synthetic construct | |
| | mol_type = protein | |
| | note = Seed: GADGVGKSA (KRAS G12D) | |
| SEQUENCE: 157 | | |
| GIDGVGKSI | | 9 |
| | | |
| SEQ ID NO: 158 | moltype = AA  length = 9 | |
| FEATURE | Location/Qualifiers | |
| source | 1..9 | |
| | organism = synthetic construct | |
| | mol_type = protein | |
| | note = Seed: GADGVGKSA (KRAS G12D) | |
| SEQUENCE: 158 | | |
| GVDGVGKSF | | 9 |
| | | |
| SEQ ID NO: 159 | moltype = AA  length = 9 | |
| FEATURE | Location/Qualifiers | |
| source | 1..9 | |
| | organism = synthetic construct | |
| | mol_type = protein | |
| | note = Seed: GADGVGKSA (KRAS G12D) | |
| SEQUENCE: 159 | | |
| GIDGVGKSV | | 9 |
| | | |
| SEQ ID NO: 160 | moltype = AA  length = 9 | |
| FEATURE | Location/Qualifiers | |
| source | 1..9 | |
| | organism = synthetic construct | |
| | mol_type = protein | |
| | note = Seed: GADGVGKSA (KRAS G12D) | |
| SEQUENCE: 160 | | |
| GVDGVGKSV | | 9 |
| | | |
| SEQ ID NO: 161 | moltype = AA  length = 9 | |
| FEATURE | Location/Qualifiers | |
| source | 1..9 | |
| | organism = synthetic construct | |
| | mol_type = protein | |
| | note = Seed: GAGDVGKSA (KRAS G13D) | |
| SEQUENCE: 161 | | |
| GAGDVGKSL | | 9 |
| | | |
| SEQ ID NO: 162 | moltype = AA  length = 9 | |
| FEATURE | Location/Qualifiers | |
| source | 1..9 | |
| | organism = synthetic construct | |
| | mol_type = protein | |
| | note = Seed: LVVVGADGV (KRAS G12D) | |
| SEQUENCE: 162 | | |
| LIVVGADGV | | 9 |
| | | |
| SEQ ID NO: 163 | moltype = AA  length = 9 | |
| FEATURE | Location/Qualifiers | |
| source | 1..9 | |
| | organism = synthetic construct | |
| | mol_type = protein | |
| | note = Seed: VVGAVGVGK (KRAS G12V) | |
| SEQUENCE: 163 | | |
| VAGAVGVGY | | 9 |
| | | |
| SEQ ID NO: 164 | moltype = AA  length = 9 | |
| FEATURE | Location/Qualifiers | |
| source | 1..9 | |
| | organism = synthetic construct | |
| | mol_type = protein | |
| | note = Seed: AGDVGKSAL (KRAS G13D) | |
| SEQUENCE: 164 | | |
| AYDVGKSAV | | 9 |
| | | |
| SEQ ID NO: 165 | moltype = AA  length = 9 | |
| FEATURE | Location/Qualifiers | |
| source | 1..9 | |
| | organism = synthetic construct | |
| | mol_type = protein | |
| | note = Seed: GARGVGKSA (KRAS G12R) | |
| SEQUENCE: 165 | | |
| GARGVGKSF | | 9 |

| | | |
|---|---|---|
| SEQ ID NO: 166<br>FEATURE<br>source<br><br>SEQUENCE: 166<br>AWDVGKSAI | moltype = AA   length = 9<br>Location/Qualifiers<br>1..9<br>organism = synthetic construct<br>mol_type = protein<br>note = Seed: AGDVGKSAL (KRAS G13D) | <br><br><br><br><br>9 |
| SEQ ID NO: 167<br>FEATURE<br>source<br><br>SEQUENCE: 167<br>GGDGVGKSL | moltype = AA   length = 9<br>Location/Qualifiers<br>1..9<br>organism = synthetic construct<br>mol_type = protein<br>note = Seed: GADGVGKSA (KRAS G12D) | <br><br><br><br><br>9 |
| SEQ ID NO: 168<br>FEATURE<br>source<br><br>SEQUENCE: 168<br>GPRGVGKSF | moltype = AA   length = 9<br>Location/Qualifiers<br>1..9<br>organism = synthetic construct<br>mol_type = protein<br>note = Seed: GARGVGKSA (KRAS G12R) | <br><br><br><br><br>9 |
| SEQ ID NO: 169<br>FEATURE<br>source<br><br>SEQUENCE: 169<br>VAGAVGVGL | moltype = AA   length = 9<br>Location/Qualifiers<br>1..9<br>organism = synthetic construct<br>mol_type = protein<br>note = Seed: VVGAVGVGK (KRAS G12V) | <br><br><br><br><br>9 |
| SEQ ID NO: 170<br>FEATURE<br>source<br><br>SEQUENCE: 170<br>GSVGVGKSY | moltype = AA   length = 9<br>Location/Qualifiers<br>1..9<br>organism = synthetic construct<br>mol_type = protein<br>note = Seed: GAVGVGKSA (KRAS G12V) | <br><br><br><br><br>9 |
| SEQ ID NO: 171<br>FEATURE<br>source<br><br>SEQUENCE: 171<br>GACGVGKSY | moltype = AA   length = 9<br>Location/Qualifiers<br>1..9<br>organism = synthetic construct<br>mol_type = protein<br>note = Seed: GACGVGKSA (KRAS G12C) | <br><br><br><br><br>9 |
| SEQ ID NO: 172<br>FEATURE<br>source<br><br>SEQUENCE: 172<br>AGDVGKSAV | moltype = AA   length = 9<br>Location/Qualifiers<br>1..9<br>organism = synthetic construct<br>mol_type = protein<br>note = Seed: AGDVGKSAL (KRAS G13D) | <br><br><br><br><br>9 |
| SEQ ID NO: 173<br>FEATURE<br>source<br><br>SEQUENCE: 173<br>ALDVGKSAF | moltype = AA   length = 9<br>Location/Qualifiers<br>1..9<br>organism = synthetic construct<br>mol_type = protein<br>note = Seed: AGDVGKSAL (KRAS G13D) | <br><br><br><br><br>9 |
| SEQ ID NO: 174<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |

```
SEQUENCE: 174
AGDVGKSAI                                                                                9

SEQ ID NO: 175          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 175
GAGDVGKSF                                                                                9

SEQ ID NO: 176          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 176
GPCGVGKSA                                                                                9

SEQ ID NO: 177          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 177
DVGKSALTF                                                                                9

SEQ ID NO: 178          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 178
AWDVGKSAV                                                                                9

SEQ ID NO: 179          moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 179
LLVVGAVGA                                                                                9

SEQ ID NO: 180          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 180
GYDGVGKSL                                                                                9

SEQ ID NO: 181          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 181
VAGARGVGL                                                                                9

SEQ ID NO: 182          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 182
GSRGVGKSY                                                                                9

SEQ ID NO: 183          moltype = AA   length = 9
FEATURE                 Location/Qualifiers
source                  1..9
                        organism = synthetic construct
```

```
                                    mol_type = protein
                                    note = Seed: AGDVGKSAL (KRAS G13D)
SEQUENCE: 183
AMDVGKSAV                                                                    9

SEQ ID NO: 184                      moltype = AA   length = 9
FEATURE                             Location/Qualifiers
source                              1..9
                                    organism = synthetic construct
                                    mol_type = protein
                                    note = Seed: AGDVGKSAL (KRAS G13D)
SEQUENCE: 184
AMDVGKSAI                                                                    9

SEQ ID NO: 185                      moltype = AA   length = 9
FEATURE                             Location/Qualifiers
source                              1..9
                                    organism = synthetic construct
                                    mol_type = protein
                                    note = Seed: DVGKSALTI (KRAS G13D)
SEQUENCE: 185
DVGKSALTW                                                                    9

SEQ ID NO: 186                      moltype = AA   length = 9
FEATURE                             Location/Qualifiers
source                              1..9
                                    organism = synthetic construct
                                    mol_type = protein
                                    note = Seed: AGDVGKSAL (KRAS G13D)
SEQUENCE: 186
ANDVGKSAL                                                                    9

SEQ ID NO: 187                      moltype = AA   length = 9
FEATURE                             Location/Qualifiers
source                              1..9
                                    organism = synthetic construct
                                    mol_type = protein
                                    note = Seed: GACGVGKSA (KRAS G12C)
SEQUENCE: 187
GACGVGKSM                                                                    9

SEQ ID NO: 188                      moltype = AA   length = 9
FEATURE                             Location/Qualifiers
source                              1..9
                                    organism = synthetic construct
                                    mol_type = protein
                                    note = Seed: AGDVGKSAL (KRAS G13D)
SEQUENCE: 188
AQDVGKSAL                                                                    9

SEQ ID NO: 189                      moltype = AA   length = 9
FEATURE                             Location/Qualifiers
source                              1..9
                                    organism = synthetic construct
                                    mol_type = protein
                                    note = Seed: GAVGVGKSA (KRAS G12V)
SEQUENCE: 189
GSVGVGKSL                                                                    9

SEQ ID NO: 190                      moltype = AA   length = 9
FEATURE                             Location/Qualifiers
source                              1..9
                                    organism = synthetic construct
                                    mol_type = protein
                                    note = Seed: GADGVGKSA (KRAS G12D)
SEQUENCE: 190
GGDGVGKSM                                                                    9

SEQ ID NO: 191                      moltype = AA   length = 9
FEATURE                             Location/Qualifiers
source                              1..9
                                    organism = synthetic construct
                                    mol_type = protein
                                    note = Seed: AGDVGKSAL (KRAS G13D)
SEQUENCE: 191
AGDVGKSAF                                                                    9

SEQ ID NO: 192                      moltype = AA   length = 9
FEATURE                             Location/Qualifiers
```

```
source                   1..9
                         organism = synthetic construct
                         mol_type = protein
                         note = Seed: GAVGVGKSA (KRAS G12V)
SEQUENCE: 192
GTVGVGKSY                                                                        9

SEQ ID NO: 193           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 193
GLDGVGKSF                                                                        9

SEQ ID NO: 194           moltype = AA   length = 9
FEATURE                  Location/Qualifiers
source                   1..9
                         organism = synthetic construct
                         mol_type = protein
                         note = Seed: LVVVGADGV (KRAS G12D)
SEQUENCE: 194
LQVVGADGV                                                                        9

SEQ ID NO: 195           moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 195
GARGVGKSL                                                                        9

SEQ ID NO: 196           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 196
GSVGVGKSF                                                                        9

SEQ ID NO: 197           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 197
ACDVGKSAL                                                                        9

SEQ ID NO: 198           moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 198
VAGAVGVGM                                                                        9

SEQ ID NO: 199           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 199
AEDVGKSAL                                                                        9

SEQ ID NO: 200           moltype = AA   length = 9
FEATURE                  Location/Qualifiers
source                   1..9
                         organism = synthetic construct
                         mol_type = protein
                         note = Seed: LVVVGADGV (KRAS G12D)
SEQUENCE: 200
LLVVGADGI                                                                        9
```

```
SEQ ID NO: 201         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 201
AEDVGKSAF                                                                  9

SEQ ID NO: 202         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 202
GLDGVGKSV                                                                  9

SEQ ID NO: 203         moltype = AA   length = 9
FEATURE                Location/Qualifiers
source                 1..9
                       organism = synthetic construct
                       mol_type = protein
                       note = Seed: VVGAVGVGK (KRAS G12V)
SEQUENCE: 203
VAGAVGVGR                                                                  9

SEQ ID NO: 204         moltype = AA   length = 9
FEATURE                Location/Qualifiers
source                 1..9
                       organism = synthetic construct
                       mol_type = protein
                       note = Seed: VVGAVGVGK (KRAS G12V)
SEQUENCE: 204
VAGAVGVGF                                                                  9

SEQ ID NO: 205         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 205
GLDGVGKSI                                                                  9

SEQ ID NO: 206         moltype = AA   length = 9
FEATURE                Location/Qualifiers
source                 1..9
                       organism = synthetic construct
                       mol_type = protein
                       note = Seed: VVGACGVGK (KRAS G12C)
SEQUENCE: 206
VTGACGVGR                                                                  9

SEQ ID NO: 207         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 207
AADVGKSAY                                                                  9

SEQ ID NO: 208         moltype = AA   length = 9
FEATURE                Location/Qualifiers
source                 1..9
                       organism = synthetic construct
                       mol_type = protein
                       note = Seed: GARGVGKSA (KRAS G12R)
SEQUENCE: 208
GVRGVGKSY                                                                  9

SEQ ID NO: 209         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 209
```

```
GFDGVGKSL                                                                        9

SEQ ID NO: 210          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 210
GVVGVGKSY                                                                        9

SEQ ID NO: 211          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 211
GSRGVGKSF                                                                        9

SEQ ID NO: 212          moltype = AA  length = 9
FEATURE                 Location/Qualifiers
source                  1..9
                        organism = synthetic construct
                        mol_type = protein
                        note = Seed: LVVVGARGV (KRAS G12R)
SEQUENCE: 212
LMVVGARGI                                                                        9

SEQ ID NO: 213          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 213
GACGVGKSF                                                                        9

SEQ ID NO: 214          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 214
GTVGVGKSF                                                                        9

SEQ ID NO: 215          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 215
DAGKSALTI                                                                        9

SEQ ID NO: 216          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 216
AQDVGKSAM                                                                        9

SEQ ID NO: 217          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 217
ANDVGKSAM                                                                        9

SEQ ID NO: 218          moltype = AA  length = 9
FEATURE                 Location/Qualifiers
source                  1..9
                        organism = synthetic construct
                        mol_type = protein
```

```
                        note = Seed: AGDVGKSAL (KRAS G13D)
SEQUENCE: 218
AYDVGKSAY                                                              9

SEQ ID NO: 219          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 219
GTRGVGKSY                                                              9

SEQ ID NO: 220          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 220
GPGDVGKSA                                                              9

SEQ ID NO: 221          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 221
GMDGVGKSV                                                              9

SEQ ID NO: 222          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 222
GVRGVGKSF                                                              9

SEQ ID NO: 223          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 223
VSGAVGVGR                                                              9

SEQ ID NO: 224          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 224
GFDGVGKSM                                                              9

SEQ ID NO: 225          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 225
AMDVGKSAF                                                              9

SEQ ID NO: 226          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 226
GCDGVGKSL                                                              9

SEQ ID NO: 227          moltype = AA  length = 9
FEATURE                 Location/Qualifiers
source                  1..9
```

```
                         organism = synthetic construct
                         mol_type = protein
                         note = Seed: GAGDVGKSA (KRAS G13D)
SEQUENCE: 227
GVGDVGKSY                                                                    9

SEQ ID NO: 228           moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 228
GTRGVGKSF                                                                    9

SEQ ID NO: 229           moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 229
GIRGVGKSY                                                                    9

SEQ ID NO: 230           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 230
GMDGVGKSI                                                                    9

SEQ ID NO: 231           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 231
ACDVGKSAM                                                                    9

SEQ ID NO: 232           moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 232
GSGDVGKSY                                                                    9

SEQ ID NO: 233           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 233
GAVGVGKSV                                                                    9

SEQ ID NO: 234           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 234
GSVGVGKSM                                                                    9

SEQ ID NO: 235           moltype = AA   length = 9
FEATURE                  Location/Qualifiers
source                   1..9
                         organism = synthetic construct
                         mol_type = protein
                         note = Seed: DVGKSALTI (KRAS G13D)
SEQUENCE: 235
DVGKSALTY                                                                    9

SEQ ID NO: 236           moltype = AA   length = 9
```

| | | |
|---|---|---|
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 236 | | |
| GVVGVGKSF | | 9 |
| | | |
| SEQ ID NO: 237 | moltype = AA  length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 237 | | |
| GIVGVGKSY | | 9 |
| | | |
| SEQ ID NO: 238 | moltype = AA  length = 9 | |
| FEATURE | Location/Qualifiers | |
| source | 1..9 | |
| | organism = synthetic construct | |
| | mol_type = protein | |
| | note = Seed: VVGACGVGK (KRAS G12C) | |
| SEQUENCE: 238 | | |
| VAGACGVGY | | 9 |
| | | |
| SEQ ID NO: 239 | moltype = AA  length = 9 | |
| FEATURE | Location/Qualifiers | |
| source | 1..9 | |
| | organism = synthetic construct | |
| | mol_type = protein | |
| | note = Seed: GACGVGKSA (KRAS G12C) | |
| SEQUENCE: 239 | | |
| GSCGVGKSY | | 9 |
| | | |
| SEQ ID NO: 240 | moltype = AA  length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 240 | | |
| GTVGVGKSL | | 9 |
| | | |
| SEQ ID NO: 241 | moltype = AA  length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 241 | | |
| GAVGVGKSH | | 9 |
| | | |
| SEQ ID NO: 242 | moltype = AA  length = 9 | |
| FEATURE | Location/Qualifiers | |
| source | 1..9 | |
| | organism = synthetic construct | |
| | mol_type = protein | |
| | note = Seed: GADGVGKSA (KRAS G12D) | |
| SEQUENCE: 242 | | |
| GMDGVGKSF | | 9 |
| | | |
| SEQ ID NO: 243 | moltype = AA  length = 9 | |
| FEATURE | Location/Qualifiers | |
| source | 1..9 | |
| | organism = synthetic construct | |
| | mol_type = protein | |
| | note = Seed: GADGVGKSA (KRAS G12D) | |
| SEQUENCE: 243 | | |
| GQDGVGKSL | | 9 |
| | | |
| SEQ ID NO: 244 | moltype = AA  length = 9 | |
| FEATURE | Location/Qualifiers | |
| source | 1..9 | |
| | organism = synthetic construct | |
| | mol_type = protein | |
| | note = Seed: GADGVGKSA (KRAS G12D) | |
| SEQUENCE: 244 | | |
| GCDGVGKSM | | 9 |

| | | |
|---|---|---|
| SEQ ID NO: 245<br>FEATURE<br>source | moltype = AA   length = 9<br>Location/Qualifiers<br>1..9<br>organism = synthetic construct<br>mol_type = protein<br>note = Seed: GAGDVGKSA (KRAS G13D) | |
| SEQUENCE: 245<br>GSGDVGKSF | | 9 |
| SEQ ID NO: 246<br>FEATURE<br>source | moltype = AA   length = 9<br>Location/Qualifiers<br>1..9<br>organism = synthetic construct<br>mol_type = protein<br>note = Seed: GAGDVGKSA (KRAS G13D) | |
| SEQUENCE: 246<br>GTGDVGKSY | | 9 |
| SEQ ID NO: 247<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 247<br>GGDGVGKSI | | 9 |
| SEQ ID NO: 248<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 248<br>ACDVGKSAV | | 9 |
| SEQ ID NO: 249<br>FEATURE<br>source | moltype = AA   length = 9<br>Location/Qualifiers<br>1..9<br>organism = synthetic construct<br>mol_type = protein<br>note = Seed: GARGVGKSA (KRAS G12R) | |
| SEQUENCE: 249<br>GSRGVGKSM | | 9 |
| SEQ ID NO: 250<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 250<br>VSGAVGVGK | | 9 |
| SEQ ID NO: 251<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 251<br>GYDGVGKSF | | 9 |
| SEQ ID NO: 252<br>FEATURE<br>source | moltype = AA   length = 9<br>Location/Qualifiers<br>1..9<br>organism = synthetic construct<br>mol_type = protein<br>note = Seed: DVGKSALTI (KRAS G13D) | |
| SEQUENCE: 252<br>DTGKSALTF | | 9 |
| SEQ ID NO: 253<br>FEATURE<br>source | moltype = AA   length = 9<br>Location/Qualifiers<br>1..9<br>organism = synthetic construct<br>mol_type = protein<br>note = Seed: GARGVGKSA (KRAS G12R) | |

```
SEQUENCE: 253
GPRGVGKSP                                                                       9

SEQ ID NO: 254          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 254
GPVGVGKSL                                                                       9

SEQ ID NO: 255          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 255
GGDGVGKSF                                                                       9

SEQ ID NO: 256          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 256
GPCGVGKSV                                                                       9

SEQ ID NO: 257          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 257
GVGDVGKSF                                                                       9

SEQ ID NO: 258          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 258
GIGDVGKSY                                                                       9

SEQ ID NO: 259          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 259
GGVGVGKSY                                                                       9

SEQ ID NO: 260          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 260
GPRGVGKST                                                                       9

SEQ ID NO: 261          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 261
GGDGVGKSV                                                                       9

SEQ ID NO: 262          moltype = AA  length = 9
FEATURE                 Location/Qualifiers
source                  1..9
                        organism = synthetic construct
```

```
                        mol_type = protein
                        note = Seed: AGDVGKSAL (KRAS G13D)
SEQUENCE: 262
ACDVGKSAF                                                                       9

SEQ ID NO: 263          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 263
GAVGVGKSI                                                                       9

SEQ ID NO: 264          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 264
GIRGVGKSF                                                                       9

SEQ ID NO: 265          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 265
GTGDVGKSF                                                                       9

SEQ ID NO: 266          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 266
GNDGVGKSL                                                                       9

SEQ ID NO: 267          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 267
VAGARGVGF                                                                       9

SEQ ID NO: 268          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 268
GVCGVGKSY                                                                       9

SEQ ID NO: 269          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 269
GVRGVGKSM                                                                       9

SEQ ID NO: 270          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 270
VTGARGVGR                                                                       9

SEQ ID NO: 271          moltype = AA   length = 9
FEATURE                 Location/Qualifiers
```

-continued

| | | |
|---|---|---|
| source | 1..9<br>organism = synthetic construct<br>mol_type = protein<br>note = Seed: VVGAVGVGK (KRAS G12V) | |
| SEQUENCE: 271<br>VAGAVGVGK | | 9 |
| SEQ ID NO: 272<br>FEATURE<br>source | moltype = AA   length = 9<br>Location/Qualifiers<br>1..9<br>organism = synthetic construct<br>mol_type = protein<br>note = Seed: VVGADGVGK (KRAS G12D) | |
| SEQUENCE: 272<br>VAGADGVGY | | 9 |
| SEQ ID NO: 273<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 273<br>GQDGVGKSM | | 9 |
| SEQ ID NO: 274<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 274<br>GPVGVGKST | | 9 |
| SEQ ID NO: 275<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 275<br>AEDVGKSAI | | 9 |
| SEQ ID NO: 276<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 276<br>VIGAVGVGK | | 9 |
| SEQ ID NO: 277<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 277<br>GVVGVGKSL | | 9 |
| SEQ ID NO: 278<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 278<br>GVVGVGKSM | | 9 |
| SEQ ID NO: 279<br>FEATURE<br>source | moltype = AA   length = 9<br>Location/Qualifiers<br>1..9<br>organism = synthetic construct<br>mol_type = protein<br>note = Seed: VVGARGVGK (KRAS G12R) | |
| SEQUENCE: 279<br>VAGARGVGY | | 9 |

-continued

```
SEQ ID NO: 280           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 280
GTVGVGKSM                                                                  9

SEQ ID NO: 281           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 281
ACDVGKSAI                                                                  9

SEQ ID NO: 282           moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 282
GPRGVGKSC                                                                  9

SEQ ID NO: 283           moltype = AA   length = 9
FEATURE                  Location/Qualifiers
source                   1..9
                         organism = synthetic construct
                         mol_type = protein
                         note = Seed: LVVVGARGV (KRAS G12R)
SEQUENCE: 283
LLVVGARGI                                                                  9

SEQ ID NO: 284           moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 284
GVRGVGKSL                                                                  9

SEQ ID NO: 285           moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 285
GTCGVGKSY                                                                  9

SEQ ID NO: 286           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 286
GPVGVGKSP                                                                  9

SEQ ID NO: 287           moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 287
VSGAVGVGY                                                                  9

SEQ ID NO: 288           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 288
```

```
GFDGVGKSV                                                                              9

SEQ ID NO: 289          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 289
DIGKSALTW                                                                              9

SEQ ID NO: 290          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 290
GYDGVGKSI                                                                              9

SEQ ID NO: 291          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 291
GARGVGKSV                                                                              9

SEQ ID NO: 292          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 292
GPDGVGKSA                                                                              9

SEQ ID NO: 293          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 293
GGRGVGKSY                                                                              9

SEQ ID NO: 294          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 294
GTRGVGKSM                                                                              9

SEQ ID NO: 295          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 295
GIVGVGKSF                                                                              9

SEQ ID NO: 296          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 296
AEDVGKSAV                                                                              9

SEQ ID NO: 297          moltype = AA  length = 9
FEATURE                 Location/Qualifiers
source                  1..9
                        organism = synthetic construct
                        mol_type = protein
```

```
                        note = Seed: GAVGVGKSA (KRAS G12V)
SEQUENCE: 297
GPVGVGKSI                                                                       9

SEQ ID NO: 298          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 298
ADDVGKSAF                                                                       9

SEQ ID NO: 299          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 299
GSCGVGKSF                                                                       9

SEQ ID NO: 300          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 300
ARDVGKSAL                                                                       9

SEQ ID NO: 301          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 301
GSGDVGKSM                                                                       9

SEQ ID NO: 302          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 302
AQDVGKSAI                                                                       9

SEQ ID NO: 303          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 303
GVGDVGKSM                                                                       9

SEQ ID NO: 304          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 304
GFDGVGKSF                                                                       9

SEQ ID NO: 305          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 305
GSRGVGKSL                                                                       9

SEQ ID NO: 306          moltype = AA   length = 9
FEATURE                 Location/Qualifiers
source                  1..9
```

```
SEQUENCE: 306
ANDVGKSAI                                                                        9
                            organism = synthetic construct
                            mol_type = protein
                            note = Seed: AGDVGKSAL (KRAS G13D)

SEQ ID NO: 307              moltype = AA  length = 9
FEATURE                     Location/Qualifiers
source                      1..9
                            organism = synthetic construct
                            mol_type = protein
                            note = Seed: GAVGVGKSA (KRAS G12V)
SEQUENCE: 307
GPVGVGKSM                                                                        9

SEQ ID NO: 308              moltype = AA  length = 9
FEATURE                     Location/Qualifiers
source                      1..9
                            organism = synthetic construct
                            mol_type = protein
                            note = Seed: GADGVGKSA (KRAS G12D)
SEQUENCE: 308
GNDGVGKSM                                                                        9

SEQ ID NO: 309              moltype = AA  length = 9
FEATURE                     Location/Qualifiers
source                      1..9
                            organism = synthetic construct
                            mol_type = protein
                            note = Seed: VVGAVGVGK (KRAS G12V)
SEQUENCE: 309
VLGAVGVGR                                                                        9

SEQ ID NO: 310              moltype = AA  length = 9
FEATURE                     Location/Qualifiers
source                      1..9
                            organism = synthetic construct
                            mol_type = protein
                            note = Seed: LVVGARGV (KRAS G12R)
SEQUENCE: 310
LMVVGARGL                                                                        9

SEQ ID NO: 311              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 311
ANDVGKSAV                                                                        9

SEQ ID NO: 312              moltype = AA  length = 9
FEATURE                     Location/Qualifiers
source                      1..9
                            organism = synthetic construct
                            mol_type = protein
                            note = Seed: GADGVGKSA (KRAS G12D)
SEQUENCE: 312
GWDGVGKSL                                                                        9

SEQ ID NO: 313              moltype = AA  length = 9
FEATURE                     Location/Qualifiers
source                      1..9
                            organism = synthetic construct
                            mol_type = protein
                            note = Seed: VVGACGVGK (KRAS G12C)
SEQUENCE: 313
VAGACGVGR                                                                        9

SEQ ID NO: 314              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 314
ADDVGKSAL                                                                        9

SEQ ID NO: 315              moltype = AA  length = 9
```

```
FEATURE              Location/Qualifiers
source               1..9
                     organism = synthetic construct
                     mol_type = protein
                     note = Seed: GACGVGKSA (KRAS G12C)
SEQUENCE: 315
GSCGVGKSL                                                                    9

SEQ ID NO: 316       moltype = AA  length = 9
FEATURE              Location/Qualifiers
source               1..9
                     organism = synthetic construct
                     mol_type = protein
                     note = Seed: DVGKSALTI (KRAS G13D)
SEQUENCE: 316
DAGKSALTL                                                                    9

SEQ ID NO: 317       moltype = AA  length = 9
FEATURE              Location/Qualifiers
source               1..9
                     organism = synthetic construct
                     mol_type = protein
                     note = Seed: AGDVGKSAL (KRAS G13D)
SEQUENCE: 317
AQDVGKSAV                                                                    9

SEQ ID NO: 318       moltype = AA  length = 9
FEATURE              Location/Qualifiers
source               1..9
                     organism = synthetic construct
                     mol_type = protein
                     note = Seed: VVGAGDVGK (KRAS G13D)
SEQUENCE: 318
VTGAGDVGR                                                                    9

SEQ ID NO: 319       moltype = AA  length = 9
FEATURE              Location/Qualifiers
source               1..9
                     organism = synthetic construct
                     mol_type = protein
                     note = Seed: VVGADGVGK (KRAS G12D)
SEQUENCE: 319
VTGADGVGR                                                                    9

SEQ ID NO: 320       moltype = AA  length = 9
FEATURE              Location/Qualifiers
source               1..9
                     organism = synthetic construct
                     mol_type = protein
                     note = Seed: VVGAVGVGK (KRAS G12V)
SEQUENCE: 320
VTGAVGVGY                                                                    9

SEQ ID NO: 321       moltype = AA  length = 9
FEATURE              Location/Qualifiers
source               1..9
                     organism = synthetic construct
                     mol_type = protein
                     note = Seed: VVGAVGVGK (KRAS G12V)
SEQUENCE: 321
VVGAVGVGY                                                                    9

SEQ ID NO: 322       moltype = AA  length = 9
FEATURE              Location/Qualifiers
source               1..9
                     organism = synthetic construct
                     mol_type = protein
                     note = Seed: VVGAVGVGK (KRAS G12V)
SEQUENCE: 322
VIGAVGVGR                                                                    9

SEQ ID NO: 323       moltype = AA  length = 9
FEATURE              Location/Qualifiers
source               1..9
                     organism = synthetic construct
                     mol_type = protein
                     note = Seed: GACGVGKSA (KRAS G12C)
SEQUENCE: 323
GICGVGKSY                                                                    9
```

-continued

```
SEQ ID NO: 324          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 324
VVGARGVGR                                                                    9

SEQ ID NO: 325          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 325
GIGDVGKSF                                                                    9

SEQ ID NO: 326          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 326
VMGARGVGR                                                                    9

SEQ ID NO: 327          moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 327
VAGACGVGF                                                                    9

SEQ ID NO: 328          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 328
AQDVGKSAF                                                                    9

SEQ ID NO: 329          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 329
AVDVGKSAY                                                                    9

SEQ ID NO: 330          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 330
VAGAGDVGY                                                                    9

SEQ ID NO: 331          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 331
DPGKSALTV                                                                    9

SEQ ID NO: 332          moltype = AA   length = 9
FEATURE                 Location/Qualifiers
source                  1..9
                        organism = synthetic construct
                        mol_type = protein
                        note = Seed: GADGVGKSA (KRAS G12D)
```

```
SEQUENCE: 332
GCDGVGKSV                                                                   9

SEQ ID NO: 333         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 333
GFDGVGKSI                                                                   9

SEQ ID NO: 334         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 334
GIRGVGKSM                                                                   9

SEQ ID NO: 335         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 335
GCDGVGKSF                                                                   9

SEQ ID NO: 336         moltype = AA  length = 9
FEATURE                Location/Qualifiers
source                 1..9
                       organism = synthetic construct
                       mol_type = protein
                       note = Seed: VVGACGVGK (KRAS G12C)
SEQUENCE: 336
VAGACGVGL                                                                   9

SEQ ID NO: 337         moltype = AA  length = 9
FEATURE                Location/Qualifiers
source                 1..9
                       organism = synthetic construct
                       mol_type = protein
                       note = Seed: LVVVGACGV (KRAS G12C)
SEQUENCE: 337
LVVVGACGI                                                                   9

SEQ ID NO: 338         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 338
ASDVGKSAY                                                                   9

SEQ ID NO: 339         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 339
GYDGVGKSV                                                                   9

SEQ ID NO: 340         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 340
ADDVGKSAM                                                                   9

SEQ ID NO: 341         moltype = AA  length = 9
FEATURE                Location/Qualifiers
source                 1..9
                       organism = synthetic construct
```

```
                                mol_type = protein
                                note = Seed: DVGKSALTI (KRAS G13D)
SEQUENCE: 341
DTGKSALTW                                                                       9

SEQ ID NO: 342                  moltype = AA  length = 9
FEATURE                         Location/Qualifiers
source                          1..9
                                organism = synthetic construct
                                mol_type = protein
                                note = Seed: GACGVGKSA (KRAS G12C)
SEQUENCE: 342
GPCGVGKSL                                                                       9

SEQ ID NO: 343                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 343
GRDGVGKSL                                                                       9

SEQ ID NO: 344                  moltype = AA  length = 9
FEATURE                         Location/Qualifiers
source                          1..9
                                organism = synthetic construct
                                mol_type = protein
                                note = Seed: GACGVGKSA (KRAS G12C)
SEQUENCE: 344
GVCGVGKSF                                                                       9

SEQ ID NO: 345                  moltype = AA  length = 9
FEATURE                         Location/Qualifiers
source                          1..9
                                organism = synthetic construct
                                mol_type = protein
                                note = Seed: GARGVGKSA (KRAS G12R)
SEQUENCE: 345
GLRGVGKSY                                                                       9

SEQ ID NO: 346                  moltype = AA  length = 9
FEATURE                         Location/Qualifiers
source                          1..9
                                organism = synthetic construct
                                mol_type = protein
                                note = Seed: GACGVGKSA (KRAS G12C)
SEQUENCE: 346
GACGVGKSV                                                                       9

SEQ ID NO: 347                  moltype = AA  length = 9
FEATURE                         Location/Qualifiers
source                          1..9
                                organism = synthetic construct
                                mol_type = protein
                                note = Seed: GACGVGKSA (KRAS G12C)
SEQUENCE: 347
GTCGVGKSF                                                                       9

SEQ ID NO: 348                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 348
GSDGVGKSY                                                                       9

SEQ ID NO: 349                  moltype = AA  length = 9
FEATURE                         Location/Qualifiers
source                          1..9
                                organism = synthetic construct
                                mol_type = protein
                                note = Seed: GACGVGKSA (KRAS G12C)
SEQUENCE: 349
GACGVGKSI                                                                       9

SEQ ID NO: 350                  moltype = AA  length = 9
FEATURE                         Location/Qualifiers
```

```
source                  1..9
                        organism = synthetic construct
                        mol_type = protein
                        note = Seed: GAGDVGKSA (KRAS G13D)
SEQUENCE: 350
GTGDVGKSM                                                                         9

SEQ ID NO: 351          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 351
VSGARGVGM                                                                         9

SEQ ID NO: 352          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 352
VTGADGVGK                                                                         9

SEQ ID NO: 353          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 353
VLGAVGVGK                                                                         9

SEQ ID NO: 354          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 354
ARDVGKSAY                                                                         9

SEQ ID NO: 355          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 355
GSGDVGKSL                                                                         9

SEQ ID NO: 356          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 356
VVGAGDVGR                                                                         9

SEQ ID NO: 357          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 357
GPGDVGKSV                                                                         9

SEQ ID NO: 358          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 358
DTGKSALTY                                                                         9
```

| | | |
|---|---|---|
| SEQ ID NO: 359
FEATURE
source | moltype = AA   length = 9
Location/Qualifiers
1..9
organism = synthetic construct
mol_type = protein
note = Seed: AGDVGKSAL (KRAS G13D) | |
| SEQUENCE: 359
ARDVGKSAF | | 9 |
| SEQ ID NO: 360
FEATURE
source | moltype = AA   length = 9
Location/Qualifiers
1..9
organism = synthetic construct
mol_type = protein
note = Seed: GACGVGKSA (KRAS G12C) | |
| SEQUENCE: 360
GSCGVGKSM | | 9 |
| SEQ ID NO: 361
FEATURE
source | moltype = AA   length = 9
Location/Qualifiers
1..9
organism = synthetic construct
mol_type = protein
note = Seed: AGDVGKSAL (KRAS G13D) | |
| SEQUENCE: 361
ATDVGKSAY | | 9 |
| SEQ ID NO: 362
FEATURE
source | moltype = AA   length = 9
Location/Qualifiers
1..9
organism = synthetic construct
mol_type = protein
note = Seed: GARGVGKSA (KRAS G12R) | |
| SEQUENCE: 362
GMRGVGKSY | | 9 |
| SEQ ID NO: 363
FEATURE
source | moltype = AA   length = 9
Location/Qualifiers
1..9
organism = synthetic construct
mol_type = protein
note = Seed: GAGDVGKSA (KRAS G13D) | |
| SEQUENCE: 363
GAGDVGKSH | | 9 |
| SEQ ID NO: 364
FEATURE
source | moltype = AA   length = 9
Location/Qualifiers
1..9
organism = synthetic construct
mol_type = protein
note = Seed: GADGVGKSA (KRAS G12D) | |
| SEQUENCE: 364
GCDGVGKSI | | 9 |
| SEQ ID NO: 365
FEATURE
source | moltype = AA   length = 9
Location/Qualifiers
1..9
organism = synthetic construct
mol_type = protein
note = Seed: GARGVGKSA (KRAS G12R) | |
| SEQUENCE: 365
GARGVGKSI | | 9 |
| SEQ ID NO: 366
FEATURE
source | moltype = AA   length = 9
Location/Qualifiers
1..9
organism = synthetic construct
mol_type = protein
note = Seed: VVGADGVGK (KRAS G12D) | |
| SEQUENCE: 366
VVGADGVGR | | 9 |
| SEQ ID NO: 367
FEATURE
source | moltype = AA   length = 9
Location/Qualifiers
1..9
organism = synthetic construct
mol_type = protein
note = Seed: AGDVGKSAL (KRAS G13D) | |
| SEQUENCE: 367 | | |

```
ANDVGKSAF                                                                    9

SEQ ID NO: 368       moltype = AA  length = 9
FEATURE              Location/Qualifiers
source               1..9
                     organism = synthetic construct
                     mol_type = protein
                     note = Seed: VVGACGVGK (KRAS G12C)
SEQUENCE: 368
VSGACGVGK                                                                    9

SEQ ID NO: 369       moltype = AA  length = 9
FEATURE              Location/Qualifiers
source               1..9
                     organism = synthetic construct
                     mol_type = protein
                     note = Seed: VVGAVGVGK (KRAS G12V)
SEQUENCE: 369
VSGAVGVGF                                                                    9

SEQ ID NO: 370       moltype = AA  length = 9
FEATURE              Location/Qualifiers
source               1..9
                     organism = synthetic construct
                     mol_type = protein
                     note = Seed: GADGVGKSA (KRAS G12D)
SEQUENCE: 370
GWDGVGKSM                                                                    9

SEQ ID NO: 371       moltype = AA  length = 9
FEATURE              Location/Qualifiers
source               1..9
                     organism = synthetic construct
                     mol_type = protein
                     note = Seed: GARGVGKSA (KRAS G12R)
SEQUENCE: 371
GTRGVGKSL                                                                    9

SEQ ID NO: 372       moltype = AA  length = 9
FEATURE              Location/Qualifiers
source               1..9
                     organism = synthetic construct
                     mol_type = protein
                     note = Seed: GAVGVGKSA (KRAS G12V)
SEQUENCE: 372
GIVGVGKSM                                                                    9

SEQ ID NO: 373       moltype = AA  length = 9
FEATURE              Location/Qualifiers
source               1..9
                     organism = synthetic construct
                     mol_type = protein
                     note = Seed: VVGACGVGK (KRAS G12C)
SEQUENCE: 373
VIGACGVGK                                                                    9

SEQ ID NO: 374       moltype = AA  length = 9
FEATURE              Location/Qualifiers
source               1..9
                     organism = synthetic construct
                     mol_type = protein
                     note = Seed: GAGDVGKSA (KRAS G13D)
SEQUENCE: 374
GAGDVGKSV                                                                    9

SEQ ID NO: 375       moltype = AA  length = 9
FEATURE              Location/Qualifiers
source               1..9
                     organism = synthetic construct
                     mol_type = protein
                     note = Seed: GAGDVGKSA (KRAS G13D)
SEQUENCE: 375
GGGDVGKSY                                                                    9

SEQ ID NO: 376       moltype = AA  length = 9
FEATURE              Location/Qualifiers
source               1..9
                     organism = synthetic construct
                     mol_type = protein
```

-continued

```
                        note = Seed: LVVVGACGV (KRAS G12C)
SEQUENCE: 376
LQVVGACGL                                                               9

SEQ ID NO: 377          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 377
GVGDVGKSL                                                               9

SEQ ID NO: 378          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 378
VAGADGVGF                                                               9

SEQ ID NO: 379          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 379
GARGVGKSH                                                               9

SEQ ID NO: 380          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 380
GVDGVGKSY                                                               9

SEQ ID NO: 381          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 381
VAGACGVGM                                                               9

SEQ ID NO: 382          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 382
GPCGVGKSM                                                               9

SEQ ID NO: 383          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 383
VTGADGVGY                                                               9

SEQ ID NO: 384          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 384
AADVGKSAA                                                               9

SEQ ID NO: 385          moltype = AA  length = 9
FEATURE                 Location/Qualifiers
source                  1..9
```

```
                         organism = synthetic construct
                         mol_type = protein
                         note = Seed: GACGVGKSA (KRAS G12C)
SEQUENCE: 385
GGCGVGKSY                                                                 9

SEQ ID NO: 386           moltype = AA  length = 9
FEATURE                  Location/Qualifiers
source                   1..9
                         organism = synthetic construct
                         mol_type = protein
                         note = Seed: GAVGVGKSA (KRAS G12V)
SEQUENCE: 386
GSVGVGKSH                                                                 9

SEQ ID NO: 387           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 387
AADVGKSAC                                                                 9

SEQ ID NO: 388           moltype = AA  length = 9
FEATURE                  Location/Qualifiers
source                   1..9
                         organism = synthetic construct
                         mol_type = protein
                         note = Seed: DVGKSALTI (KRAS G13D)
SEQUENCE: 388
DIGKSALTF                                                                 9

SEQ ID NO: 389           moltype = AA  length = 9
FEATURE                  Location/Qualifiers
source                   1..9
                         organism = synthetic construct
                         mol_type = protein
                         note = Seed: VVGAVGVGK (KRAS G12V)
SEQUENCE: 389
VAGAVGVGH                                                                 9

SEQ ID NO: 390           moltype = AA  length = 9
FEATURE                  Location/Qualifiers
source                   1..9
                         organism = synthetic construct
                         mol_type = protein
                         note = Seed: GARGVGKSA (KRAS G12R)
SEQUENCE: 390
GQRGVGKSY                                                                 9

SEQ ID NO: 391           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 391
AFDVGKSAY                                                                 9

SEQ ID NO: 392           moltype = AA  length = 9
FEATURE                  Location/Qualifiers
source                   1..9
                         organism = synthetic construct
                         mol_type = protein
                         note = Seed: VVGARGVGK (KRAS G12R)
SEQUENCE: 392
VSGARGVGL                                                                 9

SEQ ID NO: 393           moltype = AA  length = 9
FEATURE                  Location/Qualifiers
source                   1..9
                         organism = synthetic construct
                         mol_type = protein
                         note = Seed: GACGVGKSA (KRAS G12C)
SEQUENCE: 393
GPCGVGKSI                                                                 9

SEQ ID NO: 394           moltype = AA  length = 9
```

| FEATURE | Location/Qualifiers |
|---|---|
| source | 1..9<br>organism = synthetic construct<br>mol_type = protein<br>note = Seed: GAVGVGKSA (KRAS G12V) |

SEQUENCE: 394
GQVGVGKSY                                                          9

| SEQ ID NO: 395 | moltype = AA  length = 9 |
|---|---|
| FEATURE | Location/Qualifiers |
| source | 1..9<br>organism = synthetic construct<br>mol_type = protein<br>note = Seed: VVGACGVGK (KRAS G12C) |

SEQUENCE: 395
VTGACGVGY                                                          9

| SEQ ID NO: 396 | moltype = AA  length = 9 |
|---|---|
| FEATURE | Location/Qualifiers |
| source | 1..9<br>organism = synthetic construct<br>mol_type = protein<br>note = Seed: GACGVGKSA (KRAS G12C) |

SEQUENCE: 396
GPCGVGKSP                                                          9

| SEQ ID NO: 397 | moltype = AA  length = 9 |
|---|---|
| FEATURE | Location/Qualifiers |
| source | 1..9<br>organism = synthetic construct<br>mol_type = protein<br>note = Seed: VVGACGVGK (KRAS G12C) |

SEQUENCE: 397
VSGACGVGR                                                          9

| SEQ ID NO: 398 | moltype = AA  length = 9 |
|---|---|
| FEATURE | Location/Qualifiers |
| source | 1..9<br>organism = synthetic construct<br>mol_type = protein<br>note = Seed: GAGDVGKSA (KRAS G13D) |

SEQUENCE: 398
GIGDVGKSM                                                          9

| SEQ ID NO: 399 | moltype = AA  length = 9 |
|---|---|
| FEATURE | Location/Qualifiers |
| source | 1..9<br>organism = synthetic construct<br>mol_type = protein<br>note = Seed: LVVVGAVGV (KRAS G12V) |

SEQUENCE: 399
LMVVGAVGM                                                          9

| SEQ ID NO: 400 | moltype = AA  length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 400
ARDVGKSAM                                                          9

| SEQ ID NO: 401 | moltype = AA  length = 9 |
|---|---|
| FEATURE | Location/Qualifiers |
| source | 1..9<br>organism = synthetic construct<br>mol_type = protein<br>note = Seed: LVVVGAVGV (KRAS G12V) |

SEQUENCE: 401
LQVVGAVGL                                                          9

| SEQ ID NO: 402 | moltype = AA  length = 9 |
|---|---|
| FEATURE | Location/Qualifiers |
| source | 1..9<br>organism = synthetic construct<br>mol_type = protein<br>note = Seed: GACGVGKSA (KRAS G12C) |

SEQUENCE: 402
GACGVGKSH                                                          9

| | | |
|---|---|---|
| SEQ ID NO: 403<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |
| SEQUENCE: 403<br>GVCGVGKSM | | 9 |
| SEQ ID NO: 404<br>FEATURE<br>source | moltype = AA   length = 9<br>Location/Qualifiers<br>1..9<br>organism = synthetic construct<br>mol_type = protein<br>note = Seed: LVVVGARGV (KRAS G12R) | |
| SEQUENCE: 404<br>LLVVGARGL | | 9 |
| SEQ ID NO: 405<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |
| SEQUENCE: 405<br>GTCGVGKSL | | 9 |
| SEQ ID NO: 406<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 406<br>AFDVGKSAC | | 9 |
| SEQ ID NO: 407<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 407<br>GLVGVGKSY | | 9 |
| SEQ ID NO: 408<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 408<br>GMVGVGKSY | | 9 |
| SEQ ID NO: 409<br>FEATURE<br>source | moltype = AA   length = 9<br>Location/Qualifiers<br>1..9<br>organism = synthetic construct<br>mol_type = protein<br>note = Seed: VVGARGVGK (KRAS G12R) | |
| SEQUENCE: 409<br>VSGARGVGF | | 9 |
| SEQ ID NO: 410<br>FEATURE<br>source | moltype = AA   length = 9<br>Location/Qualifiers<br>1..9<br>organism = synthetic construct<br>mol_type = protein<br>note = Seed: VVGACGVGK (KRAS G12C) | |
| SEQUENCE: 410<br>VLGACGVGK | | 9 |
| SEQ ID NO: 411<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |

| | | |
|---|---|---|
| SEQUENCE: 411 GTCGVGKSM | | 9 |
| SEQ ID NO: 412 FEATURE source | moltype = AA  length = 9 Location/Qualifiers 1..9 organism = synthetic construct mol_type = protein note = Seed: GADGVGKSA (KRAS G12D) | |
| SEQUENCE: 412 GTDGVGKSY | | 9 |
| SEQ ID NO: 413 FEATURE source | moltype = AA  length = 9 Location/Qualifiers 1..9 organism = synthetic construct mol_type = protein note = Seed: GAVGVGKSA (KRAS G12V) | |
| SEQUENCE: 413 GGVGVGKSF | | 9 |
| SEQ ID NO: 414 FEATURE source | moltype = AA  length = 9 Location/Qualifiers 1..9 organism = synthetic construct mol_type = protein note = Seed: GAGDVGKSA (KRAS G13D) | |
| SEQUENCE: 414 GTGDVGKSL | | 9 |
| SEQ ID NO: 415 FEATURE source | moltype = AA  length = 9 Location/Qualifiers 1..9 organism = synthetic construct mol_type = protein note = Seed: LVVVGACGV (KRAS G12C) | |
| SEQUENCE: 415 LIVVGACGI | | 9 |
| SEQ ID NO: 416 FEATURE source | moltype = AA  length = 9 Location/Qualifiers 1..9 organism = synthetic construct mol_type = protein note = Seed: VVGARGVGK (KRAS G12R) | |
| SEQUENCE: 416 VLGARGVGK | | 9 |
| SEQ ID NO: 417 FEATURE source | moltype = AA  length = 9 Location/Qualifiers 1..9 organism = synthetic construct mol_type = protein note = Seed: LVVVGARGV (KRAS G12R) | |
| SEQUENCE: 417 LMVVGARGA | | 9 |
| SEQ ID NO: 418 FEATURE source | moltype = AA  length = 9 Location/Qualifiers 1..9 organism = synthetic construct mol_type = protein note = Seed: GACGVGKSA (KRAS G12C) | |
| SEQUENCE: 418 GPCGVGKST | | 9 |
| SEQ ID NO: 419 FEATURE source | moltype = AA  length = 9 Location/Qualifiers 1..9 organism = synthetic construct mol_type = protein note = Seed: VVGAVGVGK (KRAS G12V) | |
| SEQUENCE: 419 VIGAVGVGY | | 9 |
| SEQ ID NO: 420 FEATURE source | moltype = AA  length = 9 Location/Qualifiers 1..9 organism = synthetic construct | |

```
                            mol_type = protein
                            note = Seed: GARGVGKSA (KRAS G12R)
SEQUENCE: 420
GPRGVGKSS                                                               9

SEQ ID NO: 421              moltype = AA  length = 9
FEATURE                     Location/Qualifiers
source                      1..9
                            organism = synthetic construct
                            mol_type = protein
                            note = Seed: LVVVGACGV (KRAS G12C)
SEQUENCE: 421
LAVVGACGV                                                               9

SEQ ID NO: 422              moltype = AA  length = 9
FEATURE                     Location/Qualifiers
source                      1..9
                            organism = synthetic construct
                            mol_type = protein
                            note = Seed: GARGVGKSA (KRAS G12R)
SEQUENCE: 422
GIRGVGKSL                                                               9

SEQ ID NO: 423              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 423
AYDVGKSAC                                                               9

SEQ ID NO: 424              moltype = AA  length = 9
FEATURE                     Location/Qualifiers
source                      1..9
                            organism = synthetic construct
                            mol_type = protein
                            note = Seed: LVVVGADGV (KRAS G12D)
SEQUENCE: 424
LMVVGADGA                                                               9

SEQ ID NO: 425              moltype = AA  length = 9
FEATURE                     Location/Qualifiers
source                      1..9
                            organism = synthetic construct
                            mol_type = protein
                            note = Seed: DVGKSALTI (KRAS G13D)
SEQUENCE: 425
DPGKSALTI                                                               9

SEQ ID NO: 426              moltype = AA  length = 9
FEATURE                     Location/Qualifiers
source                      1..9
                            organism = synthetic construct
                            mol_type = protein
                            note = Seed: VVGAGDVGK (KRAS G13D)
SEQUENCE: 426
VTGAGDVGK                                                               9

SEQ ID NO: 427              moltype = AA  length = 9
FEATURE                     Location/Qualifiers
source                      1..9
                            organism = synthetic construct
                            mol_type = protein
                            note = Seed: VVGACGVGK (KRAS G12C)
SEQUENCE: 427
VAGACGVGK                                                               9

SEQ ID NO: 428              moltype = AA  length = 9
FEATURE                     Location/Qualifiers
source                      1..9
                            organism = synthetic construct
                            mol_type = protein
                            note = Seed: GADGVGKSA (KRAS G12D)
SEQUENCE: 428
GADGVGKSC                                                               9

SEQ ID NO: 429              moltype = AA  length = 9
FEATURE                     Location/Qualifiers
```

```
                                    -continued source                   1..9
                         organism = synthetic construct
                         mol_type = protein
                         note = Seed: GACGVGKSA (KRAS G12C)
SEQUENCE: 429
GICGVGKSF                                                                9

SEQ ID NO: 430           moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 430
VVGAVGVGF                                                                9

SEQ ID NO: 431           moltype = AA   length = 9
FEATURE                  Location/Qualifiers
source                   1..9
                         organism = synthetic construct
                         mol_type = protein
                         note = Seed: VVGADGVGK (KRAS G12D)
SEQUENCE: 431
VAGADGVGL                                                                9

SEQ ID NO: 432           moltype = AA   length = 9
FEATURE                  Location/Qualifiers
source                   1..9
                         organism = synthetic construct
                         mol_type = protein
                         note = Seed: VVGARGVGK (KRAS G12R)
SEQUENCE: 432
VSGARGVGY                                                                9

SEQ ID NO: 433           moltype = AA   length = 9
FEATURE                  Location/Qualifiers
source                   1..9
                         organism = synthetic construct
                         mol_type = protein
                         note = Seed: LVVVGACGV (KRAS G12C)
SEQUENCE: 433
LVVVGACGL                                                                9

SEQ ID NO: 434           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 434
AHDVGKSAL                                                                9

SEQ ID NO: 435           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 435
GRDGVGKSM                                                                9

SEQ ID NO: 436           moltype = AA   length = 9
FEATURE                  Location/Qualifiers
source                   1..9
                         organism = synthetic construct
                         mol_type = protein
                         note = Seed: VVGAGDVGK (KRAS G13D)
SEQUENCE: 436
VTGAGDVGY                                                                9

SEQ ID NO: 437           moltype = AA   length = 9
FEATURE                  Location/Qualifiers
source                   1..9
                         organism = synthetic construct
                         mol_type = protein
                         note = Seed: LVVVGACGV (KRAS G12C)
SEQUENCE: 437
LTVVGACGI                                                                9
```

| | | |
|---|---|---|
| SEQ ID NO: 438<br>FEATURE<br>source | moltype = AA   length = 9<br>Location/Qualifiers<br>1..9<br>organism = synthetic construct<br>mol_type = protein<br>note = Seed: VVGARGVGK (KRAS G12R) | |
| SEQUENCE: 438<br>VTGARGVGM | | 9 |
| SEQ ID NO: 439<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 439<br>APDVGKSAL | | 9 |
| SEQ ID NO: 440<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |
| SEQUENCE: 440<br>GVCGVGKSL | | 9 |
| SEQ ID NO: 441<br>FEATURE<br>source | moltype = AA   length = 9<br>Location/Qualifiers<br>1..9<br>organism = synthetic construct<br>mol_type = protein<br>note = Seed: VVGAGDVGK (KRAS G13D) | |
| SEQUENCE: 441<br>VAGAGDVGF | | 9 |
| SEQ ID NO: 442<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 442<br>GIVGVGKSL | | 9 |
| SEQ ID NO: 443<br>FEATURE<br>source | moltype = AA   length = 9<br>Location/Qualifiers<br>1..9<br>organism = synthetic construct<br>mol_type = protein<br>note = Seed: VVGAGDVGK (KRAS G13D) | |
| SEQUENCE: 443<br>VAGAGDVGL | | 9 |
| SEQ ID NO: 444<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 444<br>AIDVGKSAY | | 9 |
| SEQ ID NO: 445<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 445<br>GPVGVGKSC | | 9 |
| SEQ ID NO: 446<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 446 | | |

```
GHDGVGKSL                                                                    9

SEQ ID NO: 447         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 447
GPVGVGKSS                                                                    9

SEQ ID NO: 448         moltype = AA  length = 9
FEATURE                Location/Qualifiers
source                 1..9
                       organism = synthetic construct
                       mol_type = protein
                       note = Seed: VVGARGVGK (KRAS G12R)
SEQUENCE: 448
VTGARGVGL                                                                    9

SEQ ID NO: 449         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 449
GQDGVGKSF                                                                    9

SEQ ID NO: 450         moltype = AA  length = 9
FEATURE                Location/Qualifiers
source                 1..9
                       organism = synthetic construct
                       mol_type = protein
                       note = Seed: VVGACGVGK (KRAS G12C)
SEQUENCE: 450
VLGACGVGR                                                                    9

SEQ ID NO: 451         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 451
AHDVGKSAM                                                                    9

SEQ ID NO: 452         moltype = AA  length = 9
FEATURE                Location/Qualifiers
source                 1..9
                       organism = synthetic construct
                       mol_type = protein
                       note = Seed: LVVVGACGV (KRAS G12C)
SEQUENCE: 452
LQVVGACGI                                                                    9

SEQ ID NO: 453         moltype = AA  length = 9
FEATURE                Location/Qualifiers
source                 1..9
                       organism = synthetic construct
                       mol_type = protein
                       note = Seed: VVGARGVGK (KRAS G12R)
SEQUENCE: 453
VTGARGVGF                                                                    9

SEQ ID NO: 454         moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 454
GAGDVGKSI                                                                    9

SEQ ID NO: 455         moltype = AA  length = 9
FEATURE                Location/Qualifiers
source                 1..9
                       organism = synthetic construct
                       mol_type = protein
```

```
                        note = Seed: VVGADGVGK (KRAS G12D)
SEQUENCE: 455
VAGADGVGM                                                              9

SEQ ID NO: 456          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 456
GQGDVGKSY                                                              9

SEQ ID NO: 457          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 457
VAGARGVGK                                                              9

SEQ ID NO: 458          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 458
GLGDVGKSY                                                              9

SEQ ID NO: 459          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 459
VLGARGVGR                                                              9

SEQ ID NO: 460          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 460
GGVGVGKSM                                                              9

SEQ ID NO: 461          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 461
GQDGVGKSV                                                              9

SEQ ID NO: 462          moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 462
LQVVGAVGI                                                              9

SEQ ID NO: 463          moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 463
LVVVGAVGI                                                              9

SEQ ID NO: 464          moltype = AA   length = 9
FEATURE                 Location/Qualifiers
source                  1..9
```

```
                        organism = synthetic construct
                        mol_type = protein
                        note = Seed: VVGAVGVGK (KRAS G12V)
SEQUENCE: 464
VTGAVGVGF                                                                9

SEQ ID NO: 465          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 465
GGRGVGKSF                                                                9

SEQ ID NO: 466          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 466
GLRGVGKSF                                                                9

SEQ ID NO: 467          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 467
GMGDVGKSY                                                                9

SEQ ID NO: 468          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 468
GQDGVGKSI                                                                9

SEQ ID NO: 469          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 469
VSGAVGVGM                                                                9

SEQ ID NO: 470          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 470
GPVGVGKSF                                                                9

SEQ ID NO: 471          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 471
DQGKSALTV                                                                9

SEQ ID NO: 472          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 472
VSGARGVGK                                                                9

SEQ ID NO: 473          moltype = AA   length = 9
```

-continued

| FEATURE | Location/Qualifiers |
|---|---|
| source | 1..9<br>organism = synthetic construct<br>mol_type = protein<br>note = Seed: GADGVGKSA (KRAS G12D) |

SEQUENCE: 473
GPDGVGKSL                                                                9

SEQ ID NO: 474    moltype = AA  length = 9
FEATURE           Location/Qualifiers
source            1..9
                  organism = synthetic construct
                  mol_type = protein
                  note = Seed: VVGARGVGK (KRAS G12R)
SEQUENCE: 474
VAGARGVGR                                                                9

SEQ ID NO: 475    moltype = AA  length = 9
FEATURE           Location/Qualifiers
source            1..9
                  organism = synthetic construct
                  mol_type = protein
                  note = Seed: GADGVGKSA (KRAS G12D)
SEQUENCE: 475
GPDGVGKSV                                                                9

SEQ ID NO: 476    moltype = AA  length = 9
FEATURE           Location/Qualifiers
source            1..9
                  organism = synthetic construct
                  mol_type = protein
                  note = Seed: GADGVGKSA (KRAS G12D)
SEQUENCE: 476
GWDGVGKSF                                                                9

SEQ ID NO: 477    moltype = AA  length = 9
FEATURE           Location/Qualifiers
source            1..9
                  organism = synthetic construct
                  mol_type = protein
                  note = Seed: GAVGVGKSA (KRAS G12V)
SEQUENCE: 477
GVVGVGKSH                                                                9

SEQ ID NO: 478    moltype = AA  length = 9
FEATURE           Location/Qualifiers
source            1..9
                  organism = synthetic construct
                  mol_type = protein
                  note = Seed: VVGARGVGK (KRAS G12R)
SEQUENCE: 478
VIGARGVGK                                                                9

SEQ ID NO: 479    moltype = AA  length = 9
FEATURE           Location/Qualifiers
source            1..9
                  organism = synthetic construct
                  mol_type = protein
                  note = Seed: DVGKSALTI (KRAS G13D)
SEQUENCE: 479
DSGKSALTV                                                                9

SEQ ID NO: 480    moltype = AA  length = 9
FEATURE           Location/Qualifiers
source            1..9
                  organism = synthetic construct
                  mol_type = protein
                  note = Seed: DVGKSALTI (KRAS G13D)
SEQUENCE: 480
DAGKSALTF                                                                9

SEQ ID NO: 481    moltype = AA  length = 9
FEATURE           Location/Qualifiers
source            1..9
                  organism = synthetic construct
                  mol_type = protein
                  note = Seed: GADGVGKSA (KRAS G12D)
SEQUENCE: 481
GNDGVGKSF                                                                9

| | | |
|---|---|---|
| SEQ ID NO: 482<br>FEATURE<br>source<br><br>SEQUENCE: 482<br>GHDGVGKSM | moltype = AA  length = 9<br>Location/Qualifiers<br>1..9<br>organism = synthetic construct<br>mol_type = protein<br>note = Seed: GADGVGKSA (KRAS G12D) | 9 |
| SEQ ID NO: 483<br>FEATURE<br>source<br><br>SEQUENCE: 483<br>GICGVGKSM | moltype = AA  length = 9<br>Location/Qualifiers<br>1..9<br>organism = synthetic construct<br>mol_type = protein<br>note = Seed: GACGVGKSA (KRAS G12C) | 9 |
| SEQ ID NO: 484<br>FEATURE<br>source<br><br>SEQUENCE: 484<br>ADDVGKSAI | moltype = AA  length = 9<br>Location/Qualifiers<br>1..9<br>organism = synthetic construct<br>mol_type = protein<br>note = Seed: AGDVGKSAL (KRAS G13D) | 9 |
| SEQ ID NO: 485<br>FEATURE<br>source<br><br>SEQUENCE: 485<br>GMRGVGKSF | moltype = AA  length = 9<br>Location/Qualifiers<br>1..9<br>organism = synthetic construct<br>mol_type = protein<br>note = Seed: GARGVGKSA (KRAS G12R) | 9 |
| SEQ ID NO: 486<br>FEATURE<br>source<br><br>SEQUENCE: 486<br>GPRGVGKSG | moltype = AA  length = 9<br>Location/Qualifiers<br>1..9<br>organism = synthetic construct<br>mol_type = protein<br>note = Seed: GARGVGKSA (KRAS G12R) | 9 |
| SEQ ID NO: 487<br>FEATURE<br>source<br><br>SEQUENCE: 487<br>LAVVGAVGV | moltype = AA  length = 9<br>Location/Qualifiers<br>1..9<br>organism = synthetic construct<br>mol_type = protein<br>note = Seed: LVVVGAVGV (KRAS G12V) | 9 |
| SEQ ID NO: 488<br>FEATURE<br>source<br><br>SEQUENCE: 488<br>ARDVGKSAI | moltype = AA  length = 9<br>Location/Qualifiers<br>1..9<br>organism = synthetic construct<br>mol_type = protein<br>note = Seed: AGDVGKSAL (KRAS G13D) | 9 |
| SEQ ID NO: 489<br>FEATURE<br>source<br><br>SEQUENCE: 489<br>LIVVGACGL | moltype = AA  length = 9<br>Location/Qualifiers<br>1..9<br>organism = synthetic construct<br>mol_type = protein<br>note = Seed: LVVVGACGV (KRAS G12C) | 9 |
| SEQ ID NO: 490<br>FEATURE<br>source | moltype = AA  length = 9<br>Location/Qualifiers<br>1..9<br>organism = synthetic construct<br>mol_type = protein<br>note = Seed: LVVVGAVGV (KRAS G12V) | |

```
SEQUENCE: 490
LLVVGAVGM                                                                        9

SEQ ID NO: 491       moltype = AA  length = 9
FEATURE              Location/Qualifiers
source               1..9
                     organism = synthetic construct
                     mol_type = protein
                     note = Seed: GADGVGKSA (KRAS G12D)
SEQUENCE: 491
GNDGVGKSI                                                                        9

SEQ ID NO: 492       moltype = AA  length = 9
FEATURE              Location/Qualifiers
source               1..9
                     organism = synthetic construct
                     mol_type = protein
                     note = Seed: VVGACGVGK (KRAS G12C)
SEQUENCE: 492
VSGACGVGY                                                                        9

SEQ ID NO: 493       moltype = AA  length = 9
FEATURE              Location/Qualifiers
source               1..9
                     organism = synthetic construct
                     mol_type = protein
                     note = Seed: DVGKSALTI (KRAS G13D)
SEQUENCE: 493
DAGKSALTW                                                                        9

SEQ ID NO: 494       moltype = AA  length = 9
FEATURE              Location/Qualifiers
source               1..9
                     organism = synthetic construct
                     mol_type = protein
                     note = Seed: VVGADGVGK (KRAS G12D)
SEQUENCE: 494
VSGADGVGY                                                                        9

SEQ ID NO: 495       moltype = AA  length = 9
FEATURE              Location/Qualifiers
source               1..9
                     organism = synthetic construct
                     mol_type = protein
                     note = Seed: GAVGVGKSA (KRAS G12V)
SEQUENCE: 495
GTVGVGKSH                                                                        9

SEQ ID NO: 496       moltype = AA  length = 9
FEATURE              Location/Qualifiers
source               1..9
                     organism = synthetic construct
                     mol_type = protein
                     note = Seed: GARGVGKSA (KRAS G12R)
SEQUENCE: 496
GVRGVGKSA                                                                        9

SEQ ID NO: 497       moltype = AA  length = 9
FEATURE              Location/Qualifiers
source               1..9
                     organism = synthetic construct
                     mol_type = protein
                     note = Seed: LVVVGAGDV (KRAS G13D)
SEQUENCE: 497
LMVVGAGDV                                                                        9

SEQ ID NO: 498       moltype = AA  length = 9
FEATURE              Location/Qualifiers
source               1..9
                     organism = synthetic construct
                     mol_type = protein
                     note = Seed: VVGACGVGK (KRAS G12C)
SEQUENCE: 498
VVGACGVGY                                                                        9

SEQ ID NO: 499       moltype = AA  length = 9
FEATURE              Location/Qualifiers
source               1..9
                     organism = synthetic construct
```

```
                        mol_type = protein
                        note = Seed: DVGKSALTI (KRAS G13D)
SEQUENCE: 499
DIGKSALTY                                                               9

SEQ ID NO: 500          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 500
GSVGVGKSV                                                               9

SEQ ID NO: 501          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 501
GNDGVGKSV                                                               9

SEQ ID NO: 502          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 502
GRDGVGKSF                                                               9

SEQ ID NO: 503          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 503
VTGARGVGY                                                               9

SEQ ID NO: 504          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 504
GIGDVGKSL                                                               9

SEQ ID NO: 505          moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 505
LIVVGAVGI                                                               9

SEQ ID NO: 506          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 506
GIDGVGKSY                                                               9

SEQ ID NO: 507          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 507
GTDGVGKSC                                                               9

SEQ ID NO: 508          moltype = AA  length = 9
FEATURE                 Location/Qualifiers
```

```
source                  1..9
                        organism = synthetic construct
                        mol_type = protein
                        note = Seed: GACGVGKSA (KRAS G12C)
SEQUENCE: 508
GQCGVGKSY                                                                           9

SEQ ID NO: 509          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 509
VGGAVGVGY                                                                           9

SEQ ID NO: 510          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 510
AHDVGKSAF                                                                           9

SEQ ID NO: 511          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 511
GMVGVGKSF                                                                           9

SEQ ID NO: 512          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 512
GMCGVGKSY                                                                           9

SEQ ID NO: 513          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 513
AFDVGKSAW                                                                           9

SEQ ID NO: 514          moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 514
LTVVGAVGI                                                                           9

SEQ ID NO: 515          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 515
GLCGVGKSY                                                                           9

SEQ ID NO: 516          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 516
DGGKSALTV                                                                           9
```

```
SEQ ID NO: 517          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 517
GNRGVGKSY                                                                9

SEQ ID NO: 518          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 518
VAGAGDVGR                                                                9

SEQ ID NO: 519          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 519
APDVGKSAM                                                                9

SEQ ID NO: 520          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 520
AHDVGKSAY                                                                9

SEQ ID NO: 521          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 521
VAGAGDVGM                                                                9

SEQ ID NO: 522          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 522
VIGACGVGR                                                                9

SEQ ID NO: 523          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 523
GRDGVGKSI                                                                9

SEQ ID NO: 524          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 524
VSGAVGVGL                                                                9

SEQ ID NO: 525          moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 525
```

```
LVVVGAVGL                                                                    9

SEQ ID NO: 526        moltype = AA   length = 9
FEATURE               Location/Qualifiers
source                1..9
                      organism = synthetic construct
                      mol_type = protein
                      note = Seed: VVGARGVGK (KRAS G12R)
SEQUENCE: 526
VIGARGVGR                                                                    9

SEQ ID NO: 527        moltype = AA   length = 9
FEATURE               Location/Qualifiers
source                1..9
                      organism = synthetic construct
                      mol_type = protein
                      note = Seed: GAGDVGKSA (KRAS G13D)
SEQUENCE: 527
GPGDVGKSL                                                                    9

SEQ ID NO: 528        moltype = AA   length = 9
FEATURE               Location/Qualifiers
source                1..9
                      organism = synthetic construct
                      mol_type = protein
                      note = Seed: GARGVGKSA (KRAS G12R)
SEQUENCE: 528
GSRGVGKSH                                                                    9

SEQ ID NO: 529        moltype = AA   length = 9
FEATURE               Location/Qualifiers
source                1..9
                      organism = synthetic construct
                      mol_type = protein
                      note = Seed: AGDVGKSAL (KRAS G13D)
SEQUENCE: 529
ARDVGKSAV                                                                    9

SEQ ID NO: 530        moltype = AA   length = 9
FEATURE               Location/Qualifiers
source                1..9
                      organism = synthetic construct
                      mol_type = protein
                      note = Seed: GAGDVGKSA (KRAS G13D)
SEQUENCE: 530
GPGDVGKSI                                                                    9

SEQ ID NO: 531        moltype = AA   length = 9
FEATURE               Location/Qualifiers
source                1..9
                      organism = synthetic construct
                      mol_type = protein
                      note = Seed: GAGDVGKSA (KRAS G13D)
SEQUENCE: 531
GPGDVGKSP                                                                    9

SEQ ID NO: 532        moltype = AA   length = 9
FEATURE               Location/Qualifiers
source                1..9
                      organism = synthetic construct
                      mol_type = protein
                      note = Seed: AGDVGKSAL (KRAS G13D)
SEQUENCE: 532
ATDVGKSAC                                                                    9

SEQ ID NO: 533        moltype = AA   length = 9
FEATURE               Location/Qualifiers
source                1..9
                      organism = synthetic construct
                      mol_type = protein
                      note = Seed: VVGAGDVGK (KRAS G13D)
SEQUENCE: 533
VSGAGDVGY                                                                    9

SEQ ID NO: 534        moltype = AA   length = 9
FEATURE               Location/Qualifiers
source                1..9
                      organism = synthetic construct
                      mol_type = protein
```

-continued

| | | |
|---|---|---|
| | note = Seed: VVGADGVGK (KRAS G12D) | |
| SEQUENCE: 534 | | |
| VVGADGVGY | | 9 |
| | | |
| SEQ ID NO: 535 | moltype = AA   length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 535 | | |
| GQVGVGKSF | | 9 |
| | | |
| SEQ ID NO: 536 | moltype = AA   length = 9 | |
| FEATURE | Location/Qualifiers | |
| source | 1..9 | |
| | organism = synthetic construct | |
| | mol_type = protein | |
| | note = Seed: VVGADGVGK (KRAS G12D) | |
| SEQUENCE: 536 | | |
| VAGADGVGK | | 9 |
| | | |
| SEQ ID NO: 537 | moltype = AA   length = 9 | |
| FEATURE | Location/Qualifiers | |
| source | 1..9 | |
| | organism = synthetic construct | |
| | mol_type = protein | |
| | note = Seed: DVGKSALTI (KRAS G13D) | |
| SEQUENCE: 537 | | |
| DVGKSALTV | | 9 |
| | | |
| SEQ ID NO: 538 | moltype = AA   length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 538 | | |
| GNVGVGKSY | | 9 |
| | | |
| SEQ ID NO: 539 | moltype = AA   length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 539 | | |
| GCVGVGKSY | | 9 |
| | | |
| SEQ ID NO: 540 | moltype = AA   length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 540 | | |
| GLVGVGKSF | | 9 |
| | | |
| SEQ ID NO: 541 | moltype = AA   length = 9 | |
| FEATURE | Location/Qualifiers | |
| source | 1..9 | |
| | organism = synthetic construct | |
| | mol_type = protein | |
| | note = Seed: GARGVGKSA (KRAS G12R) | |
| SEQUENCE: 541 | | |
| GQRGVGKSF | | 9 |
| | | |
| SEQ ID NO: 542 | moltype = AA   length = 9 | |
| FEATURE | Location/Qualifiers | |
| source | 1..9 | |
| | organism = synthetic construct | |
| | mol_type = protein | |
| | note = Seed: AGDVGKSAL (KRAS G13D) | |
| SEQUENCE: 542 | | |
| ADDVGKSAV | | 9 |
| | | |
| SEQ ID NO: 543 | moltype = AA   length = 9 | |
| FEATURE | Location/Qualifiers | |
| source | 1..9 | |

```
                            organism = synthetic construct
                            mol_type = protein
                            note = Seed: LVVVGADGV (KRAS G12D)
SEQUENCE: 543
LQVVGADGL                                                                        9

SEQ ID NO: 544              moltype = AA   length = 9
FEATURE                     Location/Qualifiers
source                      1..9
                            organism = synthetic construct
                            mol_type = protein
                            note = Seed: GAGDVGKSA (KRAS G13D)
SEQUENCE: 544
GGGDVGKSF                                                                        9

SEQ ID NO: 545              moltype = AA   length = 9
FEATURE                     Location/Qualifiers
source                      1..9
                            organism = synthetic construct
                            mol_type = protein
                            note = Seed: VVGARGVGK (KRAS G12R)
SEQUENCE: 545
VAGARGVGV                                                                        9

SEQ ID NO: 546              moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 546
GSRGVGKSV                                                                        9

SEQ ID NO: 547              moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 547
GCRGVGKSY                                                                        9

SEQ ID NO: 548              moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 548
GGRGVGKSM                                                                        9

SEQ ID NO: 549              moltype = AA   length = 9
FEATURE                     Location/Qualifiers
source                      1..9
                            organism = synthetic construct
                            mol_type = protein
                            note = Seed: VVGAVGVGK (KRAS G12V)
SEQUENCE: 549
VPGAVGVGR                                                                        9

SEQ ID NO: 550              moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 550
AADVGKSAW                                                                        9

SEQ ID NO: 551              moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 551
ASDVGKSAC                                                                        9

SEQ ID NO: 552              moltype = AA   length = 9
```

-continued

| FEATURE | Location/Qualifiers |
|---|---|
| source | 1..9<br>organism = synthetic construct<br>mol_type = protein<br>note = Seed: LVVVGACGV (KRAS G12C) |

SEQUENCE: 552
LSVVGACGV                                                                        9

| SEQ ID NO: 553<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) |
|---|---|

SEQUENCE: 553
GDDGVGKSL                                                                        9

| SEQ ID NO: 554<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) |
|---|---|

SEQUENCE: 554
GSDGVGKSC                                                                        9

| SEQ ID NO: 555<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) |
|---|---|

SEQUENCE: 555
GRDGVGKSV                                                                        9

| SEQ ID NO: 556<br>FEATURE<br>source | moltype = AA   length = 9<br>Location/Qualifiers<br>1..9<br>organism = synthetic construct<br>mol_type = protein<br>note = Seed: VVGADGVGK (KRAS G12D) |
|---|---|

SEQUENCE: 556
VAGADGVGR                                                                        9

| SEQ ID NO: 557<br>FEATURE<br>source | moltype = AA   length = 9<br>Location/Qualifiers<br>1..9<br>organism = synthetic construct<br>mol_type = protein<br>note = Seed: VVGADGVGK (KRAS G12D) |
|---|---|

SEQUENCE: 557
VMGADGVGK                                                                        9

| SEQ ID NO: 558<br>FEATURE<br>source | moltype = AA   length = 9<br>Location/Qualifiers<br>1..9<br>organism = synthetic construct<br>mol_type = protein<br>note = Seed: GAGDVGKSA (KRAS G13D) |
|---|---|

SEQUENCE: 558
GQGDVGKSF                                                                        9

| SEQ ID NO: 559<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) |
|---|---|

SEQUENCE: 559
AYDVGKSAW                                                                        9

| SEQ ID NO: 560<br>FEATURE<br>source | moltype = AA   length = 9<br>Location/Qualifiers<br>1..9<br>organism = synthetic construct<br>mol_type = protein<br>note = Seed: LVVVGARGV (KRAS G12R) |
|---|---|

SEQUENCE: 560
LQVVGARGV                                                                        9

-continued

```
SEQ ID NO: 561           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 561
ASDVGKSAA                                                                9

SEQ ID NO: 562           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 562
AGDVGKSAY                                                                9

SEQ ID NO: 563           moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 563
VTGAVGVGM                                                                9

SEQ ID NO: 564           moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 564
VVGAVGVGM                                                                9

SEQ ID NO: 565           moltype = AA   length = 9
FEATURE                  Location/Qualifiers
source                   1..9
                         organism = synthetic construct
                         mol_type = protein
                         note = Seed: LVVVGADGV (KRAS G12D)
SEQUENCE: 565
LLVVGADGA                                                                9

SEQ ID NO: 566           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 566
GAVGVGKSK                                                                9

SEQ ID NO: 567           moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 567
GVGDVGKSH                                                                9

SEQ ID NO: 568           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 568
AEDVGKSAY                                                                9

SEQ ID NO: 569           moltype = AA   length = 9
FEATURE                  Location/Qualifiers
source                   1..9
                         organism = synthetic construct
                         mol_type = protein
                         note = Seed: GAGDVGKSA (KRAS G13D)
```

| | | |
|---|---|---|
| SEQUENCE: 569<br>GPGDVGKST | | 9 |
| SEQ ID NO: 570<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 570<br>GPVGVGKSG | | 9 |
| SEQ ID NO: 571<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 571<br>GPDGVGKSM | | 9 |
| SEQ ID NO: 572<br>FEATURE<br>source | moltype = AA   length = 9<br>Location/Qualifiers<br>1..9<br>organism = synthetic construct<br>mol_type = protein<br>note = Seed: LVVVGAVGV (KRAS G12V) | |
| SEQUENCE: 572<br>LIVVGAVGL | | 9 |
| SEQ ID NO: 573<br>FEATURE<br>source | moltype = AA   length = 9<br>Location/Qualifiers<br>1..9<br>organism = synthetic construct<br>mol_type = protein<br>note = Seed: VVGAGDVGK (KRAS G13D) | |
| SEQUENCE: 573<br>VMGAGDVGK | | 9 |
| SEQ ID NO: 574<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |
| SEQUENCE: 574<br>GPCGVGKSF | | 9 |
| SEQ ID NO: 575<br>FEATURE<br>source | moltype = AA   length = 9<br>Location/Qualifiers<br>1..9<br>organism = synthetic construct<br>mol_type = protein<br>note = Seed: DVGKSALTI (KRAS G13D) | |
| SEQUENCE: 575<br>DVGKSALTL | | 9 |
| SEQ ID NO: 576<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 576<br>VTGAVGVGL | | 9 |
| SEQ ID NO: 577<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 577<br>AWDVGKSAC | | 9 |
| SEQ ID NO: 578<br>FEATURE<br>source | moltype = AA   length = 9<br>Location/Qualifiers<br>1..9<br>organism = synthetic construct | |

```
                            mol_type = protein
                            note = Seed: AGDVGKSAL (KRAS G13D)
SEQUENCE: 578
AEDVGKSAW                                                                    9

SEQ ID NO: 579          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 579
DQGKSALTI                                                                    9

SEQ ID NO: 580          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 580
VYGAVGVGR                                                                    9

SEQ ID NO: 581          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 581
GSDGVGKSA                                                                    9

SEQ ID NO: 582          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 582
VGGAVGVGK                                                                    9

SEQ ID NO: 583          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 583
GLGDVGKSF                                                                    9

SEQ ID NO: 584          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 584
GSVGVGKSI                                                                    9

SEQ ID NO: 585          moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 585
LMVVGACGM                                                                    9

SEQ ID NO: 586          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 586
GAVGVGKSW                                                                    9

SEQ ID NO: 587          moltype = AA  length = 9
FEATURE                 Location/Qualifiers
```

```
source                    1..9
                          organism = synthetic construct
                          mol_type = protein
                          note = Seed: GAGDVGKSA (KRAS G13D)
SEQUENCE: 587
GMGDVGKSF                                                                       9

SEQ ID NO: 588            moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 588
AWDVGKSAY                                                                       9

SEQ ID NO: 589            moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 589
GADGVGKSW                                                                       9

SEQ ID NO: 590            moltype = AA   length = 9
FEATURE                   Location/Qualifiers
source                    1..9
                          organism = synthetic construct
                          mol_type = protein
                          note = Seed: VVGAGDVGK (KRAS G13D)
SEQUENCE: 590
VAGAGDVGK                                                                       9

SEQ ID NO: 591            moltype = AA   length = 9
FEATURE                   Location/Qualifiers
source                    1..9
                          organism = synthetic construct
                          mol_type = protein
                          note = Seed: LVVVGAVGV (KRAS G12V)
SEQUENCE: 591
LSVVGAVGV                                                                       9

SEQ ID NO: 592            moltype = AA   length = 9
FEATURE                   Location/Qualifiers
source                    1..9
                          organism = synthetic construct
                          mol_type = protein
                          note = Seed: VVGAVGVGK (KRAS G12V)
SEQUENCE: 592
VIGAVGVGF                                                                       9

SEQ ID NO: 593            moltype = AA   length = 9
FEATURE                   Location/Qualifiers
source                    1..9
                          organism = synthetic construct
                          mol_type = protein
                          note = Seed: VVGARGVGK (KRAS G12R)
SEQUENCE: 593
VAGARGVGI                                                                       9

SEQ ID NO: 594            moltype = AA   length = 9
FEATURE                   Location/Qualifiers
source                    1..9
                          organism = synthetic construct
                          mol_type = protein
                          note = Seed: GARGVGKSA (KRAS G12R)
SEQUENCE: 594
GLRGVGKSM                                                                       9

SEQ ID NO: 595            moltype = AA   length = 9
FEATURE                   Location/Qualifiers
source                    1..9
                          organism = synthetic construct
                          mol_type = protein
                          note = Seed: GAVGVGKSA (KRAS G12V)
SEQUENCE: 595
GIVGVGKSH                                                                       9
```

-continued

| | | |
|---|---|---|
| SEQ ID NO: 596<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 596<br>GMVGVGKSM | | 9 |
| SEQ ID NO: 597<br>FEATURE<br>source | moltype = AA   length = 9<br>Location/Qualifiers<br>1..9<br>organism = synthetic construct<br>mol_type = protein<br>note = Seed: GARGVGKSA (KRAS G12R) | |
| SEQUENCE: 597<br>GSRGVGKSI | | 9 |
| SEQ ID NO: 598<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 598<br>AADVGKSAT | | 9 |
| SEQ ID NO: 599<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |
| SEQUENCE: 599<br>GGCGVGKSF | | 9 |
| SEQ ID NO: 600<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 600<br>GGDGVGKSY | | 9 |
| SEQ ID NO: 601<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 601<br>GAVGVGKSR | | 9 |
| SEQ ID NO: 602<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 602<br>GWDGVGKSI | | 9 |
| SEQ ID NO: 603<br>FEATURE<br>source | moltype = AA   length = 9<br>Location/Qualifiers<br>1..9<br>organism = synthetic construct<br>mol_type = protein<br>note = Seed: DVGKSALTI (KRAS G13D) | |
| SEQUENCE: 603<br>DSGKSALTI | | 9 |
| SEQ ID NO: 604<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 604 | | |

```
AMDVGKSAY                                                                         9

SEQ ID NO: 605          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 605
GICGVGKSL                                                                         9

SEQ ID NO: 606          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 606
GSGDVGKSH                                                                         9

SEQ ID NO: 607          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 607
VSGARGVGR                                                                         9

SEQ ID NO: 608          moltype = AA  length = 9
FEATURE                 Location/Qualifiers
source                  1..9
                        organism = synthetic construct
                        mol_type = protein
                        note = Seed: LVVVGADGV (KRAS G12D)
SEQUENCE: 608
LVVVGADGL                                                                         9

SEQ ID NO: 609          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 609
GHDGVGKSF                                                                         9

SEQ ID NO: 610          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 610
DAGKSALTM                                                                         9

SEQ ID NO: 611          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 611
AQDVGKSAY                                                                         9

SEQ ID NO: 612          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 612
VSGACGVGF                                                                         9

SEQ ID NO: 613          moltype = AA  length = 9
FEATURE                 Location/Qualifiers
source                  1..9
                        organism = synthetic construct
                        mol_type = protein
```

-continued

```
                        note = Seed: GAGDVGKSA (KRAS G13D)
SEQUENCE: 613
GPGDVGKSM                                                               9

SEQ ID NO: 614          moltype = AA   length = 9
FEATURE                 Location/Qualifiers
source                  1..9
                        organism = synthetic construct
                        mol_type = protein
                        note = Seed: LVVVGAGDV (KRAS G13D)
SEQUENCE: 614
LLVVGAGDV                                                               9

SEQ ID NO: 615          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 615
AADVGKSAH                                                               9

SEQ ID NO: 616          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 616
VGGAVGVGR                                                               9

SEQ ID NO: 617          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 617
GWDGVGKSV                                                               9

SEQ ID NO: 618          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 618
GMRGVGKSM                                                               9

SEQ ID NO: 619          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 619
VSGAGDVGR                                                               9

SEQ ID NO: 620          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 620
GQVGVGKSM                                                               9

SEQ ID NO: 621          moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 621
VMGADGVGR                                                               9

SEQ ID NO: 622          moltype = AA   length = 9
FEATURE                 Location/Qualifiers
source                  1..9
```

```
                          -continued organism = synthetic construct
                          mol_type = protein
                          note = Seed: GAVGVGKSA (KRAS G12V)
SEQUENCE: 622
GVVGVGKSK                                                              9

SEQ ID NO: 623            moltype = AA  length = 9
FEATURE                   Location/Qualifiers
source                    1..9
                          organism = synthetic construct
                          mol_type = protein
                          note = Seed: VVGADGVGK (KRAS G12D)
SEQUENCE: 623
VIGADGVGK                                                              9

SEQ ID NO: 624            moltype = AA  length = 9
FEATURE                   Location/Qualifiers
source                    1..9
                          organism = synthetic construct
                          mol_type = protein
                          note = Seed: GAVGVGKSA (KRAS G12V)
SEQUENCE: 624
GGVGVGKSL                                                              9

SEQ ID NO: 625            moltype = AA  length = 9
FEATURE                   Location/Qualifiers
source                    1..9
                          organism = synthetic construct
                          mol_type = protein
                          note = Seed: GAGDVGKSA (KRAS G13D)
SEQUENCE: 625
GNGDVGKSY                                                              9

SEQ ID NO: 626            moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 626
GADGVGKST                                                              9

SEQ ID NO: 627            moltype = AA  length = 9
FEATURE                   Location/Qualifiers
source                    1..9
                          organism = synthetic construct
                          mol_type = protein
                          note = Seed: AGDVGKSAL (KRAS G13D)
SEQUENCE: 627
AFDVGKSAA                                                              9

SEQ ID NO: 628            moltype = AA  length = 9
FEATURE                   Location/Qualifiers
source                    1..9
                          organism = synthetic construct
                          mol_type = protein
                          note = Seed: DVGKSALTI (KRAS G13D)
SEQUENCE: 628
DAGKSALTY                                                              9

SEQ ID NO: 629            moltype = AA  length = 9
FEATURE                   Location/Qualifiers
source                    1..9
                          organism = synthetic construct
                          mol_type = protein
                          note = Seed: GACGVGKSA (KRAS G12C)
SEQUENCE: 629
GNCGVGKSY                                                              9

SEQ ID NO: 630            moltype = AA  length = 9
FEATURE                   Location/Qualifiers
source                    1..9
                          organism = synthetic construct
                          mol_type = protein
                          note = Seed: VVGADGVGK (KRAS G12D)
SEQUENCE: 630
VSGADGVGK                                                              9

SEQ ID NO: 631            moltype = AA  length = 9
```

-continued

| FEATURE | Location/Qualifiers |
|---|---|
| source | 1..9<br>organism = synthetic construct<br>mol_type = protein<br>note = Seed: VVGAGDVGK (KRAS G13D) |

SEQUENCE: 631
VMGAGDVGR                                                                      9

SEQ ID NO: 632           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 632
AKDVGKSAL                                                                      9

SEQ ID NO: 633           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 633
AIDVGKSAC                                                                      9

SEQ ID NO: 634           moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 634
GSCGVGKSH                                                                      9

SEQ ID NO: 635           moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 635
GAGDVGKSK                                                                      9

SEQ ID NO: 636           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 636
AYDVGKSAA                                                                      9

SEQ ID NO: 637           moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 637
GPCGVGKSC                                                                      9

SEQ ID NO: 638           moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 638
VQGAVGVGR                                                                      9

SEQ ID NO: 639           moltype = AA   length = 9
FEATURE                  Location/Qualifiers
source                   1..9
                         organism = synthetic construct
                         mol_type = protein
                         note = Seed: LVVVGARGV (KRAS G12R)
SEQUENCE: 639
LLVVGARGA                                                                      9

```
SEQ ID NO: 640          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 640
GQDGVGKSY                                                                     9

SEQ ID NO: 641          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 641
VVGAGDVGY                                                                     9

SEQ ID NO: 642          moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 642
VIGADGVGR                                                                     9

SEQ ID NO: 643          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 643
GTDGVGKSA                                                                     9

SEQ ID NO: 644          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 644
VQGAVGVGK                                                                     9

SEQ ID NO: 645          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 645
GVGDVGKSK                                                                     9

SEQ ID NO: 646          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 646
GVDGVGKSC                                                                     9

SEQ ID NO: 647          moltype = AA   length = 9
FEATURE                 Location/Qualifiers
source                  1..9
                        organism = synthetic construct
                        mol_type = protein
                        note = Seed: LVVVGACGV (KRAS G12C)
SEQUENCE: 647
LLVVGACGM                                                                     9

SEQ ID NO: 648          moltype = AA   length = 9
FEATURE                 Location/Qualifiers
source                  1..9
                        organism = synthetic construct
                        mol_type = protein
                        note = Seed: DVGKSALTI (KRAS G13D)
```

```
SEQUENCE: 648
DSGKSALTF                                                                              9

SEQ ID NO: 649         moltype = AA   length = 9
FEATURE                Location/Qualifiers
source                 1..9
                       organism = synthetic construct
                       mol_type = protein
                       note = Seed: DVGKSALTI (KRAS G13D)
SEQUENCE: 649
DPGKSALTL                                                                              9

SEQ ID NO: 650         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 650
GIDGVGKSC                                                                              9

SEQ ID NO: 651         moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 651
GIVGVGKSK                                                                              9

SEQ ID NO: 652         moltype = AA   length = 9
FEATURE                Location/Qualifiers
source                 1..9
                       organism = synthetic construct
                       mol_type = protein
                       note = Seed: GARGVGKSA (KRAS G12R)
SEQUENCE: 652
GVRGVGKSH                                                                              9

SEQ ID NO: 653         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 653
GMDGVGKSY                                                                              9

SEQ ID NO: 654         moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 654
GAGDVGKSR                                                                              9

SEQ ID NO: 655         moltype = AA   length = 9
FEATURE                Location/Qualifiers
source                 1..9
                       organism = synthetic construct
                       mol_type = protein
                       note = Seed: VVGAGDVGK (KRAS G13D)
SEQUENCE: 655
VIGAGDVGK                                                                              9

SEQ ID NO: 656         moltype = AA   length = 9
FEATURE                Location/Qualifiers
source                 1..9
                       organism = synthetic construct
                       mol_type = protein
                       note = Seed: GARGVGKSA (KRAS G12R)
SEQUENCE: 656
GERGVGKSY                                                                              9

SEQ ID NO: 657         moltype = AA   length = 9
FEATURE                Location/Qualifiers
source                 1..9
                       organism = synthetic construct
```

```
                        mol_type = protein
                        note = Seed: GAGDVGKSA (KRAS G13D)
SEQUENCE: 657
GVGDVGKSR                                                                   9

SEQ ID NO: 658          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 658
GSVGVGKSK                                                                   9

SEQ ID NO: 659          moltype = AA  length = 9
FEATURE                 Location/Qualifiers
source                  1..9
                        organism = synthetic construct
                        mol_type = protein
                        note = Seed: LVVVGADGV (KRAS G12D)
SEQUENCE: 659
LVVVGADGI                                                                   9

SEQ ID NO: 660          moltype = AA  length = 9
FEATURE                 Location/Qualifiers
source                  1..9
                        organism = synthetic construct
                        mol_type = protein
                        note = Seed: LVVVGARGV (KRAS G12R)
SEQUENCE: 660
LIVVGARGV                                                                   9

SEQ ID NO: 661          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 661
GTVGVGKSV                                                                   9

SEQ ID NO: 662          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 662
GPCGVGKSS                                                                   9

SEQ ID NO: 663          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 663
GVVGVGKSR                                                                   9

SEQ ID NO: 664          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 664
APDVGKSAV                                                                   9

SEQ ID NO: 665          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 665
GVDGVGKSR                                                                   9

SEQ ID NO: 666          moltype = AA  length = 9
FEATURE                 Location/Qualifiers
```

```
                   -continued source              1..9
                    organism = synthetic construct
                    mol_type = protein
                    note = Seed: GADGVGKSA (KRAS G12D)
SEQUENCE: 666
GDDGVGKSM                                                                          9

SEQ ID NO: 667      moltype = AA   length = 9
FEATURE             Location/Qualifiers
source              1..9
                    organism = synthetic construct
                    mol_type = protein
                    note = Seed: GAGDVGKSA (KRAS G13D)
SEQUENCE: 667
GGGDVGKSM                                                                          9

SEQ ID NO: 668      moltype = AA   length = 9
FEATURE             Location/Qualifiers
source              1..9
                    organism = synthetic construct
                    mol_type = protein
                    note = Seed: AGDVGKSAL (KRAS G13D)
SEQUENCE: 668
ALDVGKSAY                                                                          9

SEQ ID NO: 669      moltype = AA   length = 9
FEATURE             Location/Qualifiers
source              1..9
                    organism = synthetic construct
                    mol_type = protein
                    note = Seed: VVGADGVGK (KRAS G12D)
SEQUENCE: 669
VSGADGVGR                                                                          9

SEQ ID NO: 670      moltype = AA   length = 9
FEATURE             Location/Qualifiers
source              1..9
                    organism = synthetic construct
                    mol_type = protein
                    note = Seed: VVGAVGVGK (KRAS G12V)
SEQUENCE: 670
VRGAVGVGL                                                                          9

SEQ ID NO: 671      moltype = AA   length = 9
FEATURE             Location/Qualifiers
source              1..9
                    organism = synthetic construct
                    mol_type = protein
                    note = Seed: GADGVGKSA (KRAS G12D)
SEQUENCE: 671
GADGVGKSH                                                                          9

SEQ ID NO: 672      moltype = AA   length = 9
FEATURE             Location/Qualifiers
source              1..9
                    organism = synthetic construct
                    mol_type = protein
                    note = Seed: GAVGVGKSA (KRAS G12V)
SEQUENCE: 672
GTVGVGKSI                                                                          9

SEQ ID NO: 673      moltype = AA   length = 9
FEATURE             Location/Qualifiers
source              1..9
                    organism = synthetic construct
                    mol_type = protein
                    note = Seed: VVGACGVGK (KRAS G12C)
SEQUENCE: 673
VIGACGVGY                                                                          9

SEQ ID NO: 674      moltype = AA   length = 9
FEATURE             Location/Qualifiers
source              1..9
                    organism = synthetic construct
                    mol_type = protein
                    note = Seed: VVGAVGVGK (KRAS G12V)
SEQUENCE: 674
VAGAVGVGI                                                                          9
```

```
SEQ ID NO: 675          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 675
GVRGVGKSV                                                                  9

SEQ ID NO: 676          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 676
AVDVGKSAC                                                                  9

SEQ ID NO: 677          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 677
GMCGVGKSF                                                                  9

SEQ ID NO: 678          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 678
GADGVGKSK                                                                  9

SEQ ID NO: 679          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 679
APDVGKSAI                                                                  9

SEQ ID NO: 680          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 680
GQRGVGKSM                                                                  9

SEQ ID NO: 681          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 681
GVDGVGKSK                                                                  9

SEQ ID NO: 682          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 682
GKDGVGKSL                                                                  9

SEQ ID NO: 683          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 683
```

GLVGVGKSM                                                                                           9

SEQ ID NO: 684        moltype = AA  length = 9
FEATURE               Location/Qualifiers
source                1..9
                      organism = synthetic construct
                      mol_type = protein
                      note = Seed: GADGVGKSA (KRAS G12D)
SEQUENCE: 684
GADGVGKSR                                                                                           9

SEQ ID NO: 685        moltype = AA  length = 9
FEATURE               Location/Qualifiers
source                1..9
                      organism = synthetic construct
                      mol_type = protein
                      note = Seed: VVGAGDVGK (KRAS G13D)
SEQUENCE: 685
VIGAGDVGR                                                                                           9

SEQ ID NO: 686        moltype = AA  length = 9
FEATURE               Location/Qualifiers
source                1..9
                      organism = synthetic construct
                      mol_type = protein
                      note = Seed: VVGACGVGK (KRAS G12C)
SEQUENCE: 686
VVGACGVGF                                                                                           9

SEQ ID NO: 687        moltype = AA  length = 9
FEATURE               Location/Qualifiers
source                1..9
                      organism = synthetic construct
                      mol_type = protein
                      note = Seed: GARGVGKSA (KRAS G12R)
SEQUENCE: 687
GVRGVGKSI                                                                                           9

SEQ ID NO: 688        moltype = AA  length = 9
FEATURE               Location/Qualifiers
source                1..9
                      organism = synthetic construct
                      mol_type = protein
                      note = Seed: GAVGVGKSA (KRAS G12V)
SEQUENCE: 688
GIVGVGKSR                                                                                           9

SEQ ID NO: 689        moltype = AA  length = 9
FEATURE               Location/Qualifiers
source                1..9
                      organism = synthetic construct
                      mol_type = protein
                      note = Seed: GAGDVGKSA (KRAS G13D)
SEQUENCE: 689
GIGDVGKSR                                                                                           9

SEQ ID NO: 690        moltype = AA  length = 9
FEATURE               Location/Qualifiers
source                1..9
                      organism = synthetic construct
                      mol_type = protein
                      note = Seed: VVGAVGVGK (KRAS G12V)
SEQUENCE: 690
VAGAVGVGV                                                                                           9

SEQ ID NO: 691        moltype = AA  length = 9
FEATURE               Location/Qualifiers
source                1..9
                      organism = synthetic construct
                      mol_type = protein
                      note = Seed: GAVGVGKSA (KRAS G12V)
SEQUENCE: 691
GTVGVGKSK                                                                                           9

SEQ ID NO: 692        moltype = AA  length = 9
FEATURE               Location/Qualifiers
source                1..9
                      organism = synthetic construct
                      mol_type = protein

```
                              note = Seed: VVGAVGVGK (KRAS G12V)
SEQUENCE: 692
VMGAVGVGY                                                                    9

SEQ ID NO: 693                moltype = AA   length = 9
FEATURE                       Location/Qualifiers
source                        1..9
                              organism = synthetic construct
                              mol_type = protein
                              note = Seed: GAGDVGKSA (KRAS G13D)
SEQUENCE: 693
GIGDVGKSK                                                                    9

SEQ ID NO: 694                moltype = AA   length = 9
FEATURE                       Location/Qualifiers
source                        1..9
                              organism = synthetic construct
                              mol_type = protein
                              note = Seed: LVVVGADGV (KRAS G12D)
SEQUENCE: 694
LIVVGADGL                                                                    9

SEQ ID NO: 695                moltype = AA   length = 9
FEATURE                       Location/Qualifiers
source                        1..9
                              organism = synthetic construct
                              mol_type = protein
                              note = Seed: GARGVGKSA (KRAS G12R)
SEQUENCE: 695
GARGVGKSW                                                                    9

SEQ ID NO: 696                moltype = AA   length = 9
FEATURE                       Location/Qualifiers
source                        1..9
                              organism = synthetic construct
                              mol_type = protein
                              note = Seed: LVVVGACGV (KRAS G12C)
SEQUENCE: 696
LTVVGACGL                                                                    9

SEQ ID NO: 697                moltype = AA   length = 9
FEATURE                       Location/Qualifiers
source                        1..9
                              organism = synthetic construct
                              mol_type = protein
                              note = Seed: GAGDVGKSA (KRAS G13D)
SEQUENCE: 697
GQGDVGKSM                                                                    9

SEQ ID NO: 698                moltype = AA   length = 9
FEATURE                       Location/Qualifiers
source                        1..9
                              organism = synthetic construct
                              mol_type = protein
                              note = Seed: AGDVGKSAL (KRAS G13D)
SEQUENCE: 698
ATDVGKSAA                                                                    9

SEQ ID NO: 699                moltype = AA   length = 9
FEATURE                       Location/Qualifiers
source                        1..9
                              organism = synthetic construct
                              mol_type = protein
                              note = Seed: GACGVGKSA (KRAS G12C)
SEQUENCE: 699
GQCGVGKSF                                                                    9

SEQ ID NO: 700                moltype = AA   length = 9
FEATURE                       Location/Qualifiers
source                        1..9
                              organism = synthetic construct
                              mol_type = protein
                              note = Seed: VVGADGVGK (KRAS G12D)
SEQUENCE: 700
VSGADGVGF                                                                    9

SEQ ID NO: 701                moltype = AA   length = 9
FEATURE                       Location/Qualifiers
source                        1..9
```

```
                        organism = synthetic construct
                        mol_type = protein
                        note = Seed: GADGVGKSA (KRAS G12D)
SEQUENCE: 701
GPDGVGKSI                                                                          9

SEQ ID NO: 702          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 702
GSVGVGKSR                                                                          9

SEQ ID NO: 703          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 703
VLGAGDVGR                                                                          9

SEQ ID NO: 704          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 704
GIDGVGKSR                                                                          9

SEQ ID NO: 705          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 705
DGGKSALTI                                                                          9

SEQ ID NO: 706          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 706
GTRGVGKSH                                                                          9

SEQ ID NO: 707          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 707
GAGDVGKSW                                                                          9

SEQ ID NO: 708          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 708
DSGKSALTW                                                                          9

SEQ ID NO: 709          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 709
VSGAGDVGK                                                                          9

SEQ ID NO: 710          moltype = AA   length = 9
```

```
FEATURE              Location/Qualifiers
source               1..9
                     organism = synthetic construct
                     mol_type = protein
                     note = Seed: GACGVGKSA (KRAS G12C)
SEQUENCE: 710
GGCGVGKSM                                                                      9

SEQ ID NO: 711       moltype = AA  length = 9
FEATURE              Location/Qualifiers
source               1..9
                     organism = synthetic construct
                     mol_type = protein
                     note = Seed: GARGVGKSA (KRAS G12R)
SEQUENCE: 711
GMRGVGKSL                                                                      9

SEQ ID NO: 712       moltype = AA  length = 9
FEATURE              Location/Qualifiers
source               1..9
                     organism = synthetic construct
                     mol_type = protein
                     note = Seed: GAVGVGKSA (KRAS G12V)
SEQUENCE: 712
GTVGVGKSR                                                                      9

SEQ ID NO: 713       moltype = AA  length = 9
FEATURE              Location/Qualifiers
source               1..9
                     organism = synthetic construct
                     mol_type = protein
                     note = Seed: GAGDVGKSA (KRAS G13D)
SEQUENCE: 713
GMGDVGKSM                                                                      9

SEQ ID NO: 714       moltype = AA  length = 9
FEATURE              Location/Qualifiers
source               1..9
                     organism = synthetic construct
                     mol_type = protein
                     note = Seed: VVGADGVGK (KRAS G12D)
SEQUENCE: 714
VLGADGVGK                                                                      9

SEQ ID NO: 715       moltype = AA  length = 9
FEATURE              Location/Qualifiers
source               1..9
                     organism = synthetic construct
                     mol_type = protein
                     note = Seed: GAVGVGKSA (KRAS G12V)
SEQUENCE: 715
GEVGVGKSY                                                                      9

SEQ ID NO: 716       moltype = AA  length = 9
FEATURE              Location/Qualifiers
source               1..9
                     organism = synthetic construct
                     mol_type = protein
                     note = Seed: VVGACGVGK (KRAS G12C)
SEQUENCE: 716
VAGACGVGH                                                                      9

SEQ ID NO: 717       moltype = AA  length = 9
FEATURE              Location/Qualifiers
source               1..9
                     organism = synthetic construct
                     mol_type = protein
                     note = Seed: LVVVGADGV (KRAS G12D)
SEQUENCE: 717
LQVVGADGI                                                                      9

SEQ ID NO: 718       moltype = AA  length = 9
FEATURE              Location/Qualifiers
source               1..9
                     organism = synthetic construct
                     mol_type = protein
                     note = Seed: VVGAVGVGK (KRAS G12V)
SEQUENCE: 718
VFGAVGVGR                                                                      9
```

```
SEQ ID NO: 719          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 719
DQGKSALTL                                                                    9

SEQ ID NO: 720          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 720
GGVGVGKSK                                                                    9

SEQ ID NO: 721          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 721
GLCGVGKSF                                                                    9

SEQ ID NO: 722          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 722
VLGADGVGR                                                                    9

SEQ ID NO: 723          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 723
GLGDVGKSM                                                                    9

SEQ ID NO: 724          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 724
VGGADGVGK                                                                    9

SEQ ID NO: 725          moltype = AA  length = 9
FEATURE                 Location/Qualifiers
source                  1..9
                        organism = synthetic construct
                        mol_type = protein
                        note = Seed: LVVVGARGV (KRAS G12R)
SEQUENCE: 725
LTVVGARGV                                                                    9

SEQ ID NO: 726          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 726
ALDVGKSAC                                                                    9

SEQ ID NO: 727          moltype = AA  length = 9
FEATURE                 Location/Qualifiers
source                  1..9
                        organism = synthetic construct
                        mol_type = protein
                        note = Seed: GACGVGKSA (KRAS G12C)
```

```
SEQUENCE: 727
GVCGVGKSH                                                                          9

SEQ ID NO: 728         moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 728
VLGAGDVGK                                                                          9

SEQ ID NO: 729         moltype = AA  length = 9
FEATURE                Location/Qualifiers
source                 1..9
                       organism = synthetic construct
                       mol_type = protein
                       note = Seed: LVVVGAVGV (KRAS G12V)
SEQUENCE: 729
LTVVGAVGL                                                                          9

SEQ ID NO: 730         moltype = AA  length = 9
FEATURE                Location/Qualifiers
source                 1..9
                       organism = synthetic construct
                       mol_type = protein
                       note = Seed: LVVVGADGV (KRAS G12D)
SEQUENCE: 730
LIVVGADGI                                                                          9

SEQ ID NO: 731         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 731
VGGADGVGR                                                                          9

SEQ ID NO: 732         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 732
VAGADGVGH                                                                          9

SEQ ID NO: 733         moltype = AA  length = 9
FEATURE                Location/Qualifiers
source                 1..9
                       organism = synthetic construct
                       mol_type = protein
                       note = Seed: DVGKSALTI (KRAS G13D)
SEQUENCE: 733
DLGKSALTW                                                                          9

SEQ ID NO: 734         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 734
GEDGVGKSL                                                                          9

SEQ ID NO: 735         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 735
GGVGVGKSR                                                                          9

SEQ ID NO: 736         moltype = AA  length = 9
FEATURE                Location/Qualifiers
source                 1..9
                       organism = synthetic construct
```

```
                              mol_type = protein
                              note = Seed: GADGVGKSA (KRAS G12D)
SEQUENCE: 736
GLDGVGKSY                                                               9

SEQ ID NO: 737            moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 737
GIDGVGKSK                                                               9

SEQ ID NO: 738            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 738
GTGDVGKSH                                                               9

SEQ ID NO: 739            moltype = AA   length = 9
FEATURE                   Location/Qualifiers
source                    1..9
                          organism = synthetic construct
                          mol_type = protein
                          note = Seed: VVGADGVGK (KRAS G12D)
SEQUENCE: 739
VVGADGVGF                                                               9

SEQ ID NO: 740            moltype = AA   length = 9
FEATURE                   Location/Qualifiers
source                    1..9
                          organism = synthetic construct
                          mol_type = protein
                          note = Seed: LVVVGACGV (KRAS G12C)
SEQUENCE: 740
LTVVGACGA                                                               9

SEQ ID NO: 741            moltype = AA   length = 9
FEATURE                   Location/Qualifiers
source                    1..9
                          organism = synthetic construct
                          mol_type = protein
                          note = Seed: VVGADGVGK (KRAS G12D)
SEQUENCE: 741
VIGADGVGY                                                               9

SEQ ID NO: 742            moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 742
GYDGVGKSC                                                               9

SEQ ID NO: 743            moltype = AA   length = 9
FEATURE                   Location/Qualifiers
source                    1..9
                          organism = synthetic construct
                          mol_type = protein
                          note = Seed: DVGKSALTI (KRAS G13D)
SEQUENCE: 743
DVGKSALTM                                                               9

SEQ ID NO: 744            moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 744
AHDVGKSAI                                                               9

SEQ ID NO: 745            moltype = AA   length = 9
FEATURE                   Location/Qualifiers
```

```
source                    1..9
                          organism = synthetic construct
                          mol_type = protein
                          note = Seed: GAGDVGKSA (KRAS G13D)
SEQUENCE: 745
GSGDVGKSK                                                                        9

SEQ ID NO: 746            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 746
GIGDVGKSH                                                                        9

SEQ ID NO: 747            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 747
GTGDVGKSK                                                                        9

SEQ ID NO: 748            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 748
GTGDVGKSR                                                                        9

SEQ ID NO: 749            moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 749
GTDGVGKSR                                                                        9

SEQ ID NO: 750            moltype = AA   length = 9
FEATURE                   Location/Qualifiers
source                    1..9
                          organism = synthetic construct
                          mol_type = protein
                          note = Seed: GACGVGKSA (KRAS G12C)
SEQUENCE: 750
GSCGVGKSV                                                                        9

SEQ ID NO: 751            moltype = AA   length = 9
FEATURE                   Location/Qualifiers
source                    1..9
                          organism = synthetic construct
                          mol_type = protein
                          note = Seed: GARGVGKSA (KRAS G12R)
SEQUENCE: 751
GGRGVGKSL                                                                        9

SEQ ID NO: 752            moltype = AA   length = 9
FEATURE                   Location/Qualifiers
source                    1..9
                          organism = synthetic construct
                          mol_type = protein
                          note = Seed: VVGAGDVGK (KRAS G13D)
SEQUENCE: 752
VGGAGDVGK                                                                        9

SEQ ID NO: 753            moltype = AA   length = 9
FEATURE                   Location/Qualifiers
source                    1..9
                          organism = synthetic construct
                          mol_type = protein
                          note = Seed: GAVGVGKSA (KRAS G12V)
SEQUENCE: 753
GVVGVGKSV                                                                        9
```

-continued

| | | |
|---|---|---|
| SEQ ID NO: 754<br>FEATURE<br>source | moltype = AA   length = 9<br>Location/Qualifiers<br>1..9<br>organism = synthetic construct<br>mol_type = protein<br>note = Seed: GAGDVGKSA (KRAS G13D) | |
| SEQUENCE: 754<br>GSGDVGKSR | | 9 |
| SEQ ID NO: 755<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 755<br>VPGAVGVGK | | 9 |
| SEQ ID NO: 756<br>FEATURE<br>source | moltype = AA   length = 9<br>Location/Qualifiers<br>1..9<br>organism = synthetic construct<br>mol_type = protein<br>note = Seed: LVVVGACGV (KRAS G12C) | |
| SEQUENCE: 756<br>LIVVGACGA | | 9 |
| SEQ ID NO: 757<br>FEATURE<br>source | moltype = AA   length = 9<br>Location/Qualifiers<br>1..9<br>organism = synthetic construct<br>mol_type = protein<br>note = Seed: GAGDVGKSA (KRAS G13D) | |
| SEQUENCE: 757<br>GCGDVGKSY | | 9 |
| SEQ ID NO: 758<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 758<br>AWDVGKSAW | | 9 |
| SEQ ID NO: 759<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 759<br>GTDGVGKSK | | 9 |
| SEQ ID NO: 760<br>FEATURE<br>source | moltype = AA   length = 9<br>Location/Qualifiers<br>1..9<br>organism = synthetic construct<br>mol_type = protein<br>note = Seed: VVGACGVGK (KRAS G12C) | |
| SEQUENCE: 760<br>VPGACGVGR | | 9 |
| SEQ ID NO: 761<br>FEATURE<br>source | moltype = AA   length = 9<br>Location/Qualifiers<br>1..9<br>organism = synthetic construct<br>mol_type = protein<br>note = Seed: GARGVGKSA (KRAS G12R) | |
| SEQUENCE: 761<br>GTRGVGKSV | | 9 |
| SEQ ID NO: 762<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 762 | | |

```
AIDVGKSAW                                                                    9

SEQ ID NO: 763         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 763
GPVGVGKSY                                                                    9

SEQ ID NO: 764         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 764
VVGAVGVGL                                                                    9

SEQ ID NO: 765         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 765
GVCGVGKSK                                                                    9

SEQ ID NO: 766         moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 766
GEGDVGKSY                                                                    9

SEQ ID NO: 767         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 767
VQGAVGVGY                                                                    9

SEQ ID NO: 768         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 768
VNGAVGVGK                                                                    9

SEQ ID NO: 769         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 769
GACGVGKSW                                                                    9

SEQ ID NO: 770         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 770
GGDGVGKSR                                                                    9

SEQ ID NO: 771         moltype = AA  length = 9
FEATURE                Location/Qualifiers
source                 1..9
                       organism = synthetic construct
                       mol_type = protein
```

-continued

```
                        note = Seed: GARGVGKSA (KRAS G12R)
SEQUENCE: 771
GPRGVGKSY                                                                    9

SEQ ID NO: 772          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 772
GACGVGKSK                                                                    9

SEQ ID NO: 773          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 773
VSGAGDVGF                                                                    9

SEQ ID NO: 774          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 774
GHDGVGKSI                                                                    9

SEQ ID NO: 775          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 775
VYGACGVGR                                                                    9

SEQ ID NO: 776          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 776
AMDVGKSAC                                                                    9

SEQ ID NO: 777          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 777
GMCGVGKSM                                                                    9

SEQ ID NO: 778          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 778
GSDGVGKSR                                                                    9

SEQ ID NO: 779          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 779
GPRGVGKSW                                                                    9

SEQ ID NO: 780          moltype = AA  length = 9
FEATURE                 Location/Qualifiers
source                  1..9
```

```
                              organism = synthetic construct
                              mol_type = protein
                              note = Seed: GAVGVGKSA (KRAS G12V)
SEQUENCE: 780
GGVGVGKSH                                                                     9

SEQ ID NO: 781                moltype = AA   length = 9
FEATURE                       Location/Qualifiers
source                        1..9
                              organism = synthetic construct
                              mol_type = protein
                              note = Seed: VVGAVGVGK (KRAS G12V)
SEQUENCE: 781
VLGAVGVGY                                                                     9

SEQ ID NO: 782                moltype = AA   length = 9
FEATURE                       Location/Qualifiers
source                        1..9
                              organism = synthetic construct
                              mol_type = protein
                              note = Seed: GACGVGKSA (KRAS G12C)
SEQUENCE: 782
GQCGVGKSM                                                                     9

SEQ ID NO: 783                moltype = AA   length = 9
FEATURE                       Location/Qualifiers
source                        1..9
                              organism = synthetic construct
                              mol_type = protein
                              note = Seed: GAVGVGKSA (KRAS G12V)
SEQUENCE: 783
GVVGVGKSI                                                                     9

SEQ ID NO: 784                moltype = AA   length = 9
FEATURE                       Location/Qualifiers
source                        1..9
                              organism = synthetic construct
                              mol_type = protein
                              note = Seed: GAGDVGKSA (KRAS G13D)
SEQUENCE: 784
GVGDVGKSV                                                                     9

SEQ ID NO: 785                moltype = AA   length = 9
FEATURE                       Location/Qualifiers
source                        1..9
                              organism = synthetic construct
                              mol_type = protein
                              note = Seed: GADGVGKSA (KRAS G12D)
SEQUENCE: 785
GPDGVGKST                                                                     9

SEQ ID NO: 786                moltype = AA   length = 9
FEATURE                       Location/Qualifiers
source                        1..9
                              organism = synthetic construct
                              mol_type = protein
                              note = Seed: AGDVGKSAL (KRAS G13D)
SEQUENCE: 786
AKDVGKSAM                                                                     9

SEQ ID NO: 787                moltype = AA   length = 9
FEATURE                       Location/Qualifiers
source                        1..9
                              organism = synthetic construct
                              mol_type = protein
                              note = Seed: AGDVGKSAL (KRAS G13D)
SEQUENCE: 787
APDVGKSAF                                                                     9

SEQ ID NO: 788                moltype = AA   length = 9
FEATURE                       Location/Qualifiers
source                        1..9
                              organism = synthetic construct
                              mol_type = protein
                              note = Seed: VVGAVGVGK (KRAS G12V)
SEQUENCE: 788
VNGAVGVGR                                                                     9

SEQ ID NO: 789                moltype = AA   length = 9
```

```
FEATURE              Location/Qualifiers
source               1..9
                     organism = synthetic construct
                     mol_type = protein
                     note = Seed: VVGAGDVGK (KRAS G13D)
SEQUENCE: 789
VGGAGDVGR                                                                         9

SEQ ID NO: 790       moltype = AA  length = 9
FEATURE              Location/Qualifiers
source               1..9
                     organism = synthetic construct
                     mol_type = protein
                     note = Seed: LVVVGACGV (KRAS G12C)
SEQUENCE: 790
LVVVGACGA                                                                         9

SEQ ID NO: 791       moltype = AA  length = 9
FEATURE              Location/Qualifiers
source               1..9
                     organism = synthetic construct
                     mol_type = protein
                     note = Seed: AGDVGKSAL (KRAS G13D)
SEQUENCE: 791
AEDVGKSAC                                                                         9

SEQ ID NO: 792       moltype = AA  length = 9
FEATURE              Location/Qualifiers
source               1..9
                     organism = synthetic construct
                     mol_type = protein
                     note = Seed: GAGDVGKSA (KRAS G13D)
SEQUENCE: 792
GPGDVGKSC                                                                         9

SEQ ID NO: 793       moltype = AA  length = 9
FEATURE              Location/Qualifiers
source               1..9
                     organism = synthetic construct
                     mol_type = protein
                     note = Seed: AGDVGKSAL (KRAS G13D)
SEQUENCE: 793
AHDVGKSAV                                                                         9

SEQ ID NO: 794       moltype = AA  length = 9
FEATURE              Location/Qualifiers
source               1..9
                     organism = synthetic construct
                     mol_type = protein
                     note = Seed: DVGKSALTI (KRAS G13D)
SEQUENCE: 794
DMGKSALTW                                                                         9

SEQ ID NO: 795       moltype = AA  length = 9
FEATURE              Location/Qualifiers
source               1..9
                     organism = synthetic construct
                     mol_type = protein
                     note = Seed: GARGVGKSA (KRAS G12R)
SEQUENCE: 795
GLRGVGKSL                                                                         9

SEQ ID NO: 796       moltype = AA  length = 9
FEATURE              Location/Qualifiers
source               1..9
                     organism = synthetic construct
                     mol_type = protein
                     note = Seed: VVGAVGVGK (KRAS G12V)
SEQUENCE: 796
VSGAVGVGH                                                                         9

SEQ ID NO: 797       moltype = AA  length = 9
FEATURE              Location/Qualifiers
source               1..9
                     organism = synthetic construct
                     mol_type = protein
                     note = Seed: GADGVGKSA (KRAS G12D)
SEQUENCE: 797
GDDGVGKSF                                                                         9
```

```
SEQ ID NO: 798            moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 798
GGDGVGKSK                                                                  9

SEQ ID NO: 799            moltype = AA  length = 9
FEATURE                   Location/Qualifiers
source                    1..9
                          organism = synthetic construct
                          mol_type = protein
                          note = Seed: GAVGVGKSA (KRAS G12V)
SEQUENCE: 799
GMVGVGKSL                                                                  9

SEQ ID NO: 800            moltype = AA  length = 9
FEATURE                   Location/Qualifiers
source                    1..9
                          organism = synthetic construct
                          mol_type = protein
                          note = Seed: VVGACGVGK (KRAS G12C)
SEQUENCE: 800
VGGACGVGK                                                                  9

SEQ ID NO: 801            moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 801
GSDGVGKSW                                                                  9

SEQ ID NO: 802            moltype = AA  length = 9
FEATURE                   Location/Qualifiers
source                    1..9
                          organism = synthetic construct
                          mol_type = protein
                          note = Seed: GAVGVGKSA (KRAS G12V)
SEQUENCE: 802
GCVGVGKSF                                                                  9

SEQ ID NO: 803            moltype = AA  length = 9
FEATURE                   Location/Qualifiers
source                    1..9
                          organism = synthetic construct
                          mol_type = protein
                          note = Seed: GAGDVGKSA (KRAS G13D)
SEQUENCE: 803
GSGDVGKSV                                                                  9

SEQ ID NO: 804            moltype = AA  length = 9
FEATURE                   Location/Qualifiers
source                    1..9
                          organism = synthetic construct
                          mol_type = protein
                          note = Seed: GACGVGKSA (KRAS G12C)
SEQUENCE: 804
GTCGVGKSH                                                                  9

SEQ ID NO: 805            moltype = AA  length = 9
FEATURE                   Location/Qualifiers
source                    1..9
                          organism = synthetic construct
                          mol_type = protein
                          note = Seed: VVGACGVGK (KRAS G12C)
SEQUENCE: 805
VFGACGVGR                                                                  9

SEQ ID NO: 806            moltype = AA  length = 9
FEATURE                   Location/Qualifiers
source                    1..9
                          organism = synthetic construct
                          mol_type = protein
                          note = Seed: VVGACGVGK (KRAS G12C)
```

```
SEQUENCE: 806
VQGACGVGK                                                                       9

SEQ ID NO: 807         moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 807
GSVGVGKSA                                                                       9

SEQ ID NO: 808         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 808
GLDGVGKSR                                                                       9

SEQ ID NO: 809         moltype = AA   length = 9
FEATURE                Location/Qualifiers
source                 1..9
                       organism = synthetic construct
                       mol_type = protein
                       note = Seed: LVVVGADGV (KRAS G12D)
SEQUENCE: 809
LAVVGADGV                                                                       9

SEQ ID NO: 810         moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 810
GECGVGKSY                                                                       9

SEQ ID NO: 811         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 811
GSDGVGKSK                                                                       9

SEQ ID NO: 812         moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 812
GGGDVGKSR                                                                       9

SEQ ID NO: 813         moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 813
GPCGVGKSG                                                                       9

SEQ ID NO: 814         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 814
AIDVGKSAA                                                                       9

SEQ ID NO: 815         moltype = AA   length = 9
FEATURE                Location/Qualifiers
source                 1..9
                       organism = synthetic construct
```

```
                                mol_type = protein
                                note = Seed: GACGVGKSA (KRAS G12C)
SEQUENCE: 815
GACGVGKSR                                                                      9

SEQ ID NO: 816                  moltype = AA   length = 9
FEATURE                         Location/Qualifiers
source                          1..9
                                organism = synthetic construct
                                mol_type = protein
                                note = Seed: VVGAVGVGK (KRAS G12V)
SEQUENCE: 816
VDGAVGVGK                                                                      9

SEQ ID NO: 817                  moltype = AA   length = 9
FEATURE                         Location/Qualifiers
source                          1..9
                                organism = synthetic construct
                                mol_type = protein
                                note = Seed: GACGVGKSA (KRAS G12C)
SEQUENCE: 817
GLCGVGKSM                                                                      9

SEQ ID NO: 818                  moltype = AA   length = 9
FEATURE                         Location/Qualifiers
source                          1..9
                                organism = synthetic construct
                                mol_type = protein
                                note = Seed: GACGVGKSA (KRAS G12C)
SEQUENCE: 818
GSCGVGKSI                                                                      9

SEQ ID NO: 819                  moltype = AA   length = 9
FEATURE                         Location/Qualifiers
source                          1..9
                                organism = synthetic construct
                                mol_type = protein
                                note = Seed: GARGVGKSA (KRAS G12R)
SEQUENCE: 819
GIRGVGKSH                                                                      9

SEQ ID NO: 820                  moltype = AA   length = 9
FEATURE                         Location/Qualifiers
source                          1..9
                                organism = synthetic construct
                                mol_type = protein
                                note = Seed: GADGVGKSA (KRAS G12D)
SEQUENCE: 820
GLDGVGKSC                                                                      9

SEQ ID NO: 821                  moltype = AA   length = 9
FEATURE                         Location/Qualifiers
source                          1..9
                                organism = synthetic construct
                                mol_type = protein
                                note = Seed: GAVGVGKSA (KRAS G12V)
SEQUENCE: 821
GNVGVGKSF                                                                      9

SEQ ID NO: 822                  moltype = AA   length = 9
FEATURE                         Location/Qualifiers
source                          1..9
                                organism = synthetic construct
                                mol_type = protein
                                note = Seed: GADGVGKSA (KRAS G12D)
SEQUENCE: 822
GHDGVGKSV                                                                      9

SEQ ID NO: 823                  moltype = AA   length = 9
FEATURE                         Location/Qualifiers
source                          1..9
                                organism = synthetic construct
                                mol_type = protein
                                note = Seed: GACGVGKSA (KRAS G12C)
SEQUENCE: 823
GICGVGKSK                                                                      9

SEQ ID NO: 824                  moltype = AA   length = 9
FEATURE                         Location/Qualifiers
```

| | | |
|---|---|---|
| source | 1..9<br>organism = synthetic construct<br>mol_type = protein<br>note = Seed: GARGVGKSA (KRAS G12R) | |
| SEQUENCE: 824<br>GTRGVGKSI | | 9 |
| SEQ ID NO: 825<br>FEATURE<br>source | moltype = AA length = 9<br>Location/Qualifiers<br>1..9<br>organism = synthetic construct<br>mol_type = protein<br>note = Seed: GACGVGKSA (KRAS G12C) | |
| SEQUENCE: 825<br>GCCGVGKSY | | 9 |
| SEQ ID NO: 826<br>FEATURE<br>source | moltype = AA length = 9<br>Location/Qualifiers<br>1..9<br>organism = synthetic construct<br>mol_type = protein<br>note = Seed: GAVGVGKSA (KRAS G12V) | |
| SEQUENCE: 826<br>GLVGVGKSK | | 9 |
| SEQ ID NO: 827<br>FEATURE<br>source | moltype = AA length = 9<br>Location/Qualifiers<br>1..9<br>organism = synthetic construct<br>mol_type = protein<br>note = Seed: VVGARGVGK (KRAS G12R) | |
| SEQUENCE: 827<br>VYGARGVGR | | 9 |
| SEQ ID NO: 828<br>FEATURE<br>source | moltype = AA length = 9<br>Location/Qualifiers<br>1..9<br>organism = synthetic construct<br>mol_type = protein<br>note = Seed: DVGKSALTI (KRAS G13D) | |
| SEQUENCE: 828<br>DSGKSALTY | | 9 |
| SEQ ID NO: 829<br>FEATURE<br>source | moltype = AA length = 9<br>Location/Qualifiers<br>1..9<br>organism = synthetic construct<br>mol_type = protein<br>note = Seed: VVGACGVGK (KRAS G12C) | |
| SEQUENCE: 829<br>VGGACGVGY | | 9 |
| SEQ ID NO: 830<br>FEATURE<br>source | moltype = AA length = 9<br>Location/Qualifiers<br>1..9<br>organism = synthetic construct<br>mol_type = protein<br>note = Seed: GARGVGKSA (KRAS G12R) | |
| SEQUENCE: 830<br>GNRGVGKSF | | 9 |
| SEQ ID NO: 831<br>FEATURE<br>source | moltype = AA length = 9<br>Location/Qualifiers<br>1..9<br>organism = synthetic construct<br>mol_type = protein<br>note = Seed: VVGADGVGK (KRAS G12D) | |
| SEQUENCE: 831<br>VTGADGVGF | | 9 |
| SEQ ID NO: 832<br>FEATURE<br>source | moltype = AA length = 9<br>Location/Qualifiers<br>1..9<br>organism = synthetic construct<br>mol_type = protein<br>note = Seed: GACGVGKSA (KRAS G12C) | |
| SEQUENCE: 832<br>GVCGVGKSV | | 9 |

-continued

```
SEQ ID NO: 833          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 833
GGGDVGKSK                                                                  9

SEQ ID NO: 834          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 834
GIDGVGKSW                                                                  9

SEQ ID NO: 835          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 835
GVDGVGKSA                                                                  9

SEQ ID NO: 836          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 836
AVDVGKSAA                                                                  9

SEQ ID NO: 837          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 837
ASDVGKSAW                                                                  9

SEQ ID NO: 838          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 838
VSGACGVGM                                                                  9

SEQ ID NO: 839          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 839
GLDGVGKSK                                                                  9

SEQ ID NO: 840          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 840
GVCGVGKSR                                                                  9

SEQ ID NO: 841          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 841
```

```
GEDGVGKSM                                                                                9

SEQ ID NO: 842         moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 842
GTGDVGKSV                                                                                9

SEQ ID NO: 843         moltype = AA   length = 9
FEATURE                Location/Qualifiers
source                 1..9
                       organism = synthetic construct
                       mol_type = protein
                       note = Seed: VVGACGVGK (KRAS G12C)
SEQUENCE: 843
VTGACGVGF                                                                                9

SEQ ID NO: 844         moltype = AA   length = 9
FEATURE                Location/Qualifiers
source                 1..9
                       organism = synthetic construct
                       mol_type = protein
                       note = Seed: GARGVGKSA (KRAS G12R)
SEQUENCE: 844
GIRGVGKSA                                                                                9

SEQ ID NO: 845         moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 845
GLGDVGKSR                                                                                9

SEQ ID NO: 846         moltype = AA   length = 9
FEATURE                Location/Qualifiers
source                 1..9
                       organism = synthetic construct
                       mol_type = protein
                       note = Seed: VVGAGDVGK (KRAS G13D)
SEQUENCE: 846
VVGAGDVGF                                                                                9

SEQ ID NO: 847         moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 847
GNVGVGKSK                                                                                9

SEQ ID NO: 848         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 848
GPDGVGKSP                                                                                9

SEQ ID NO: 849         moltype = AA   length = 9
FEATURE                Location/Qualifiers
source                 1..9
                       organism = synthetic construct
                       mol_type = protein
                       note = Seed: LVVVGADGV (KRAS G12D)
SEQUENCE: 849
LMVVGADGM                                                                                9

SEQ ID NO: 850         moltype = AA   length = 9
FEATURE                Location/Qualifiers
source                 1..9
                       organism = synthetic construct
                       mol_type = protein
```

-continued

```
                        note = Seed: VVGACGVGK (KRAS G12C)
SEQUENCE: 850
VQGACGVGR                                                               9

SEQ ID NO: 851          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 851
VEGAVGVGK                                                               9

SEQ ID NO: 852          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 852
GICGVGKSR                                                               9

SEQ ID NO: 853          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 853
AVDVGKSAW                                                               9

SEQ ID NO: 854          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 854
GCRGVGKSF                                                               9

SEQ ID NO: 855          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 855
VFGARGVGR                                                               9

SEQ ID NO: 856          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 856
DAGKSALTC                                                               9

SEQ ID NO: 857          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 857
DTGKSALTV                                                               9

SEQ ID NO: 858          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 858
AEDVGKSAA                                                               9

SEQ ID NO: 859          moltype = AA  length = 9
FEATURE                 Location/Qualifiers
source                  1..9
```

-continued

```
                            organism = synthetic construct
                            mol_type = protein
                            note = Seed: GADGVGKSA (KRAS G12D)
SEQUENCE: 859
GYDGVGKSY                                                                        9

SEQ ID NO: 860              moltype = AA  length = 9
FEATURE                     Location/Qualifiers
source                      1..9
                            organism = synthetic construct
                            mol_type = protein
                            note = Seed: VVGAVGVGK (KRAS G12V)
SEQUENCE: 860
VGGAVGVGF                                                                        9

SEQ ID NO: 861              moltype = AA  length = 9
FEATURE                     Location/Qualifiers
source                      1..9
                            organism = synthetic construct
                            mol_type = protein
                            note = Seed: VVGARGVGK (KRAS G12R)
SEQUENCE: 861
VVGARGVGY                                                                        9

SEQ ID NO: 862              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 862
ALDVGKSAW                                                                        9

SEQ ID NO: 863              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 863
AVDVGKSAK                                                                        9

SEQ ID NO: 864              moltype = AA  length = 9
FEATURE                     Location/Qualifiers
source                      1..9
                            organism = synthetic construct
                            mol_type = protein
                            note = Seed: GADGVGKSA (KRAS G12D)
SEQUENCE: 864
GIDGVGKSA                                                                        9

SEQ ID NO: 865              moltype = AA  length = 9
FEATURE                     Location/Qualifiers
source                      1..9
                            organism = synthetic construct
                            mol_type = protein
                            note = Seed: VVGACGVGK (KRAS G12C)
SEQUENCE: 865
VGGACGVGR                                                                        9

SEQ ID NO: 866              moltype = AA  length = 9
FEATURE                     Location/Qualifiers
source                      1..9
                            organism = synthetic construct
                            mol_type = protein
                            note = Seed: GAGDVGKSA (KRAS G13D)
SEQUENCE: 866
GLGDVGKSK                                                                        9

SEQ ID NO: 867              moltype = AA  length = 9
FEATURE                     Location/Qualifiers
source                      1..9
                            organism = synthetic construct
                            mol_type = protein
                            note = Seed: GAVGVGKSA (KRAS G12V)
SEQUENCE: 867
GLVGVGKSR                                                                        9

SEQ ID NO: 868              moltype = AA  length = 9
```

-continued

| FEATURE | Location/Qualifiers |
|---|---|
| source | 1..9<br>organism = synthetic construct<br>mol_type = protein<br>note = Seed: VVGAVGVGK (KRAS G12V) |

SEQUENCE: 868
VIGAVGVGM                                                                                      9

SEQ ID NO: 869      moltype = AA   length = 9
FEATURE             Location/Qualifiers
source              1..9
                    organism = synthetic construct
                    mol_type = protein
                    note = Seed: GAVGVGKSA (KRAS G12V)
SEQUENCE: 869
GQVGVGKSL                                                                                      9

SEQ ID NO: 870      moltype = AA   length = 9
FEATURE             Location/Qualifiers
source              1..9
                    organism = synthetic construct
                    mol_type = protein
                    note = Seed: AGDVGKSAL (KRAS G13D)
SEQUENCE: 870
ATDVGKSAW                                                                                      9

SEQ ID NO: 871      moltype = AA   length = 9
FEATURE             Location/Qualifiers
source              1..9
                    organism = synthetic construct
                    mol_type = protein
                    note = Seed: DVGKSALTI (KRAS G13D)
SEQUENCE: 871
DIGKSALTV                                                                                      9

SEQ ID NO: 872      moltype = AA   length = 9
FEATURE             Location/Qualifiers
source              1..9
                    organism = synthetic construct
                    mol_type = protein
                    note = Seed: VVGARGVGK (KRAS G12R)
SEQUENCE: 872
VVGARGVGM                                                                                      9

SEQ ID NO: 873      moltype = AA   length = 9
FEATURE             Location/Qualifiers
source              1..9
                    organism = synthetic construct
                    mol_type = protein
                    note = Seed: GARGVGKSA (KRAS G12R)
SEQUENCE: 873
GDRGVGKSY                                                                                      9

SEQ ID NO: 874      moltype = AA   length = 9
FEATURE             Location/Qualifiers
source              1..9
                    organism = synthetic construct
                    mol_type = protein
                    note = Seed: GAVGVGKSA (KRAS G12V)
SEQUENCE: 874
GDVGVGKSK                                                                                      9

SEQ ID NO: 875      moltype = AA   length = 9
FEATURE             Location/Qualifiers
source              1..9
                    organism = synthetic construct
                    mol_type = protein
                    note = Seed: GADGVGKSA (KRAS G12D)
SEQUENCE: 875
GVDGVGKSW                                                                                      9

SEQ ID NO: 876      moltype = AA   length = 9
FEATURE             Location/Qualifiers
source              1..9
                    organism = synthetic construct
                    mol_type = protein
                    note = Seed: VVGADGVGK (KRAS G12D)
SEQUENCE: 876
VQGADGVGK                                                                                      9

-continued

```
SEQ ID NO: 877              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 877
GPDGVGKSF                                                                  9

SEQ ID NO: 878              moltype = AA   length = 9
FEATURE                     Location/Qualifiers
source                      1..9
                            organism = synthetic construct
                            mol_type = protein
                            note = Seed: GAGDVGKSA (KRAS G13D)
SEQUENCE: 878
GSGDVGKSI                                                                  9

SEQ ID NO: 879              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 879
GMDGVGKSR                                                                  9

SEQ ID NO: 880              moltype = AA   length = 9
FEATURE                     Location/Qualifiers
source                      1..9
                            organism = synthetic construct
                            mol_type = protein
                            note = Seed: VVGARGVGK (KRAS G12R)
SEQUENCE: 880
VVGARGVGF                                                                  9

SEQ ID NO: 881              moltype = AA   length = 9
FEATURE                     Location/Qualifiers
source                      1..9
                            organism = synthetic construct
                            mol_type = protein
                            note = Seed: DVGKSALTI (KRAS G13D)
SEQUENCE: 881
DMGKSALTV                                                                  9

SEQ ID NO: 882              moltype = AA   length = 9
FEATURE                     Location/Qualifiers
source                      1..9
                            organism = synthetic construct
                            mol_type = protein
                            note = Seed: VVGAGDVGK (KRAS G13D)
SEQUENCE: 882
VAGAGDVGH                                                                  9

SEQ ID NO: 883              moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 883
GAVGVGKSC                                                                  9

SEQ ID NO: 884              moltype = AA   length = 9
FEATURE                     Location/Qualifiers
source                      1..9
                            organism = synthetic construct
                            mol_type = protein
                            note = Seed: VVGADGVGK (KRAS G12D)
SEQUENCE: 884
VSGADGVGM                                                                  9

SEQ ID NO: 885              moltype = AA   length = 9
FEATURE                     Location/Qualifiers
source                      1..9
                            organism = synthetic construct
                            mol_type = protein
                            note = Seed: AGDVGKSAL (KRAS G13D)
```

-continued

```
SEQUENCE: 885
AVDVGKSAR                                                                        9

SEQ ID NO: 886         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 886
VQGADGVGR                                                                        9

SEQ ID NO: 887         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 887
GSRGVGKSA                                                                        9

SEQ ID NO: 888         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 888
AYDVGKSAT                                                                        9

SEQ ID NO: 889         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 889
VDGAVGVGR                                                                        9

SEQ ID NO: 890         moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 890
VIGAGDVGY                                                                        9

SEQ ID NO: 891         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 891
GKDGVGKSM                                                                        9

SEQ ID NO: 892         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 892
GSCGVGKSK                                                                        9

SEQ ID NO: 893         moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 893
GNGDVGKSF                                                                        9

SEQ ID NO: 894         moltype = AA  length = 9
FEATURE                Location/Qualifiers
source                 1..9
                       organism = synthetic construct
```

```
                             mol_type = protein
                             note = Seed: LVVVGACGV (KRAS G12C)
SEQUENCE: 894
LQVVGACGA                                                                 9

SEQ ID NO: 895               moltype = AA  length = 9
FEATURE                      Location/Qualifiers
source                       1..9
                             organism = synthetic construct
                             mol_type = protein
                             note = Seed: GAGDVGKSA (KRAS G13D)
SEQUENCE: 895
GVGDVGKSI                                                                 9

SEQ ID NO: 896               moltype = AA  length = 9
FEATURE                      Location/Qualifiers
source                       1..9
                             organism = synthetic construct
                             mol_type = protein
                             note = Seed: VVGADGVGK (KRAS G12D)
SEQUENCE: 896
VNGADGVGR                                                                 9

SEQ ID NO: 897               moltype = AA  length = 9
FEATURE                      Location/Qualifiers
source                       1..9
                             organism = synthetic construct
                             mol_type = protein
                             note = Seed: AGDVGKSAL (KRAS G13D)
SEQUENCE: 897
AKDVGKSAF                                                                 9

SEQ ID NO: 898               moltype = AA  length = 9
FEATURE                      Location/Qualifiers
source                       1..9
                             organism = synthetic construct
                             mol_type = protein
                             note = Seed: GAVGVGKSA (KRAS G12V)
SEQUENCE: 898
GQVGVGKSK                                                                 9

SEQ ID NO: 899               moltype = AA  length = 9
FEATURE                      Location/Qualifiers
source                       1..9
                             organism = synthetic construct
                             mol_type = protein
                             note = Seed: VVGAVGVGK (KRAS G12V)
SEQUENCE: 899
VRGAVGVGM                                                                 9

SEQ ID NO: 900               moltype = AA  length = 9
FEATURE                      Location/Qualifiers
source                       1..9
                             organism = synthetic construct
                             mol_type = protein
                             note = Seed: AGDVGKSAL (KRAS G13D)
SEQUENCE: 900
AWDVGKSAA                                                                 9

SEQ ID NO: 901               moltype = AA  length = 9
FEATURE                      Location/Qualifiers
source                       1..9
                             organism = synthetic construct
                             mol_type = protein
                             note = Seed: VVGARGVGK (KRAS G12R)
SEQUENCE: 901
VVGARGVGL                                                                 9

SEQ ID NO: 902               moltype = AA  length = 9
FEATURE                      Location/Qualifiers
source                       1..9
                             organism = synthetic construct
                             mol_type = protein
                             note = Seed: GAVGVGKSA (KRAS G12V)
SEQUENCE: 902
GLVGVGKSL                                                                 9

SEQ ID NO: 903               moltype = AA  length = 9
FEATURE                      Location/Qualifiers
```

```
source                  1..9
                        organism = synthetic construct
                        mol_type = protein
                        note = Seed: GACGVGKSA (KRAS G12C)
SEQUENCE: 903
GTCGVGKSK                                                                           9

SEQ ID NO: 904          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 904
GSDGVGKST                                                                           9

SEQ ID NO: 905          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 905
GQRGVGKSL                                                                           9

SEQ ID NO: 906          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 906
DTGKSALTL                                                                           9

SEQ ID NO: 907          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 907
GMDGVGKSC                                                                           9

SEQ ID NO: 908          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 908
GAVGVGKST                                                                           9

SEQ ID NO: 909          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 909
AIDVGKSAK                                                                           9

SEQ ID NO: 910          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 910
GPCGVGKSY                                                                           9

SEQ ID NO: 911          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 911
AIDVGKSAR                                                                           9
```

-continued

| | | |
|---|---|---|
| SEQ ID NO: 912<br>FEATURE<br>source | moltype = AA   length = 9<br>Location/Qualifiers<br>1..9<br>organism = synthetic construct<br>mol_type = protein<br>note = Seed: GAGDVGKSA (KRAS G13D) | |
| SEQUENCE: 912<br>GQGDVGKSL | | 9 |
| SEQ ID NO: 913<br>FEATURE<br>source | moltype = AA   length = 9<br>Location/Qualifiers<br>1..9<br>organism = synthetic construct<br>mol_type = protein<br>note = Seed: VVGARGVGK (KRAS G12R) | |
| SEQUENCE: 913<br>VQGARGVGR | | 9 |
| SEQ ID NO: 914<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |
| SEQUENCE: 914<br>GICGVGKSH | | 9 |
| SEQ ID NO: 915<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |
| SEQUENCE: 915<br>GVCGVGKSI | | 9 |
| SEQ ID NO: 916<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 916<br>GMDGVGKSK | | 9 |
| SEQ ID NO: 917<br>FEATURE<br>source | moltype = AA   length = 9<br>Location/Qualifiers<br>1..9<br>organism = synthetic construct<br>mol_type = protein<br>note = Seed: GAGDVGKSA (KRAS G13D) | |
| SEQUENCE: 917<br>GFGDVGKSY | | 9 |
| SEQ ID NO: 918<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 918<br>GTDGVGKSW | | 9 |
| SEQ ID NO: 919<br>FEATURE<br>source | moltype = AA   length = 9<br>Location/Qualifiers<br>1..9<br>organism = synthetic construct<br>mol_type = protein<br>note = Seed: LVVVGADGV (KRAS G12D) | |
| SEQUENCE: 919<br>LLVVGADGM | | 9 |
| SEQ ID NO: 920<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 920 | | |

AADVGKSAK                                                                                                    9

SEQ ID NO: 921        moltype = AA  length = 9
FEATURE               Location/Qualifiers
source                1..9
                      organism = synthetic construct
                      mol_type = protein
                      note = Seed: GAGDVGKSA (KRAS G13D)
SEQUENCE: 921
GTGDVGKSI                                                                                                    9

SEQ ID NO: 922        moltype = AA  length = 9
FEATURE               Location/Qualifiers
source                1..9
                      organism = synthetic construct
                      mol_type = protein
                      note = Seed: VVGAVGVGK (KRAS G12V)
SEQUENCE: 922
VFGAVGVGK                                                                                                    9

SEQ ID NO: 923        moltype = AA  length = 9
FEATURE               Location/Qualifiers
source                1..9
                      organism = synthetic construct
                      mol_type = protein
                      note = Seed: GACGVGKSA (KRAS G12C)
SEQUENCE: 923
GSCGVGKSR                                                                                                    9

SEQ ID NO: 924        moltype = AA  length = 9
FEATURE               Location/Qualifiers
source                1..9
                      organism = synthetic construct
                      mol_type = protein
                      note = Seed: GACGVGKSA (KRAS G12C)
SEQUENCE: 924
GTCGVGKSV                                                                                                    9

SEQ ID NO: 925        moltype = AA  length = 9
FEATURE               Location/Qualifiers
source                1..9
                      organism = synthetic construct
                      mol_type = protein
                      note = Seed: DVGKSALTI (KRAS G13D)
SEQUENCE: 925
DAGKSALTA                                                                                                    9

SEQ ID NO: 926        moltype = AA  length = 9
FEATURE               Location/Qualifiers
source                1..9
                      organism = synthetic construct
                      mol_type = protein
                      note = Seed: GACGVGKSA (KRAS G12C)
SEQUENCE: 926
GTCGVGKSR                                                                                                    9

SEQ ID NO: 927        moltype = AA  length = 9
FEATURE               Location/Qualifiers
source                1..9
                      organism = synthetic construct
                      mol_type = protein
                      note = Seed: VVGAVGVGK (KRAS G12V)
SEQUENCE: 927
VYGAVGVGK                                                                                                    9

SEQ ID NO: 928        moltype = AA  length = 9
FEATURE               Location/Qualifiers
source                1..9
                      organism = synthetic construct
                      mol_type = protein
                      note = Seed: GARGVGKSA (KRAS G12R)
SEQUENCE: 928
GIRGVGKSV                                                                                                    9

SEQ ID NO: 929        moltype = AA  length = 9
FEATURE               Location/Qualifiers
source                1..9
                      organism = synthetic construct
                      mol_type = protein

```
                             note = Seed: VVGARGVGK (KRAS G12R)
SEQUENCE: 929
VSGARGVGV                                                              9

SEQ ID NO: 930          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 930
VNGAGDVGK                                                              9

SEQ ID NO: 931          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 931
VQGAGDVGK                                                              9

SEQ ID NO: 932          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 932
GQDGVGKSK                                                              9

SEQ ID NO: 933          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 933
GNVGVGKSR                                                              9

SEQ ID NO: 934          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 934
GNDGVGKSR                                                              9

SEQ ID NO: 935          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 935
VAGAVGVGA                                                              9

SEQ ID NO: 936          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 936
VNGADGVGK                                                              9

SEQ ID NO: 937          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 937
GPGDVGKSY                                                              9

SEQ ID NO: 938          moltype = AA  length = 9
FEATURE                 Location/Qualifiers
source                  1..9
```

```
                          organism = synthetic construct
                          mol_type = protein
                          note = Seed: GACGVGKSA (KRAS G12C)
SEQUENCE: 938
GGCGVGKSL                                                                  9

SEQ ID NO: 939            moltype = AA   length = 9
FEATURE                   Location/Qualifiers
source                    1..9
                          organism = synthetic construct
                          mol_type = protein
                          note = Seed: VVGAGDVGK (KRAS G13D)
SEQUENCE: 939
VQGAGDVGR                                                                  9

SEQ ID NO: 940            moltype = AA   length = 9
FEATURE                   Location/Qualifiers
source                    1..9
                          organism = synthetic construct
                          mol_type = protein
                          note = Seed: GACGVGKSA (KRAS G12C)
SEQUENCE: 940
GGCGVGKSR                                                                  9

SEQ ID NO: 941            moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 941
GQDGVGKSR                                                                  9

SEQ ID NO: 942            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 942
GGGDVGKSL                                                                  9

SEQ ID NO: 943            moltype = AA   length = 9
FEATURE                   Location/Qualifiers
source                    1..9
                          organism = synthetic construct
                          mol_type = protein
                          note = Seed: VVGAGDVGK (KRAS G13D)
SEQUENCE: 943
VTGAGDVGF                                                                  9

SEQ ID NO: 944            moltype = AA   length = 9
FEATURE                   Location/Qualifiers
source                    1..9
                          organism = synthetic construct
                          mol_type = protein
                          note = Seed: VVGARGVGK (KRAS G12R)
SEQUENCE: 944
VSGARGVGI                                                                  9

SEQ ID NO: 945            moltype = AA   length = 9
FEATURE                   Location/Qualifiers
source                    1..9
                          organism = synthetic construct
                          mol_type = protein
                          note = Seed: GARGVGKSA (KRAS G12R)
SEQUENCE: 945
GARGVGKSC                                                                  9

SEQ ID NO: 946            moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 946
ASDVGKSAT                                                                  9

SEQ ID NO: 947            moltype = AA   length = 9
```

| FEATURE | Location/Qualifiers |
|---|---|
| source | 1..9<br>organism = synthetic construct<br>mol_type = protein<br>note = Seed: VVGAVGVGK (KRAS G12V) |

SEQUENCE: 947
VVGAVGVGH                                                                  9

| SEQ ID NO: 948 | moltype = AA   length = 9 |
|---|---|
| FEATURE | Location/Qualifiers |
| source | 1..9<br>organism = synthetic construct<br>mol_type = protein<br>note = Seed: GAVGVGKSA (KRAS G12V) |

SEQUENCE: 948
GDVGVGKSR                                                                  9

| SEQ ID NO: 949 | moltype = AA   length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 949
AFDVGKSAT                                                                  9

| SEQ ID NO: 950 | moltype = AA   length = 9 |
|---|---|
| FEATURE | Location/Qualifiers |
| source | 1..9<br>organism = synthetic construct<br>mol_type = protein<br>note = Seed: VVGACGVGK (KRAS G12C) |

SEQUENCE: 950
VVGACGVGM                                                                  9

| SEQ ID NO: 951 | moltype = AA   length = 9 |
|---|---|
| FEATURE | Location/Qualifiers |
| source | 1..9<br>organism = synthetic construct<br>mol_type = protein<br>note = Seed: GARGVGKSA (KRAS G12R) |

SEQUENCE: 951
GIRGVGKSI                                                                  9

| SEQ ID NO: 952 | moltype = AA   length = 9 |
|---|---|
| FEATURE | Location/Qualifiers |
| source | 1..9<br>organism = synthetic construct<br>mol_type = protein<br>note = Seed: VVGAGDVGK (KRAS G13D) |

SEQUENCE: 952
VNGAGDVGR                                                                  9

| SEQ ID NO: 953 | moltype = AA   length = 9 |
|---|---|
| FEATURE | Location/Qualifiers |
| source | 1..9<br>organism = synthetic construct<br>mol_type = protein<br>note = Seed: GACGVGKSA (KRAS G12C) |

SEQUENCE: 953
GVCGVGKSA                                                                  9

| SEQ ID NO: 954 | moltype = AA   length = 9 |
|---|---|
| FEATURE | Location/Qualifiers |
| source | 1..9<br>organism = synthetic construct<br>mol_type = protein<br>note = Seed: VVGACGVGK (KRAS G12C) |

SEQUENCE: 954
VIGACGVGF                                                                  9

| SEQ ID NO: 955 | moltype = AA   length = 9 |
|---|---|
| FEATURE | Location/Qualifiers |
| source | 1..9<br>organism = synthetic construct<br>mol_type = protein<br>note = Seed: GACGVGKSA (KRAS G12C) |

SEQUENCE: 955
GGCGVGKSK                                                                  9

```
SEQ ID NO: 956          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 956
GFRGVGKSY                                                                     9

SEQ ID NO: 957          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 957
VMGAVGVGF                                                                     9

SEQ ID NO: 958          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 958
VPGAGDVGR                                                                     9

SEQ ID NO: 959          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 959
GPRGVGKSQ                                                                     9

SEQ ID NO: 960          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 960
GTCGVGKSI                                                                     9

SEQ ID NO: 961          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 961
GNDGVGKSK                                                                     9

SEQ ID NO: 962          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 962
GMGDVGKSL                                                                     9

SEQ ID NO: 963          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 963
GLGDVGKSL                                                                     9

SEQ ID NO: 964          moltype = AA  length = 9
FEATURE                 Location/Qualifiers
source                  1..9
                        organism = synthetic construct
                        mol_type = protein
                        note = Seed: GAVGVGKSA (KRAS G12V)
```

```
SEQUENCE: 964
GCVGVGKSM                                                                        9

SEQ ID NO: 965          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 965
VEGAVGVGR                                                                        9

SEQ ID NO: 966          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 966
GDVGVGKSY                                                                        9

SEQ ID NO: 967          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 967
GNCGVGKSF                                                                        9

SEQ ID NO: 968          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 968
AADVGKSAR                                                                        9

SEQ ID NO: 969          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 969
GNDGVGKSY                                                                        9

SEQ ID NO: 970          moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 970
LVVVGAVGA                                                                        9

SEQ ID NO: 971          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 971
DSGKSALTL                                                                        9

SEQ ID NO: 972          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 972
VPGARGVGR                                                                        9

SEQ ID NO: 973          moltype = AA   length = 9
FEATURE                 Location/Qualifiers
source                  1..9
                        organism = synthetic construct
```

```
                        mol_type = protein
                        note = Seed: VVGACGVGK (KRAS G12C)
SEQUENCE: 973
VMGACGVGY                                                                9

SEQ ID NO: 974          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 974
ADDVGKSAY                                                                9

SEQ ID NO: 975          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 975
VFGAGDVGK                                                                9

SEQ ID NO: 976          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 976
GMVGVGKSK                                                                9

SEQ ID NO: 977          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 977
GVVGVGKSA                                                                9

SEQ ID NO: 978          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 978
GFDGVGKSC                                                                9

SEQ ID NO: 979          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 979
GPGDVGKSS                                                                9

SEQ ID NO: 980          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 980
GSVGVGKSW                                                                9

SEQ ID NO: 981          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 981
GDGDVGKSK                                                                9

SEQ ID NO: 982          moltype = AA   length = 9
FEATURE                 Location/Qualifiers
```

-continued

```
source                 1..9
                       organism = synthetic construct
                       mol_type = protein
                       note = Seed: LVVVGADGV (KRAS G12D)
SEQUENCE: 982
LTVVGADGL                                                                      9

SEQ ID NO: 983         moltype = AA  length = 9
FEATURE                Location/Qualifiers
source                 1..9
                       organism = synthetic construct
                       mol_type = protein
                       note = Seed: DVGKSALTI (KRAS G13D)
SEQUENCE: 983
DIGKSALTI                                                                      9

SEQ ID NO: 984         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 984
GFDGVGKSY                                                                      9

SEQ ID NO: 985         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 985
ADDVGKSAW                                                                      9

SEQ ID NO: 986         moltype = AA  length = 9
FEATURE                Location/Qualifiers
source                 1..9
                       organism = synthetic construct
                       mol_type = protein
                       note = Seed: LVVVGAVGV (KRAS G12V)
SEQUENCE: 986
LIVVGAVGA                                                                      9

SEQ ID NO: 987         moltype = AA  length = 9
FEATURE                Location/Qualifiers
source                 1..9
                       organism = synthetic construct
                       mol_type = protein
                       note = Seed: LVVVGAVGV (KRAS G12V)
SEQUENCE: 987
LTVVGAVGA                                                                      9

SEQ ID NO: 988         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 988
GERGVGKSF                                                                      9

SEQ ID NO: 989         moltype = AA  length = 9
FEATURE                Location/Qualifiers
source                 1..9
                       organism = synthetic construct
                       mol_type = protein
                       note = Seed: DVGKSALTI (KRAS G13D)
SEQUENCE: 989
DTGKSALTI                                                                      9

SEQ ID NO: 990         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 990
GQVGVGKSR                                                                      9
```

```
SEQ ID NO: 991            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 991
GNGDVGKSK                                                                 9

SEQ ID NO: 992            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 992
GNGDVGKSR                                                                 9

SEQ ID NO: 993            moltype = AA   length = 9
FEATURE                   Location/Qualifiers
source                    1..9
                          organism = synthetic construct
                          mol_type = protein
                          note = Seed: VVGADGVGK (KRAS G12D)
SEQUENCE: 993
VMGADGVGY                                                                 9

SEQ ID NO: 994            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 994
GMGDVGKSR                                                                 9

SEQ ID NO: 995            moltype = AA   length = 9
FEATURE                   Location/Qualifiers
source                    1..9
                          organism = synthetic construct
                          mol_type = protein
                          note = Seed: VVGADGVGK (KRAS G12D)
SEQUENCE: 995
VDGADGVGK                                                                 9

SEQ ID NO: 996            moltype = AA   length = 9
FEATURE                   Location/Qualifiers
source                    1..9
                          organism = synthetic construct
                          mol_type = protein
                          note = Seed: GACGVGKSA (KRAS G12C)
SEQUENCE: 996
GMCGVGKSL                                                                 9

SEQ ID NO: 997            moltype = AA   length = 9
FEATURE                   Location/Qualifiers
source                    1..9
                          organism = synthetic construct
                          mol_type = protein
                          note = Seed: VVGADGVGK (KRAS G12D)
SEQUENCE: 997
VPGADGVGR                                                                 9

SEQ ID NO: 998            moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 998
ANDVGKSAY                                                                 9

SEQ ID NO: 999            moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 999
```

```
AGDVGKSAK                                                                            9

SEQ ID NO: 1000         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1000
VPGADGVGK                                                                            9

SEQ ID NO: 1001         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1001
GMVGVGKSH                                                                            9

SEQ ID NO: 1002         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1002
GPDGVGKSC                                                                            9

SEQ ID NO: 1003         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1003
VSGACGVGL                                                                            9

SEQ ID NO: 1004         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1004
GEGDVGKSF                                                                            9

SEQ ID NO: 1005         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1005
VLGACGVGY                                                                            9

SEQ ID NO: 1006         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1006
VGGADGVGY                                                                            9

SEQ ID NO: 1007         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1007
GMVGVGKSR                                                                            9

SEQ ID NO: 1008         moltype = AA  length = 9
FEATURE                 Location/Qualifiers
source                  1..9
                        organism = synthetic construct
                        mol_type = protein
```

```
                        note = Seed: VVGAVGVGK (KRAS G12V)
SEQUENCE: 1008
VWGAVGVGR                                                              9

SEQ ID NO: 1009         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1009
GTDGVGKST                                                              9

SEQ ID NO: 1010         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1010
VLGADGVGY                                                              9

SEQ ID NO: 1011         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1011
VSGAGDVGM                                                              9

SEQ ID NO: 1012         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1012
GMGDVGKSK                                                              9

SEQ ID NO: 1013         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1013
GDGDVGKSR                                                              9

SEQ ID NO: 1014         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1014
VPGACGVGK                                                              9

SEQ ID NO: 1015         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1015
GYDGVGKSA                                                              9

SEQ ID NO: 1016         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1016
VFGADGVGK                                                              9

SEQ ID NO: 1017         moltype = AA   length = 9
FEATURE                 Location/Qualifiers
source                  1..9
```

-continued

```
                        organism = synthetic construct
                        mol_type = protein
                        note = Seed: VVGAVGVGK (KRAS G12V)
SEQUENCE: 1017
VQGAVGVGF                                                                       9

SEQ ID NO: 1018         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1018
GCGDVGKSF                                                                       9

SEQ ID NO: 1019         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1019
ARDVGKSAW                                                                       9

SEQ ID NO: 1020         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1020
GGRGVGKSA                                                                       9

SEQ ID NO: 1021         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1021
AKDVGKSAY                                                                       9

SEQ ID NO: 1022         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1022
VRGAVGVGI                                                                       9

SEQ ID NO: 1023         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1023
VEGADGVGK                                                                       9

SEQ ID NO: 1024         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1024
GLCGVGKSR                                                                       9

SEQ ID NO: 1025         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1025
GDDGVGKSI                                                                       9

SEQ ID NO: 1026         moltype = AA  length = 9
```

```
FEATURE                 Location/Qualifiers
source                  1..9
                        organism = synthetic construct
                        mol_type = protein
                        note = Seed: GAVGVGKSA (KRAS G12V)
SEQUENCE: 1026
GFVGVGKSY                                                                     9

SEQ ID NO: 1027         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1027
DTGKSALTM                                                                     9

SEQ ID NO: 1028         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1028
VIGARGVGY                                                                     9

SEQ ID NO: 1029         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1029
VTGAVGVGH                                                                     9

SEQ ID NO: 1030         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1030
AGDVGKSAR                                                                     9

SEQ ID NO: 1031         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1031
GQCGVGKSL                                                                     9

SEQ ID NO: 1032         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1032
GNVGVGKSM                                                                     9

SEQ ID NO: 1033         moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 1033
VMGAGDVGY                                                                     9

SEQ ID NO: 1034         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1034
GFDGVGKSK                                                                     9
```

```
SEQ ID NO: 1035        moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 1035
VDGAGDVGK                                                              9

SEQ ID NO: 1036        moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 1036
AQDVGKSAW                                                              9

SEQ ID NO: 1037        moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 1037
GDDGVGKSK                                                              9

SEQ ID NO: 1038        moltype = AA  length = 9
FEATURE                Location/Qualifiers
source                 1..9
                       organism = synthetic construct
                       mol_type = protein
                       note = Seed: VVGARGVGK (KRAS G12R)
SEQUENCE: 1038
VTGARGVGI                                                              9

SEQ ID NO: 1039        moltype = AA  length = 9
FEATURE                Location/Qualifiers
source                 1..9
                       organism = synthetic construct
                       mol_type = protein
                       note = Seed: LVVVGADGV (KRAS G12D)
SEQUENCE: 1039
LSVVGADGV                                                              9

SEQ ID NO: 1040        moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 1040
VVGADGVGM                                                              9

SEQ ID NO: 1041        moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 1041
GNRGVGKSM                                                              9

SEQ ID NO: 1042        moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 1042
VGGAVGVGM                                                              9

SEQ ID NO: 1043        moltype = AA  length = 9
FEATURE                Location/Qualifiers
source                 1..9
                       organism = synthetic construct
                       mol_type = protein
                       note = Seed: GAVGVGKSA (KRAS G12V)
```

```
SEQUENCE: 1043
GEVGVGKSK                                                                                  9

SEQ ID NO: 1044         moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 1044
LQVVGAVGA                                                                                  9

SEQ ID NO: 1045         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1045
GPRGVGKSH                                                                                  9

SEQ ID NO: 1046         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1046
GLDGVGKSW                                                                                  9

SEQ ID NO: 1047         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1047
VTGARGVGV                                                                                  9

SEQ ID NO: 1048         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1048
GQGDVGKSR                                                                                  9

SEQ ID NO: 1049         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1049
GEDGVGKSF                                                                                  9

SEQ ID NO: 1050         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1050
VIGADGVGF                                                                                  9

SEQ ID NO: 1051         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1051
GQGDVGKSK                                                                                  9

SEQ ID NO: 1052         moltype = AA   length = 9
FEATURE                 Location/Qualifiers
source                  1..9
                        organism = synthetic construct
```

```
                            mol_type = protein
                            note = Seed: VVGARGVGK (KRAS G12R)
SEQUENCE: 1052
VGGARGVGY                                                              9

SEQ ID NO: 1053             moltype = AA   length = 9
FEATURE                     Location/Qualifiers
source                      1..9
                            organism = synthetic construct
                            mol_type = protein
                            note = Seed: VVGARGVGK (KRAS G12R)
SEQUENCE: 1053
VQGARGVGK                                                              9

SEQ ID NO: 1054             moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 1054
GKDGVGKSF                                                              9

SEQ ID NO: 1055             moltype = AA   length = 9
FEATURE                     Location/Qualifiers
source                      1..9
                            organism = synthetic construct
                            mol_type = protein
                            note = Seed: VVGAVGVGK (KRAS G12V)
SEQUENCE: 1055
VRGAVGVGV                                                              9

SEQ ID NO: 1056             moltype = AA   length = 9
FEATURE                     Location/Qualifiers
source                      1..9
                            organism = synthetic construct
                            mol_type = protein
                            note = Seed: VVGACGVGK (KRAS G12C)
SEQUENCE: 1056
VDGACGVGK                                                              9

SEQ ID NO: 1057             moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 1057
ASDVGKSAK                                                              9

SEQ ID NO: 1058             moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 1058
GQVGVGKSH                                                              9

SEQ ID NO: 1059             moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 1059
ASDVGKSAR                                                              9

SEQ ID NO: 1060             moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 1060
ASDVGKSAH                                                              9

SEQ ID NO: 1061             moltype = AA   length = 9
FEATURE                     Location/Qualifiers
```

```
source                          1..9
                                organism = synthetic construct
                                mol_type = protein
                                note = Seed: GAVGVGKSA (KRAS G12V)
SEQUENCE: 1061
GEVGVGKSF                                                                         9

SEQ ID NO: 1062                 moltype = AA   length = 9
FEATURE                         Location/Qualifiers
source                          1..9
                                organism = synthetic construct
                                mol_type = protein
                                note = Seed: VVGAGDVGK (KRAS G13D)
SEQUENCE: 1062
VLGAGDVGY                                                                         9

SEQ ID NO: 1063                 moltype = AA   length = 9
FEATURE                         Location/Qualifiers
source                          1..9
                                organism = synthetic construct
                                mol_type = protein
                                note = Seed: GARGVGKSA (KRAS G12R)
SEQUENCE: 1063
GARGVGKST                                                                         9

SEQ ID NO: 1064                 moltype = AA   length = 9
FEATURE                         Location/Qualifiers
source                          1..9
                                organism = synthetic construct
                                mol_type = protein
                                note = Seed: DVGKSALTI (KRAS G13D)
SEQUENCE: 1064
DMGKSALTI                                                                         9

SEQ ID NO: 1065                 moltype = AA   length = 9
FEATURE                         Location/Qualifiers
source                          1..9
                                organism = synthetic construct
                                mol_type = protein
                                note = Seed: LVVVGADGV (KRAS G12D)
SEQUENCE: 1065
LTVVGADGI                                                                         9

SEQ ID NO: 1066                 moltype = AA   length = 9
FEATURE                         Location/Qualifiers
source                          1..9
                                organism = synthetic construct
                                mol_type = protein
                                note = Seed: GAVGVGKSA (KRAS G12V)
SEQUENCE: 1066
GLVGVGKSH                                                                         9

SEQ ID NO: 1067                 moltype = AA   length = 9
FEATURE                         Location/Qualifiers
source                          1..9
                                organism = synthetic construct
                                mol_type = protein
                                note = Seed: GACGVGKSA (KRAS G12C)
SEQUENCE: 1067
GLCGVGKSL                                                                         9

SEQ ID NO: 1068                 moltype = AA   length = 9
FEATURE                         Location/Qualifiers
source                          1..9
                                organism = synthetic construct
                                mol_type = protein
                                note = Seed: VVGARGVGK (KRAS G12R)
SEQUENCE: 1068
VIGARGVGF                                                                         9

SEQ ID NO: 1069                 moltype = AA   length = 9
FEATURE                         Location/Qualifiers
source                          1..9
                                organism = synthetic construct
                                mol_type = protein
                                note = Seed: GADGVGKSA (KRAS G12D)
SEQUENCE: 1069
GDDGVGKSR                                                                         9
```

| | | |
|---|---|---|
| SEQ ID NO: 1070<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 1070<br>AGDVGKSAA | | 9 |
| SEQ ID NO: 1071<br>FEATURE<br>source | moltype = AA   length = 9<br>Location/Qualifiers<br>1..9<br>organism = synthetic construct<br>mol_type = protein<br>note = Seed: VVGARGVGK (KRAS G12R) | |
| SEQUENCE: 1071<br>VAGARGVGW | | 9 |
| SEQ ID NO: 1072<br>FEATURE<br>source | moltype = AA   length = 9<br>Location/Qualifiers<br>1..9<br>organism = synthetic construct<br>mol_type = protein<br>note = Seed: VVGADGVGK (KRAS G12D) | |
| SEQUENCE: 1072<br>VTGADGVGM | | 9 |
| SEQ ID NO: 1073<br>FEATURE<br>source | moltype = AA   length = 9<br>Location/Qualifiers<br>1..9<br>organism = synthetic construct<br>mol_type = protein<br>note = Seed: LVVVGACGV (KRAS G12C) | |
| SEQUENCE: 1073<br>LMVVGACGT | | 9 |
| SEQ ID NO: 1074<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 1074<br>GPDGVGKSK | | 9 |
| SEQ ID NO: 1075<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |
| SEQUENCE: 1075<br>GECGVGKSF | | 9 |
| SEQ ID NO: 1076<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 1076<br>GVDGVGKSH | | 9 |
| SEQ ID NO: 1077<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 1077<br>ALDVGKSAR | | 9 |
| SEQ ID NO: 1078<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 1078 | | |

```
ATDVGKSAK                                                                       9

SEQ ID NO: 1079      moltype = AA   length = 9
FEATURE              Location/Qualifiers
source               1..9
                     organism = synthetic construct
                     mol_type = protein
                     note = Seed: GAGDVGKSA (KRAS G13D)
SEQUENCE: 1079
GVGDVGKSA                                                                       9

SEQ ID NO: 1080      moltype = AA   length = 9
FEATURE              Location/Qualifiers
source               1..9
                     organism = synthetic construct
                     mol_type = protein
                     note = Seed: GADGVGKSA (KRAS G12D)
SEQUENCE: 1080
GRDGVGKSA                                                                       9

SEQ ID NO: 1081      moltype = AA   length = 9
FEATURE              Location/Qualifiers
source               1..9
                     organism = synthetic construct
                     mol_type = protein
                     note = Seed: GACGVGKSA (KRAS G12C)
SEQUENCE: 1081
GLCGVGKSK                                                                       9

SEQ ID NO: 1082      moltype = AA   length = 9
FEATURE              Location/Qualifiers
source               1..9
                     organism = synthetic construct
                     mol_type = protein
                     note = Seed: AGDVGKSAL (KRAS G13D)
SEQUENCE: 1082
AKDVGKSAI                                                                       9

SEQ ID NO: 1083      moltype = AA   length = 9
FEATURE              Location/Qualifiers
source               1..9
                     organism = synthetic construct
                     mol_type = protein
                     note = Seed: AGDVGKSAL (KRAS G13D)
SEQUENCE: 1083
ARDVGKSAA                                                                       9

SEQ ID NO: 1084      moltype = AA   length = 9
FEATURE              Location/Qualifiers
source               1..9
                     organism = synthetic construct
                     mol_type = protein
                     note = Seed: GAVGVGKSA (KRAS G12V)
SEQUENCE: 1084
GIVGVGKSV                                                                       9

SEQ ID NO: 1085      moltype = AA   length = 9
FEATURE              Location/Qualifiers
source               1..9
                     organism = synthetic construct
                     mol_type = protein
                     note = Seed: GADGVGKSA (KRAS G12D)
SEQUENCE: 1085
GDDGVGKSV                                                                       9

SEQ ID NO: 1086      moltype = AA   length = 9
FEATURE              Location/Qualifiers
source               1..9
                     organism = synthetic construct
                     mol_type = protein
                     note = Seed: GADGVGKSA (KRAS G12D)
SEQUENCE: 1086
GEDGVGKSY                                                                       9

SEQ ID NO: 1087      moltype = AA   length = 9
FEATURE              Location/Qualifiers
source               1..9
                     organism = synthetic construct
                     mol_type = protein
```

```
                          note = Seed: DVGKSALTI (KRAS G13D)
SEQUENCE: 1087
DGGKSALTL                                                              9

SEQ ID NO: 1088           moltype = AA  length = 9
FEATURE                   Location/Qualifiers
source                    1..9
                          organism = synthetic construct
                          mol_type = protein
                          note = Seed: VVGACGVGK (KRAS G12C)
SEQUENCE: 1088
VYGACGVGK                                                              9

SEQ ID NO: 1089           moltype = AA  length = 9
FEATURE                   Location/Qualifiers
source                    1..9
                          organism = synthetic construct
                          mol_type = protein
                          note = Seed: GAVGVGKSA (KRAS G12V)
SEQUENCE: 1089
GIVGVGKSI                                                              9

SEQ ID NO: 1090           moltype = AA  length = 9
FEATURE                   Location/Qualifiers
source                    1..9
                          organism = synthetic construct
                          mol_type = protein
                          note = Seed: GAVGVGKSA (KRAS G12V)
SEQUENCE: 1090
GFVGVGKSK                                                              9

SEQ ID NO: 1091           moltype = AA  length = 9
FEATURE                   Location/Qualifiers
source                    1..9
                          organism = synthetic construct
                          mol_type = protein
                          note = Seed: VVGACGVGK (KRAS G12C)
SEQUENCE: 1091
VNGACGVGK                                                              9

SEQ ID NO: 1092           moltype = AA  length = 9
FEATURE                   Location/Qualifiers
source                    1..9
                          organism = synthetic construct
                          mol_type = protein
                          note = Seed: GAGDVGKSA (KRAS G13D)
SEQUENCE: 1092
GFGDVGKSK                                                              9

SEQ ID NO: 1093           moltype = AA  length = 9
FEATURE                   Location/Qualifiers
source                    1..9
                          organism = synthetic construct
                          mol_type = protein
                          note = Seed: AGDVGKSAL (KRAS G13D)
SEQUENCE: 1093
ATDVGKSAR                                                              9

SEQ ID NO: 1094           moltype = AA  length = 9
FEATURE                   Location/Qualifiers
source                    1..9
                          organism = synthetic construct
                          mol_type = protein
                          note = Seed: VVGAVGVGK (KRAS G12V)
SEQUENCE: 1094
VCGAVGVGK                                                              9

SEQ ID NO: 1095           moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 1095
GRDGVGKSC                                                              9

SEQ ID NO: 1096           moltype = AA  length = 9
FEATURE                   Location/Qualifiers
source                    1..9
```

```
                            organism = synthetic construct
                            mol_type = protein
                            note = Seed: GAVGVGKSA (KRAS G12V)
SEQUENCE: 1096
GAVGVGKSQ                                                                    9

SEQ ID NO: 1097             moltype = AA  length = 9
FEATURE                     Location/Qualifiers
source                      1..9
                            organism = synthetic construct
                            mol_type = protein
                            note = Seed: VVGAVGVGK (KRAS G12V)
SEQUENCE: 1097
VYGAVGVGF                                                                    9

SEQ ID NO: 1098             moltype = AA  length = 9
FEATURE                     Location/Qualifiers
source                      1..9
                            organism = synthetic construct
                            mol_type = protein
                            note = Seed: GAVGVGKSA (KRAS G12V)
SEQUENCE: 1098
GCVGVGKSK                                                                    9

SEQ ID NO: 1099             moltype = AA  length = 9
FEATURE                     Location/Qualifiers
source                      1..9
                            organism = synthetic construct
                            mol_type = protein
                            note = Seed: VVGARGVGK (KRAS G12R)
SEQUENCE: 1099
VGGARGVGK                                                                    9

SEQ ID NO: 1100             moltype = AA  length = 9
FEATURE                     Location/Qualifiers
source                      1..9
                            organism = synthetic construct
                            mol_type = protein
                            note = Seed: VVGADGVGK (KRAS G12D)
SEQUENCE: 1100
VDGADGVGR                                                                    9

SEQ ID NO: 1101             moltype = AA  length = 9
FEATURE                     Location/Qualifiers
source                      1..9
                            organism = synthetic construct
                            mol_type = protein
                            note = Seed: VVGACGVGK (KRAS G12C)
SEQUENCE: 1101
VDGACGVGR                                                                    9

SEQ ID NO: 1102             moltype = AA  length = 9
FEATURE                     Location/Qualifiers
source                      1..9
                            organism = synthetic construct
                            mol_type = protein
                            note = Seed: GADGVGKSA (KRAS G12D)
SEQUENCE: 1102
GYDGVGKSK                                                                    9

SEQ ID NO: 1103             moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 1103
ALDVGKSAK                                                                    9

SEQ ID NO: 1104             moltype = AA  length = 9
FEATURE                     Location/Qualifiers
source                      1..9
                            organism = synthetic construct
                            mol_type = protein
                            note = Seed: VVGAGDVGK (KRAS G13D)
SEQUENCE: 1104
VFGAGDVGR                                                                    9

SEQ ID NO: 1105             moltype = AA  length = 9
```

```
FEATURE              Location/Qualifiers
source               1..9
                     organism = synthetic construct
                     mol_type = protein
                     note = Seed: VVGAGDVGK (KRAS G13D)
SEQUENCE: 1105
VEGAGDVGK                                                                 9

SEQ ID NO: 1106      moltype = AA  length = 9
FEATURE              Location/Qualifiers
source               1..9
                     organism = synthetic construct
                     mol_type = protein
                     note = Seed: VVGADGVGK (KRAS G12D)
SEQUENCE: 1106
VFGADGVGR                                                                 9

SEQ ID NO: 1107      moltype = AA  length = 9
FEATURE              Location/Qualifiers
source               1..9
                     organism = synthetic construct
                     mol_type = protein
                     note = Seed: AGDVGKSAL (KRAS G13D)
SEQUENCE: 1107
ALDVGKSAA                                                                 9

SEQ ID NO: 1108      moltype = AA  length = 9
FEATURE              Location/Qualifiers
source               1..9
                     organism = synthetic construct
                     mol_type = protein
                     note = Seed: GADGVGKSA (KRAS G12D)
SEQUENCE: 1108
GSDGVGKSH                                                                 9

SEQ ID NO: 1109      moltype = AA  length = 9
FEATURE              Location/Qualifiers
source               1..9
                     organism = synthetic construct
                     mol_type = protein
                     note = Seed: VVGAVGVGK (KRAS G12V)
SEQUENCE: 1109
VRGAVGVGF                                                                 9

SEQ ID NO: 1110      moltype = AA  length = 9
FEATURE              Location/Qualifiers
source               1..9
                     organism = synthetic construct
                     mol_type = protein
                     note = Seed: VVGAVGVGK (KRAS G12V)
SEQUENCE: 1110
VNGAVGVGY                                                                 9

SEQ ID NO: 1111      moltype = AA  length = 9
FEATURE              Location/Qualifiers
source               1..9
                     organism = synthetic construct
                     mol_type = protein
                     note = Seed: GAGDVGKSA (KRAS G13D)
SEQUENCE: 1111
GIGDVGKSV                                                                 9

SEQ ID NO: 1112      moltype = AA  length = 9
FEATURE              Location/Qualifiers
source               1..9
                     organism = synthetic construct
                     mol_type = protein
                     note = Seed: AGDVGKSAL (KRAS G13D)
SEQUENCE: 1112
ARDVGKSAC                                                                 9

SEQ ID NO: 1113      moltype = AA  length = 9
FEATURE              Location/Qualifiers
source               1..9
                     organism = synthetic construct
                     mol_type = protein
                     note = Seed: GAVGVGKSA (KRAS G12V)
SEQUENCE: 1113
GCVGVGKSL                                                                 9
```

```
SEQ ID NO: 1114            moltype = AA  length = 9
FEATURE                    Location/Qualifiers
source                     1..9
                           organism = synthetic construct
                           mol_type = protein
                           note = Seed: AGDVGKSAL (KRAS G13D)
SEQUENCE: 1114
AEDVGKSAT                                                              9

SEQ ID NO: 1115            moltype = AA  length = 9
FEATURE                    Location/Qualifiers
source                     1..9
                           organism = synthetic construct
                           mol_type = protein
                           note = Seed: GAVGVGKSA (KRAS G12V)
SEQUENCE: 1115
GPVGVGKSK                                                              9

SEQ ID NO: 1116            moltype = AA  length = 9
FEATURE                    Location/Qualifiers
source                     1..9
                           organism = synthetic construct
                           mol_type = protein
                           note = Seed: GAVGVGKSA (KRAS G12V)
SEQUENCE: 1116
GTVGVGKSW                                                              9

SEQ ID NO: 1117            moltype = AA  length = 9
FEATURE                    Location/Qualifiers
source                     1..9
                           organism = synthetic construct
                           mol_type = protein
                           note = Seed: VVGACGVGK (KRAS G12C)
SEQUENCE: 1117
VEGACGVGK                                                              9

SEQ ID NO: 1118            moltype = AA  length = 9
FEATURE                    Location/Qualifiers
source                     1..9
                           organism = synthetic construct
                           mol_type = protein
                           note = Seed: GACGVGKSA (KRAS G12C)
SEQUENCE: 1118
GDCGVGKSY                                                              9

SEQ ID NO: 1119            moltype = AA  length = 9
FEATURE                    Location/Qualifiers
source                     1..9
                           organism = synthetic construct
                           mol_type = protein
                           note = Seed: DVGKSALTI (KRAS G13D)
SEQUENCE: 1119
DEGKSALTV                                                              9

SEQ ID NO: 1120            moltype = AA  length = 9
FEATURE                    Location/Qualifiers
source                     1..9
                           organism = synthetic construct
                           mol_type = protein
                           note = Seed: DVGKSALTI (KRAS G13D)
SEQUENCE: 1120
DQGKSALTM                                                              9

SEQ ID NO: 1121            moltype = AA  length = 9
FEATURE                    Location/Qualifiers
source                     1..9
                           organism = synthetic construct
                           mol_type = protein
                           note = Seed: GADGVGKSA (KRAS G12D)
SEQUENCE: 1121
GEDGVGKSK                                                              9

SEQ ID NO: 1122            moltype = AA  length = 9
FEATURE                    Location/Qualifiers
source                     1..9
                           organism = synthetic construct
                           mol_type = protein
                           note = Seed: VVGACGVGK (KRAS G12C)
```

```
SEQUENCE: 1122
VFGACGVGK                                                                        9

SEQ ID NO: 1123          moltype = AA   length = 9
FEATURE                  Location/Qualifiers
source                   1..9
                         organism = synthetic construct
                         mol_type = protein
                         note = Seed: VVGAGDVGK (KRAS G13D)
SEQUENCE: 1123
VGGAGDVGY                                                                        9

SEQ ID NO: 1124          moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 1124
GCVGVGKSR                                                                        9

SEQ ID NO: 1125          moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 1125
GFDGVGKSR                                                                        9

SEQ ID NO: 1126          moltype = AA   length = 9
FEATURE                  Location/Qualifiers
source                   1..9
                         organism = synthetic construct
                         mol_type = protein
                         note = Seed: VVGAGDVGK (KRAS G13D)
SEQUENCE: 1126
VDGAGDVGR                                                                        9

SEQ ID NO: 1127          moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 1127
VAGAVGVGW                                                                        9

SEQ ID NO: 1128          moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 1128
GFDGVGKSW                                                                        9

SEQ ID NO: 1129          moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 1129
VRGAVGVGY                                                                        9

SEQ ID NO: 1130          moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 1130
VIGAVGVGL                                                                        9

SEQ ID NO: 1131          moltype = AA   length = 9
FEATURE                  Location/Qualifiers
source                   1..9
                         organism = synthetic construct
```

```
                              mol_type = protein
                              note = Seed: GACGVGKSA (KRAS G12C)
SEQUENCE: 1131
GICGVGKSV                                                            9

SEQ ID NO: 1132               moltype = AA  length = 9
FEATURE                       Location/Qualifiers
source                        1..9
                              organism = synthetic construct
                              mol_type = protein
                              note = Seed: VVGACGVGK (KRAS G12C)
SEQUENCE: 1132
VTGACGVGM                                                            9

SEQ ID NO: 1133               moltype = AA  length = 9
FEATURE                       Location/Qualifiers
source                        1..9
                              organism = synthetic construct
                              mol_type = protein
                              note = Seed: AGDVGKSAL (KRAS G13D)
SEQUENCE: 1133
ACDVGKSAY                                                            9

SEQ ID NO: 1134               moltype = AA  length = 9
FEATURE                       Location/Qualifiers
source                        1..9
                              organism = synthetic construct
                              mol_type = protein
                              note = Seed: VVGAVGVGK (KRAS G12V)
SEQUENCE: 1134
VCGAVGVGR                                                            9

SEQ ID NO: 1135               moltype = AA  length = 9
FEATURE                       Location/Qualifiers
source                        1..9
                              organism = synthetic construct
                              mol_type = protein
                              note = Seed: VVGADGVGK (KRAS G12D)
SEQUENCE: 1135
VEGADGVGR                                                            9

SEQ ID NO: 1136               moltype = AA  length = 9
FEATURE                       Location/Qualifiers
source                        1..9
                              organism = synthetic construct
                              mol_type = protein
                              note = Seed: AGDVGKSAL (KRAS G13D)
SEQUENCE: 1136
AVDVGKSAH                                                            9

SEQ ID NO: 1137               moltype = AA  length = 9
FEATURE                       Location/Qualifiers
source                        1..9
                              organism = synthetic construct
                              mol_type = protein
                              note = Seed: GAGDVGKSA (KRAS G13D)
SEQUENCE: 1137
GDGDVGKSY                                                            9

SEQ ID NO: 1138               moltype = AA  length = 9
FEATURE                       Location/Qualifiers
source                        1..9
                              organism = synthetic construct
                              mol_type = protein
                              note = Seed: DVGKSALTI (KRAS G13D)
SEQUENCE: 1138
DPGKSALTM                                                            9

SEQ ID NO: 1139               moltype = AA  length = 9
FEATURE                       Location/Qualifiers
source                        1..9
                              organism = synthetic construct
                              mol_type = protein
                              note = Seed: GACGVGKSA (KRAS G12C)
SEQUENCE: 1139
GSCGVGKSA                                                            9

SEQ ID NO: 1140               moltype = AA  length = 9
FEATURE                       Location/Qualifiers
```

```
source                  1..9
                        organism = synthetic construct
                        mol_type = protein
                        note = Seed: GAGDVGKSA (KRAS G13D)
SEQUENCE: 1140
GSGDVGKSW                                                                    9

SEQ ID NO: 1141         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1141
GDCGVGKSK                                                                    9

SEQ ID NO: 1142         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1142
VYGAVGVGM                                                                    9

SEQ ID NO: 1143         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1143
VWGACGVGR                                                                    9

SEQ ID NO: 1144         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1144
GTVGVGKSA                                                                    9

SEQ ID NO: 1145         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1145
GSGDVGKSA                                                                    9

SEQ ID NO: 1146         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1146
DLGKSALTV                                                                    9

SEQ ID NO: 1147         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1147
AQDVGKSAK                                                                    9

SEQ ID NO: 1148         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1148
ATDVGKSAT                                                                    9
```

```
SEQ ID NO: 1149          moltype = AA   length = 9
FEATURE                  Location/Qualifiers
source                   1..9
                         organism = synthetic construct
                         mol_type = protein
                         note = Seed: VVGACGVGK (KRAS G12C)
SEQUENCE: 1149
VNGACGVGR                                                                 9

SEQ ID NO: 1150          moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 1150
GQCGVGKSK                                                                 9

SEQ ID NO: 1151          moltype = AA   length = 9
FEATURE                  Location/Qualifiers
source                   1..9
                         organism = synthetic construct
                         mol_type = protein
                         note = Seed: LVVVGAVGV (KRAS G12V)
SEQUENCE: 1151
LMVVGAVGT                                                                 9

SEQ ID NO: 1152          moltype = AA   length = 9
FEATURE                  Location/Qualifiers
source                   1..9
                         organism = synthetic construct
                         mol_type = protein
                         note = Seed: VVGARGVGK (KRAS G12R)
SEQUENCE: 1152
VIGARGVGL                                                                 9

SEQ ID NO: 1153          moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 1153
VYGAVGVGY                                                                 9

SEQ ID NO: 1154          moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 1154
GNCGVGKSK                                                                 9

SEQ ID NO: 1155          moltype = AA   length = 9
FEATURE                  Location/Qualifiers
source                   1..9
                         organism = synthetic construct
                         mol_type = protein
                         note = Seed: VVGACGVGK (KRAS G12C)
SEQUENCE: 1155
VTGACGVGL                                                                 9

SEQ ID NO: 1156          moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 1156
VHGAVGVGK                                                                 9

SEQ ID NO: 1157          moltype = AA   length = 9
FEATURE                  Location/Qualifiers
source                   1..9
                         organism = synthetic construct
                         mol_type = protein
                         note = Seed: VVGARGVGK (KRAS G12R)
SEQUENCE: 1157
```

```
VGGARGVGM                                                                    9

SEQ ID NO: 1158         moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 1158
VPGAGDVGK                                                                    9

SEQ ID NO: 1159         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1159
GPGDVGKSF                                                                    9

SEQ ID NO: 1160         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1160
VIGARGVGM                                                                    9

SEQ ID NO: 1161         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1161
GPRGVGKSR                                                                    9

SEQ ID NO: 1162         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1162
VFGARGVGY                                                                    9

SEQ ID NO: 1163         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1163
VQGACGVGY                                                                    9

SEQ ID NO: 1164         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1164
ADDVGKSAK                                                                    9

SEQ ID NO: 1165         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1165
VSGADGVGL                                                                    9

SEQ ID NO: 1166         moltype = AA  length = 9
FEATURE                 Location/Qualifiers
source                  1..9
                        organism = synthetic construct
                        mol_type = protein
```

-continued

```
                        note = Seed: GADGVGKSA (KRAS G12D)
SEQUENCE: 1166
GLDGVGKSA                                                               9

SEQ ID NO: 1167         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1167
VYGAGDVGK                                                               9

SEQ ID NO: 1168         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1168
VGGARGVGF                                                               9

SEQ ID NO: 1169         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1169
GVGDVGKSW                                                               9

SEQ ID NO: 1170         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1170
VCGAVGVGY                                                               9

SEQ ID NO: 1171         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1171
VVGAGDVGM                                                               9

SEQ ID NO: 1172         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1172
VGGARGVGR                                                               9

SEQ ID NO: 1173         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1173
GNGDVGKSM                                                               9

SEQ ID NO: 1174         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1174
GKDGVGKSI                                                               9

SEQ ID NO: 1175         moltype = AA   length = 9
FEATURE                 Location/Qualifiers
source                  1..9
```

```
                        organism = synthetic construct
                        mol_type = protein
                        note = Seed: VVGARGVGK (KRAS G12R)
SEQUENCE: 1175
VMGARGVGY                                                                        9

SEQ ID NO: 1176         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1176
VPGARGVGK                                                                        9

SEQ ID NO: 1177         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1177
GVVGVGKSW                                                                        9

SEQ ID NO: 1178         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1178
VAGACGVGI                                                                        9

SEQ ID NO: 1179         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1179
GCRGVGKSM                                                                        9

SEQ ID NO: 1180         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1180
AMDVGKSAW                                                                        9

SEQ ID NO: 1181         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1181
ANDVGKSAK                                                                        9

SEQ ID NO: 1182         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1182
GAVGVGKSS                                                                        9

SEQ ID NO: 1183         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1183
GEDGVGKSI                                                                        9

SEQ ID NO: 1184         moltype = AA   length = 9
```

```
FEATURE                 Location/Qualifiers
source                  1..9
                        organism = synthetic construct
                        mol_type = protein
                        note = Seed: AGDVGKSAL (KRAS G13D)
SEQUENCE: 1184
ANDVGKSAR                                                                    9

SEQ ID NO: 1185         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1185
GCDGVGKSY                                                                    9

SEQ ID NO: 1186         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1186
GEGDVGKSK                                                                    9

SEQ ID NO: 1187         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1187
AQDVGKSAR                                                                    9

SEQ ID NO: 1188         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1188
AGDVGKSAW                                                                    9

SEQ ID NO: 1189         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1189
AGDVGKSAC                                                                    9

SEQ ID NO: 1190         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1190
GPGDVGKSG                                                                    9

SEQ ID NO: 1191         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1191
GAGDVGKSC                                                                    9

SEQ ID NO: 1192         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1192
GGRGVGKSH                                                                    9
```

```
SEQ ID NO: 1193         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1193
GSRGVGKSW                                                                9

SEQ ID NO: 1194         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1194
GDRGVGKSF                                                                9

SEQ ID NO: 1195         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1195
GNCGVGKSR                                                                9

SEQ ID NO: 1196         moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 1196
VEGAGDVGR                                                                9

SEQ ID NO: 1197         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1197
VGGARGVGL                                                                9

SEQ ID NO: 1198         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1198
GFGDVGKSR                                                                9

SEQ ID NO: 1199         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1199
GPGDVGKSK                                                                9

SEQ ID NO: 1200         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1200
GFCGVGKSY                                                                9

SEQ ID NO: 1201         moltype = AA  length = 9
FEATURE                 Location/Qualifiers
source                  1..9
                        organism = synthetic construct
                        mol_type = protein
                        note = Seed: VVGADGVGK (KRAS G12D)
```

```
SEQUENCE: 1201
VYGADGVGK                                                                              9

SEQ ID NO: 1202        moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 1202
GIDGVGKST                                                                              9

SEQ ID NO: 1203        moltype = AA   length = 9
FEATURE                Location/Qualifiers
source                 1..9
                       organism = synthetic construct
                       mol_type = protein
                       note = Seed: VVGAGDVGK (KRAS G13D)
SEQUENCE: 1203
VSGAGDVGL                                                                              9

SEQ ID NO: 1204        moltype = AA   length = 9
FEATURE                Location/Qualifiers
source                 1..9
                       organism = synthetic construct
                       mol_type = protein
                       note = Seed: VVGARGVGK (KRAS G12R)
SEQUENCE: 1204
VWGARGVGR                                                                              9

SEQ ID NO: 1205        moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 1205
GVDGVGKST                                                                              9

SEQ ID NO: 1206        moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 1206
GPDGVGKSS                                                                              9

SEQ ID NO: 1207        moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 1207
GNCGVGKSM                                                                              9

SEQ ID NO: 1208        moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 1208
GEDGVGKSR                                                                              9

SEQ ID NO: 1209        moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 1209
GQCGVGKSR                                                                              9

SEQ ID NO: 1210        moltype = AA   length = 9
FEATURE                Location/Qualifiers
source                 1..9
                       organism = synthetic construct
```

```
                                mol_type = protein
                                note = Seed: GADGVGKSA (KRAS G12D)
SEQUENCE: 1210
GPDGVGKSY                                                               9

SEQ ID NO: 1211                 moltype = AA  length = 9
FEATURE                         Location/Qualifiers
source                          1..9
                                organism = synthetic construct
                                mol_type = protein
                                note = Seed: VVGACGVGK (KRAS G12C)
SEQUENCE: 1211
VEGACGVGR                                                               9

SEQ ID NO: 1212                 moltype = AA  length = 9
FEATURE                         Location/Qualifiers
source                          1..9
                                organism = synthetic construct
                                mol_type = protein
                                note = Seed: VVGAVGVGK (KRAS G12V)
SEQUENCE: 1212
VLGAVGVGF                                                               9

SEQ ID NO: 1213                 moltype = AA  length = 9
FEATURE                         Location/Qualifiers
source                          1..9
                                organism = synthetic construct
                                mol_type = protein
                                note = Seed: GAVGVGKSA (KRAS G12V)
SEQUENCE: 1213
GPVGVGKSW                                                               9

SEQ ID NO: 1214                 moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 1214
GYDGVGKSW                                                               9

SEQ ID NO: 1215                 moltype = AA  length = 9
FEATURE                         Location/Qualifiers
source                          1..9
                                organism = synthetic construct
                                mol_type = protein
                                note = Seed: GACGVGKSA (KRAS G12C)
SEQUENCE: 1215
GICGVGKSI                                                               9

SEQ ID NO: 1216                 moltype = AA  length = 9
FEATURE                         Location/Qualifiers
source                          1..9
                                organism = synthetic construct
                                mol_type = protein
                                note = Seed: GARGVGKSA (KRAS G12R)
SEQUENCE: 1216
GTRGVGKSA                                                               9

SEQ ID NO: 1217                 moltype = AA  length = 9
FEATURE                         Location/Qualifiers
source                          1..9
                                organism = synthetic construct
                                mol_type = protein
                                note = Seed: VVGAVGVGK (KRAS G12V)
SEQUENCE: 1217
VWGAVGVGK                                                               9

SEQ ID NO: 1218                 moltype = AA  length = 9
FEATURE                         Location/Qualifiers
source                          1..9
                                organism = synthetic construct
                                mol_type = protein
                                note = Seed: VVGARGVGK (KRAS G12R)
SEQUENCE: 1218
VFGARGVGF                                                               9

SEQ ID NO: 1219                 moltype = AA  length = 9
FEATURE                         Location/Qualifiers
```

```
source                   1..9
                         organism = synthetic construct
                         mol_type = protein
                         note = Seed: GAVGVGKSA (KRAS G12V)
SEQUENCE: 1219
GPVGVGKSR                                                                              9

SEQ ID NO: 1220          moltype = AA  length = 9
FEATURE                  Location/Qualifiers
source                   1..9
                         organism = synthetic construct
                         mol_type = protein
                         note = Seed: VVGAVGVGK (KRAS G12V)
SEQUENCE: 1220
VDGAVGVGY                                                                              9

SEQ ID NO: 1221          moltype = AA  length = 9
FEATURE                  Location/Qualifiers
source                   1..9
                         organism = synthetic construct
                         mol_type = protein
                         note = Seed: GAGDVGKSA (KRAS G13D)
SEQUENCE: 1221
GGGDVGKSH                                                                              9

SEQ ID NO: 1222          moltype = AA  length = 9
FEATURE                  Location/Qualifiers
source                   1..9
                         organism = synthetic construct
                         mol_type = protein
                         note = Seed: GACGVGKSA (KRAS G12C)
SEQUENCE: 1222
GGCGVGKSH                                                                              9

SEQ ID NO: 1223          moltype = AA  length = 9
FEATURE                  Location/Qualifiers
source                   1..9
                         organism = synthetic construct
                         mol_type = protein
                         note = Seed: VVGAVGVGK (KRAS G12V)
SEQUENCE: 1223
VFGAVGVGF                                                                              9

SEQ ID NO: 1224          moltype = AA  length = 9
FEATURE                  Location/Qualifiers
source                   1..9
                         organism = synthetic construct
                         mol_type = protein
                         note = Seed: VVGAGDVGK (KRAS G13D)
SEQUENCE: 1224
VIGAGDVGF                                                                              9

SEQ ID NO: 1225          moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 1225
AKDVGKSAV                                                                              9

SEQ ID NO: 1226          moltype = AA  length = 9
FEATURE                  Location/Qualifiers
source                   1..9
                         organism = synthetic construct
                         mol_type = protein
                         note = Seed: GACGVGKSA (KRAS G12C)
SEQUENCE: 1226
GDCGVGKSR                                                                              9

SEQ ID NO: 1227          moltype = AA  length = 9
FEATURE                  Location/Qualifiers
source                   1..9
                         organism = synthetic construct
                         mol_type = protein
                         note = Seed: VVGARGVGK (KRAS G12R)
SEQUENCE: 1227
VDGARGVGK                                                                              9
```

```
SEQ ID NO: 1228         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1228
GPRGVGKSE                                                                9

SEQ ID NO: 1229         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1229
APDVGKSAY                                                                9

SEQ ID NO: 1230         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1230
VYGAVGVGL                                                                9

SEQ ID NO: 1231         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1231
GMGDVGKSH                                                                9

SEQ ID NO: 1232         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1232
VTGADGVGL                                                                9

SEQ ID NO: 1233         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1233
GAGDVGKST                                                                9

SEQ ID NO: 1234         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1234
GPRGVGKSK                                                                9

SEQ ID NO: 1235         moltype = AA  length = 9
FEATURE                 Location/Qualifiers
source                  1..9
                        organism = synthetic construct
                        mol_type = protein
                        note = Seed: GADVGKSA (KRAS G12D)
SEQUENCE: 1235
GCDGVGKSK                                                                9

SEQ ID NO: 1236         moltype = AA  length = 9
FEATURE                 Location/Qualifiers
source                  1..9
                        organism = synthetic construct
                        mol_type = protein
                        note = Seed: GADVGKSA (KRAS G12D)
SEQUENCE: 1236
```

```
GGDGVGKSC                                                                         9

SEQ ID NO: 1237           moltype = AA  length = 9
FEATURE                   Location/Qualifiers
source                    1..9
                          organism = synthetic construct
                          mol_type = protein
                          note = Seed: AGDVGKSAL (KRAS G13D)
SEQUENCE: 1237
ATDVGKSAH                                                                         9

SEQ ID NO: 1238           moltype = AA  length = 9
FEATURE                   Location/Qualifiers
source                    1..9
                          organism = synthetic construct
                          mol_type = protein
                          note = Seed: VVGADGVGK (KRAS G12D)
SEQUENCE: 1238
VQGADGVGY                                                                         9

SEQ ID NO: 1239           moltype = AA  length = 9
FEATURE                   Location/Qualifiers
source                    1..9
                          organism = synthetic construct
                          mol_type = protein
                          note = Seed: VVGAGDVGK (KRAS G13D)
SEQUENCE: 1239
VTGAGDVGM                                                                         9

SEQ ID NO: 1240           moltype = AA  length = 9
FEATURE                   Location/Qualifiers
source                    1..9
                          organism = synthetic construct
                          mol_type = protein
                          note = Seed: GAGDVGKSA (KRAS G13D)
SEQUENCE: 1240
GIGDVGKSI                                                                         9

SEQ ID NO: 1241           moltype = AA  length = 9
FEATURE                   Location/Qualifiers
source                    1..9
                          organism = synthetic construct
                          mol_type = protein
                          note = Seed: GACGVGKSA (KRAS G12C)
SEQUENCE: 1241
GMCGVGKSR                                                                         9

SEQ ID NO: 1242           moltype = AA  length = 9
FEATURE                   Location/Qualifiers
source                    1..9
                          organism = synthetic construct
                          mol_type = protein
                          note = Seed: AGDVGKSAL (KRAS G13D)
SEQUENCE: 1242
AMDVGKSAR                                                                         9

SEQ ID NO: 1243           moltype = AA  length = 9
FEATURE                   Location/Qualifiers
source                    1..9
                          organism = synthetic construct
                          mol_type = protein
                          note = Seed: GACGVGKSA (KRAS G12C)
SEQUENCE: 1243
GCCGVGKSF                                                                         9

SEQ ID NO: 1244           moltype = AA  length = 9
FEATURE                   Location/Qualifiers
source                    1..9
                          organism = synthetic construct
                          mol_type = protein
                          note = Seed: AGDVGKSAL (KRAS G13D)
SEQUENCE: 1244
AEDVGKSAK                                                                         9

SEQ ID NO: 1245           moltype = AA  length = 9
FEATURE                   Location/Qualifiers
source                    1..9
                          organism = synthetic construct
                          mol_type = protein
```

```
                              note = Seed: GAVGVGKSA (KRAS G12V)
SEQUENCE: 1245
GEVGVGKSR                                                              9

SEQ ID NO: 1246       moltype = AA   length = 9
FEATURE               Location/Qualifiers
source                1..9
                      organism = synthetic construct
                      mol_type = protein
                      note = Seed: GADGVGKSA (KRAS G12D)
SEQUENCE: 1246
GWDGVGKSK                                                              9

SEQ ID NO: 1247       moltype = AA   length = 9
FEATURE               Location/Qualifiers
source                1..9
                      organism = synthetic construct
                      mol_type = protein
                      note = Seed: GACGVGKSA (KRAS G12C)
SEQUENCE: 1247
GSCGVGKSW                                                              9

SEQ ID NO: 1248       moltype = AA   length = 9
FEATURE               Location/Qualifiers
source                1..9
                      organism = synthetic construct
                      mol_type = protein
                      note = Seed: VVGACGVGK (KRAS G12C)
SEQUENCE: 1248
VVGACGVGL                                                              9

SEQ ID NO: 1249       moltype = AA   length = 9
FEATURE               Location/Qualifiers
source                1..9
                      organism = synthetic construct
                      mol_type = protein
                      note = Seed: VVGAVGVGK (KRAS G12V)
SEQUENCE: 1249
VSGAVGVGI                                                              9

SEQ ID NO: 1250       moltype = AA   length = 9
FEATURE               Location/Qualifiers
source                1..9
                      organism = synthetic construct
                      mol_type = protein
                      note = Seed: AGDVGKSAL (KRAS G13D)
SEQUENCE: 1250
AIDVGKSAT                                                              9

SEQ ID NO: 1251       moltype = AA   length = 9
FEATURE               Location/Qualifiers
source                1..9
                      organism = synthetic construct
                      mol_type = protein
                      note = Seed: GADGVGKSA (KRAS G12D)
SEQUENCE: 1251
GTDGVGKSH                                                              9

SEQ ID NO: 1252       moltype = AA   length = 9
FEATURE               Location/Qualifiers
source                1..9
                      organism = synthetic construct
                      mol_type = protein
                      note = Seed: GARGVGKSA (KRAS G12R)
SEQUENCE: 1252
GARGVGKSR                                                              9

SEQ ID NO: 1253       moltype = AA   length = 9
FEATURE               Location/Qualifiers
source                1..9
                      organism = synthetic construct
                      mol_type = protein
                      note = Seed: VVGAVGVGK (KRAS G12V)
SEQUENCE: 1253
VSGAVGVGV                                                              9

SEQ ID NO: 1254       moltype = AA   length = 9
FEATURE               Location/Qualifiers
source                1..9
```

```
                        organism = synthetic construct
                        mol_type = protein
                        note = Seed: VVGARGVGK (KRAS G12R)
SEQUENCE: 1254
VYGARGVGK                                                                    9

SEQ ID NO: 1255         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1255
AMDVGKSAA                                                                    9

SEQ ID NO: 1256         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1256
VLGARGVGY                                                                    9

SEQ ID NO: 1257         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1257
GVRGVGKSW                                                                    9

SEQ ID NO: 1258         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1258
GACGVGKST                                                                    9

SEQ ID NO: 1259         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1259
GYDGVGKSR                                                                    9

SEQ ID NO: 1260         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1260
GCDGVGKSR                                                                    9

SEQ ID NO: 1261         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1261
GGVGVGKSV                                                                    9

SEQ ID NO: 1262         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1262
VFGAVGVGY                                                                    9

SEQ ID NO: 1263         moltype = AA   length = 9
```

```
FEATURE              Location/Qualifiers
source               1..9
                     organism = synthetic construct
                     mol_type = protein
                     note = Seed: VVGAVGVGK (KRAS G12V)
SEQUENCE: 1263
VIGAVGVGH                                                                        9

SEQ ID NO: 1264      moltype = AA   length = 9
FEATURE              Location/Qualifiers
source               1..9
                     organism = synthetic construct
                     mol_type = protein
                     note = Seed: VVGACGVGK (KRAS G12C)
SEQUENCE: 1264
VAGACGVGV                                                                        9

SEQ ID NO: 1265      moltype = AA   length = 9
FEATURE              Location/Qualifiers
source               1..9
                     organism = synthetic construct
                     mol_type = protein
                     note = Seed: AGDVGKSAL (KRAS G13D)
SEQUENCE: 1265
ADDVGKSAR                                                                        9

SEQ ID NO: 1266      moltype = AA   length = 9
FEATURE              Location/Qualifiers
source               1..9
                     organism = synthetic construct
                     mol_type = protein
                     note = Seed: DVGKSALTI (KRAS G13D)
SEQUENCE: 1266
DLGKSALTI                                                                        9

SEQ ID NO: 1267      moltype = AA   length = 9
FEATURE              Location/Qualifiers
source               1..9
                     organism = synthetic construct
                     mol_type = protein
                     note = Seed: AGDVGKSAL (KRAS G13D)
SEQUENCE: 1267
AQDVGKSAC                                                                        9

SEQ ID NO: 1268      moltype = AA   length = 9
FEATURE              Location/Qualifiers
source               1..9
                     organism = synthetic construct
                     mol_type = protein
                     note = Seed: GADGVGKSA (KRAS G12D)
SEQUENCE: 1268
GKDGVGKSV                                                                        9

SEQ ID NO: 1269      moltype = AA   length = 9
FEATURE              Location/Qualifiers
source               1..9
                     organism = synthetic construct
                     mol_type = protein
                     note = Seed: GAGDVGKSA (KRAS G13D)
SEQUENCE: 1269
GCGDVGKSR                                                                        9

SEQ ID NO: 1270      moltype = AA   length = 9
FEATURE              Location/Qualifiers
source               1..9
                     organism = synthetic construct
                     mol_type = protein
                     note = Seed: GADGVGKSA (KRAS G12D)
SEQUENCE: 1270
GPDGVGKSR                                                                        9

SEQ ID NO: 1271      moltype = AA   length = 9
FEATURE              Location/Qualifiers
source               1..9
                     organism = synthetic construct
                     mol_type = protein
                     note = Seed: LVVVGAVGV (KRAS G12V)
SEQUENCE: 1271
LAVVGAVGL                                                                        9
```

```
SEQ ID NO: 1272        moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 1272
GCGDVGKSK                                                                     9

SEQ ID NO: 1273        moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 1273
GLGDVGKSH                                                                     9

SEQ ID NO: 1274        moltype = AA  length = 9
FEATURE                Location/Qualifiers
source                 1..9
                       organism = synthetic construct
                       mol_type = protein
                       note = Seed: LVVVGARGV (KRAS G12R)
SEQUENCE: 1274
LMVVGARGM                                                                     9

SEQ ID NO: 1275        moltype = AA  length = 9
FEATURE                Location/Qualifiers
source                 1..9
                       organism = synthetic construct
                       mol_type = protein
                       note = Seed: LVVVGARGV (KRAS G12R)
SEQUENCE: 1275
LLVVGARGM                                                                     9

SEQ ID NO: 1276        moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 1276
AMDVGKSAK                                                                     9

SEQ ID NO: 1277        moltype = AA  length = 9
FEATURE                Location/Qualifiers
source                 1..9
                       organism = synthetic construct
                       mol_type = protein
                       note = Seed: LVVVGACGV (KRAS G12C)
SEQUENCE: 1277
LLVVGACGT                                                                     9

SEQ ID NO: 1278        moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 1278
GARGVGKSK                                                                     9

SEQ ID NO: 1279        moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 1279
VTGAGDVGL                                                                     9

SEQ ID NO: 1280        moltype = AA  length = 9
FEATURE                Location/Qualifiers
source                 1..9
                       organism = synthetic construct
                       mol_type = protein
                       note = Seed: GADGVGKSA (KRAS G12D)
```

```
-continued

SEQUENCE: 1280
GMDGVGKSW                                                               9

SEQ ID NO: 1281         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1281
VDGARGVGR                                                               9

SEQ ID NO: 1282         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1282
GFVGVGKSR                                                               9

SEQ ID NO: 1283         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1283
GRDGVGKSY                                                               9

SEQ ID NO: 1284         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1284
DIGKSALTL                                                               9

SEQ ID NO: 1285         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1285
GFVGVGKSF                                                               9

SEQ ID NO: 1286         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1286
GADGVGKSS                                                               9

SEQ ID NO: 1287         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1287
GCGDVGKSM                                                               9

SEQ ID NO: 1288         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1288
VSGADGVGH                                                               9

SEQ ID NO: 1289         moltype = AA  length = 9
FEATURE                 Location/Qualifiers
source                  1..9
                        organism = synthetic construct
```

```
                                   mol_type = protein
                                   note = Seed: GAGDVGKSA (KRAS G13D)
SEQUENCE: 1289
GYGDVGKSY                                                                    9

SEQ ID NO: 1290              moltype = AA  length = 9
FEATURE                      Location/Qualifiers
source                       1..9
                             organism = synthetic construct
                             mol_type = protein
                             note = Seed: GAVGVGKSA (KRAS G12V)
SEQUENCE: 1290
GYVGVGKSK                                                                    9

SEQ ID NO: 1291              moltype = AA  length = 9
FEATURE                      Location/Qualifiers
source                       1..9
                             organism = synthetic construct
                             mol_type = protein
                             note = Seed: GACGVGKSA (KRAS G12C)
SEQUENCE: 1291
GFCGVGKSK                                                                    9

SEQ ID NO: 1292              moltype = AA  length = 9
FEATURE                      Location/Qualifiers
source                       1..9
                             organism = synthetic construct
                             mol_type = protein
                             note = Seed: GACGVGKSA (KRAS G12C)
SEQUENCE: 1292
GACGVGKSC                                                                    9

SEQ ID NO: 1293              moltype = AA  length = 9
FEATURE                      Location/Qualifiers
source                       1..9
                             organism = synthetic construct
                             mol_type = protein
                             note = Seed: VVGACGVGK (KRAS G12C)
SEQUENCE: 1293
VGGACGVGF                                                                    9

SEQ ID NO: 1294              moltype = AA  length = 9
FEATURE                      Location/Qualifiers
source                       1..9
                             organism = synthetic construct
                             mol_type = protein
                             note = Seed: GAGDVGKSA (KRAS G13D)
SEQUENCE: 1294
GFGDVGKSF                                                                    9

SEQ ID NO: 1295              moltype = AA  length = 9
FEATURE                      Location/Qualifiers
source                       1..9
                             organism = synthetic construct
                             mol_type = protein
                             note = Seed: GADGVGKSA (KRAS G12D)
SEQUENCE: 1295
GGDGVGKSA                                                                    9

SEQ ID NO: 1296              moltype = AA  length = 9
FEATURE                      Location/Qualifiers
source                       1..9
                             organism = synthetic construct
                             mol_type = protein
                             note = Seed: GADGVGKSA (KRAS G12D)
SEQUENCE: 1296
GWDGVGKSR                                                                    9

SEQ ID NO: 1297              moltype = AA  length = 9
FEATURE                      Location/Qualifiers
source                       1..9
                             organism = synthetic construct
                             mol_type = protein
                             note = Seed: GACGVGKSA (KRAS G12C)
SEQUENCE: 1297
GMCGVGKSK                                                                    9

SEQ ID NO: 1298              moltype = AA  length = 9
FEATURE                      Location/Qualifiers
```

```
source                     1..9
                           organism = synthetic construct
                           mol_type = protein
                           note = Seed: GAGDVGKSA (KRAS G13D)
SEQUENCE: 1298
GYGDVGKSK                                                                          9

SEQ ID NO: 1299            moltype = AA  length = 9
FEATURE                    Location/Qualifiers
source                     1..9
                           organism = synthetic construct
                           mol_type = protein
                           note = Seed: GACGVGKSA (KRAS G12C)
SEQUENCE: 1299
GECGVGKSK                                                                          9

SEQ ID NO: 1300            moltype = AA  length = 9
FEATURE                    Location/Qualifiers
source                     1..9
                           organism = synthetic construct
                           mol_type = protein
                           note = Seed: VVGAVGVGK (KRAS G12V)
SEQUENCE: 1300
VGGAVGVGL                                                                          9

SEQ ID NO: 1301            moltype = AA  length = 9
FEATURE                    Location/Qualifiers
source                     1..9
                           organism = synthetic construct
                           mol_type = protein
                           note = Seed: AGDVGKSAL (KRAS G13D)
SEQUENCE: 1301
AFDVGKSAK                                                                          9

SEQ ID NO: 1302            moltype = AA  length = 9
FEATURE                    Location/Qualifiers
source                     1..9
                           organism = synthetic construct
                           mol_type = protein
                           note = Seed: VVGADGVGK (KRAS G12D)
SEQUENCE: 1302
VVGADGVGL                                                                          9

SEQ ID NO: 1303            moltype = AA  length = 9
FEATURE                    Location/Qualifiers
source                     1..9
                           organism = synthetic construct
                           mol_type = protein
                           note = Seed: GARGVGKSA (KRAS G12R)
SEQUENCE: 1303
GERGVGKSM                                                                          9

SEQ ID NO: 1304            moltype = AA  length = 9
FEATURE                    Location/Qualifiers
source                     1..9
                           organism = synthetic construct
                           mol_type = protein
                           note = Seed: VVGAGDVGK (KRAS G13D)
SEQUENCE: 1304
VYGAGDVGR                                                                          9

SEQ ID NO: 1305            moltype = AA  length = 9
FEATURE                    Location/Qualifiers
source                     1..9
                           organism = synthetic construct
                           mol_type = protein
                           note = Seed: LVVVGACGV (KRAS G12C)
SEQUENCE: 1305
LAVVGACGL                                                                          9

SEQ ID NO: 1306            moltype = AA  length = 9
FEATURE                    Location/Qualifiers
source                     1..9
                           organism = synthetic construct
                           mol_type = protein
                           note = Seed: DVGKSALTI (KRAS G13D)
SEQUENCE: 1306
DMGKSALTL                                                                          9
```

```
SEQ ID NO: 1307         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1307
VYGADGVGR                                                                 9

SEQ ID NO: 1308         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1308
GARGVGKSP                                                                 9

SEQ ID NO: 1309         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1309
GHDGVGKSY                                                                 9

SEQ ID NO: 1310         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1310
VCGADGVGK                                                                 9

SEQ ID NO: 1311         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1311
GEDGVGKSV                                                                 9

SEQ ID NO: 1312         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1312
GEGDVGKSR                                                                 9

SEQ ID NO: 1313         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1313
VPGAVGVGY                                                                 9

SEQ ID NO: 1314         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1314
VCGADGVGR                                                                 9

SEQ ID NO: 1315         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1315
```

-continued

```
GQGDVGKSH                                                                        9

SEQ ID NO: 1316        moltype = AA   length = 9
FEATURE                Location/Qualifiers
source                 1..9
                       organism = synthetic construct
                       mol_type = protein
                       note = Seed: VVGAGDVGK (KRAS G13D)
SEQUENCE: 1316
VCGAGDVGK                                                                        9

SEQ ID NO: 1317        moltype = AA   length = 9
FEATURE                Location/Qualifiers
source                 1..9
                       organism = synthetic construct
                       mol_type = protein
                       note = Seed: GARGVGKSA (KRAS G12R)
SEQUENCE: 1317
GLRGVGKSH                                                                        9

SEQ ID NO: 1318        moltype = AA   length = 9
FEATURE                Location/Qualifiers
source                 1..9
                       organism = synthetic construct
                       mol_type = protein
                       note = Seed: GARGVGKSA (KRAS G12R)
SEQUENCE: 1318
GMRGVGKSH                                                                        9

SEQ ID NO: 1319        moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 1319
GMDGVGKSA                                                                        9

SEQ ID NO: 1320        moltype = AA   length = 9
FEATURE                Location/Qualifiers
source                 1..9
                       organism = synthetic construct
                       mol_type = protein
                       note = Seed: VVGADGVGK (KRAS G12D)
SEQUENCE: 1320
VAGADGVGI                                                                        9

SEQ ID NO: 1321        moltype = AA   length = 9
FEATURE                Location/Qualifiers
source                 1..9
                       organism = synthetic construct
                       mol_type = protein
                       note = Seed: DVGKSALTI (KRAS G13D)
SEQUENCE: 1321
DEGKSALTI                                                                        9

SEQ ID NO: 1322        moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 1322
AVDVGKSAT                                                                        9

SEQ ID NO: 1323        moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 1323
AADVGKSAS                                                                        9

SEQ ID NO: 1324        moltype = AA   length = 9
FEATURE                Location/Qualifiers
source                 1..9
                       organism = synthetic construct
                       mol_type = protein
```

```
                       note = Seed: GARGVGKSA (KRAS G12R)
SEQUENCE: 1324
GARGVGKSQ                                                            9

SEQ ID NO: 1325        moltype = AA   length = 9
FEATURE                Location/Qualifiers
source                 1..9
                       organism = synthetic construct
                       mol_type = protein
                       note = Seed: LVVVGACGV (KRAS G12C)
SEQUENCE: 1325
LAVVGACGI                                                            9

SEQ ID NO: 1326        moltype = AA   length = 9
FEATURE                Location/Qualifiers
source                 1..9
                       organism = synthetic construct
                       mol_type = protein
                       note = Seed: VVGACGVGK (KRAS G12C)
SEQUENCE: 1326
VIGACGVGM                                                            9

SEQ ID NO: 1327        moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 1327
GWDGVGKSY                                                            9

SEQ ID NO: 1328        moltype = AA   length = 9
FEATURE                Location/Qualifiers
source                 1..9
                       organism = synthetic construct
                       mol_type = protein
                       note = Seed: VVGADGVGK (KRAS G12D)
SEQUENCE: 1328
VHGADGVGK                                                            9

SEQ ID NO: 1329        moltype = AA   length = 9
FEATURE                Location/Qualifiers
source                 1..9
                       organism = synthetic construct
                       mol_type = protein
                       note = Seed: GARGVGKSA (KRAS G12R)
SEQUENCE: 1329
GQRGVGKSH                                                            9

SEQ ID NO: 1330        moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 1330
GAVGVGKSP                                                            9

SEQ ID NO: 1331        moltype = AA   length = 9
FEATURE                Location/Qualifiers
source                 1..9
                       organism = synthetic construct
                       mol_type = protein
                       note = Seed: VVGADGVGK (KRAS G12D)
SEQUENCE: 1331
VAGADGVGV                                                            9

SEQ ID NO: 1332        moltype = AA   length = 9
FEATURE                Location/Qualifiers
source                 1..9
                       organism = synthetic construct
                       mol_type = protein
                       note = Seed: VVGAGDVGK (KRAS G13D)
SEQUENCE: 1332
VQGAGDVGY                                                            9

SEQ ID NO: 1333        moltype = AA   length = 9
FEATURE                Location/Qualifiers
source                 1..9
```

-continued

```
                          organism = synthetic construct
                          mol_type = protein
                          note = Seed: VVGAVGVGK (KRAS G12V)
SEQUENCE: 1333
VEGAVGVGY                                                               9

SEQ ID NO: 1334           moltype = AA  length = 9
FEATURE                   Location/Qualifiers
source                    1..9
                          organism = synthetic construct
                          mol_type = protein
                          note = Seed: VVGACGVGK (KRAS G12C)
SEQUENCE: 1334
VDGACGVGY                                                               9

SEQ ID NO: 1335           moltype = AA  length = 9
FEATURE                   Location/Qualifiers
source                    1..9
                          organism = synthetic construct
                          mol_type = protein
                          note = Seed: VVGAVGVGK (KRAS G12V)
SEQUENCE: 1335
VFGAVGVGM                                                               9

SEQ ID NO: 1336           moltype = AA  length = 9
FEATURE                   Location/Qualifiers
source                    1..9
                          organism = synthetic construct
                          mol_type = protein
                          note = Seed: LVVVGAVGV (KRAS G12V)
SEQUENCE: 1336
LAVVGAVGI                                                               9

SEQ ID NO: 1337           moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 1337
GFDGVGKSA                                                               9

SEQ ID NO: 1338           moltype = AA  length = 9
FEATURE                   Location/Qualifiers
source                    1..9
                          organism = synthetic construct
                          mol_type = protein
                          note = Seed: GAGDVGKSA (KRAS G13D)
SEQUENCE: 1338
GTGDVGKSW                                                               9

SEQ ID NO: 1339           moltype = AA  length = 9
FEATURE                   Location/Qualifiers
source                    1..9
                          organism = synthetic construct
                          mol_type = protein
                          note = Seed: VVGADGVGK (KRAS G12D)
SEQUENCE: 1339
VWGADGVGK                                                               9

SEQ ID NO: 1340           moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 1340
GGDGVGKSW                                                               9

SEQ ID NO: 1341           moltype = AA  length = 9
FEATURE                   Location/Qualifiers
source                    1..9
                          organism = synthetic construct
                          mol_type = protein
                          note = Seed: VVGARGVGK (KRAS G12R)
SEQUENCE: 1341
VEGARGVGK                                                               9

SEQ ID NO: 1342           moltype = AA  length = 9
```

```
FEATURE                 Location/Qualifiers
source                  1..9
                        organism = synthetic construct
                        mol_type = protein
                        note = Seed: VVGAVGVGK (KRAS G12V)
SEQUENCE: 1342
VTGAVGVGV                                                                        9

SEQ ID NO: 1343         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1343
GEGDVGKSM                                                                        9

SEQ ID NO: 1344         moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 1344
DLGKSALTF                                                                        9

SEQ ID NO: 1345         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1345
GPDGVGKSG                                                                        9

SEQ ID NO: 1346         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1346
GWVGVGKSK                                                                        9

SEQ ID NO: 1347         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1347
GWGDVGKSK                                                                        9

SEQ ID NO: 1348         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1348
VHGAGDVGK                                                                        9

SEQ ID NO: 1349         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1349
VWGAGDVGK                                                                        9

SEQ ID NO: 1350         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1350
VTGAVGVGI                                                                        9
```

```
SEQ ID NO: 1351         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1351
VFGARGVGK                                                                9

SEQ ID NO: 1352         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1352
DMGKSALTF                                                                9

SEQ ID NO: 1353         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1353
GMCGVGKSH                                                                9

SEQ ID NO: 1354         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1354
VVGADGVGH                                                                9

SEQ ID NO: 1355         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1355
GYVGVGKSY                                                                9

SEQ ID NO: 1356         moltype = AA  length = 9
FEATURE                 Location/Qualifiers
source                  1..9
                        organism = synthetic construct
                        mol_type = protein
                        note = Seed: LVVVGARGV (KRAS G12R)
SEQUENCE: 1356
LIVVGARGL                                                                9

SEQ ID NO: 1357         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1357
GYRGVGKSY                                                                9

SEQ ID NO: 1358         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1358
GDVGVGKSF                                                                9

SEQ ID NO: 1359         moltype = AA  length = 9
FEATURE                 Location/Qualifiers
source                  1..9
                        organism = synthetic construct
                        mol_type = protein
                        note = Seed: GACGVGKSA (KRAS G12C)
```

```
SEQUENCE: 1359
GVCGVGKSW                                                                    9

SEQ ID NO: 1360         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1360
AEDVGKSAR                                                                    9

SEQ ID NO: 1361         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1361
GIDGVGKSH                                                                    9

SEQ ID NO: 1362         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1362
VSGACGVGH                                                                    9

SEQ ID NO: 1363         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1363
GEVGVGKSM                                                                    9

SEQ ID NO: 1364         moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 1364
VCGAGDVGR                                                                    9

SEQ ID NO: 1365         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1365
GQCGVGKSH                                                                    9

SEQ ID NO: 1366         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1366
AFDVGKSAR                                                                    9

SEQ ID NO: 1367         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1367
VDGARGVGY                                                                    9

SEQ ID NO: 1368         moltype = AA  length = 9
FEATURE                 Location/Qualifiers
source                  1..9
                        organism = synthetic construct
```

```
                                   mol_type = protein
                                   note = Seed: GARGVGKSA (KRAS G12R)
SEQUENCE: 1368
GMRGVGKSA                                                                    9

SEQ ID NO: 1369        moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 1369
ADDVGKSAC                                                                    9

SEQ ID NO: 1370        moltype = AA   length = 9
FEATURE                Location/Qualifiers
source                 1..9
                       organism = synthetic construct
                       mol_type = protein
                       note = Seed: VVGAVGVGK (KRAS G12V)
SEQUENCE: 1370
VQGAVGVGM                                                                    9

SEQ ID NO: 1371        moltype = AA   length = 9
FEATURE                Location/Qualifiers
source                 1..9
                       organism = synthetic construct
                       mol_type = protein
                       note = Seed: LVVVGAVGV (KRAS G12V)
SEQUENCE: 1371
LIVVGAVGM                                                                    9

SEQ ID NO: 1372        moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 1372
GPGDVGKSR                                                                    9

SEQ ID NO: 1373        moltype = AA   length = 9
FEATURE                Location/Qualifiers
source                 1..9
                       organism = synthetic construct
                       mol_type = protein
                       note = Seed: VVGACGVGK (KRAS G12C)
SEQUENCE: 1373
VTGACGVGH                                                                    9

SEQ ID NO: 1374        moltype = AA   length = 9
FEATURE                Location/Qualifiers
source                 1..9
                       organism = synthetic construct
                       mol_type = protein
                       note = Seed: VVGARGVGK (KRAS G12R)
SEQUENCE: 1374
VMGARGVGF                                                                    9

SEQ ID NO: 1375        moltype = AA   length = 9
FEATURE                Location/Qualifiers
source                 1..9
                       organism = synthetic construct
                       mol_type = protein
                       note = Seed: DVGKSALTI (KRAS G13D)
SEQUENCE: 1375
DIGKSALTM                                                                    9

SEQ ID NO: 1376        moltype = AA   length = 9
FEATURE                Location/Qualifiers
source                 1..9
                       organism = synthetic construct
                       mol_type = protein
                       note = Seed: VVGARGVGK (KRAS G12R)
SEQUENCE: 1376
VNGARGVGK                                                                    9

SEQ ID NO: 1377        moltype = AA   length = 9
FEATURE                Location/Qualifiers
```

```
source                  1..9
                        organism = synthetic construct
                        mol_type = protein
                        note = Seed: GADGVGKSA (KRAS G12D)
SEQUENCE: 1377
GWDGVGKSC                                                                       9

SEQ ID NO: 1378         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1378
GQDGVGKSW                                                                       9

SEQ ID NO: 1379         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1379
VMGACGVGF                                                                       9

SEQ ID NO: 1380         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1380
GLRGVGKSA                                                                       9

SEQ ID NO: 1381         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1381
GAGDVGKSQ                                                                       9

SEQ ID NO: 1382         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1382
VHGAVGVGR                                                                       9

SEQ ID NO: 1383         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1383
AYDVGKSAK                                                                       9

SEQ ID NO: 1384         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1384
GPRGVGKSN                                                                       9

SEQ ID NO: 1385         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1385
GIVGVGKSW                                                                       9
```

```
SEQ ID NO: 1386          moltype = AA  length = 9
FEATURE                  Location/Qualifiers
source                   1..9
                         organism = synthetic construct
                         mol_type = protein
                         note = Seed: GARGVGKSA (KRAS G12R)

SEQUENCE: 1386
GFRGVGKSF                                                                  9

SEQ ID NO: 1387          moltype = AA  length = 9
FEATURE                  Location/Qualifiers
source                   1..9
                         organism = synthetic construct
                         mol_type = protein
                         note = Seed: GADGVGKSA (KRAS G12D)

SEQUENCE: 1387
GCDGVGKSA                                                                  9

SEQ ID NO: 1388          moltype = AA  length = 9
FEATURE                  Location/Qualifiers
source                   1..9
                         organism = synthetic construct
                         mol_type = protein
                         note = Seed: AGDVGKSAL (KRAS G13D)

SEQUENCE: 1388
ADDVGKSAA                                                                  9

SEQ ID NO: 1389          moltype = AA  length = 9
FEATURE                  Location/Qualifiers
source                   1..9
                         organism = synthetic construct
                         mol_type = protein
                         note = Seed: GAVGVGKSA (KRAS G12V)

SEQUENCE: 1389
GQVGVGKSW                                                                  9

SEQ ID NO: 1390          moltype = AA  length = 9
FEATURE                  Location/Qualifiers
source                   1..9
                         organism = synthetic construct
                         mol_type = protein
                         note = Seed: GAVGVGKSA (KRAS G12V)

SEQUENCE: 1390
GGVGVGKSI                                                                  9

SEQ ID NO: 1391          moltype = AA  length = 9
FEATURE                  Location/Qualifiers
source                   1..9
                         organism = synthetic construct
                         mol_type = protein
                         note = Seed: GAGDVGKSA (KRAS G13D)

SEQUENCE: 1391
GIGDVGKSW                                                                  9

SEQ ID NO: 1392          moltype = AA  length = 9
FEATURE                  Location/Qualifiers
source                   1..9
                         organism = synthetic construct
                         mol_type = protein
                         note = Seed: LVVVGAGDV (KRAS G13D)

SEQUENCE: 1392
LMVVGAGDL                                                                  9

SEQ ID NO: 1393          moltype = AA  length = 9
FEATURE                  Location/Qualifiers
source                   1..9
                         organism = synthetic construct
                         mol_type = protein
                         note = Seed: VVGADGVGK (KRAS G12D)

SEQUENCE: 1393
VGGADGVGF                                                                  9

SEQ ID NO: 1394          moltype = AA  length = 9
FEATURE                  Location/Qualifiers
source                   1..9
                         organism = synthetic construct
                         mol_type = protein
                         note = Seed: GACGVGKSA (KRAS G12C)

SEQUENCE: 1394
```

```
GLCGVGKSH                                                                              9

SEQ ID NO: 1395          moltype = AA  length = 9
FEATURE                  Location/Qualifiers
source                   1..9
                         organism = synthetic construct
                         mol_type = protein
                         note = Seed: LVVVGARGV (KRAS G12R)
SEQUENCE: 1395
LQVVGARGL                                                                              9

SEQ ID NO: 1396          moltype = AA  length = 9
FEATURE                  Location/Qualifiers
source                   1..9
                         organism = synthetic construct
                         mol_type = protein
                         note = Seed: VVGAGDVGK (KRAS G13D)
SEQUENCE: 1396
VAGAGDVGI                                                                              9

SEQ ID NO: 1397          moltype = AA  length = 9
FEATURE                  Location/Qualifiers
source                   1..9
                         organism = synthetic construct
                         mol_type = protein
                         note = Seed: GACGVGKSA (KRAS G12C)
SEQUENCE: 1397
GTCGVGKSW                                                                              9

SEQ ID NO: 1398          moltype = AA  length = 9
FEATURE                  Location/Qualifiers
source                   1..9
                         organism = synthetic construct
                         mol_type = protein
                         note = Seed: LVVVGADGV (KRAS G12D)
SEQUENCE: 1398
LVVVGADGA                                                                              9

SEQ ID NO: 1399          moltype = AA  length = 9
FEATURE                  Location/Qualifiers
source                   1..9
                         organism = synthetic construct
                         mol_type = protein
                         note = Seed: GACGVGKSA (KRAS G12C)
SEQUENCE: 1399
GTCGVGKSA                                                                              9

SEQ ID NO: 1400          moltype = AA  length = 9
FEATURE                  Location/Qualifiers
source                   1..9
                         organism = synthetic construct
                         mol_type = protein
                         note = Seed: GADGVGKSA (KRAS G12D)
SEQUENCE: 1400
GHDGVGKSK                                                                              9

SEQ ID NO: 1401          moltype = AA  length = 9
FEATURE                  Location/Qualifiers
source                   1..9
                         organism = synthetic construct
                         mol_type = protein
                         note = Seed: GAVGVGKSA (KRAS G12V)
SEQUENCE: 1401
GNVGVGKSL                                                                              9

SEQ ID NO: 1402          moltype = AA  length = 9
FEATURE                  Location/Qualifiers
source                   1..9
                         organism = synthetic construct
                         mol_type = protein
                         note = Seed: VVGARGVGK (KRAS G12R)
SEQUENCE: 1402
VFGARGVGM                                                                              9

SEQ ID NO: 1403          moltype = AA  length = 9
FEATURE                  Location/Qualifiers
source                   1..9
                         organism = synthetic construct
                         mol_type = protein
```

```
                        note = Seed: GARGVGKSA (KRAS G12R)
SEQUENCE: 1403
GNRGVGKSL                                                                9

SEQ ID NO: 1404         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1404
GPCGVGKSW                                                                9

SEQ ID NO: 1405         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1405
GTGDVGKSA                                                                9

SEQ ID NO: 1406         moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 1406
LSVVGAVGL                                                                9

SEQ ID NO: 1407         moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 1407
DMGKSALTY                                                                9

SEQ ID NO: 1408         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1408
GECGVGKSM                                                                9

SEQ ID NO: 1409         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1409
GADGVGKSP                                                                9

SEQ ID NO: 1410         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1410
VGGAVGVGH                                                                9

SEQ ID NO: 1411         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1411
GARGVGKSS                                                                9

SEQ ID NO: 1412         moltype = AA   length = 9
FEATURE                 Location/Qualifiers
source                  1..9
```

```
                        organism = synthetic construct
                        mol_type = protein
                        note = Seed: GACGVGKSA (KRAS G12C)
SEQUENCE: 1412
GPCGVGKSK                                                             9

SEQ ID NO: 1413         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1413
GPCGVGKSR                                                             9

SEQ ID NO: 1414         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1414
VDGADGVGY                                                             9

SEQ ID NO: 1415         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1415
VMGARGVGM                                                             9

SEQ ID NO: 1416         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1416
GPVGVGKSQ                                                             9

SEQ ID NO: 1417         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1417
VMGARGVGL                                                             9

SEQ ID NO: 1418         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1418
VFGAVGVGL                                                             9

SEQ ID NO: 1419         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1419
VWGADGVGR                                                             9

SEQ ID NO: 1420         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1420
DNGKSALTV                                                             9

SEQ ID NO: 1421         moltype = AA  length = 9
```

```
FEATURE                 Location/Qualifiers
source                  1..9
                        organism = synthetic construct
                        mol_type = protein
                        note = Seed: VVGACGVGK (KRAS G12C)
SEQUENCE: 1421
VNGACGVGY                                                                       9

SEQ ID NO: 1422         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1422
VVGAGDVGL                                                                       9

SEQ ID NO: 1423         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1423
GCRGVGKSL                                                                       9

SEQ ID NO: 1424         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1424
VLGARGVGF                                                                       9

SEQ ID NO: 1425         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1425
GIRGVGKSW                                                                       9

SEQ ID NO: 1426         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1426
VCGACGVGK                                                                       9

SEQ ID NO: 1427         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1427
VMGAVGVGL                                                                       9

SEQ ID NO: 1428         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1428
GGRGVGKSV                                                                       9

SEQ ID NO: 1429         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1429
AADVGKSAP                                                                       9
```

```
SEQ ID NO: 1430          moltype = AA  length = 9
FEATURE                  Location/Qualifiers
source                   1..9
                         organism = synthetic construct
                         mol_type = protein
                         note = Seed: VVGAGDVGK (KRAS G13D)
SEQUENCE: 1430
VWGAGDVGR                                                                  9

SEQ ID NO: 1431          moltype = AA  length = 9
FEATURE                  Location/Qualifiers
source                   1..9
                         organism = synthetic construct
                         mol_type = protein
                         note = Seed: VVGAVGVGK (KRAS G12V)
SEQUENCE: 1431
VLGAVGVGL                                                                  9

SEQ ID NO: 1432          moltype = AA  length = 9
FEATURE                  Location/Qualifiers
source                   1..9
                         organism = synthetic construct
                         mol_type = protein
                         note = Seed: VVGARGVGK (KRAS G12R)
SEQUENCE: 1432
VTGARGVGH                                                                  9

SEQ ID NO: 1433          moltype = AA  length = 9
FEATURE                  Location/Qualifiers
source                   1..9
                         organism = synthetic construct
                         mol_type = protein
                         note = Seed: VVGAVGVGK (KRAS G12V)
SEQUENCE: 1433
VMGAVGVGM                                                                  9

SEQ ID NO: 1434          moltype = AA  length = 9
FEATURE                  Location/Qualifiers
source                   1..9
                         organism = synthetic construct
                         mol_type = protein
                         note = Seed: GAVGVGKSA (KRAS G12V)
SEQUENCE: 1434
GHVGVGKSK                                                                  9

SEQ ID NO: 1435          moltype = AA  length = 9
FEATURE                  Location/Qualifiers
source                   1..9
                         organism = synthetic construct
                         mol_type = protein
                         note = Seed: VVGAVGVGK (KRAS G12V)
SEQUENCE: 1435
VAGAVGVGQ                                                                  9

SEQ ID NO: 1436          moltype = AA  length = 9
FEATURE                  Location/Qualifiers
source                   1..9
                         organism = synthetic construct
                         mol_type = protein
                         note = Seed: GADGVGKSA (KRAS G12D)
SEQUENCE: 1436
GRDGVGKSW                                                                  9

SEQ ID NO: 1437          moltype = AA  length = 9
FEATURE                  Location/Qualifiers
source                   1..9
                         organism = synthetic construct
                         mol_type = protein
                         note = Seed: GAGDVGKSA (KRAS G13D)
SEQUENCE: 1437
GIGDVGKSA                                                                  9

SEQ ID NO: 1438          moltype = AA  length = 9
FEATURE                  Location/Qualifiers
source                   1..9
                         organism = synthetic construct
                         mol_type = protein
                         note = Seed: DVGKSALTI (KRAS G13D)
```

| | | |
|---|---|---|
| SEQUENCE: 1438 DCGKSALTV | | 9 |
| SEQ ID NO: 1439 FEATURE source | moltype = AA  length = 9 Location/Qualifiers 1..9 organism = synthetic construct mol_type = protein note = Seed: VVGACGVGK (KRAS G12C) | |
| SEQUENCE: 1439 VVGACGVGH | | 9 |
| SEQ ID NO: 1440 FEATURE source | moltype = AA  length = 9 Location/Qualifiers 1..9 organism = synthetic construct mol_type = protein note = Seed: DVGKSALTI (KRAS G13D) | |
| SEQUENCE: 1440 DLGKSALTY | | 9 |
| SEQ ID NO: 1441 FEATURE source | moltype = AA  length = 9 Location/Qualifiers 1..9 organism = synthetic construct mol_type = protein note = Seed: GACGVGKSA (KRAS G12C) | |
| SEQUENCE: 1441 GYCGVGKSK | | 9 |
| SEQ ID NO: 1442 FEATURE source | moltype = AA  length = 9 Location/Qualifiers 1..9 organism = synthetic construct mol_type = protein note = Seed: AGDVGKSAL (KRAS G13D) | |
| SEQUENCE: 1442 ACDVGKSAC | | 9 |
| SEQ ID NO: 1443 FEATURE source | moltype = AA  length = 9 Location/Qualifiers 1..9 organism = synthetic construct mol_type = protein note = Seed: GADGVGKSA (KRAS G12D) | |
| SEQUENCE: 1443 GDDGVGKSY | | 9 |
| SEQ ID NO: 1444 FEATURE source | moltype = AA  length = 9 Location/Qualifiers 1..9 organism = synthetic construct mol_type = protein note = Seed: GAVGVGKSA (KRAS G12V) | |
| SEQUENCE: 1444 GPVGVGKSE | | 9 |
| SEQ ID NO: 1445 FEATURE source | moltype = AA  length = 9 Location/Qualifiers 1..9 organism = synthetic construct mol_type = protein note = Seed: VVGADGVGK (KRAS G12D) | |
| SEQUENCE: 1445 VIGADGVGM | | 9 |
| SEQ ID NO: 1446 FEATURE source | moltype = AA  length = 9 Location/Qualifiers 1..9 organism = synthetic construct mol_type = protein note = Seed: AGDVGKSAL (KRAS G13D) | |
| SEQUENCE: 1446 ACDVGKSAA | | 9 |
| SEQ ID NO: 1447 FEATURE source | moltype = AA  length = 9 Location/Qualifiers 1..9 organism = synthetic construct | |

```
                                       mol_type = protein
                                       note = Seed: VVGADGVGK (KRAS G12D)
SEQUENCE: 1447
VNGADGVGY                                                                      9

SEQ ID NO: 1448                        moltype = AA  length = 9
FEATURE                                Location/Qualifiers
source                                 1..9
                                       organism = synthetic construct
                                       mol_type = protein
                                       note = Seed: GAVGVGKSA (KRAS G12V)
SEQUENCE: 1448
GFVGVGKSM                                                                      9

SEQ ID NO: 1449                        moltype = AA  length = 9
FEATURE                                Location/Qualifiers
source                                 1..9
                                       organism = synthetic construct
                                       mol_type = protein
                                       note = Seed: VVGARGVGK (KRAS G12R)
SEQUENCE: 1449
VNGARGVGR                                                                      9

SEQ ID NO: 1450                        moltype = AA  length = 9
FEATURE                                Location/Qualifiers
source                                 1..9
                                       organism = synthetic construct
                                       mol_type = protein
                                       note = Seed: VVGARGVGK (KRAS G12R)
SEQUENCE: 1450
VLGARGVGM                                                                      9

SEQ ID NO: 1451                        moltype = AA  length = 9
FEATURE                                Location/Qualifiers
source                                 1..9
                                       organism = synthetic construct
                                       mol_type = protein
                                       note = Seed: GAGDVGKSA (KRAS G13D)
SEQUENCE: 1451
GQGDVGKSW                                                                      9

SEQ ID NO: 1452                        moltype = AA  length = 9
FEATURE                                Location/Qualifiers
source                                 1..9
                                       organism = synthetic construct
                                       mol_type = protein
                                       note = Seed: LVVGADGV (KRAS G12D)
SEQUENCE: 1452
LIVVGADGA                                                                      9

SEQ ID NO: 1453                        moltype = AA  length = 9
FEATURE                                Location/Qualifiers
source                                 1..9
                                       organism = synthetic construct
                                       mol_type = protein
                                       note = Seed: GAVGVGKSA (KRAS G12V)
SEQUENCE: 1453
GIVGVGKSA                                                                      9

SEQ ID NO: 1454                        moltype = AA  length = 9
FEATURE                                Location/Qualifiers
source                                 1..9
                                       organism = synthetic construct
                                       mol_type = protein
                                       note = Seed: VVGACGVGK (KRAS G12C)
SEQUENCE: 1454
VHGACGVGK                                                                      9

SEQ ID NO: 1455                        moltype = AA  length = 9
FEATURE                                Location/Qualifiers
source                                 1..9
                                       organism = synthetic construct
                                       mol_type = protein
                                       note = Seed: LVVGAGDV (KRAS G13D)
SEQUENCE: 1455
LIVVGAGDV                                                                      9

SEQ ID NO: 1456                        moltype = AA  length = 9
FEATURE                                Location/Qualifiers
```

```
source                      1..9
                            organism = synthetic construct
                            mol_type = protein
                            note = Seed: VVGAGDVGK (KRAS G13D)
SEQUENCE: 1456
VAGAGDVGV                                                                      9

SEQ ID NO: 1457             moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 1457
GDCGVGKSF                                                                      9

SEQ ID NO: 1458             moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 1458
GFCGVGKSR                                                                      9

SEQ ID NO: 1459             moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 1459
GECGVGKSR                                                                      9

SEQ ID NO: 1460             moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 1460
GTRGVGKSW                                                                      9

SEQ ID NO: 1461             moltype = AA   length = 9
FEATURE                     Location/Qualifiers
source                      1..9
                            organism = synthetic construct
                            mol_type = protein
                            note = Seed: GAGDVGKSA (KRAS G13D)
SEQUENCE: 1461
GDGDVGKSF                                                                      9

SEQ ID NO: 1462             moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 1462
GNVGVGKSH                                                                      9

SEQ ID NO: 1463             moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 1463
GICGVGKSA                                                                      9

SEQ ID NO: 1464             moltype = AA   length = 9
FEATURE                     Location/Qualifiers
source                      1..9
                            organism = synthetic construct
                            mol_type = protein
                            note = Seed: VVGACGVGK (KRAS G12C)
SEQUENCE: 1464
VWGACGVGK                                                                      9
```

```
SEQ ID NO: 1465        moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 1465
GCCGVGKSM                                                                  9

SEQ ID NO: 1466        moltype = AA  length = 9
FEATURE                Location/Qualifiers
source                 1..9
                       organism = synthetic construct
                       mol_type = protein
                       note = Seed: LVVVGAGDV (KRAS G13D)
SEQUENCE: 1466
LMVVGAGDI                                                                  9

SEQ ID NO: 1467        moltype = AA  length = 9
FEATURE                Location/Qualifiers
source                 1..9
                       organism = synthetic construct
                       mol_type = protein
                       note = Seed: VVGACGVGK (KRAS G12C)
SEQUENCE: 1467
VAGACGVGW                                                                  9

SEQ ID NO: 1468        moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 1468
GYGDVGKSR                                                                  9

SEQ ID NO: 1469        moltype = AA  length = 9
FEATURE                Location/Qualifiers
source                 1..9
                       organism = synthetic construct
                       mol_type = protein
                       note = Seed: LVVVGARGV (KRAS G12R)
SEQUENCE: 1469
LQVVGARGI                                                                  9

SEQ ID NO: 1470        moltype = AA  length = 9
FEATURE                Location/Qualifiers
source                 1..9
                       organism = synthetic construct
                       mol_type = protein
                       note = Seed: LVVVGAVGV (KRAS G12V)
SEQUENCE: 1470
LLVVGAVGT                                                                  9

SEQ ID NO: 1471        moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 1471
VSGAGDVGH                                                                  9

SEQ ID NO: 1472        moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 1472
AIDVGKSAH                                                                  9

SEQ ID NO: 1473        moltype = AA  length = 9
FEATURE                Location/Qualifiers
source                 1..9
                       organism = synthetic construct
                       mol_type = protein
                       note = Seed: VVGARGVGK (KRAS G12R)
SEQUENCE: 1473
```

```
VSGARGVGW                                                                         9

SEQ ID NO: 1474         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1474
GACGVGKSQ                                                                         9

SEQ ID NO: 1475         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1475
VQGACGVGF                                                                         9

SEQ ID NO: 1476         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1476
VCGACGVGY                                                                         9

SEQ ID NO: 1477         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1477
VCGADGVGY                                                                         9

SEQ ID NO: 1478         moltype = AA  length = 9
FEATURE                 Location/Qualifiers
source                  1..9
                        organism = synthetic construct
                        mol_type = protein
                        note = Seed: LVVVGAGDV (KRAS G13D)
SEQUENCE: 1478
LLVVGAGDL                                                                         9

SEQ ID NO: 1479         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1479
ACDVGKSAW                                                                         9

SEQ ID NO: 1480         moltype = AA  length = 9
FEATURE                 Location/Qualifiers
source                  1..9
                        organism = synthetic construct
                        mol_type = protein
                        note = Seed: LVVVGADGV (KRAS G12D)
SEQUENCE: 1480
LAVVGADGL                                                                         9

SEQ ID NO: 1481         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1481
VCGAVGVGF                                                                         9

SEQ ID NO: 1482         moltype = AA  length = 9
FEATURE                 Location/Qualifiers
source                  1..9
                        organism = synthetic construct
                        mol_type = protein
```

```
                        note = Seed: VVGADGVGK (KRAS G12D)
SEQUENCE: 1482
VHGADGVGR                                                                     9

SEQ ID NO: 1483         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1483
GCCGVGKSK                                                                     9

SEQ ID NO: 1484         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1484
AWDVGKSAT                                                                     9

SEQ ID NO: 1485         moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 1485
LSVVGACGI                                                                     9

SEQ ID NO: 1486         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1486
GCCGVGKSR                                                                     9

SEQ ID NO: 1487         moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 1487
LSVVGAVGI                                                                     9

SEQ ID NO: 1488         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1488
AYDVGKSAR                                                                     9

SEQ ID NO: 1489         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1489
VLGARGVGL                                                                     9

SEQ ID NO: 1490         moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 1490
LQVVGAVGM                                                                     9

SEQ ID NO: 1491         moltype = AA  length = 9
FEATURE                 Location/Qualifiers
source                  1..9
```

```
SEQUENCE: 1491
LTVVGAVGM                                                                          9

SEQ ID NO: 1492          moltype = AA   length = 9
FEATURE                  Location/Qualifiers
source                   1..9
                         organism = synthetic construct
                         mol_type = protein
                         note = Seed: VVGADGVGK (KRAS G12D)
SEQUENCE: 1492
VTGADGVGH                                                                          9

SEQ ID NO: 1493          moltype = AA   length = 9
FEATURE                  Location/Qualifiers
source                   1..9
                         organism = synthetic construct
                         mol_type = protein
                         note = Seed: VVGADGVGK (KRAS G12D)
SEQUENCE: 1493
VQGADGVGF                                                                          9

SEQ ID NO: 1494          moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 1494
GYDGVGKST                                                                          9

SEQ ID NO: 1495          moltype = AA   length = 9
FEATURE                  Location/Qualifiers
source                   1..9
                         organism = synthetic construct
                         mol_type = protein
                         note = Seed: VVGACGVGK (KRAS G12C)
SEQUENCE: 1495
VIGACGVGL                                                                          9

SEQ ID NO: 1496          moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 1496
VLGAVGVGM                                                                          9

SEQ ID NO: 1497          moltype = AA   length = 9
FEATURE                  Location/Qualifiers
source                   1..9
                         organism = synthetic construct
                         mol_type = protein
                         note = Seed: LVVVGACGV (KRAS G12C)
SEQUENCE: 1497
LSVVGACGL                                                                          9

SEQ ID NO: 1498          moltype = AA   length = 9
FEATURE                  Location/Qualifiers
source                   1..9
                         organism = synthetic construct
                         mol_type = protein
                         note = Seed: VVGAGDVGK (KRAS G13D)
SEQUENCE: 1498
VNGAGDVGY                                                                          9

SEQ ID NO: 1499          moltype = AA   length = 9
FEATURE                  Location/Qualifiers
source                   1..9
                         organism = synthetic construct
                         mol_type = protein
                         note = Seed: VVGADGVGK (KRAS G12D)
SEQUENCE: 1499
VMGADGVGF                                                                          9

SEQ ID NO: 1500          moltype = AA   length = 9
```

```
FEATURE                 Location/Qualifiers
source                  1..9
                        organism = synthetic construct
                        mol_type = protein
                        note = Seed: GAGDVGKSA (KRAS G13D)
SEQUENCE: 1500
GWGDVGKSR                                                                      9

SEQ ID NO: 1501         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1501
AWDVGKSAK                                                                      9

SEQ ID NO: 1502         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1502
GNGDVGKSL                                                                      9

SEQ ID NO: 1503         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1503
VSGAVGVGW                                                                      9

SEQ ID NO: 1504         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1504
GQRGVGKSV                                                                      9

SEQ ID NO: 1505         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1505
VFGARGVGL                                                                      9

SEQ ID NO: 1506         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1506
VGGACGVGM                                                                      9

SEQ ID NO: 1507         moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 1507
DLGKSALTL                                                                      9

SEQ ID NO: 1508         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1508
GVRGVGKSC                                                                      9
```

```
SEQ ID NO: 1509         moltype = AA   length = 9
FEATURE                 Location/Qualifiers
source                  1..9
                        organism = synthetic construct
                        mol_type = protein
                        note = Seed: LVVVGACGV (KRAS G12C)
SEQUENCE: 1509
LQVVGACGM                                                                       9

SEQ ID NO: 1510         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1510
VYGARGVGY                                                                       9

SEQ ID NO: 1511         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1511
VYGADGVGY                                                                       9

SEQ ID NO: 1512         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1512
GGCGVGKSV                                                                       9

SEQ ID NO: 1513         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1513
VEGARGVGR                                                                       9

SEQ ID NO: 1514         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1514
VCGACGVGR                                                                       9

SEQ ID NO: 1515         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1515
GGRGVGKSI                                                                       9

SEQ ID NO: 1516         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1516
GYCGVGKSY                                                                       9

SEQ ID NO: 1517         moltype = AA   length = 9
FEATURE                 Location/Qualifiers
source                  1..9
                        organism = synthetic construct
                        mol_type = protein
                        note = Seed: AGDVGKSAL (KRAS G13D)
```

```
SEQUENCE: 1517
APDVGKSAK                                                                        9

SEQ ID NO: 1518        moltype = AA  length = 9
FEATURE                Location/Qualifiers
source                 1..9
                       organism = synthetic construct
                       mol_type = protein
                       note = Seed: DVGKSALTI (KRAS G13D)
SEQUENCE: 1518
DEGKSALTL                                                                        9

SEQ ID NO: 1519        moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 1519
GERGVGKSL                                                                        9

SEQ ID NO: 1520        moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 1520
GCDGVGKSW                                                                        9

SEQ ID NO: 1521        moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 1521
GWGDVGKSY                                                                        9

SEQ ID NO: 1522        moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 1522
ACDVGKSAK                                                                        9

SEQ ID NO: 1523        moltype = AA  length = 321
FEATURE                Location/Qualifiers
source                 1..321
                       organism = synthetic construct
                       mol_type = protein
SEQUENCE: 1523
MRVTAPRTLI LLLSGALALT ETWAGSGGSG GGGSGGGADG VGKSMGGSGG GGSGGLMVVG    60
ADGVGGSGGG GSGGGAVGVG KSLGGSGGGG SGGLMVVGAV GVGGSGGGGS GGVTGARGVG   120
KGGSGGGGSG GEYKFVVLGT VGHGKSGGSG GGGSGGEYKI VVAGNVGIGK SGGSGGGGSG   180
GEYKFVVFGS DGAGKSGGSG GGGSGGMTEY KFVVSGADGI GKSALTGGSG GGGSGGMTEY   240
KFVVIGNRGV GKSALTGGSL GGGGSGIVGI VAGLAVLAVV VIGAVVATVM CRRKSSGGKG   300
GSYSQAASSD SAQGSDVSLT A                                            321
```